US012527218B2

(12) United States Patent
Hong et al.

(10) Patent No.: US 12,527,218 B2
(45) Date of Patent: Jan. 13, 2026

(54) ORGANIC COMPOUND, ORGANIC LIGHT EMITTING DIODE AND ORGANIC LIGHT EMITTING DEVICE INCLUDING THE ORGANIC COMPOUND

(71) Applicants: LG DISPLAY CO., LTD., Seoul (KR); LT Materials Co., Ltd., Yongin-si (KR)

(72) Inventors: Tae-Ryang Hong, Paju-si (KR); Suk-Young Bae, Paju-si (KR); Jun-Yun Kim, Paju-si (KR); Yong-Woo Kim, Yongin-si (KR); Yong-Geun Jung, Yongin-si (KR); Jin-Hwan Shin, Yongin-si (KR); Yeon-Jun Shim, Yongin-si (KR)

(73) Assignees: LG DISPLAY CO., LTD., Seoul (KR); LT MATERIALS CO., LTD., Yongin-si (KR)

( * ) Notice: Subject to any disclaimer, the term of this patent is extended or adjusted under 35 U.S.C. 154(b) by 851 days.

(21) Appl. No.: 17/385,831

(22) Filed: Jul. 26, 2021

(65) Prior Publication Data

US 2022/0077401 A1 Mar. 10, 2022

(30) Foreign Application Priority Data

Sep. 10, 2020 (KR) ........................ 10-2020-0115964

(51) Int. Cl.
*H01L 51/50* (2006.01)
*C07D 487/04* (2006.01)
(Continued)

(52) U.S. Cl.
CPC ....... *H10K 85/6572* (2023.02); *C07D 487/04* (2013.01); *C09K 11/06* (2013.01);
(Continued)

(58) Field of Classification Search
None
See application file for complete search history.

(56) References Cited

U.S. PATENT DOCUMENTS

2006/0273713 A1* 12/2006 Mehta .................... H10K 71/16 428/917
2009/0302313 A1* 12/2009 Choi ...................... H10K 71/00 438/45
(Continued)

FOREIGN PATENT DOCUMENTS

CN 107619412 * 1/2018 ............. H01L 51/54
CN 110041268 * 7/2019 ........... C07D 239/26
(Continued)

OTHER PUBLICATIONS

Office Action issued Sep. 25, 2023 for counterpart Korean Patent Application No. 10-2020-0115964.
(Continued)

*Primary Examiner* — Gregory D Clark
(74) *Attorney, Agent, or Firm* — Morgan, Lewis & Bockius LLP

(57) ABSTRACT

The present disclosure relates to an organic compound in which an electron acceptor moiety and an electron donor moiety of a fused aromatic ring or a hetero aromatic ring are directly linked or through an linker moiety and they are connected via carbon-carbon bond, and an organic light emitting diode (OLED) and an organic light emitting device including the organic compound. The organic compound includes both the electron acceptor and donor moieties that are linked directly or through a linker moiety via a carbon-carbon bond having strong bond energy within its molecule, thus charges can be transported easily within the molecule. The OLED and the organic light emitting device including
(Continued)

the organic compound in an emissive layer can implement excellent luminous efficiency and luminous lifespan.

15 Claims, 15 Drawing Sheets

(51) Int. Cl.

| | |
|---|---|
| ***C09K 11/06*** | (2006.01) |
| ***H10K 85/60*** | (2023.01) |
| *H10K 50/11* | (2023.01) |
| *H10K 101/10* | (2023.01) |

(52) U.S. Cl.

CPC .... *H10K 85/654* (2023.02); *C09K 2211/1018* (2013.01); *H10K 50/11* (2023.02); *H10K 2101/10* (2023.02)

(56) References Cited

U.S. PATENT DOCUMENTS

| | | | | |
|---|---|---|---|---|
| 2016/0315268 | A1 | 10/2016 | Stoessel | |
| 2020/0270278 | A1 * | 8/2020 | Gao | H10K 85/658 |
| 2022/0109111 | A1 | 4/2022 | Oh et al. | |

FOREIGN PATENT DOCUMENTS

| | | | |
|---|---|---|---|
| KR | 10-2015-0140322 | A | 12/2015 |
| KR | 10-2017-0129468 | A | 11/2017 |
| KR | 10-2020-0068396 | A | 6/2020 |
| KR | 10-2020-0070892 | A | 6/2020 |
| KR | 10-2021-0001936 | A | 1/2021 |
| WO | 2020020602 | A1 † | 1/2020 |
| WO | 2020096421 | A1 | 5/2020 |

OTHER PUBLICATIONS

First Office Action with partial translation issued Mar. 1, 2024 for counterpart China National Intellectual Property Administration Application 202110907647.2.

Second Office Action with partial translation issued Jul. 23, 2024 for counterpart China National Intellectual Property Administration Application 202110907647.2.

* cited by examiner
† cited by third party

ORGANIC COMPOUND, ORGANIC LIGHT EMITTING DIODE AND ORGANIC LIGHT EMITTING DEVICE INCLUDING THE ORGANIC COMPOUND

CROSS-REFERENCE TO RELATED APPLICATIONS

This application claims the priority benefit under 35 U.S.C. § 119(a) to Korean Patent Application No. 10-2020-0115964, filed on Sep. 10, 2020, which is hereby incorporated by reference in its entirety.

BACKGROUND

Technical Field

The present disclosure relates to an organic compound, and more specifically, to an organic compound having excellent luminous properties, an organic light emitting diode and an organic light emitting device including the organic compound.

Discussion of the Related Art

As display devices have become larger, there exists a need for a flat display device with a lower space requirement. Among the flat display devices used widely at present, displays having organic light emitting diodes (OLEDs) are rapidly replacing liquid crystal display devices (LCDs).

The OLED can be formed as a thin film having a thickness less than 2000 Å and can be implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high. Particularly, the OLED can implement red, green and blue colors, thus it has attracted a lot of attention as a light emitting device.

In the OLED, holes injected from an anode and electrons injected from a cathode are recombined in an EML to form excitons as an unstable excites state, and then the light emits as the exciton is shifted to a stable ground state. The common fluorescent materials in which only singlet excitons involved in the luminescence process have low luminous efficiency. The common phosphorescent materials in which triplet excitons as well as singlet excitons involved in the luminescence process have relatively high luminous efficiency. However, the metal complex, representative phosphorescent materials, has too short luminous lifespan to be applicable to commercial devices.

SUMMARY

Accordingly, embodiments of the present disclosure are directed to an organic compound and an OLED and an organic light emitting device including the organic compound that substantially obviates one or more of the problems due to the limitations and disadvantages of the related art.

An aspect of the present disclosure is to provide an organic compound having excellent luminous efficiency, an OLED and an organic light emitting device into which the organic compound is applied.

A further aspect of the present disclosure is to provide an OLED improving its color purity and an organic light emitting device having the OLED.

Additional features and aspects will be set forth in the description that follows, and in part will be apparent from the description, or may be learned by practice of the inventive concepts provided herein. Other features and aspects of the inventive concept may be realized and attained by the structure particularly pointed out in the written description, or derivable therefrom, and the claims hereof as well as the appended drawings.

To achieve these and other aspects of the present disclosure, as embodied and broadly described, the present disclosure provides an organic compound having the following structure of Formula 1:

$$A\text{-}[L\text{-}D]_m \qquad \text{[Formula 1]}$$

wherein A is an aromatic ring or a hetero aromatic ring having the following structure of Formula 2; L is a single bond or an aromatic ring or a hetero aromatic ring having the following structure of Formula 3; D is a fused aromatic ring or a fused hetero aromatic ring having the following structure of Formula 4; and m is an integer of 1 to 5;

[Formula 2]

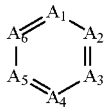

wherein one to five of $A_1$ to $A_6$ is a carbon atom linked to L or D and the rest of $A_1$ to $A_6$ is independently $CR_1$ or N, wherein $R_1$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two of the rest of $A_1$ to $A_6$ form an unsubstituted or substituted $C_6$-$C_{20}$ aromatic ring or an unsubstituted or substituted $C_3$-$C_{20}$ hetero aromatic ring;

[Formula 3]

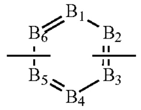

wherein two of $B_1$ to $B_6$ are carbon atoms each of which is linked to A and D, respectively, and the rest of $B_1$ to $B_6$ is independently $CR_2$ or N, wherein $R_2$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two of the rest of $B_1$ to $B_6$ form an unsubstituted or substituted $C_6$-$C_{20}$ aromatic ring or an unsubstituted or substituted $C_3$-$C_{20}$ hetero aromatic ring;

[Formula 4]

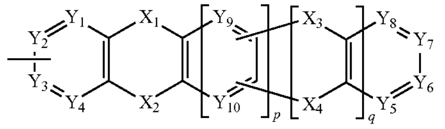

wherein each of $X_1$ to $X_4$ is independently a single bond, $CR_3R_4$, $NR_5$, O or S, wherein each of $R_3$ to $R_5$ is independently hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, and wherein at least one of $X_1$ and $X_2$ is not a single bond and at least one of $X_3$ and $X_4$ is not a single bond; one of $Y_1$ to $Y_{10}$ is a carbon atom linked to A or L and the rest of $Y_1$ to $Y_{10}$ is independently $CR_6$ or N, wherein $R_6$ is independently is hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, or two of the rest of $Y_1$ to $Y_{10}$ form an unsubstituted or substituted $C_6$-$C_{20}$ aromatic ring or an unsubstituted or substituted $C_3$-$C_{20}$ hetero aromatic ring; and each of p and q is independently an integer of 0 to 2.

In another aspect, the present disclosure provides an OLED that comprises a first electrode; a second electrode facing the first electrode; and an emissive layer disposed between the first and second electrodes, wherein the emissive layer comprises the organic compound.

For example, at least one emitting material in the emissive layer may comprise the organic compound as a delayed fluorescent material. The at least one emitting material layer may further comprise at least one host, and optionally at least one fluorescent or phosphorescent material.

As an example, the emissive layer may have a mono emitting part or multiple emitting parts and at least one charge generation layer disposed between the multiple emitting parts to form a tandem structure.

At least one emitting material layer in at least one emitting part of the multiple emitting parts may comprise the organic compound.

In still another aspect, the present disclosure provides an organic light emitting device, such as an organic light emitting display device and an organic light emitting illumination device that comprises a substrate and an OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of the present disclosure, illustrate aspects of the disclosure and together with the description serve to explain principles of the disclosure.

DETAILED DESCRIPTION

Figure 1:
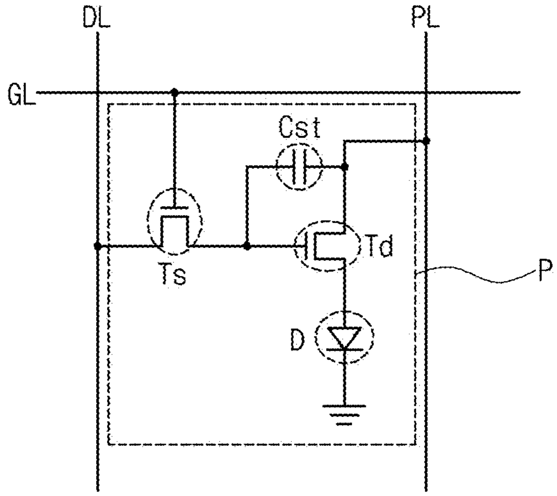
FIG. 1 is a schematic circuit diagram illustrating an organic light emitting display device in accordance with an exemplary aspect of the present disclosure.

Reference and discussions will now be made below in detail to aspects, and examples of the disclosure, some examples of which are illustrated in the accompanying drawings.

[Organic Compound]

An organic compound applied in to an organic light emitting diode (OLED) should have excellent luminous properties, high affinity to charges and maintain stable properties in driving the OLED. Particularly, luminous material applied into the OLED is the most important factor determining the luminous efficiency of the OLED. The luminous material should have high quantum efficiency, large mobility for charges and adequate energy levels with regard to other materials applied into the same or adjacent layers.

An organic compound of the present disclosure has both an electron donor moiety and an electron acceptor moiety within its molecular structure, thus it can show delayed fluorescent property. The organic compound of the present disclosure may have the following structure of Formula 1:

$$A\text{-}[L\text{-}D]_m \quad \text{[Formula 1]}$$

wherein A is an aromatic ring or a hetero aromatic ring having the following structure of Formula 2; L is a single bond or an aromatic ring or a hetero aromatic ring having the following structure of Formula 3; D is a fused aromatic ring or a fused hetero aromatic ring having the following structure of Formula 4; and m is an integer of 1 to 5;

[Formula 2]

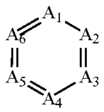

wherein one to five of $A_1$ to $A_6$ is a carbon atom linked to L or D and the rest of $A_1$ to $A_6$ is independently $CR_1$ or N, wherein $R_1$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two of the rest of $A_1$ to $A_6$ form an unsubstituted or substituted $C_6$-$C_{20}$ aromatic ring or an unsubstituted or substituted $C_3$-$C_{20}$ hetero aromatic ring;

[Formula 3]

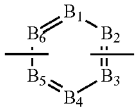

wherein two of $B_1$ to $B_6$ are carbon atoms each of which is linked to A and D, respectively, and the rest of $B_1$ to $B_6$ is independently $CR_2$ or N, wherein $R_2$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two of the rest of $B_1$ to $B_6$ form an unsubstituted or substituted $C_6$-$C_{20}$ aromatic ring or an unsubstituted or substituted $C_3$-$C_{20}$ hetero aromatic ring;

[Formula 4]

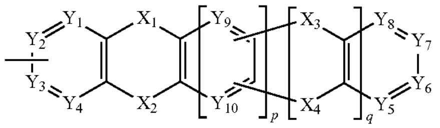

wherein each of $X_1$ to $X_4$ is independently a single bond, $CR_3R_4$, $NR_5$, O or S, wherein each of $R_3$ to $R_5$ is independently hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, and wherein at least one of $X_1$ and $X_2$ is not a single bond and at least one of $X_3$ and $X_4$ is not a single bond; one of $Y_1$ to $Y_{10}$ is a carbon atom linked to A or L and the rest of $Y_1$ to $Y_{10}$ is independently $CR_6$ or N, wherein $R_6$ is independently is hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, or two of the rest of $Y_1$ to $Y_{10}$ form an unsubstituted or substituted $C_6$-$C_{20}$ aromatic ring or an unsubstituted or substituted $C_3$-$C_{20}$ hetero aromatic ring; and each of p and q is independently an integer of 0 to 2.

As used herein, the term 'unsubstituted" means that hydrogen is linked, and in this case, hydrogen comprises protium, deuterium and tritium.

As used herein, substituent in the term "substituted" comprises, but is not limited to, unsubstituted or halogen-substituted $C_1$-$C_{20}$ alkyl, unsubstituted or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term 'hetero" in such as "a hetero aromatic ring", "a hetero cycloalkylene group", "a hetero arylene group", "a hetero aryl alkylene group", "a hetero aryl oxylene group", "a hetero cycloalkyl group", "a hetero aryl group", "a hetero aryl alkyl group", "a hetero aryloxyl group", "a hetero aryl amino group" means that at least one carbon atom, for example 1-5 carbons atoms, constituting an aromatic ring or an alicyclic ring is substituted with at least one hetero atom selected from the group consisting of N, O, S, P and combination thereof.

As an example, each of the alkyl group and the alkyl amino group of $R_1$ to $R_6$ may be independently, but is not limited to, unsubstituted or substituted with at least one halogen atom, respectively. Each of the aromatic group, the hetero aromatic group, the aromatic ring and the hetero aromatic ring of $R_1$ to $R_6$ may be independently, but is not limited to, unsubstituted or substituted with at least one of a cyano group, a nitro group, a halogen group.

In one exemplary aspect, when each of $R_1$ to $R_6$ is independently a $C_6$-$C_{30}$ aromatic group, each of $R_1$ to $R_6$ is independently may be, but is not limited to, a $C_6$-$C_{30}$ aryl group, a $C_7$-$C_{30}$ aryl alkyl group, a $C_6$-$C_{30}$ aryl oxy group and a $C_6$-$C_{30}$ aryl amino group. In another exemplary aspect, when each of $R_1$ to $R_6$ is independently a $C_3$-$C_{30}$ hetero aromatic group, each of $R_1$ to $R_6$ is independently may be, but is not limited to, a $C_3$-$C_{30}$ hetero aryl group, a $C_4$-$C_{30}$ hetero aryl alkyl group, a $C_3$-$C_{30}$ hetero aryl oxy group and a $C_3$-$C_{30}$ hetero aryl amino group.

As an example, when each of $R_1$ to $R_6$ is independently a $C_6$-$C_{30}$ aryl group, each of $R_1$ to $R_6$ is independently may comprise, but is not limited to, an unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spiro-fluorenyl.

In another exemplary aspect, when each of $R_1$ to $R_6$ is independently a $C_3$-$C_{30}$ hetero aryl group, each of $R_1$ to $R_6$ is independently may comprise, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzo-furo-carbazolyl, benzo-thieno-carbazolyl, carbolinyl, quinolinyl, iso-quinolinyl, phthlazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzo-furanyl, dibenzo-furanyl, thiopyranyl, xanthenyl, chromenyl, iso-chromenyl, thioazinyl, thiophenyl, benzo-thiophenyl, dibenzo-thiophenyl, difuro-pyrazinyl, benzofuro-dibenzo-furanyl, benzothieno-benzo-thiophenyl, benzothieno-dibenzo-thiophenyl, benzo-thieno-benzo-furanyl, benzothieno-dibenzo-furanyl, xanthen-linked spiro acridinyl, dihydroacridinyl substituted with at least one $C_1$-$C_{10}$ alkyl and N-substituted spiro fluorenyl.

As an example, when each of $R_1$ to $R_6$ is the aromatic group or the hetero aromatic group, each of $R_1$ to $R_6$ may be independently, but is not limited to, phenyl, biphenyl, pyrrolyl, triazinyl, imidazolyl, pyrazolyl, pyridinyl, pyrazinyl, pyrimidinyl, pyridazinyl, furanyl, benzo-furanyl, dibenzo-furanyl, thiophenyl, benzo-thiophenyl, dibenzo-thiophenyl and carbazolyl.

Alternatively, adjacent two of each of $R_1$, each of $R_2$, $R_3$ to $R_5$ and each of $R_6$ may form a $C_6$-$C_{20}$ aromatic ring or a $C_3$-$C_{20}$ hetero aromatic ring. As an example, when adjacent two of each of $R_1$, each of $R_2$, $R_3$ to $R_5$ and each of $R_6$ in Formulae 2 to 4 form the aromatic ring or the hetero aromatic ring, the formed aromatic ring or the hetero aromatic ring may be, but is not limited to, an aryl ring such as a benzene ring and/or a naphthalene ring or a hetero aryl ring such as a pyrimidine ring and/or a carbazole ring.

In one exemplary aspect, at least one of $R_1$ and $R_2$ may comprise, but is not limited to, a cyano group, a nitro group, a halogen atom, a $C_1$-$C_{10}$ alkyl group substituted with halogen, a $C_6$-$C_{30}$ aromatic group substituted with at least one of a cyano group, a nitro group and halogen and a $C_3$-$C_{30}$ hetero aromatic group substituted with at least one of a cyano group, a nitro group and halogen.

In another exemplary aspect, one of $X_1$ and $X_2$ may be a single bond and the other of $X_1$ and $X_2$ may be $NR_5$, one of $X_3$ and $X_4$ may be a single bond and the other of $X_3$ and $X_4$ may be $NR_5$, and each of p and q may be independently 1, one of $Y_1$ to $Y_{10}$ may be a carbon atom linked to L, and the rest of $Y_1$ to $Y_{10}$ may be independently $CR_6$, but is not limited thereto.

The organic compound having the structure of Formula 1 has an aromatic or hetero aromatic moiety (A moiety) of an electron acceptor moiety, a fused aromatic or fused hetero aromatic moiety (D moiety) of an electron donor moiety, and optionally an aromatic or hetero aromatic linker moiety (L moiety) between the electron acceptor moiety and the electron donor moiety.

As a steric hindrance between the fused aromatic or fused hetero aromatic moiety of the electron donor and the aromatic or hetero aromatic moiety of the electron acceptor, the formation of the conjugation structure between those moieties are limited. The molecule are divided easily into a highest occupied molecular orbital (HOMO) energy state and a lowest unoccupied molecular orbital (LUMO) energy state, and dipole between the electron acceptor moiety and the electron donor moiety, and therefore, the organic compound has excellent luminous efficiency as the dipole moment within the molecule increases.

Figure 4:
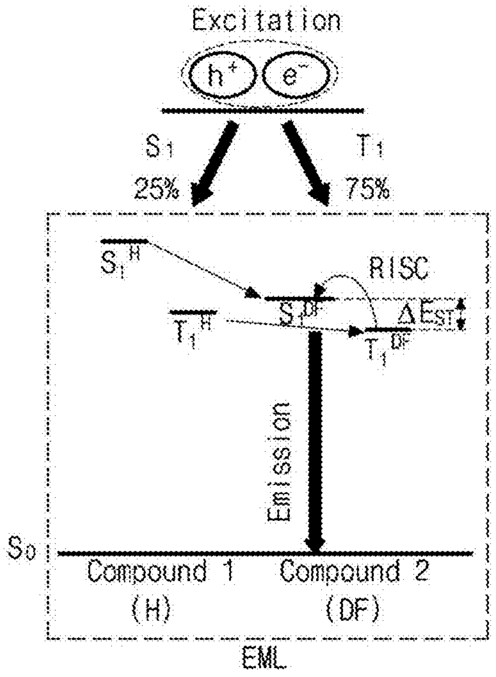
FIG. 4 is a schematic diagram illustrating luminous mechanism by energy level bandgap among luminous materials in accordance with an exemplary aspect of the present disclosure.

As the electron donor moiety is separated from the electron acceptor moiety, the energy overlapping between the HOMO energy state and the LUMO energy state within the molecule is decreased. Accordingly, the organic compound having the structure of Formula 1 has very narrow energy bandgap $\Delta E_{ST}$ between a singlet energy level $S_1^{DF}$ and a triplet energy level $T_1^{DF}$ (FIG. 4).

As an example, the organic compound having the structure of Formula 1 may have the energy bandgap $\Delta E_{ST}$ between the singlet energy level $S_1^{DF}$ and the triplet energy level $T_1^{DF}$ of equal to or less than about 0.3 eV, for example, between about 0.05 eV and about 0.3 eV. In case of driving the OLED D1 including the organic compound having the structure of Formula 1, the excitons of singlet energy level $S_1^{DF}$ as well as the excitons of triplet energy level $T_1^{DF}$ can be transferred to an intermediate energy level state, i.e. ICT (intramolecular charge transfer) state ($S_1^{DF} \rightarrow ICT \leftarrow T_1^{DF}$) by heat, and then the intermediate state excitons can be shifted to a ground state ($ICT \rightarrow S_0$). Since the organic compound emits light with the excitons at ICT state shifting to the ground state, it may have an internal quantum efficiency of 100% in theory.

In other words, since the organic compound having the structure of Formula 1 has little energy bandgap between the singlet state and the triplet state, it can exhibit common fluorescence with Inter system Crossing (ISC) in which the excitons of singlet energy level $S_1$ can be shifted to its ground state $S_0$, as well as delayed fluorescence with Reverser Inter System Crossing (RISC) in which the excitons of triplet energy level $T_1$ can be converted upwardly to the excitons of singlet energy level $S_1$, and then the exciton of singlet energy level $S_1$ can be shifted to the ground state $S_0$ with implementing delayed fluorescence.

In addition, the organic compound having the structure of Formula 1 includes a rigid electron donor moiety (D moiety) of the fused aromatic or hetero aromatic ring so that its molecular conformation is much limited. Since there is little energy loss owing to changes of molecular conformation when the organic compound emits light and the photoluminescence spectra of the organic compound can be specific ranges, it is possible to realize high color purity.

Moreover, organic compound having the structure of Formula 1 may have triplet energy level $T_1^{DF}$ less than the triplet energy level of common phosphorescent material and may have narrower energy bandgap narrower than the phosphorescent material. Accordingly, it is not necessary to use organic compounds as a host with high triplet energy level and wide energy bandgap, which limits the utilization of the common phosphorescent material as a dopant. In addition, it is possible to minimize delays of charge injections and transportations caused by the host with wider energy bandgap Moreover, the organic compound having the structure of Formula 1 includes the electron acceptor moiety (A moiety), the aromatic or hetero aromatic linker moiety (L moiety) and the electron donor moiety (D moiety) each of which is linked by a carbon-carbon link, respectively. Owing to the carbon-carbon link having strong bond energy, the organic compound having the structure of Formula 1 has excellent thermal stability. Since the organic compound is not deteriorated by heat generated in driving the OLED, it can implement excellent luminous efficiency and luminous lifespan.

In one exemplary aspect, one of $A_1$ to $A_6$ constituting the electron acceptor moiety (A moiety) may be a carbon atom linked to the linker moiety (L moiety) or the electron donor moiety (D moiety) and at least one of $A_1$ to $A_6$ not linked to the L moiety or the D moiety may be nitrogen (N). In another exemplary aspect, one of $A_1$ to $A_6$ constituting the electron acceptor moiety (A moiety) may be a carbon atom linked to the linker moiety (L moiety) or the electron donor moiety (D moiety) and at least two of $A_1$ to $A_6$ not linked to the L moiety or the D moiety may be nitrogen (N).

Alternatively, at least one carbon atom, not linked to the L moiety or the D moiety, of carbon atoms constituting the A moiety may be, but is not limited to, substituted with a halogen atom, a cyano group, a nitro group, a $C_1$-$C_{10}$ alkyl group unsubstituted or substituted with halogen, a $C_1$-$C_{10}$ alkyl amino group unsubstituted or substituted with halogen, a $C_6$-$C_{30}$ aryl group unsubstituted or substituted with halogen, a cyano group, a nitro group or combination thereof, or a $C_3$-$C_{30}$ hetero aryl group unsubstituted or substituted with halogen, a cyano group, a nitro group or combination thereof.

In one exemplary aspect, the D moiety of the electron donor moiety may have a structure of two six-membered rings at both sides and a fused ring of at least one five-membered ring and at least one six membered ring between two six-membered ring. Such a D moiety may have the following structure of Formula 5 or Formula 6:

[Formula 5]

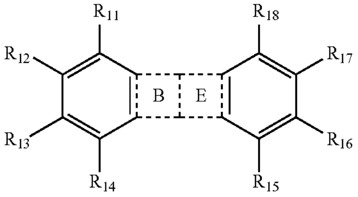

[Formula 6]

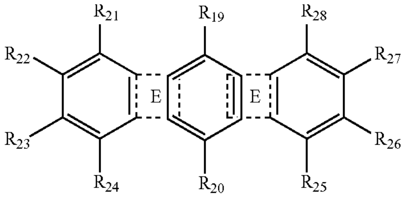

wherein B has the following structure of Formula 7; E has the following structure of Formula 8; one of $R_{11}$ to $R_{18}$ is a carbon atom linked to A or L and the rest of $R_{11}$ to $R_{18}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group; one of $R_{19}$ to $R_{28}$ is a carbon atom linked to A or L and the rest of $R_{19}$ to $R_{28}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group;

[Formula 7]

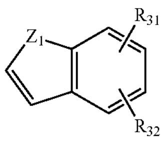

[Formula 8]

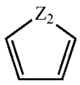

wherein each of $R_{31}$ and $R_{32}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group; each of $Z_1$ and $Z_2$ is independently $NR_{33}$, O or S, wherein $R_{33}$ is hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group.

Also, the A moiety of the electron acceptor moiety in Formula 1 may comprise a triazine moiety with three nitrogen atoms as a nuclear atom. An organic compound including the triazine moiety as the A moiety may be selected from the following compounds of Formula 9:

[Formula 9]

1-1

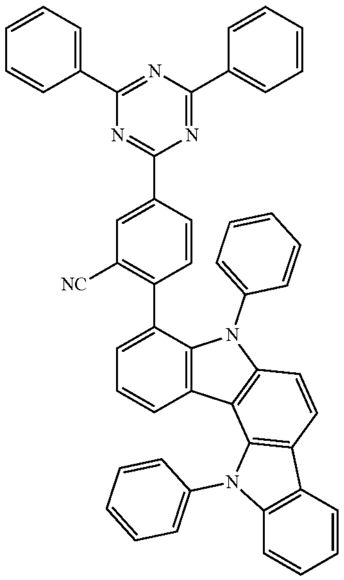

1-2

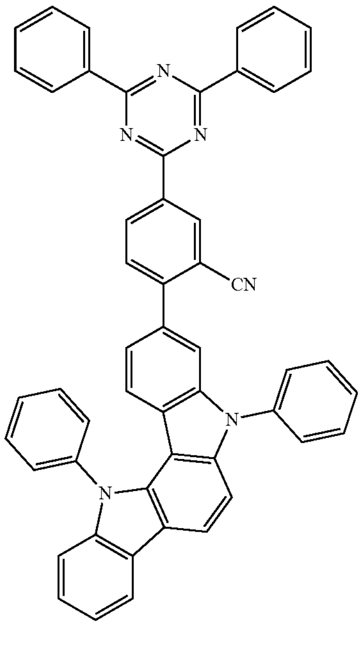

1-3
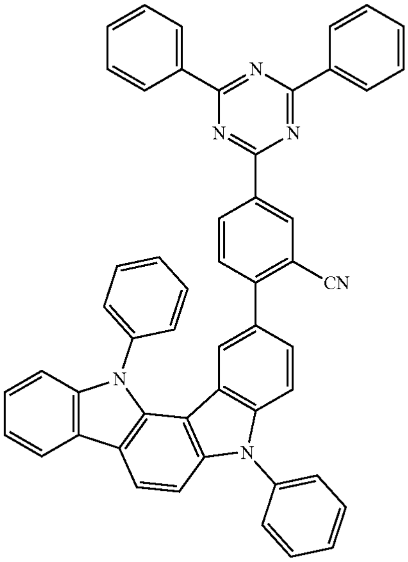
1-4
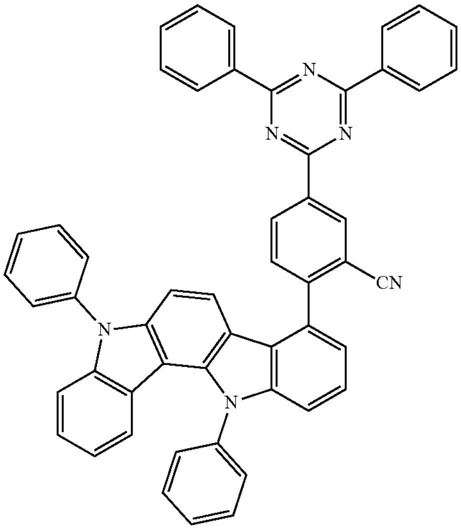
1-5
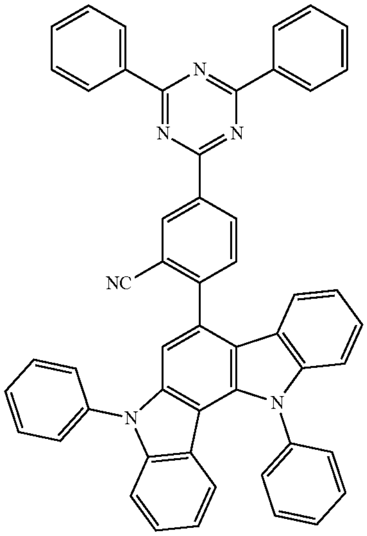
1-6
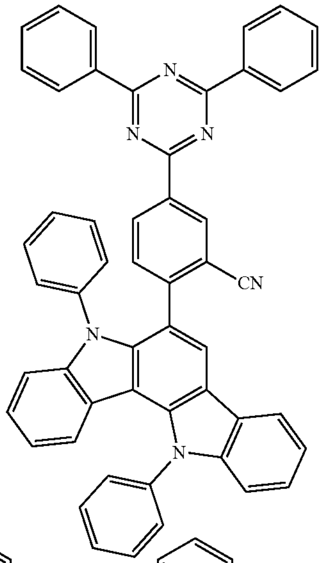
1-7
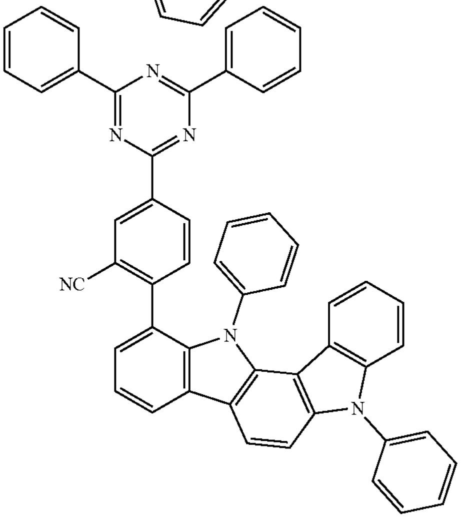
1-8
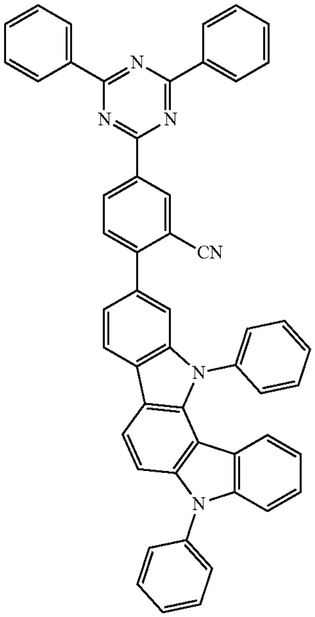

1-9
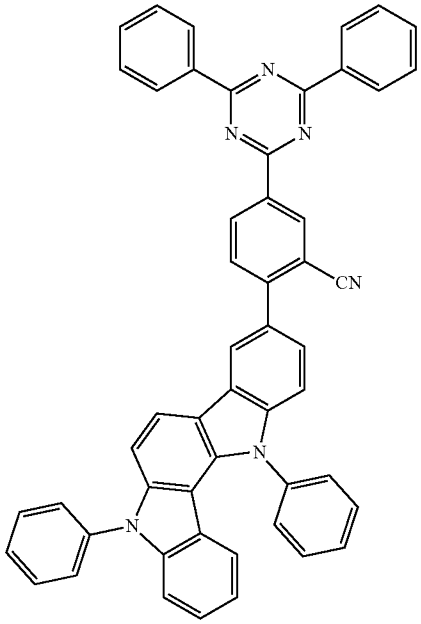
1-11
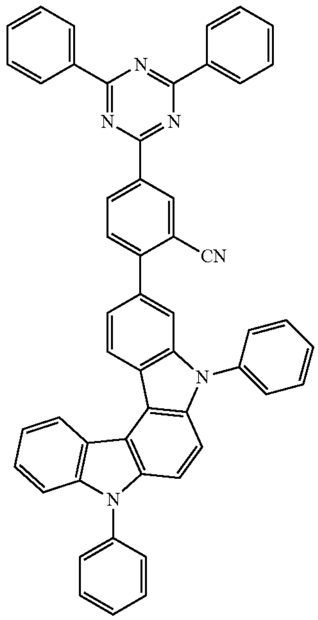
1-10
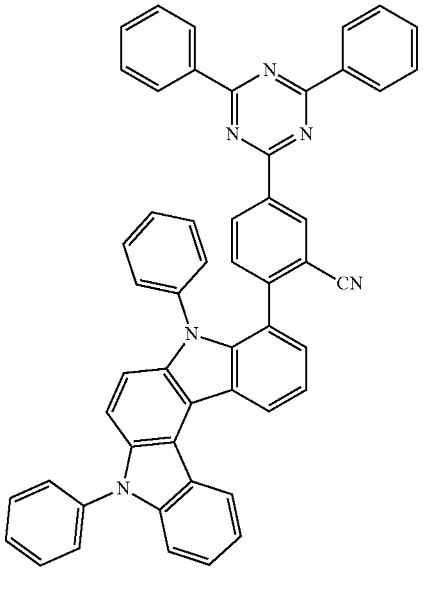
1-12
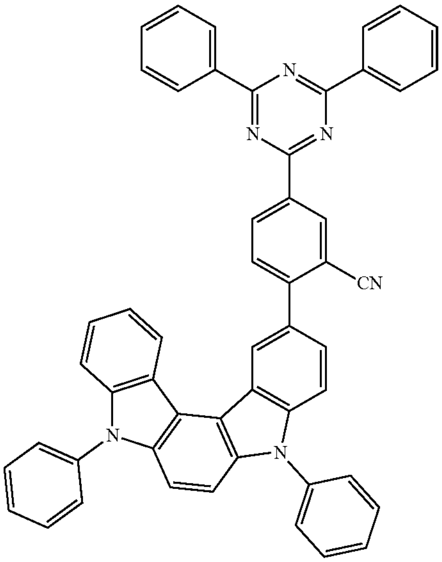

-continued
1-13
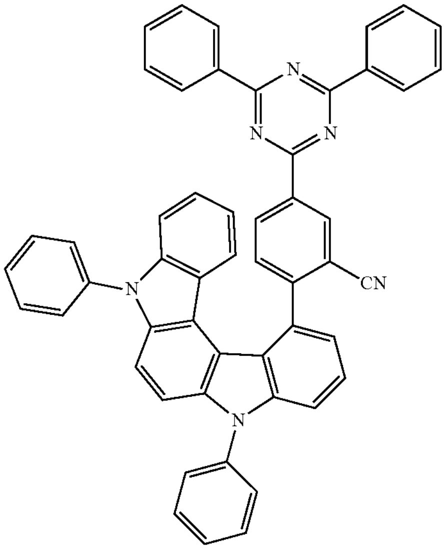
1-14
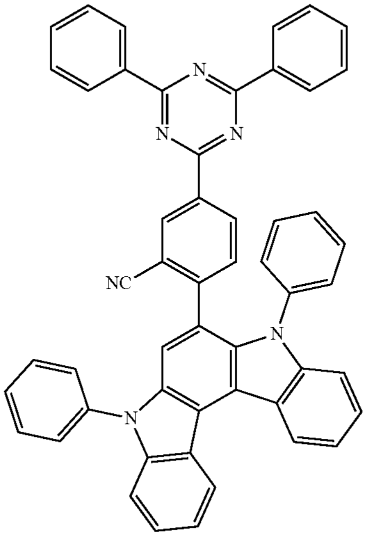
1-15
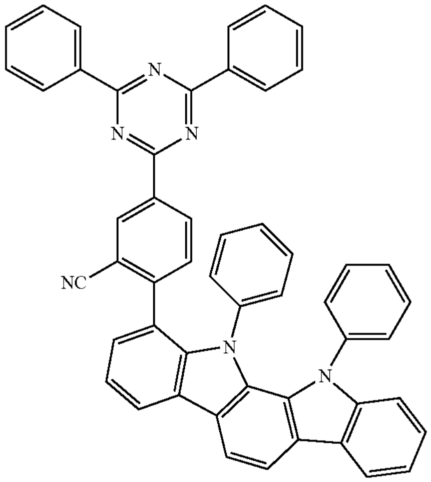
-continued
1-16
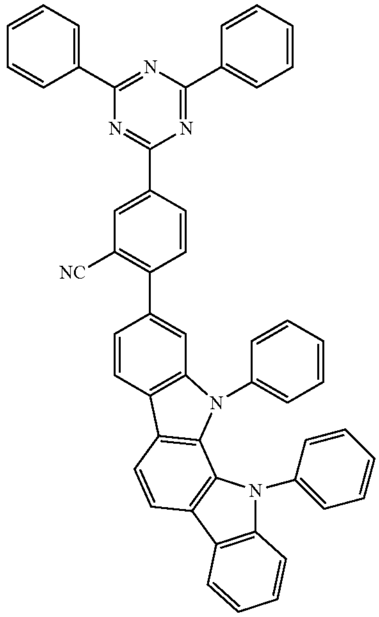
1-17
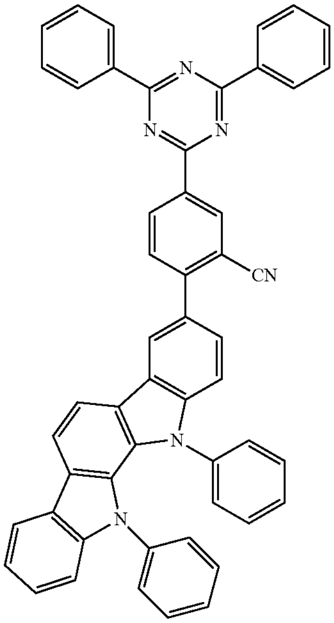

1-18
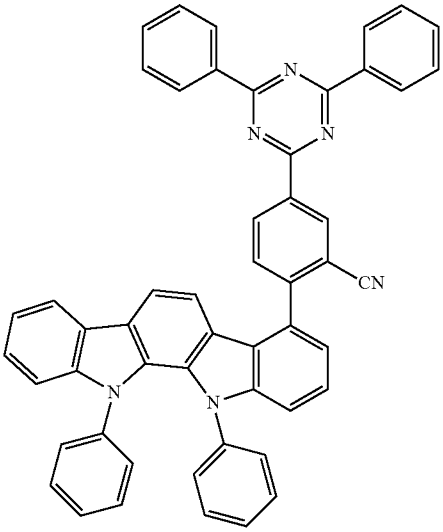
1-20
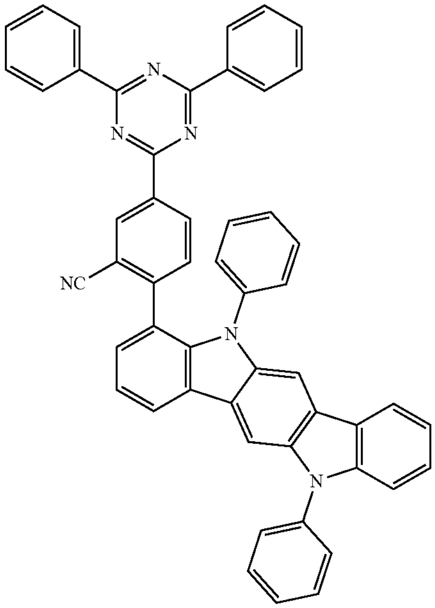
1-19
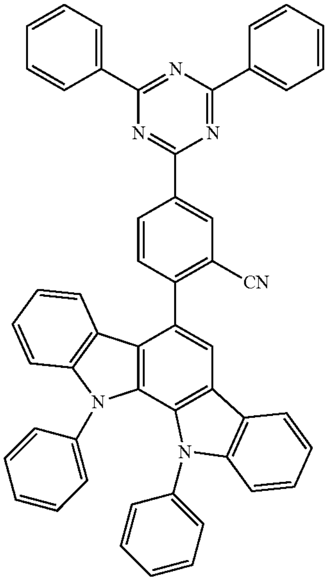
1-21
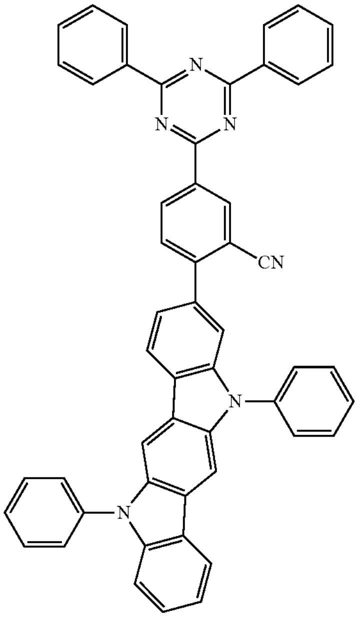

-continued
1-22
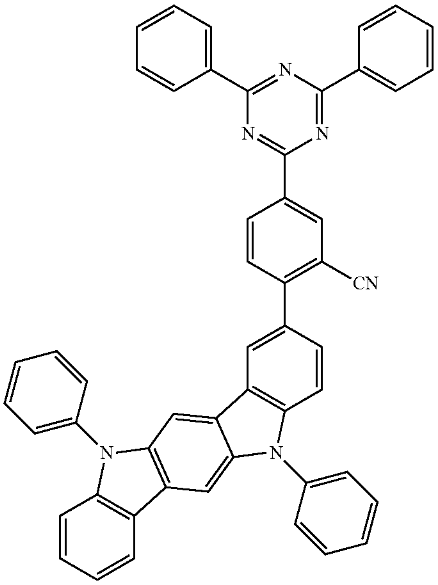
1-23
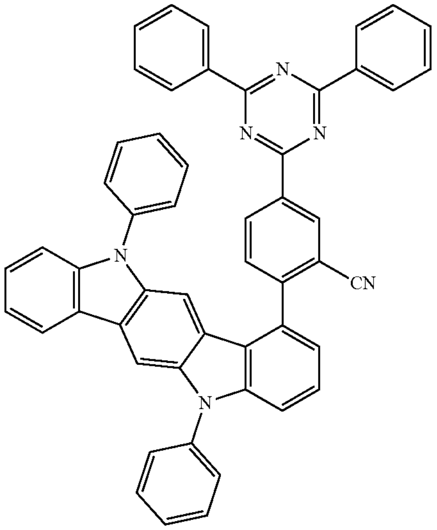
1-24
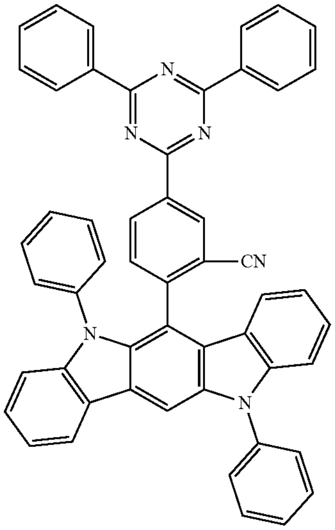
-continued
1-25
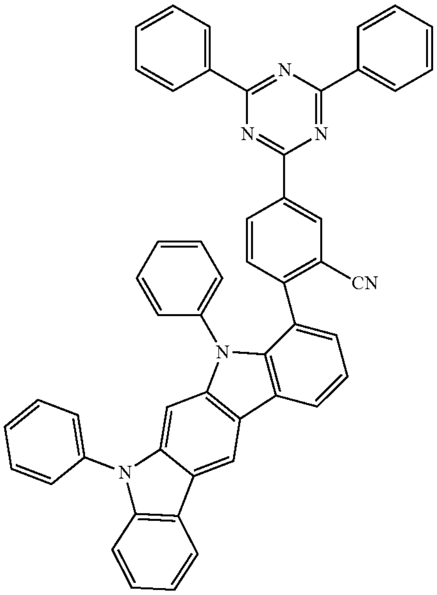
1-26
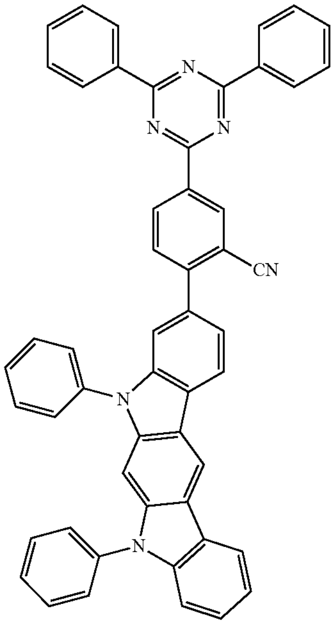

-continued
1-27
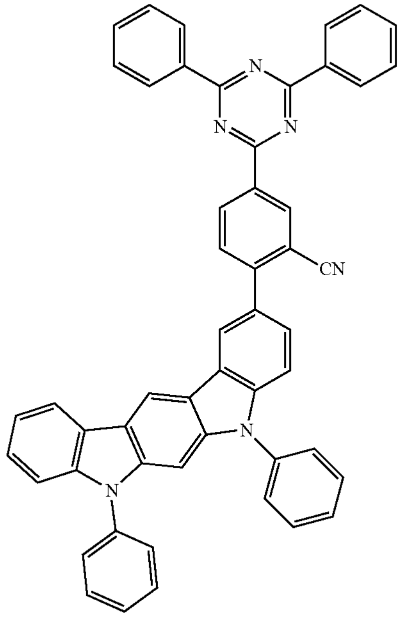
1-28
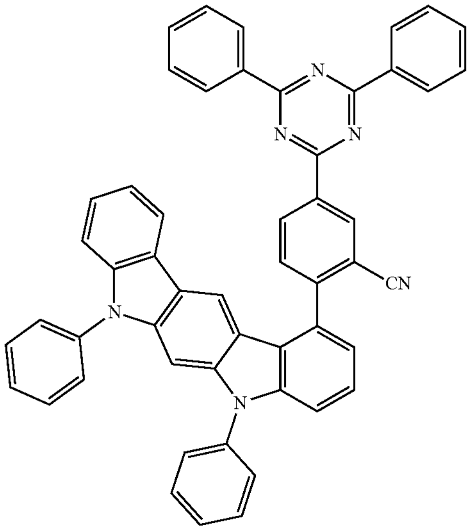
-continued
1-29
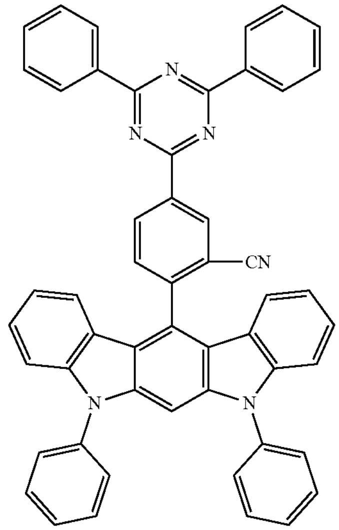
1-30
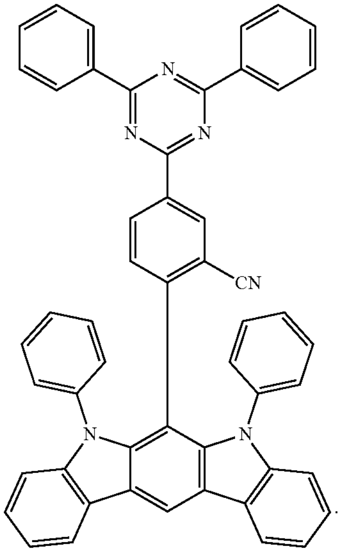
Alternatively, the A moiety in Formula 1 may comprise a pyrimidine moiety or a pyrazine moiety with two nitrogen atoms as a nuclear atom. An organic compound including the pyrimidine moiety or the pyrazine moiety as the A moiety may be selected from the following compounds of Formula 10:

[Formula 10]
2-1
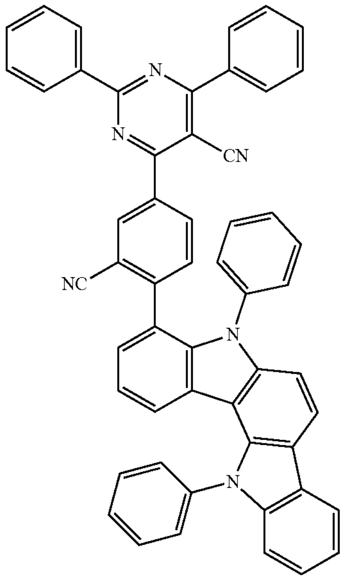
2-2
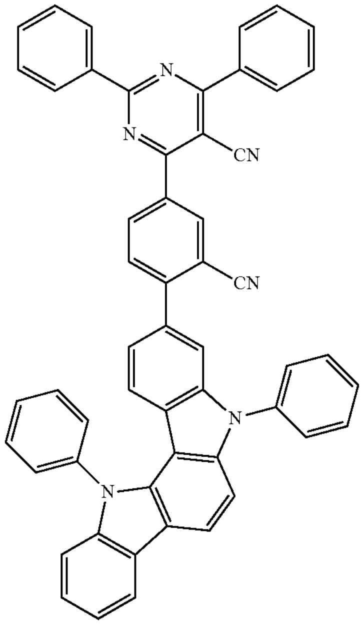
-continued
2-3
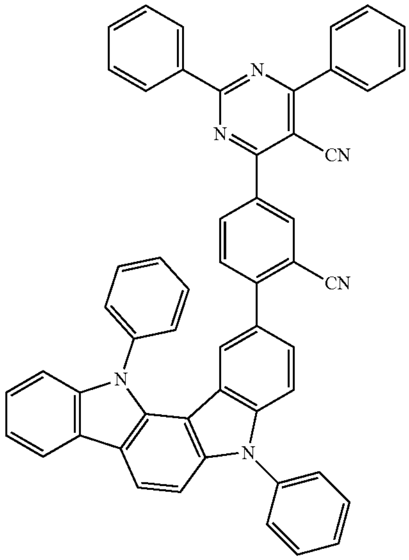
2-4
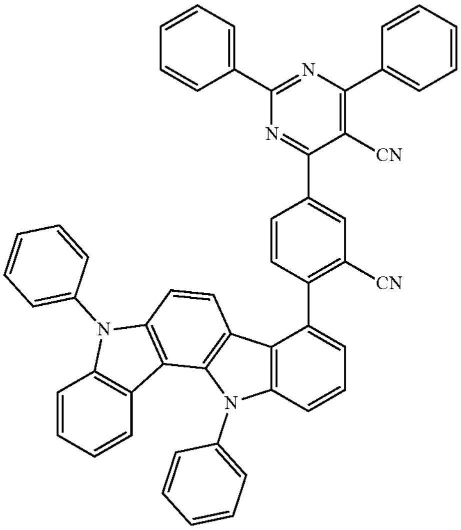
2-5
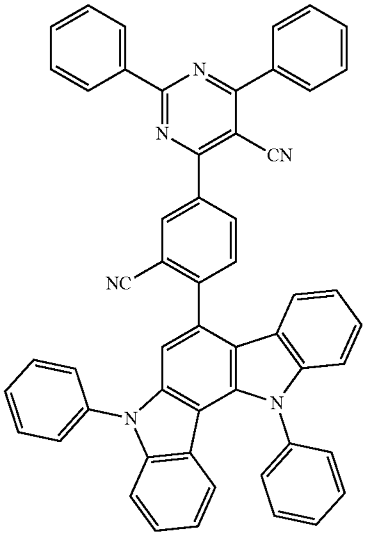

-continued
2-6
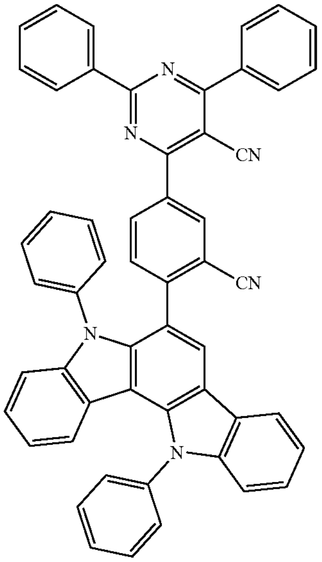
2-7
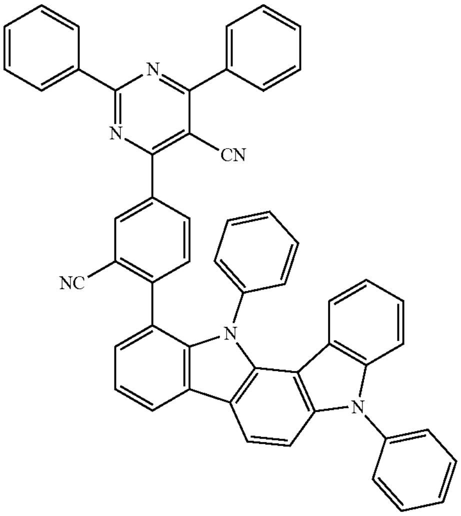
-continued
2-8
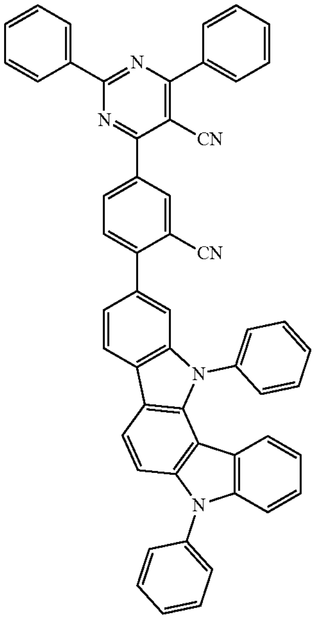
2-9
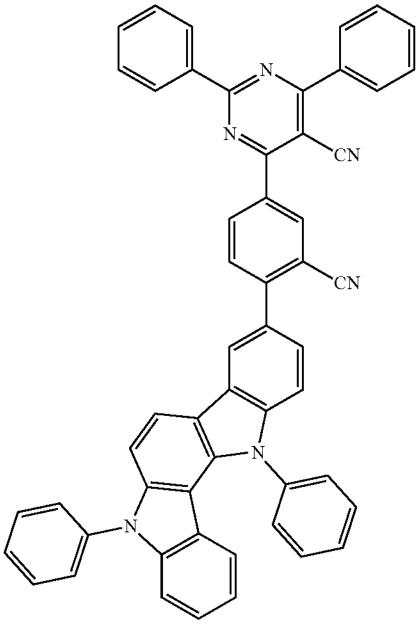

-continued
2-10
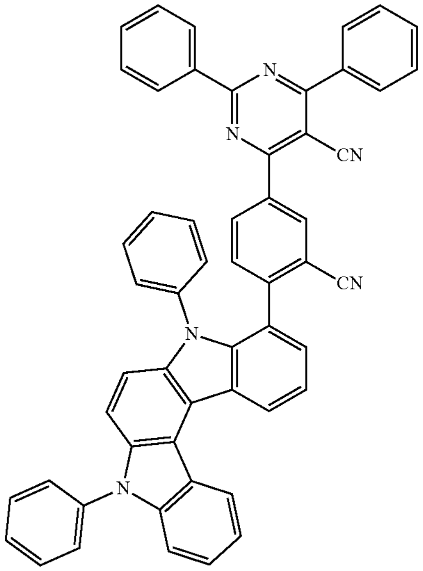
2-11
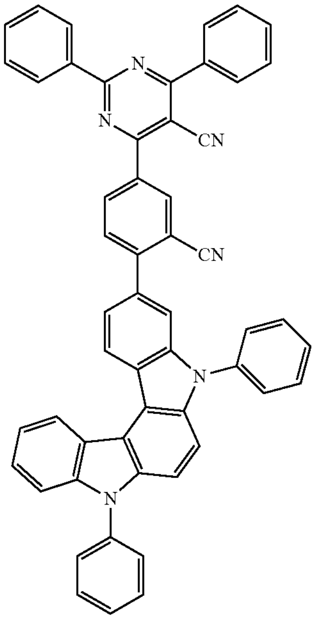
-continued
2-12
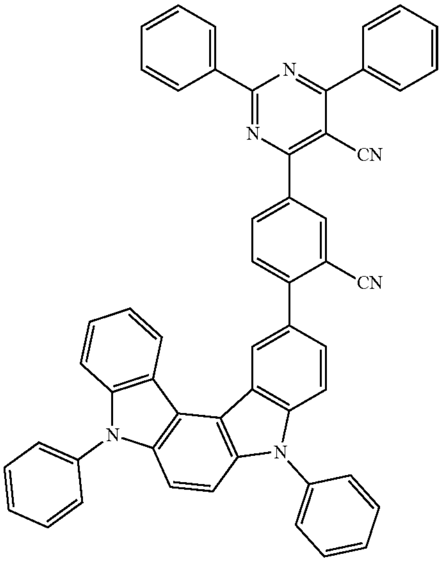
2-13
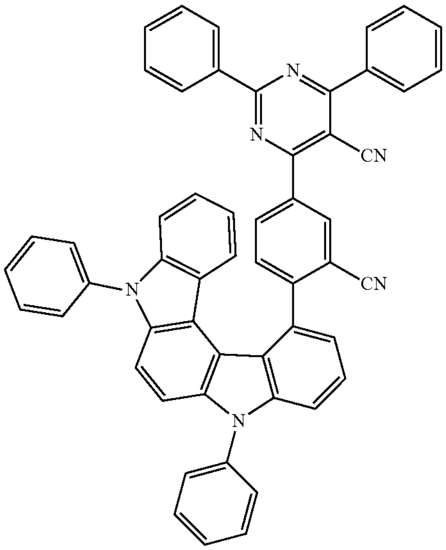
2-14
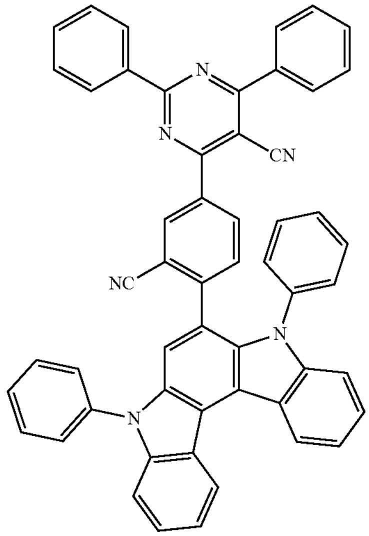

-continued
2-15
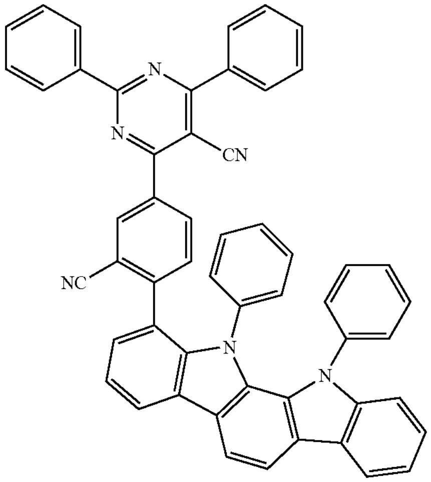
2-16
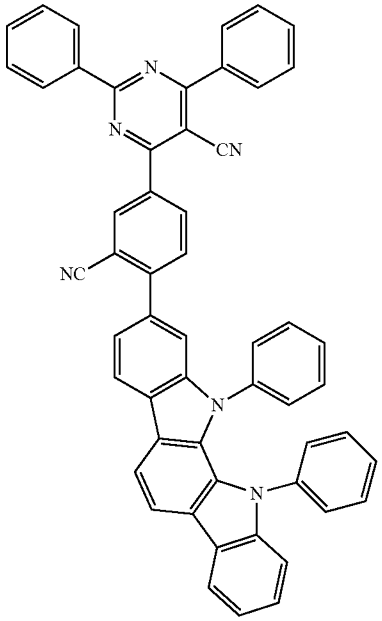
-continued
2-17
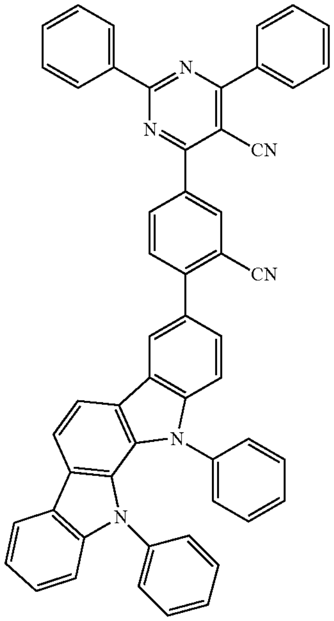
2-18
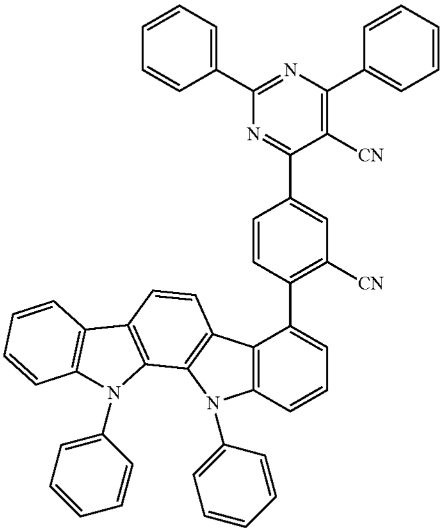

-continued
2-19
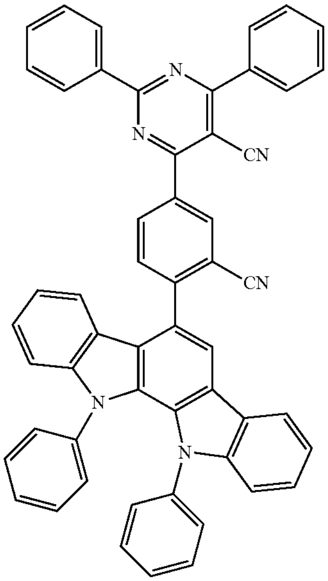
2-20
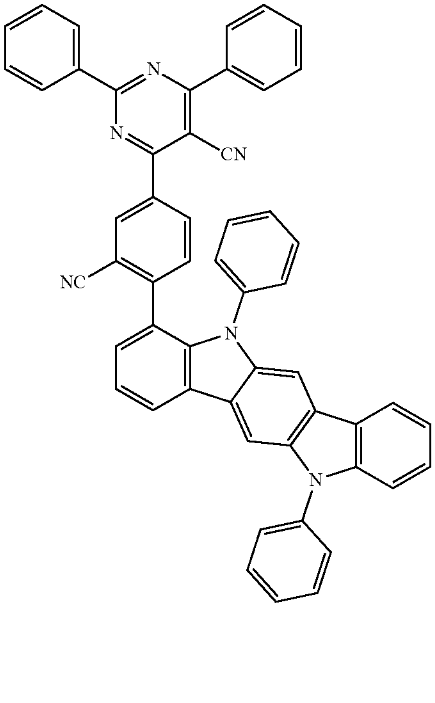
-continued
2-21
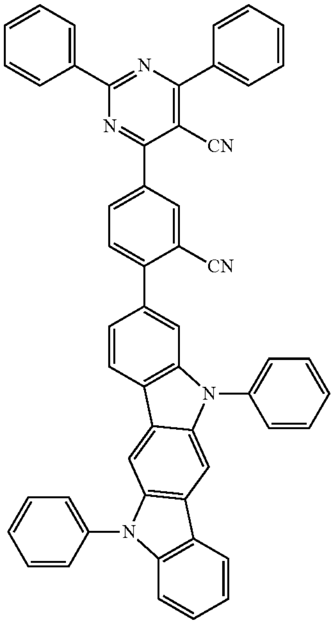
2-22
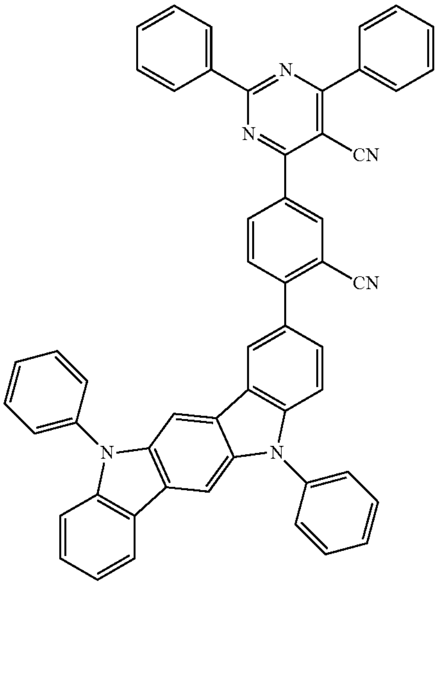

-continued
2-23
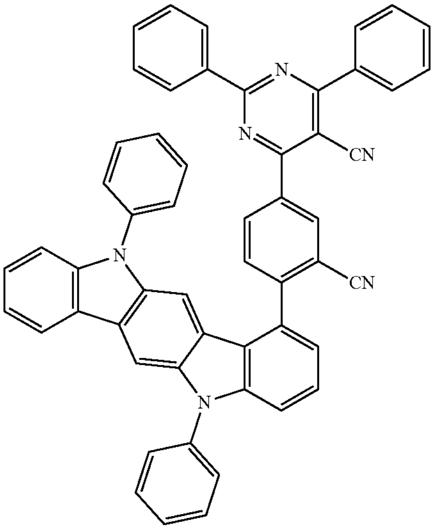
2-24
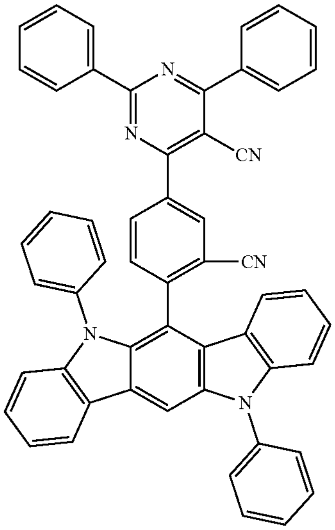
2-25
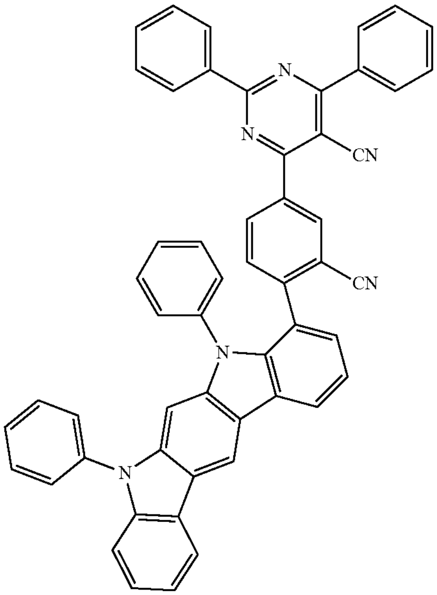
-continued
2-26
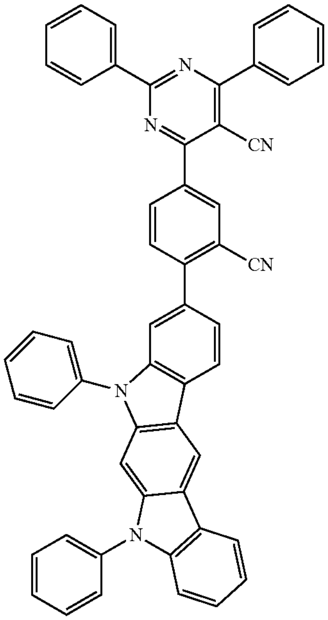
2-27
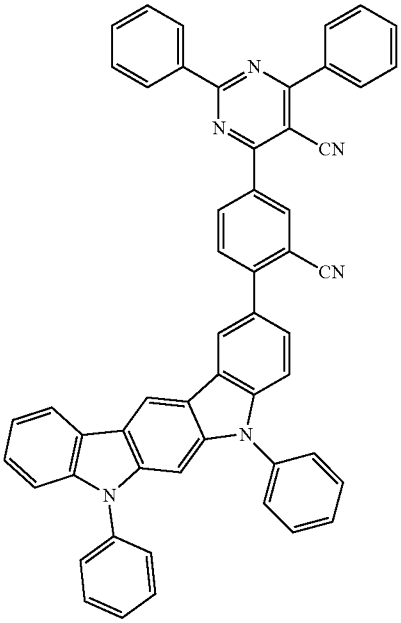

-continued
2-28
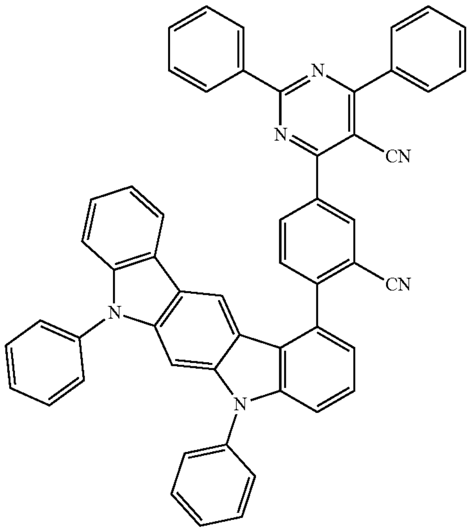
2-29
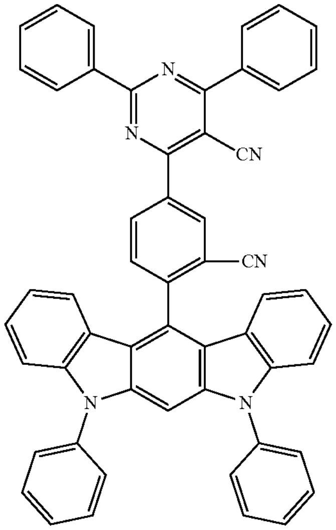
2-30
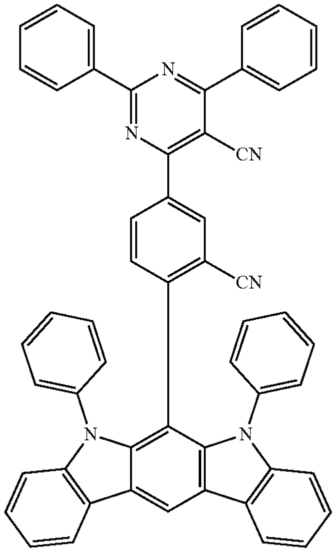
-continued
2-31
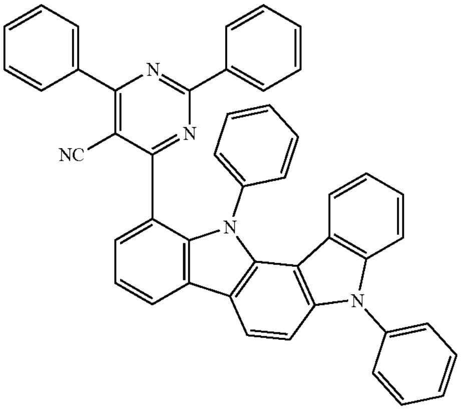
2-32
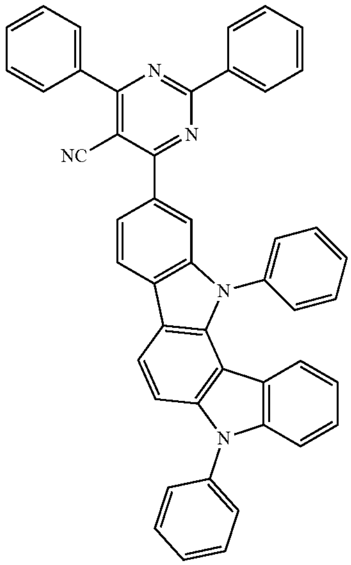
2-33
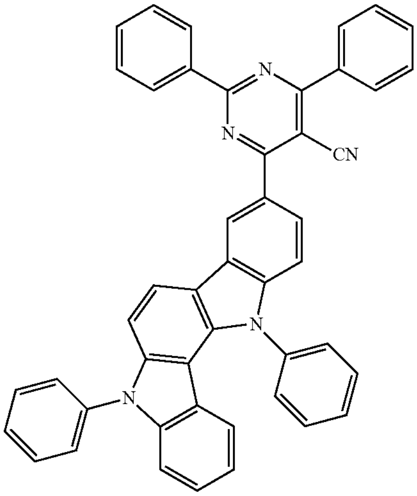

2-34
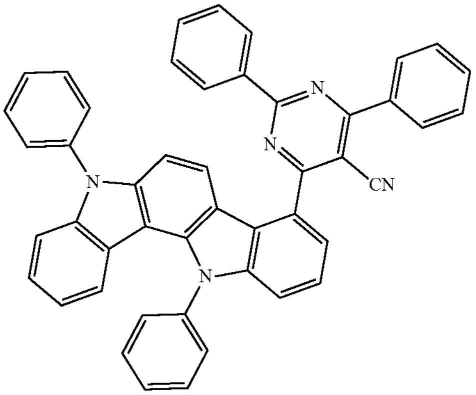
2-35
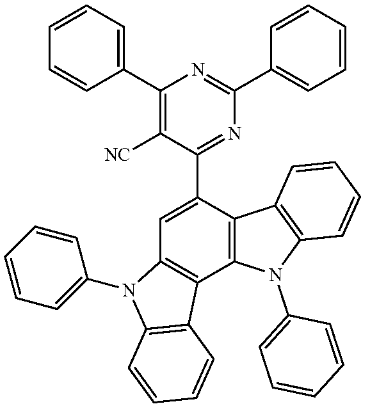
2-36
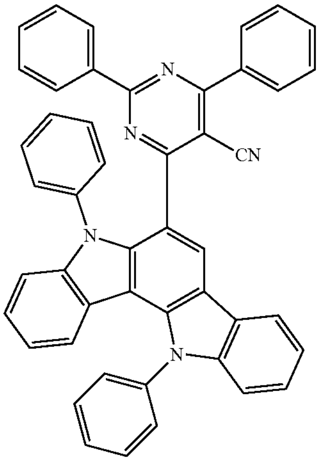
2-37
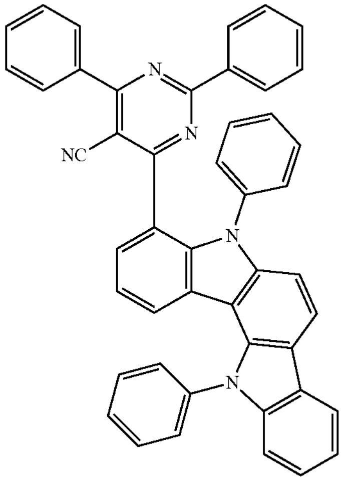
2-38
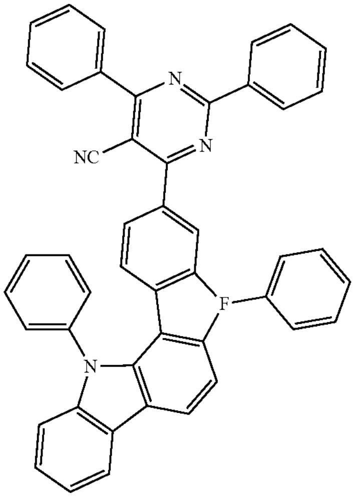
2-39
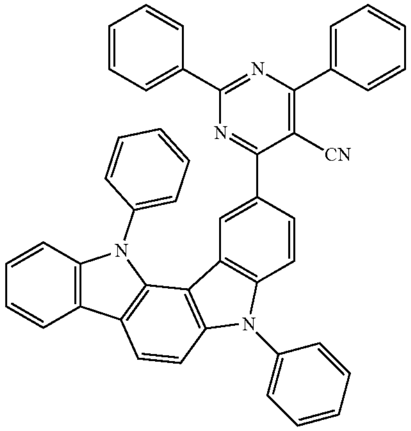

-continued
2-40
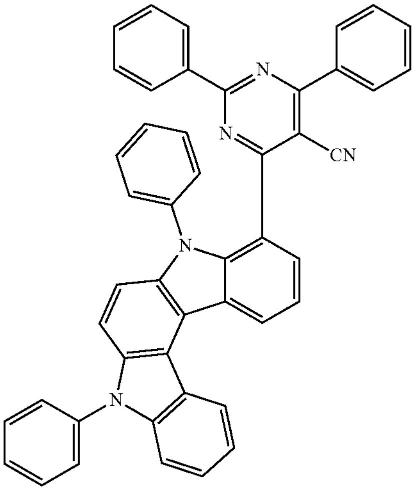
2-41
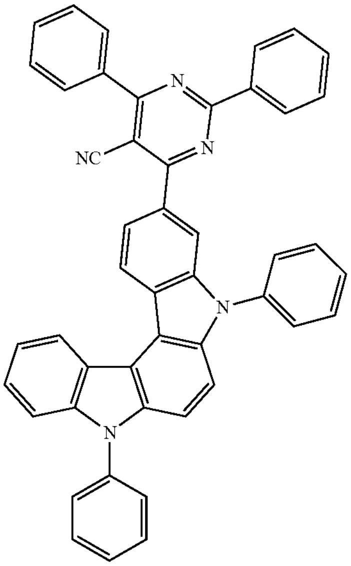
2-42
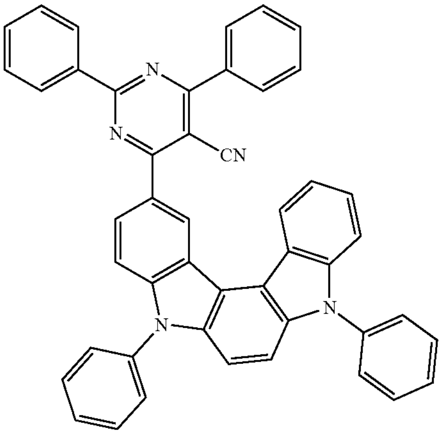
-continued
2-43
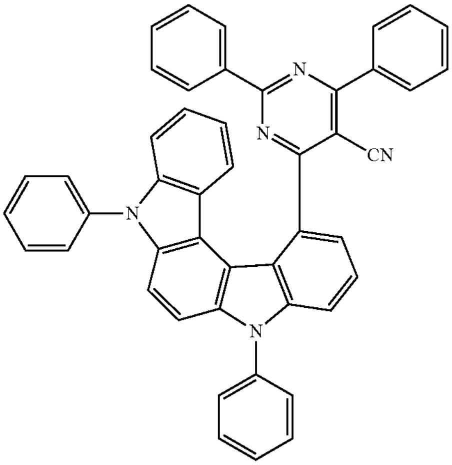
2-44
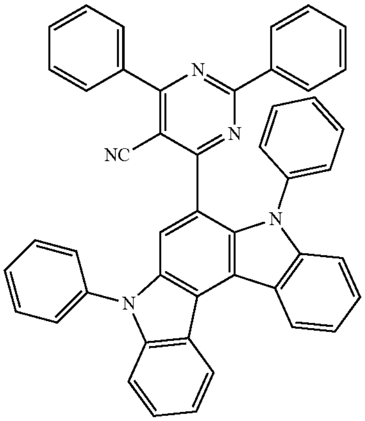
2-45
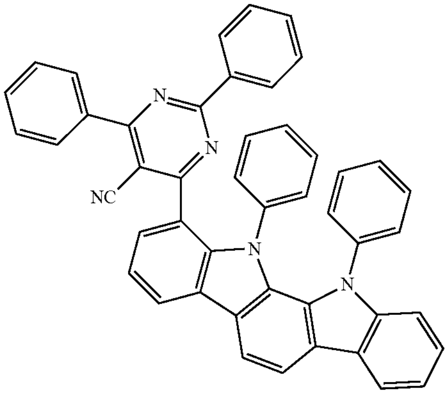

-continued
2-46
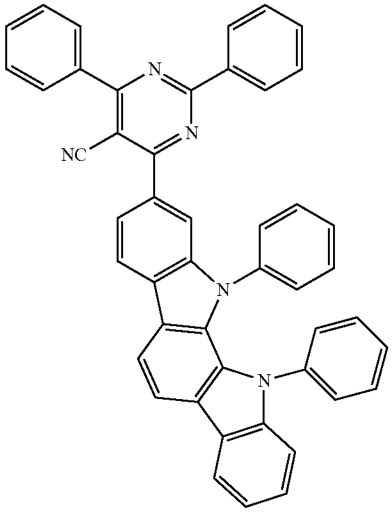
2-47
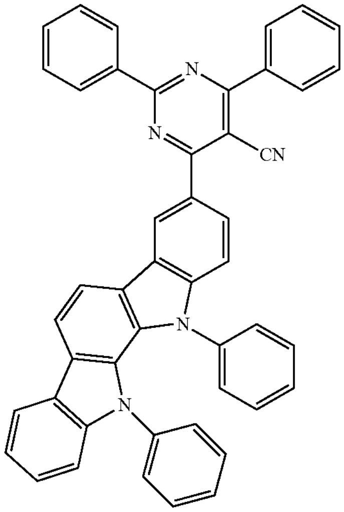
2-48
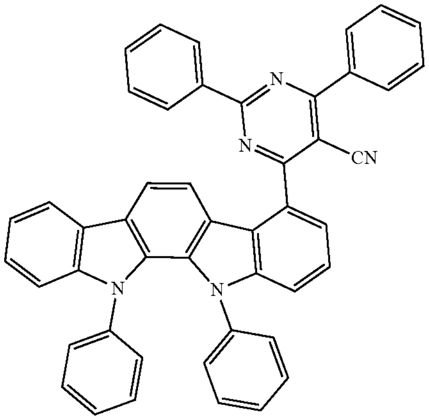
-continued
2-49
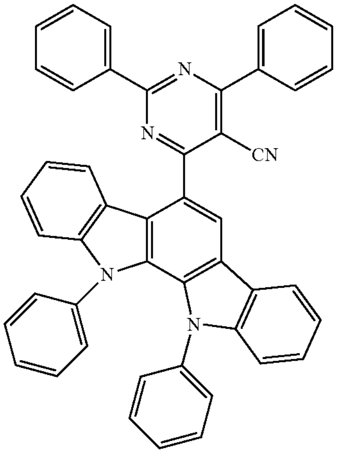
2-50
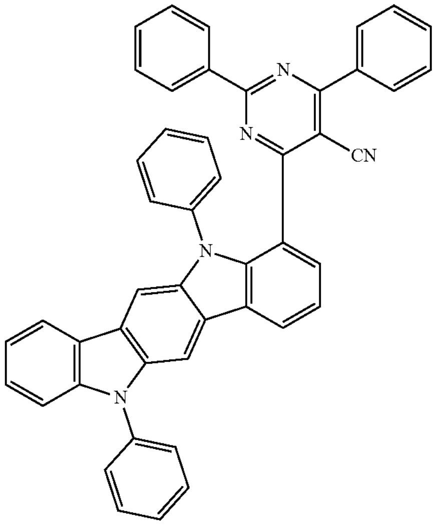
2-51
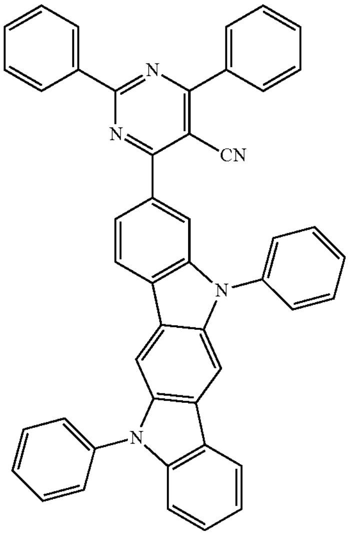

-continued
2-52
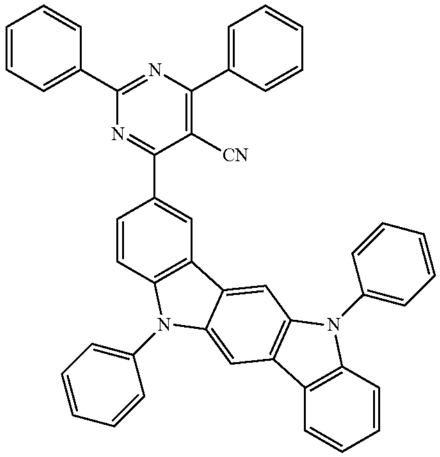
2-53
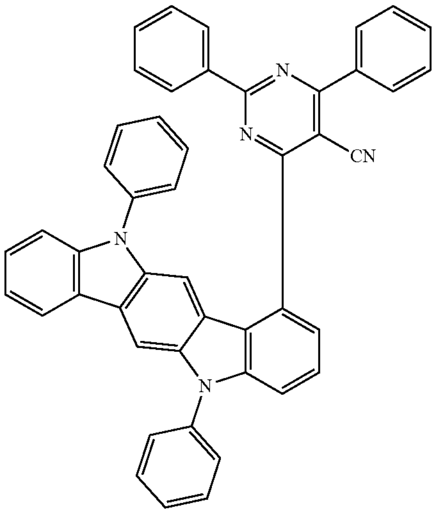
2-54
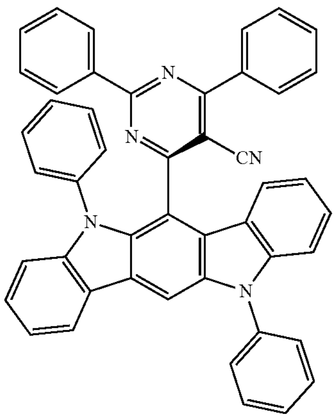
-continued
2-55
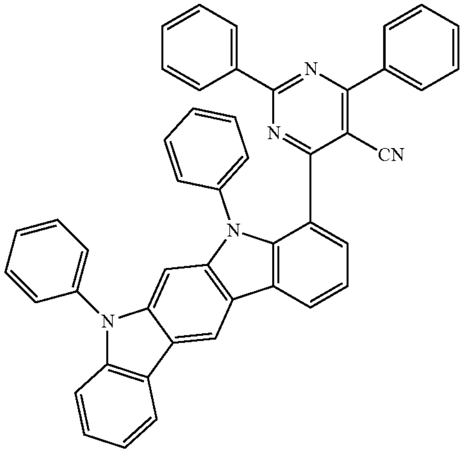
2-56
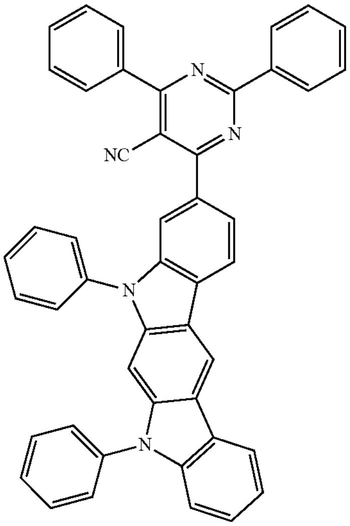
2-57
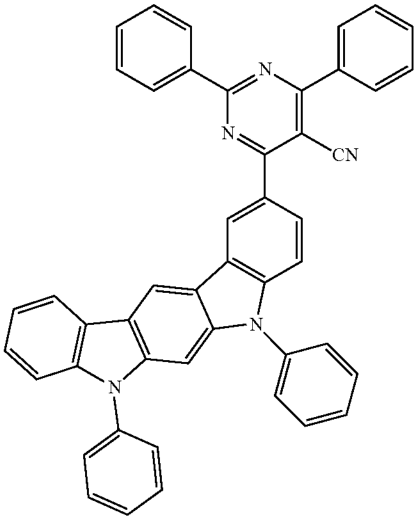

-continued
2-58
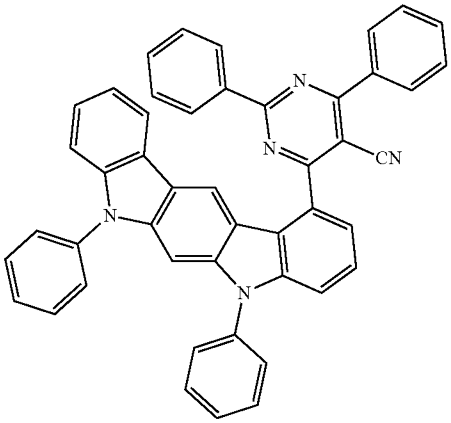
2-59
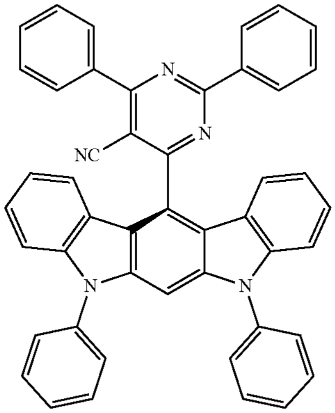
2-60
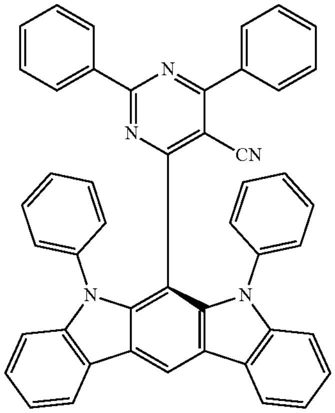
-continued
2-61
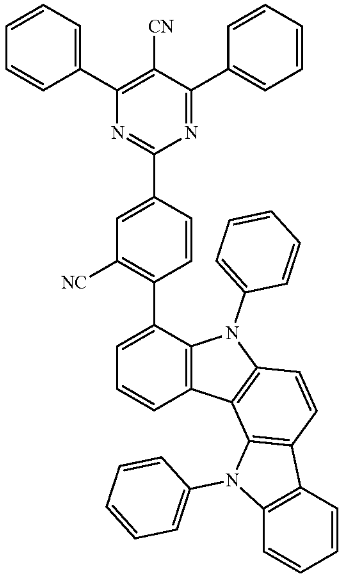
2-62
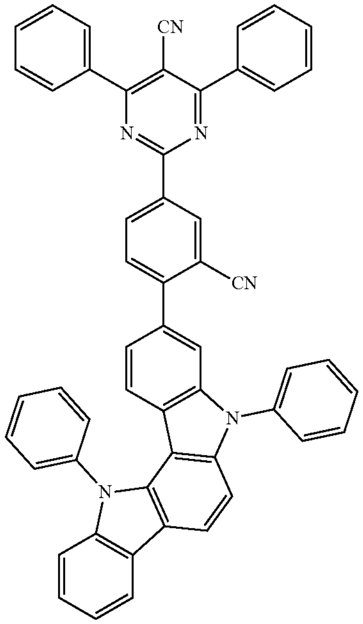

-continued
2-63
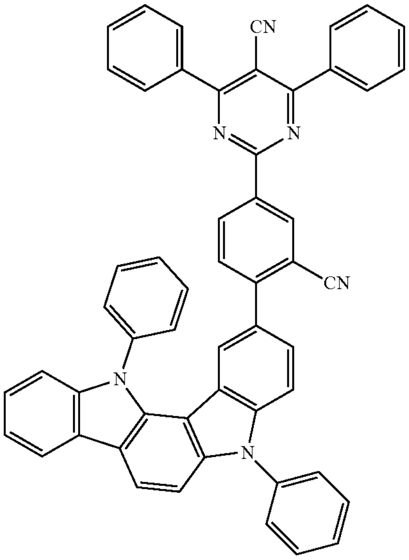
2-64
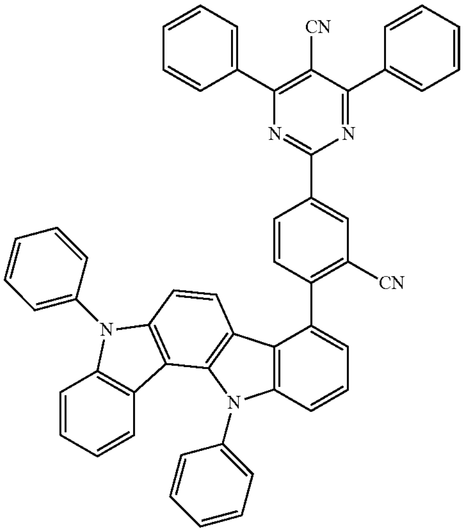
2-65
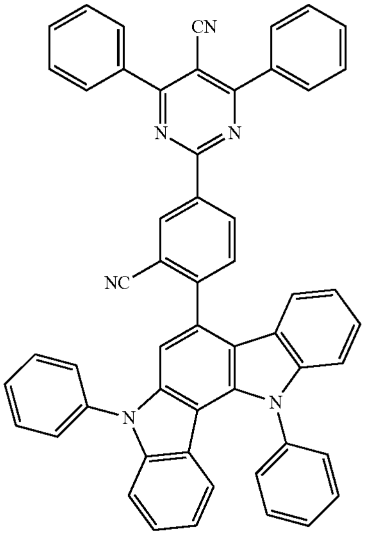
-continued
2-66
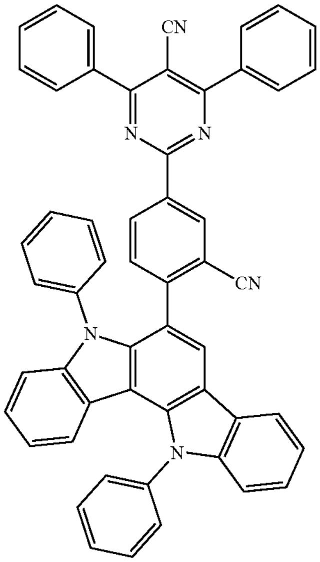
2-67
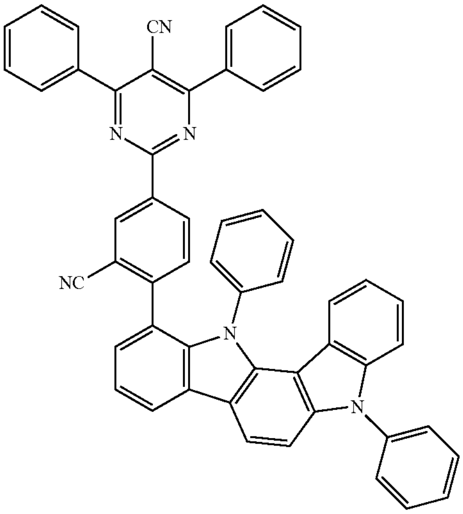

-continued
2-68
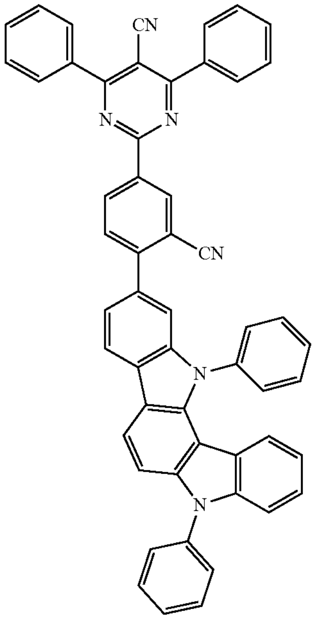
2-69
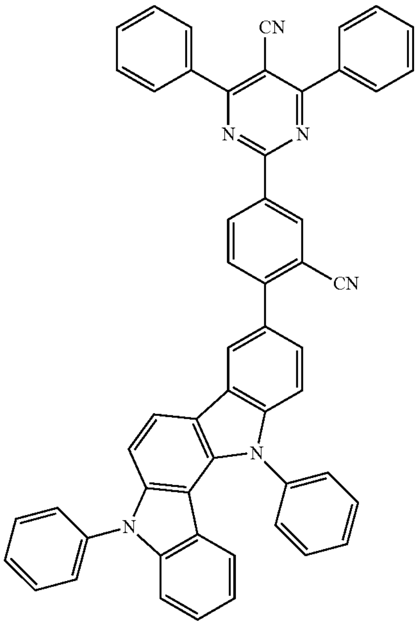
-continued
2-70
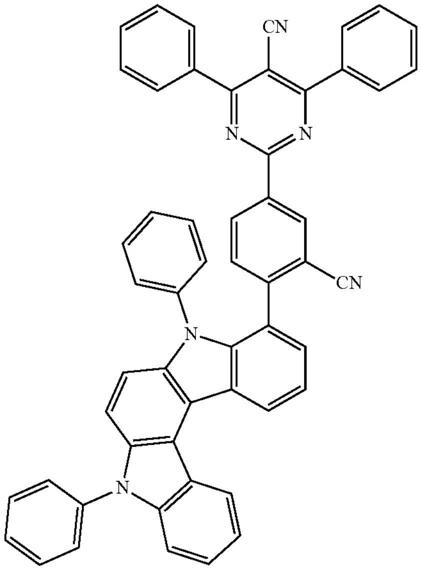
2-71
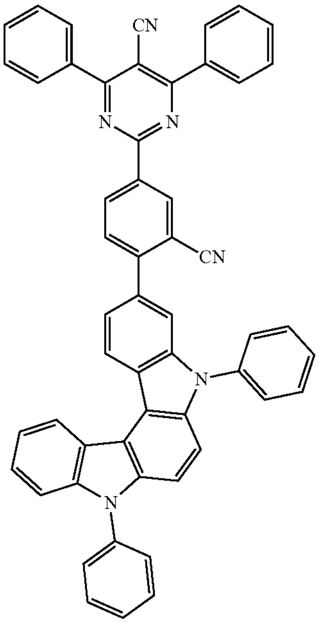

-continued
2-72
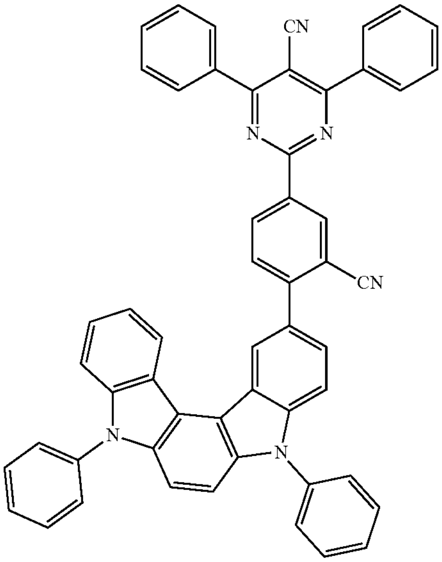
2-73
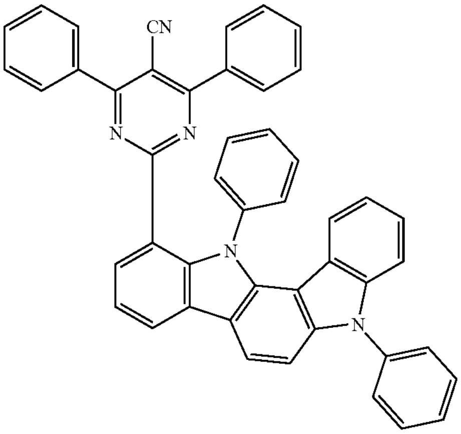
2-74
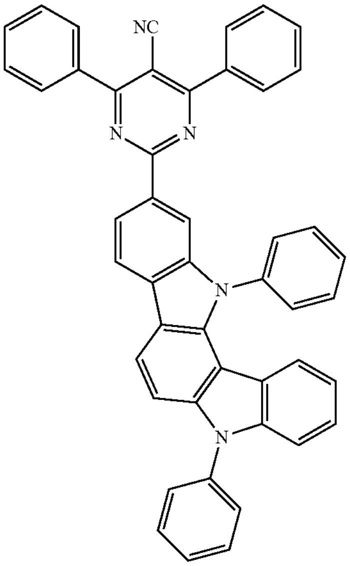
-continued
2-75
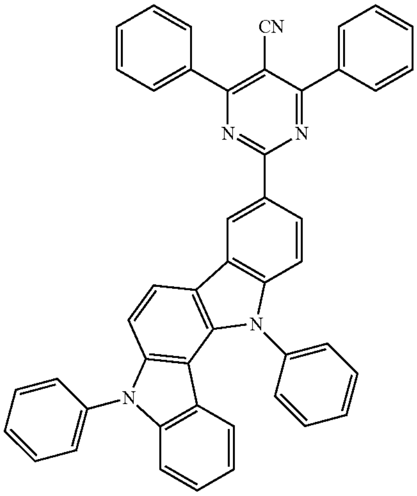
2-76
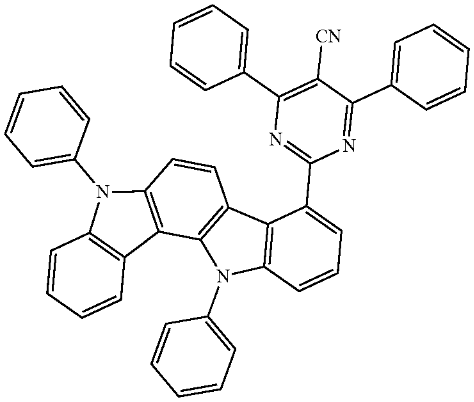
2-77
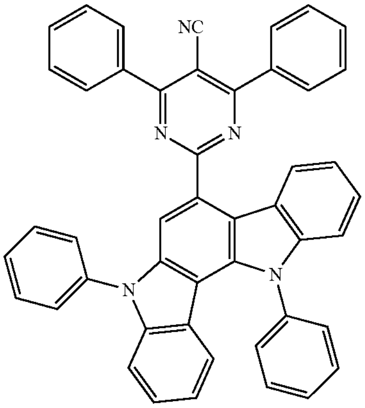

-continued
2-78
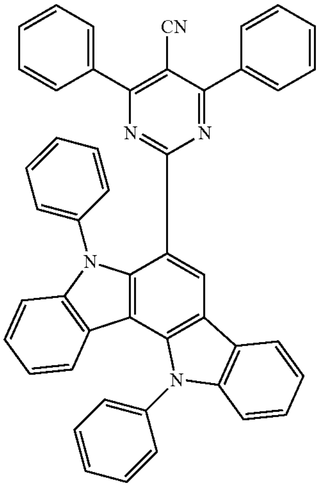
2-79
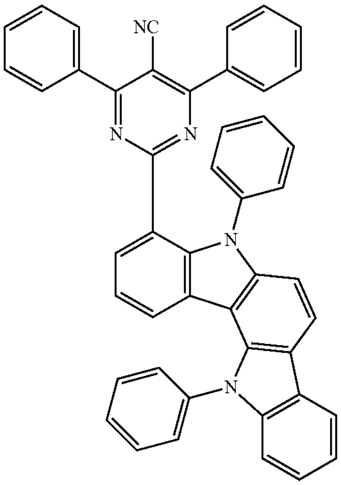
2-80
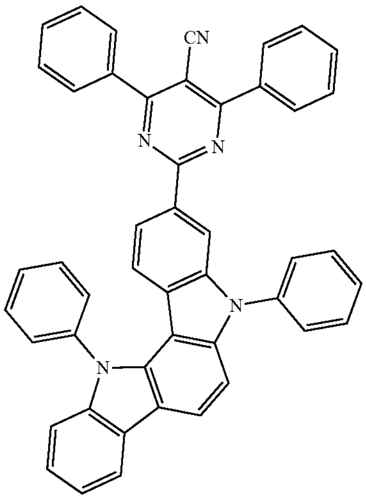
-continued
2-81
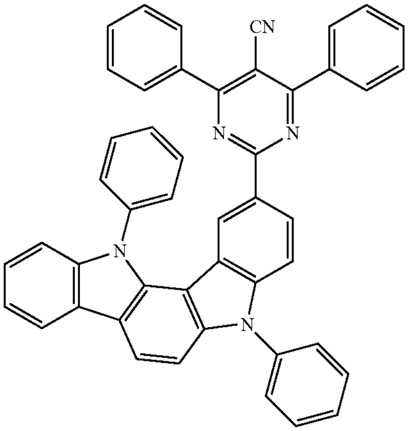
2-82
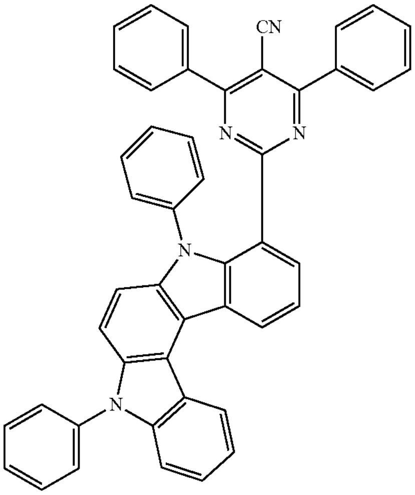
2-83
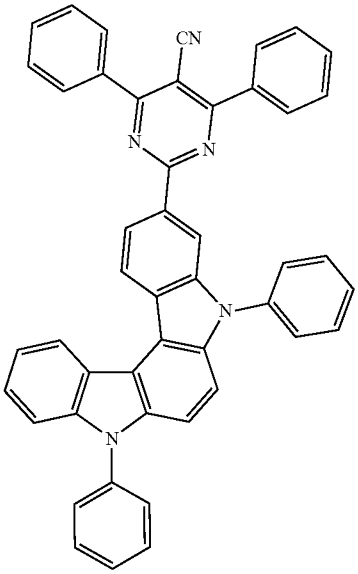

-continued
2-84
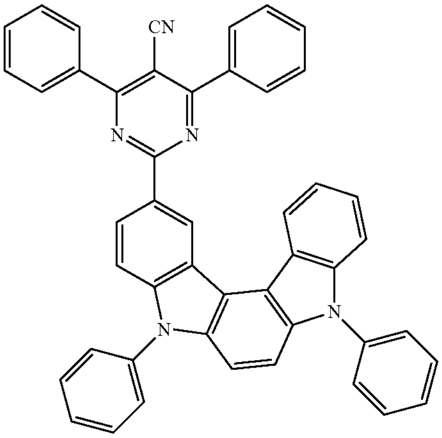
2-85
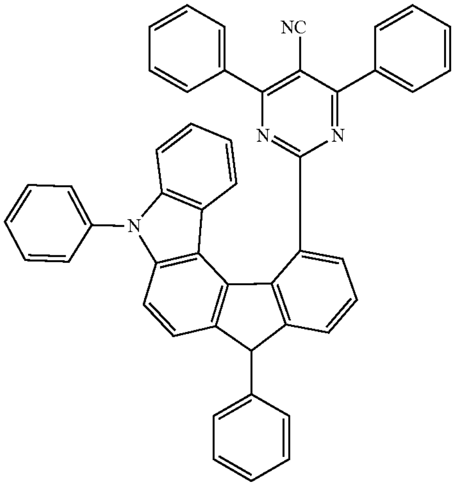
2-86
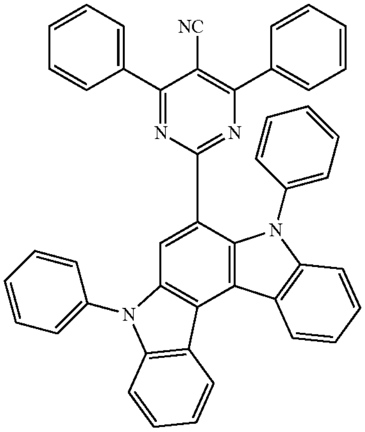
-continued
2-87
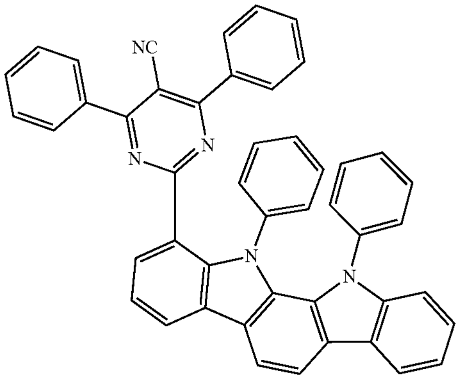
2-88
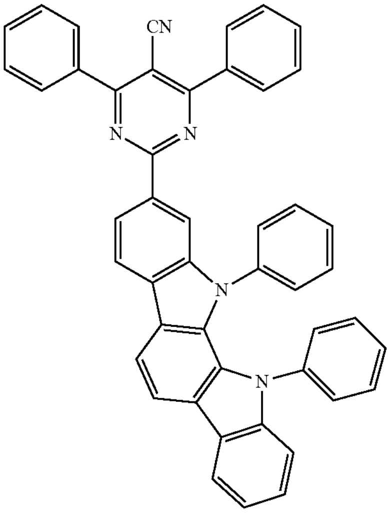
2-89
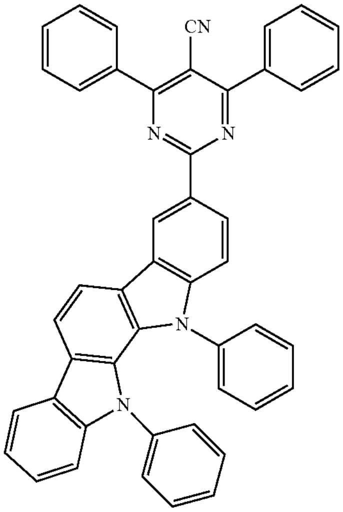

-continued
2-90
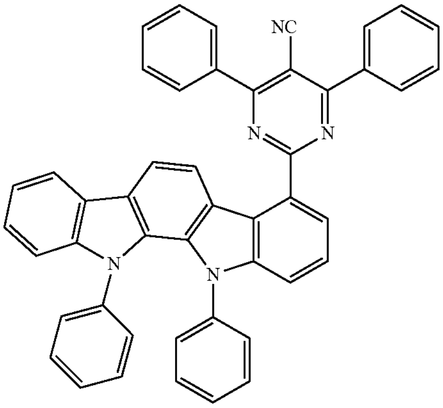
2-91
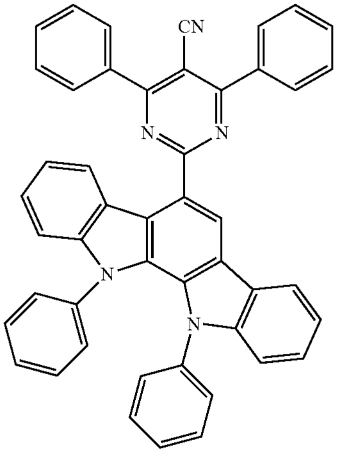
2-92
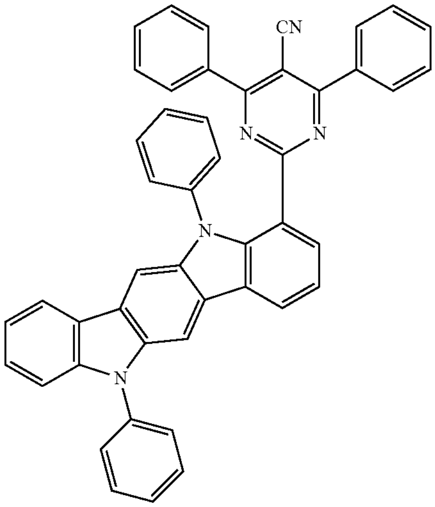
-continued
2-93
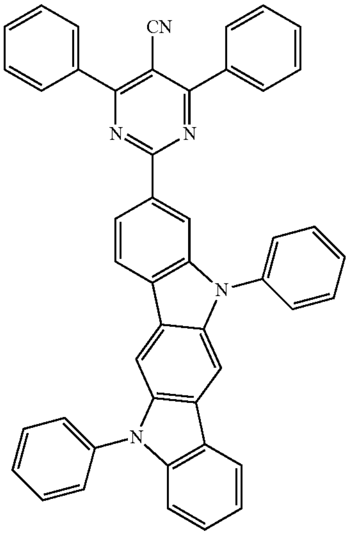
2-94
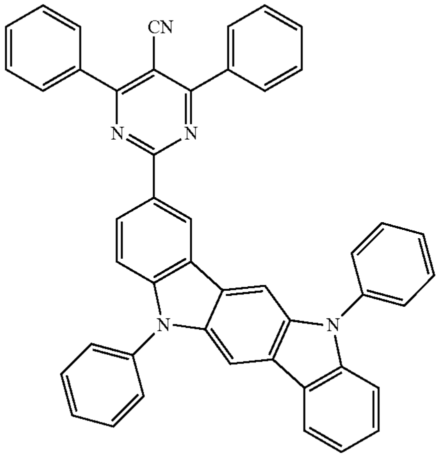
2-95
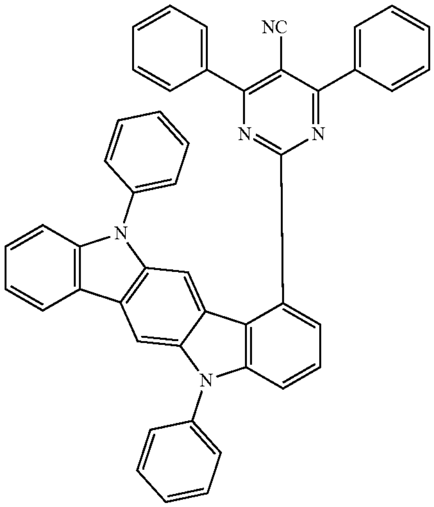

-continued
2-96
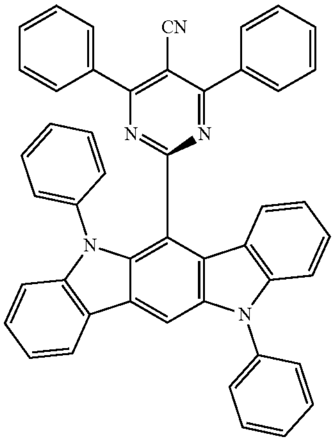
2-97
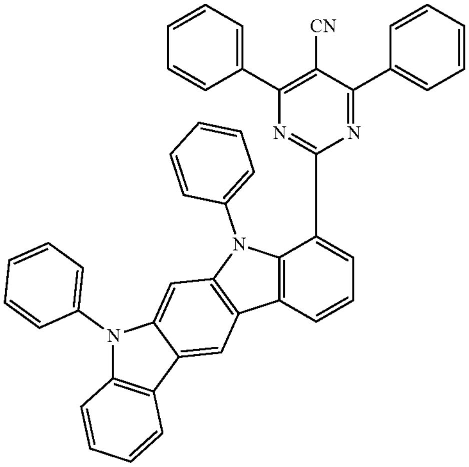
2-98
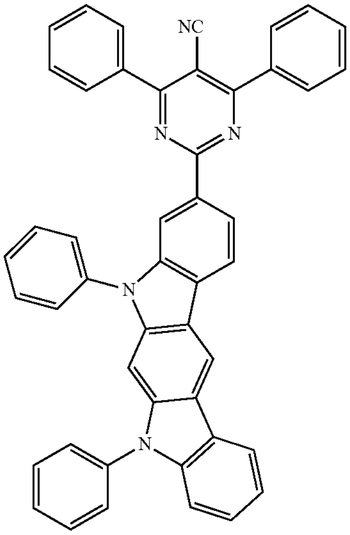
-continued
2-99
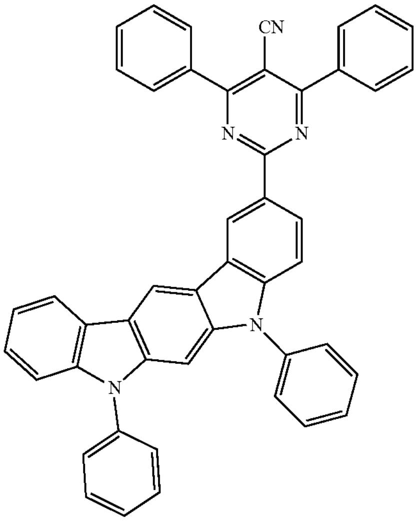
2-100
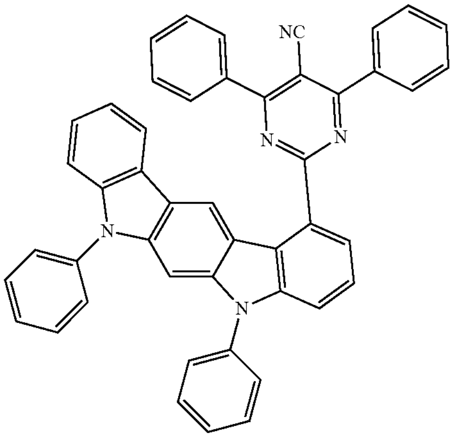
2-101
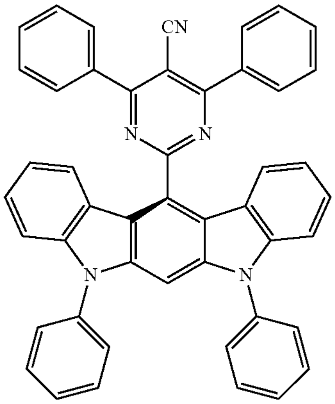

-continued
2-102
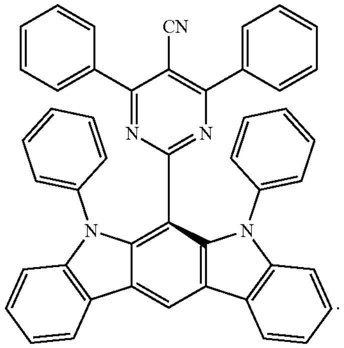
In still another aspect, the A moiety in Formula 1 may comprise a pyridine moiety with one nitrogen atom as a nuclear atom. An organic compound including the pyridine moiety as the A moiety may be selected from the following compounds of Formula 11:
[Formula 11]
3-1
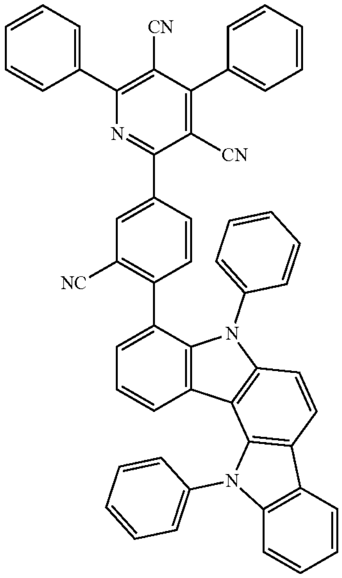
-continued
3-2
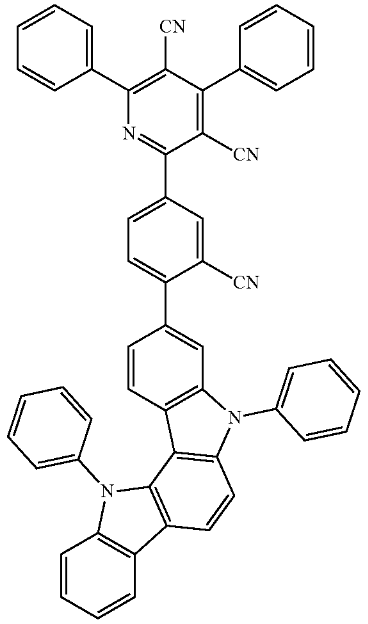
3-3
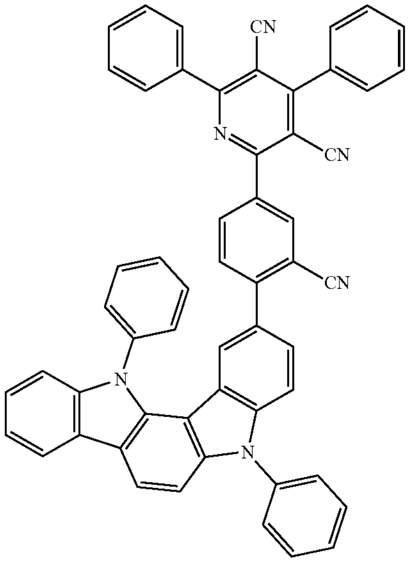

-continued
3-4
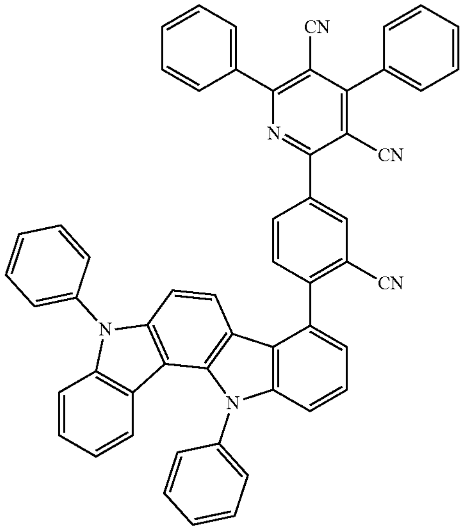
3-5
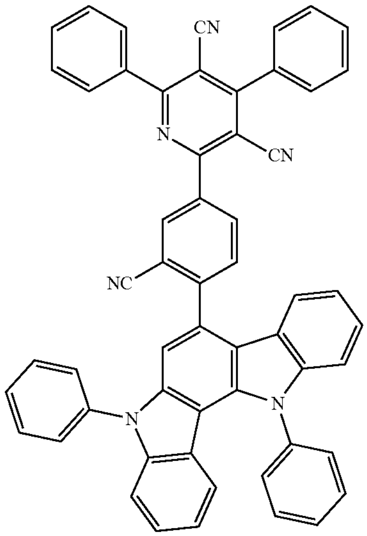
3-6
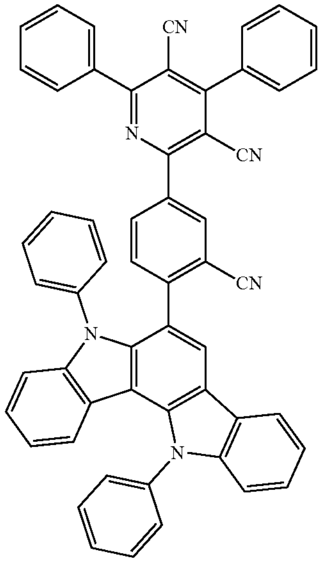
-continued
3-7
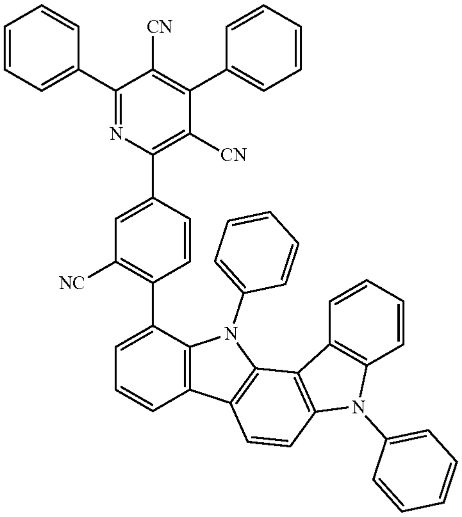
3-8
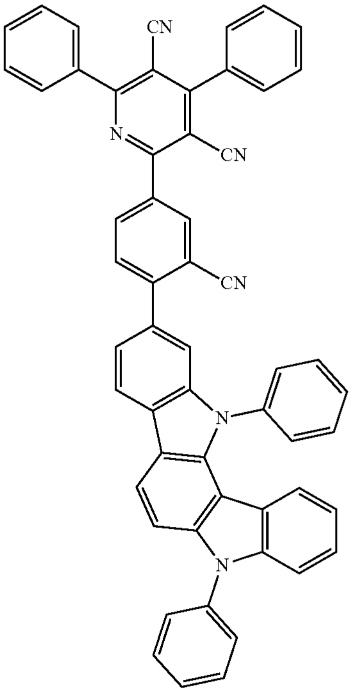

-continued
3-9
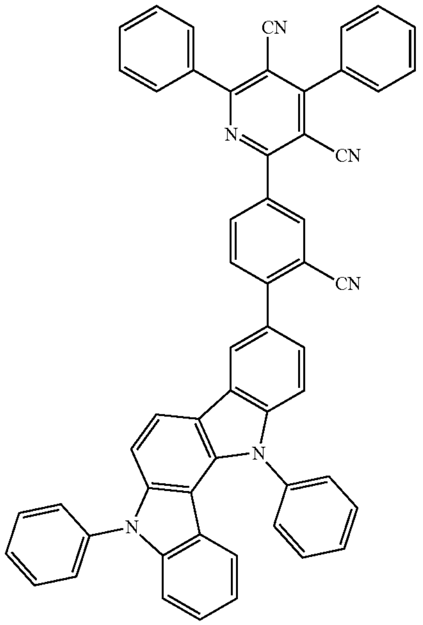
3-10
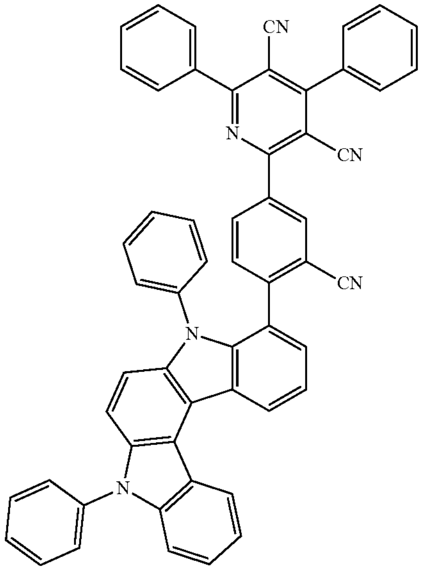
-continued
3-11
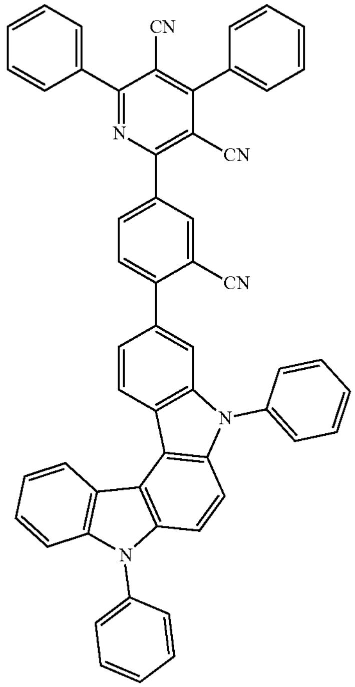
3-12
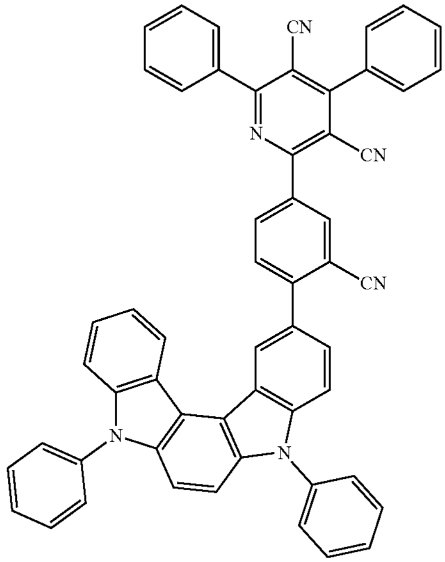

-continued
3-13
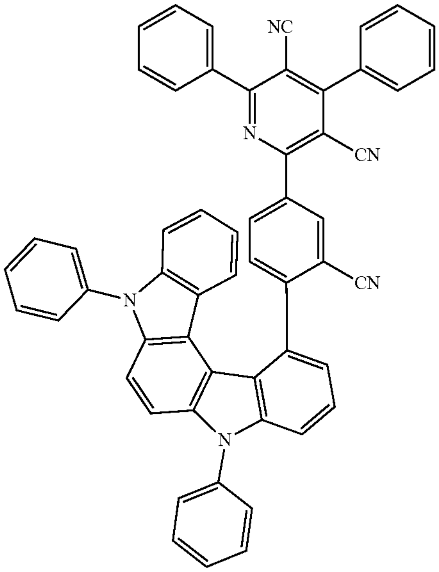
3-14
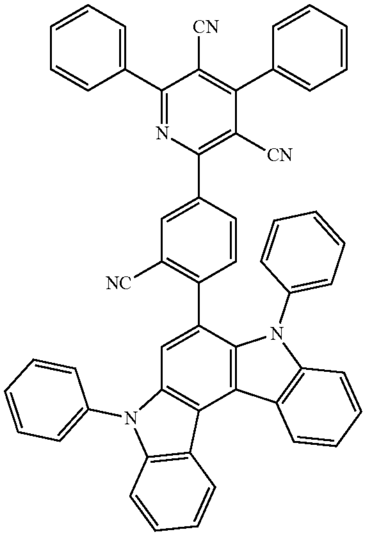
3-15
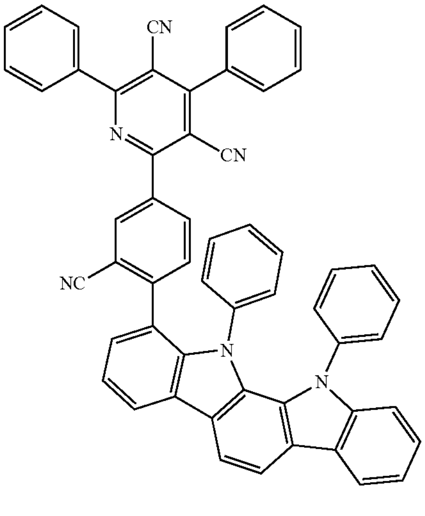
-continued
3-16
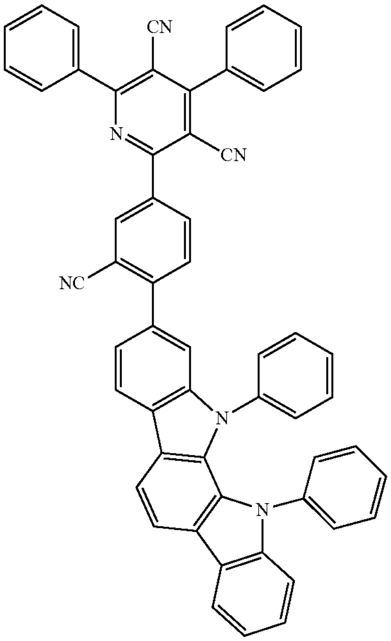
3-17
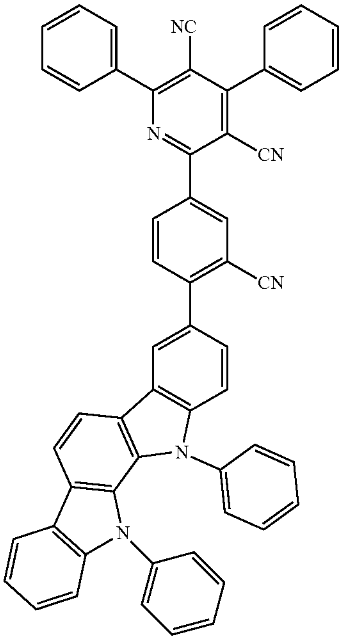

-continued
3-18
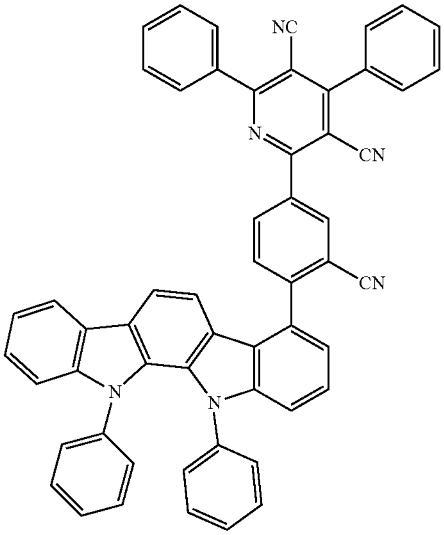
3-19
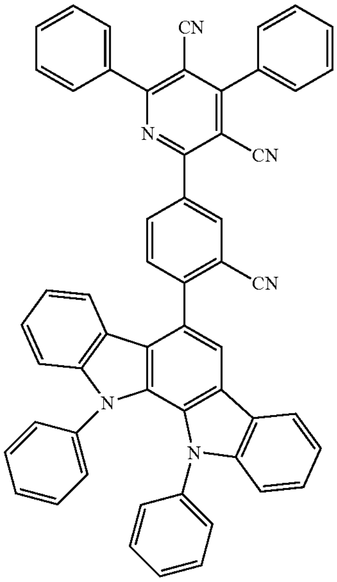
3-20
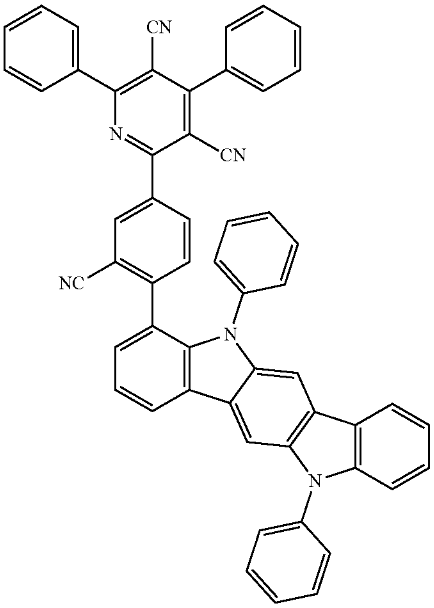
3-21
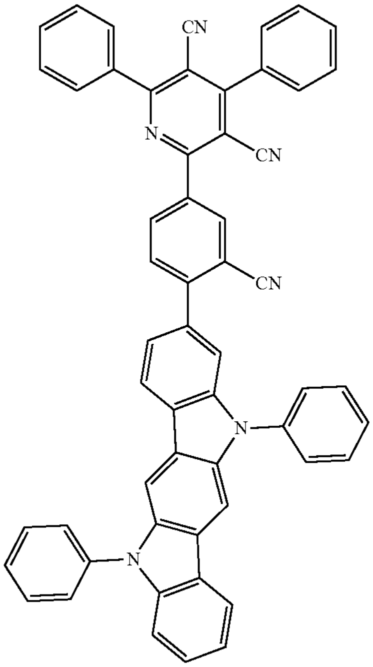

3-22
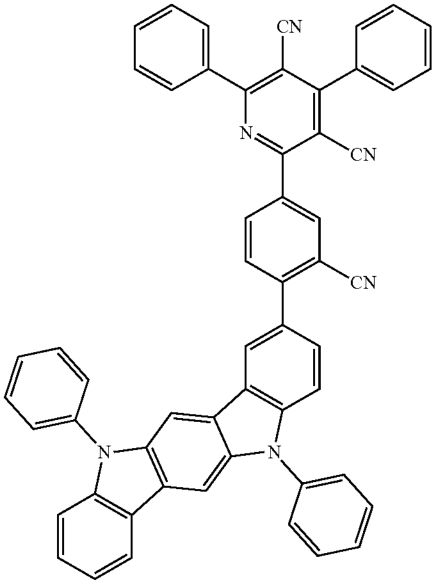
3-23
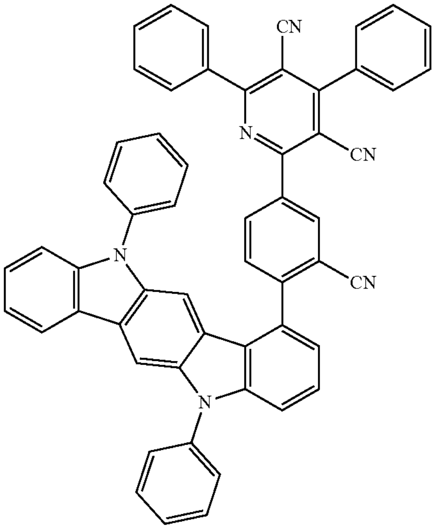
3-24
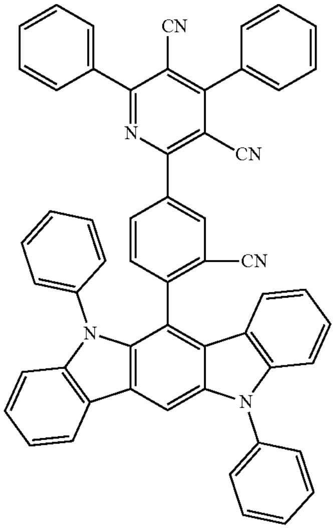
3-25
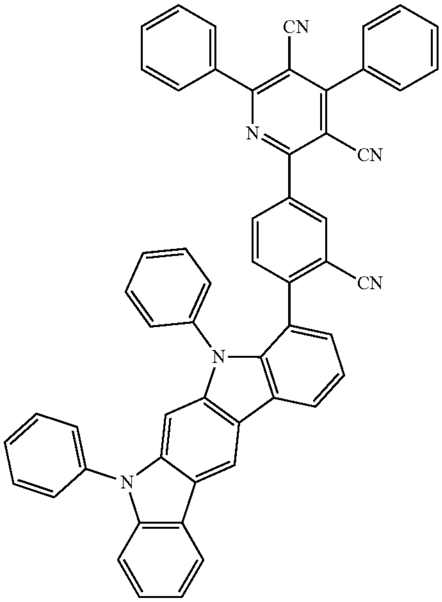
3-26
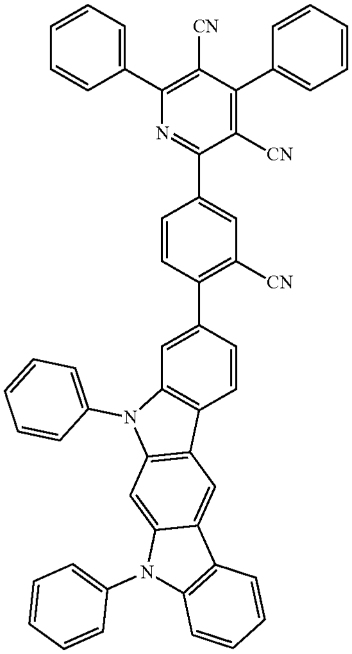

-continued
3-27
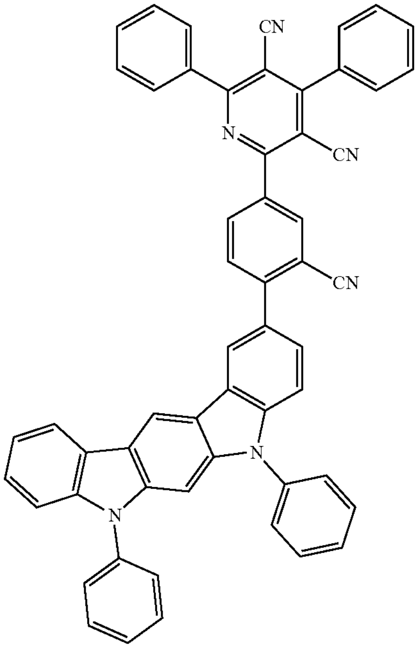
3-28
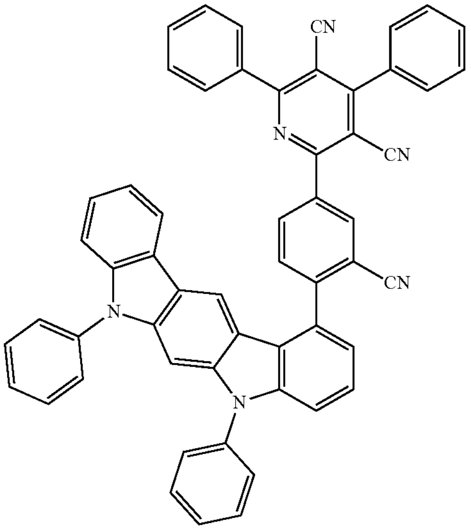
-continued
3-29
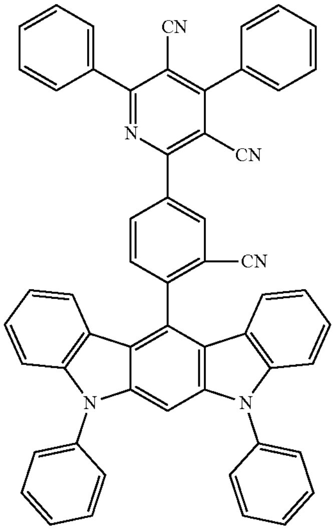
3-30
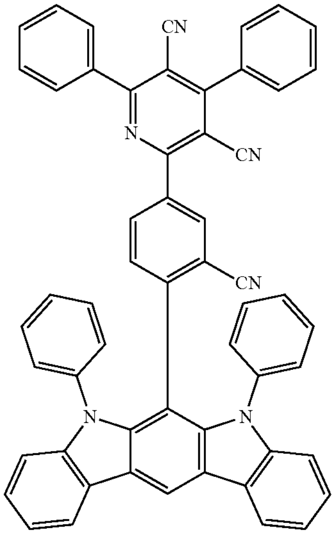
3-31
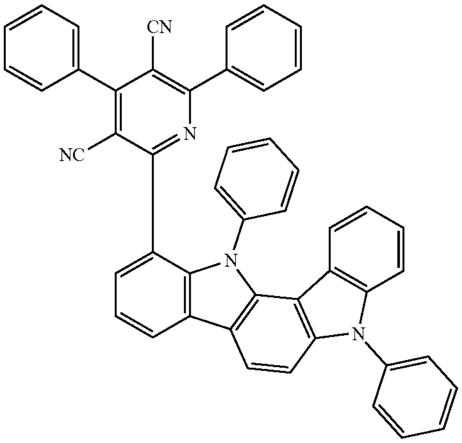

-continued
3-32
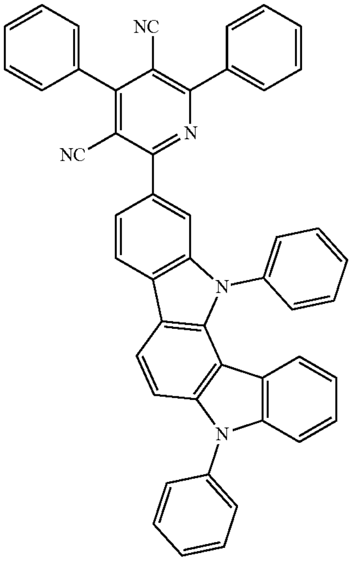
3-33
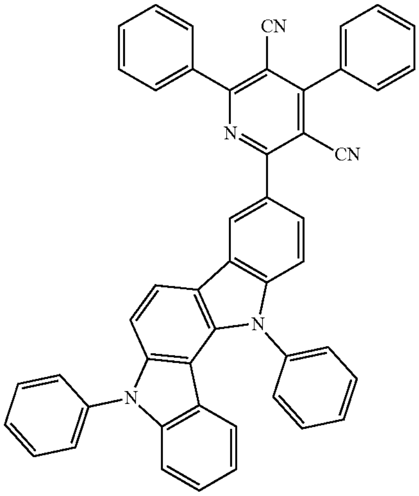
2-34
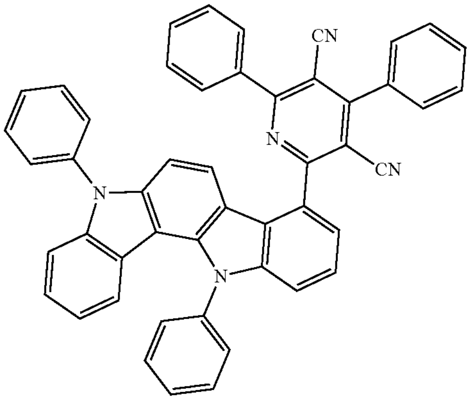
-continued
3-35
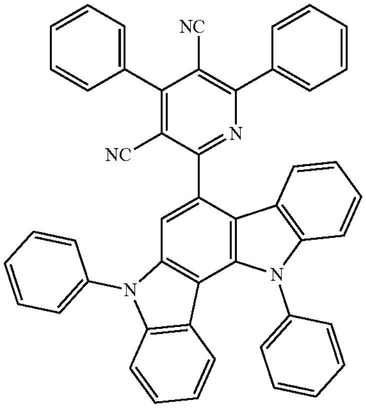
3-36
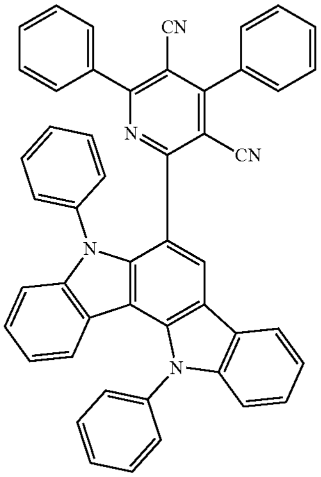
3-37
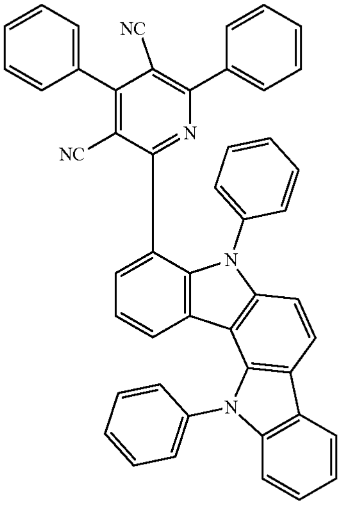

-continued
3-38
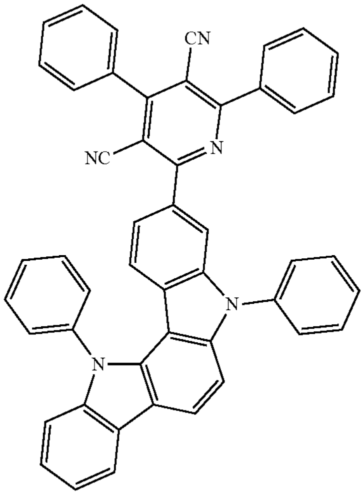
3-39
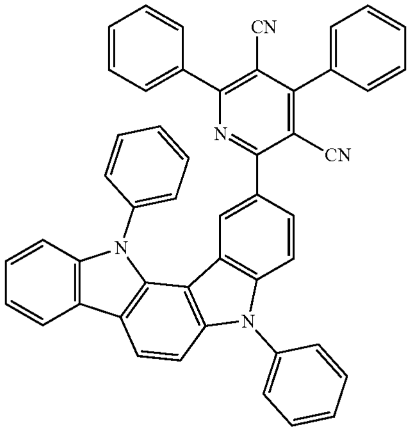
3-40
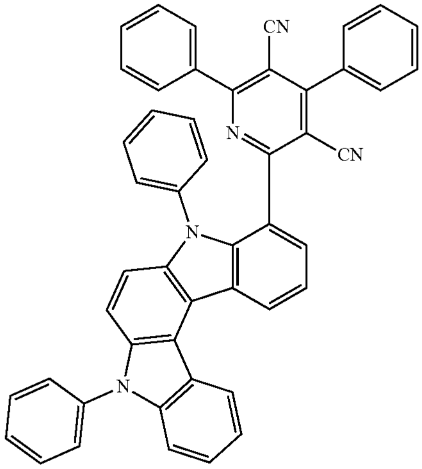
-continued
3-41
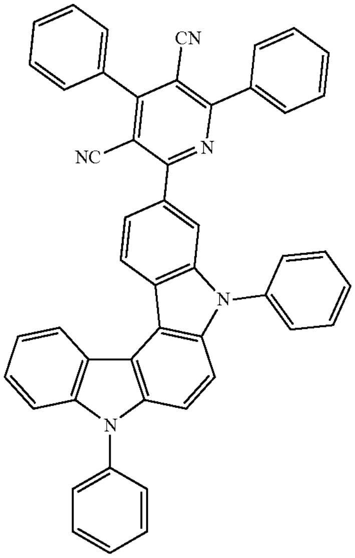
3-42
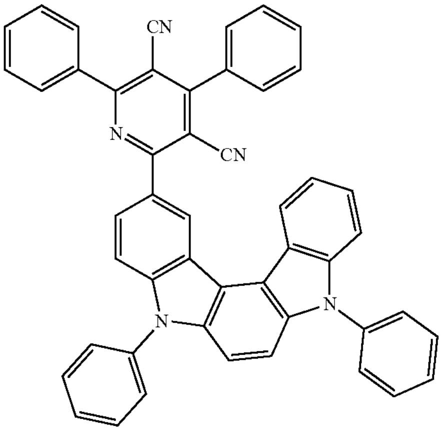
3-43
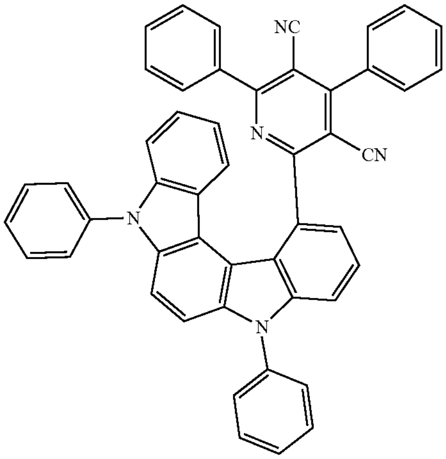

-continued
3-44
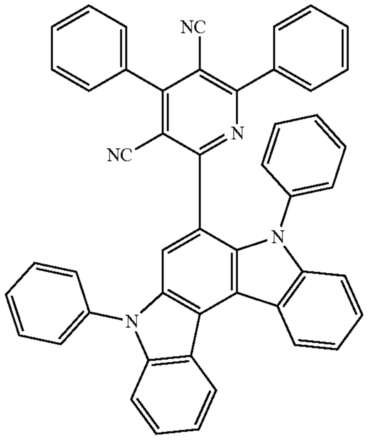
3-45
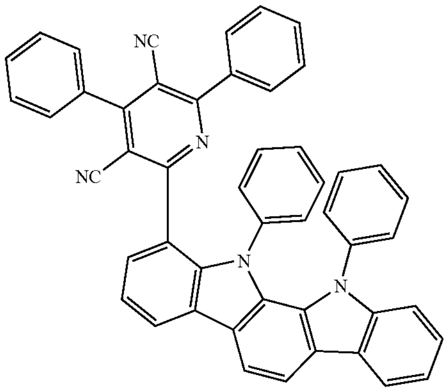
3-46
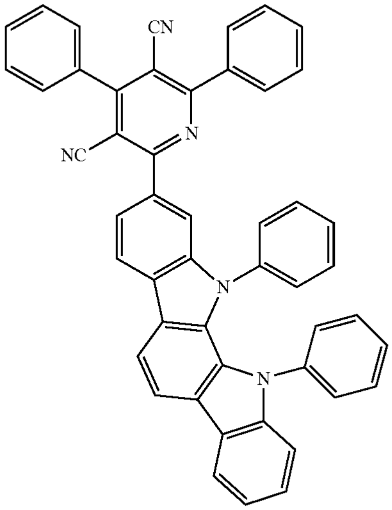
-continued
3-47
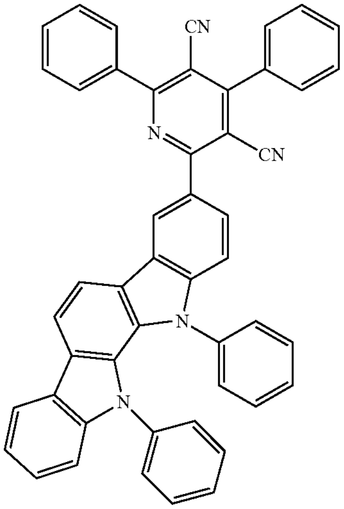
3-48
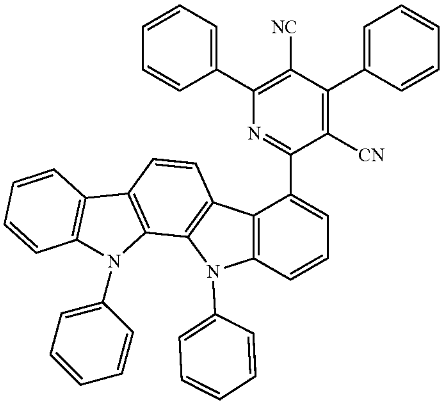
3-49
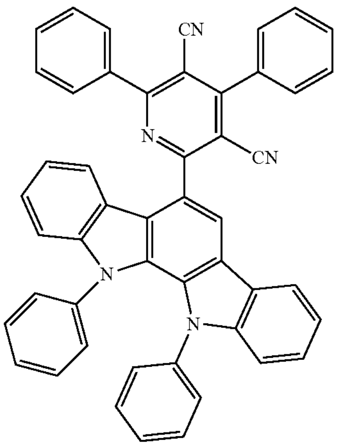

-continued
3-50
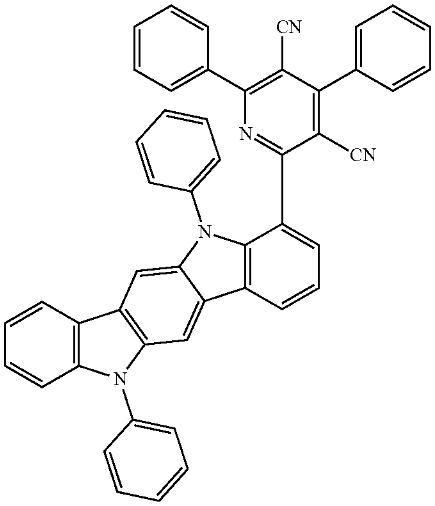
3-51
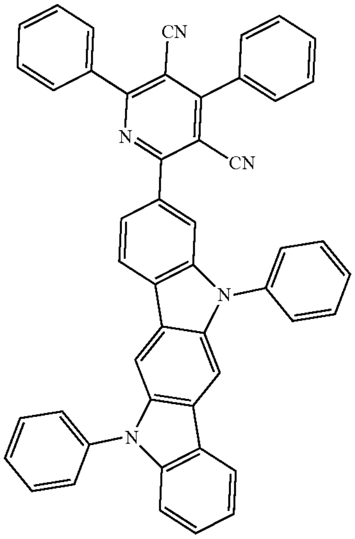
3-52
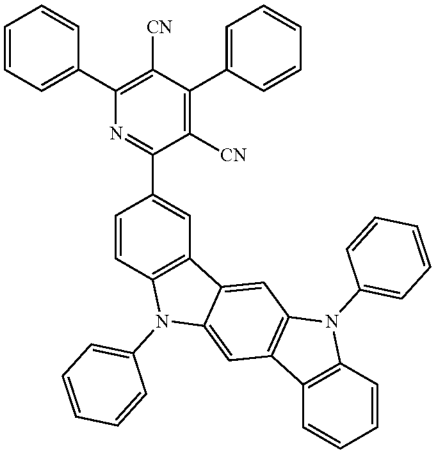
-continued
3-53
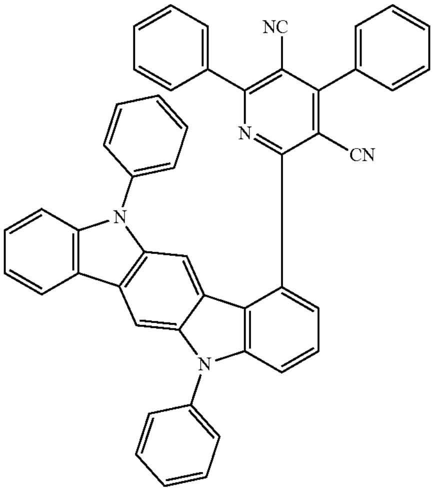
3-54
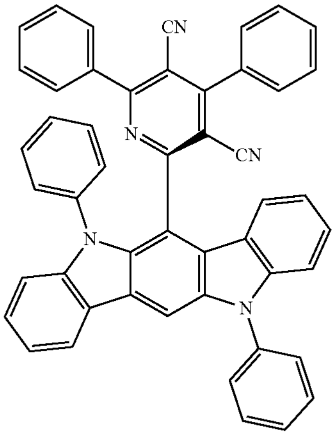
3-55
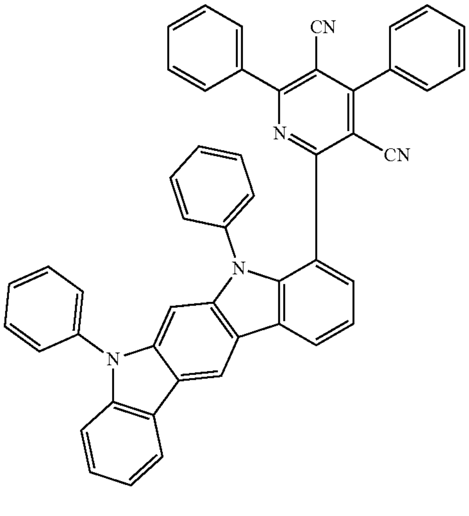

-continued 3-56

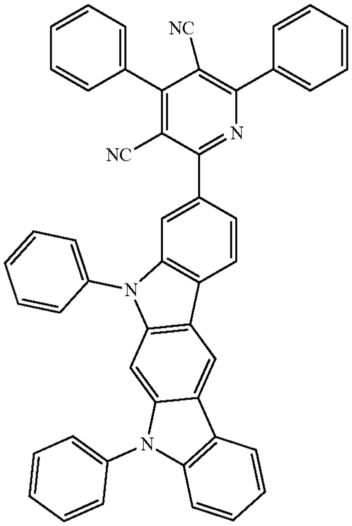

3-57

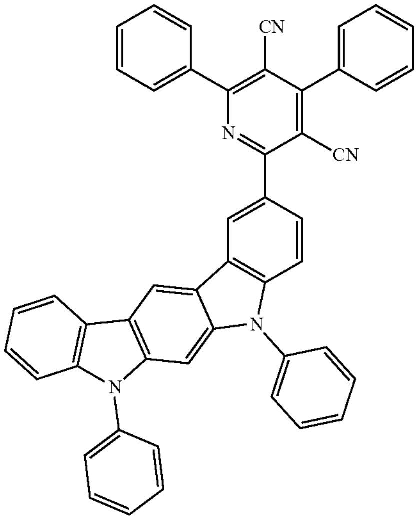

3-58

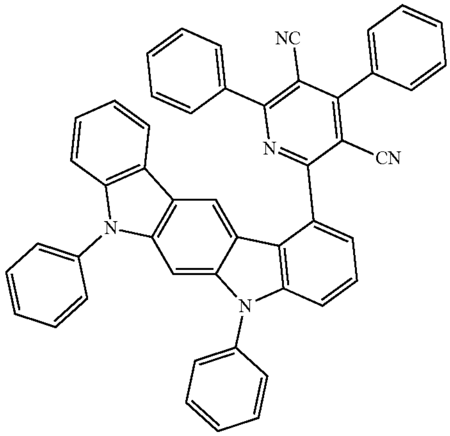

-continued 3-59

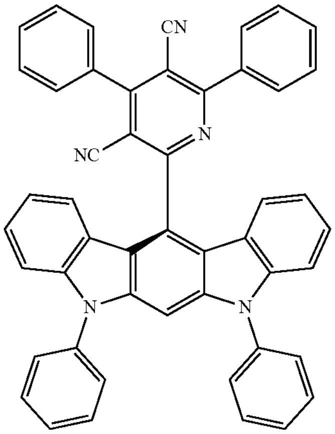

3-60

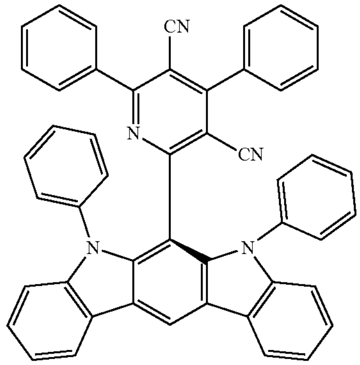

.

In further still another aspect, the A moiety in Formula 1 may comprise a phenyl moiety with only carbon atoms as a nuclear atom. In this case, the at least one carbon atom, for example, two carbon atoms of the phenyl moiety as the nuclear atom may be, but is not limited to, substituted with a cyano group, a nitro group and combination thereof. As an example, an organic compound including the phenyl moiety as the A moiety may be selected from the following compounds of Formula 12:

[Formula 12]

4-4

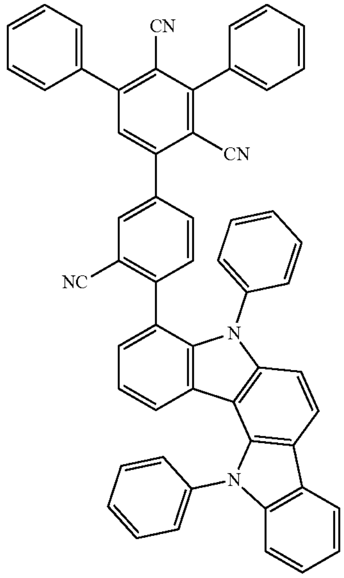

-continued
4-5
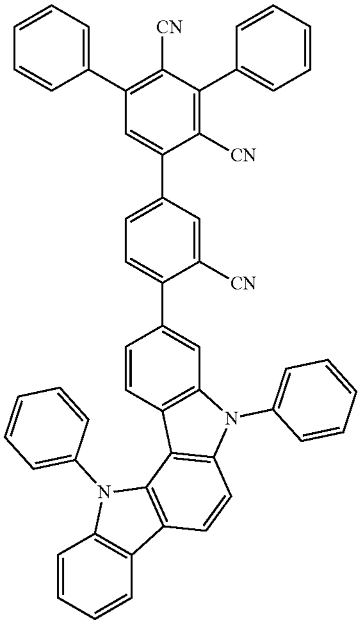
4-6
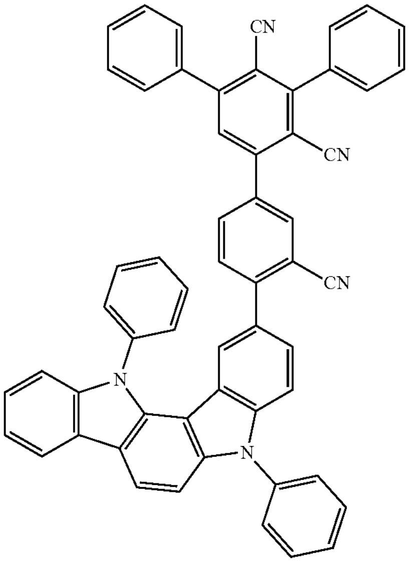
-continued
4-7
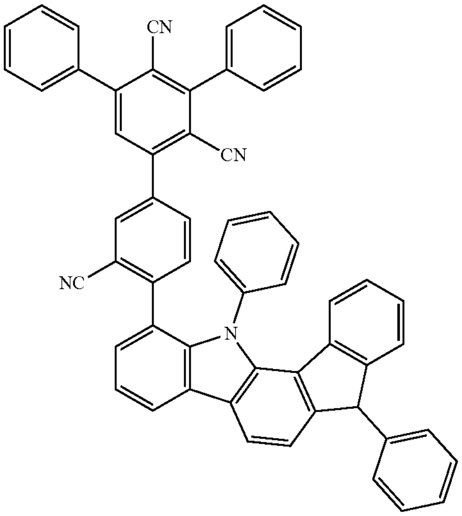
4-8
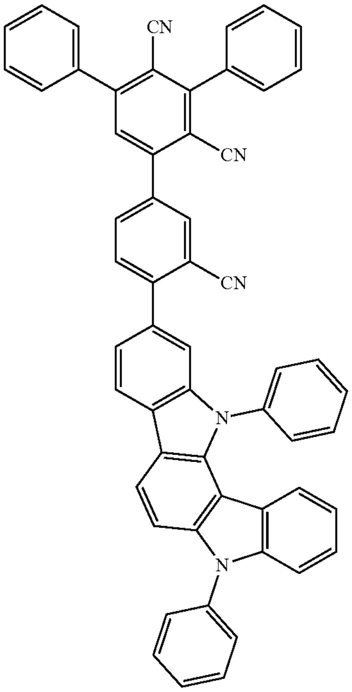

-continued
4-9
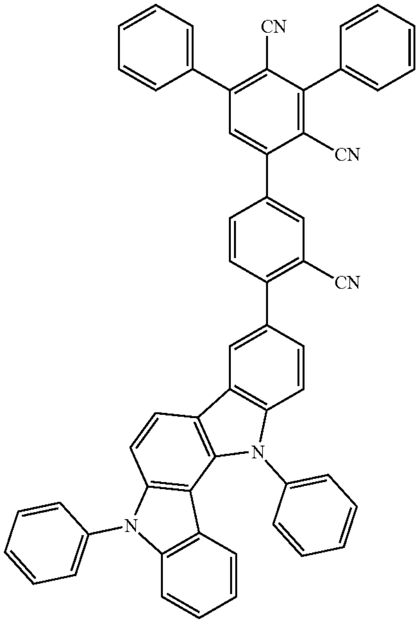
4-10
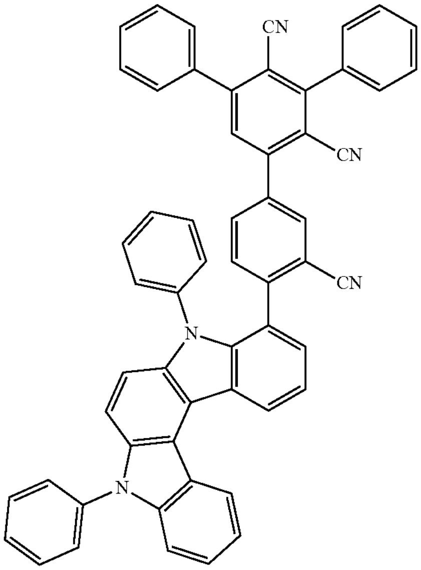
-continued
4-11
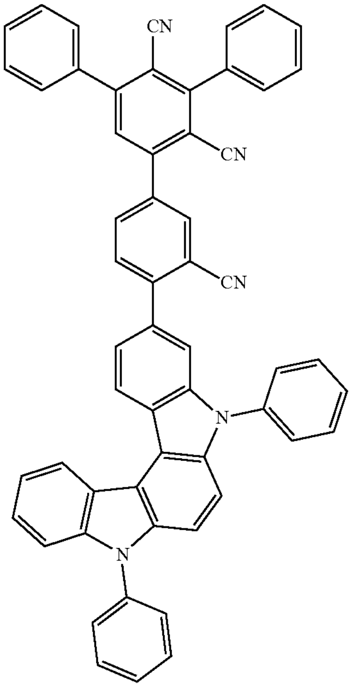
4-12
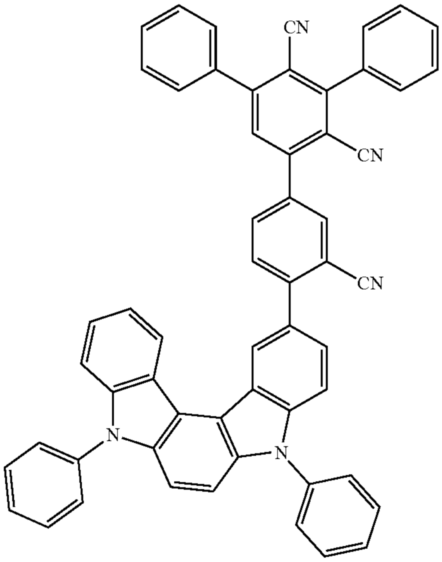

4-13
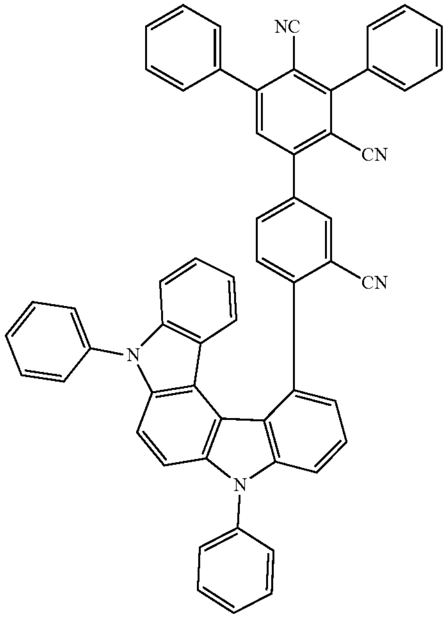
4-14
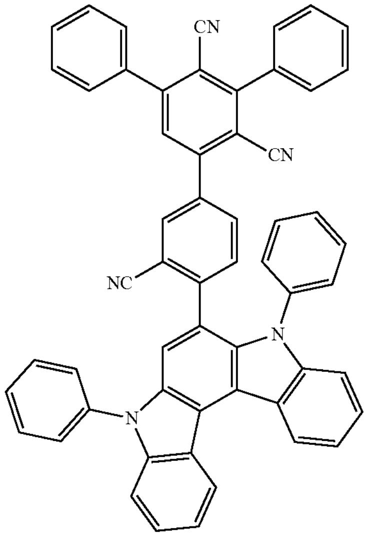
4-15
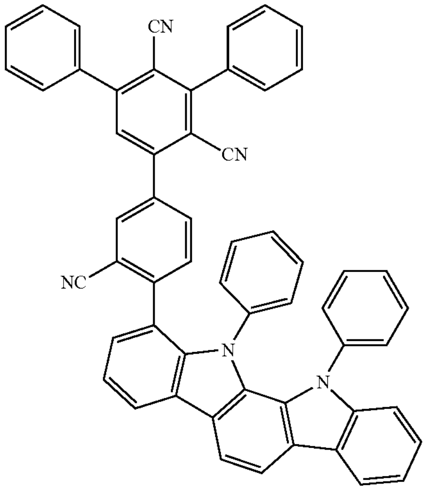
4-16
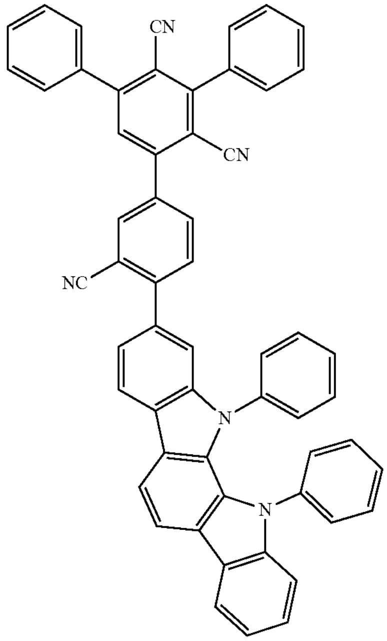
4-17
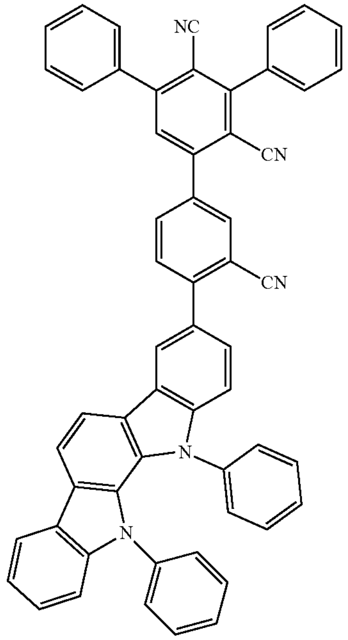

-continued
4-18
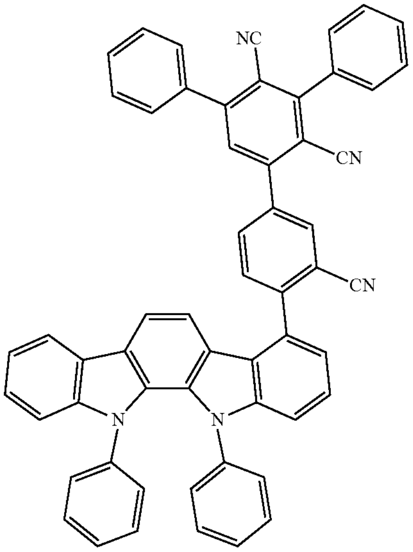
4-19
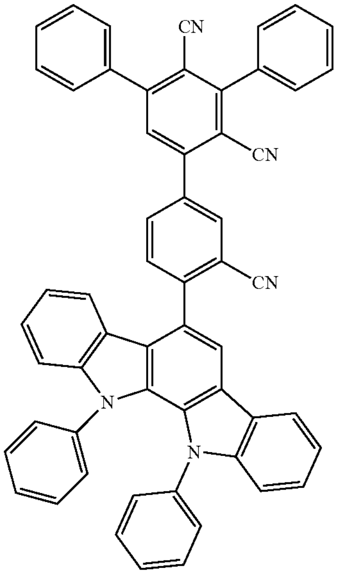
-continued
4-20
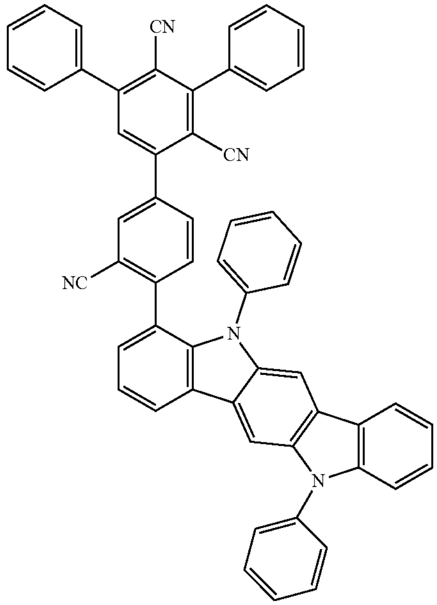
4-21
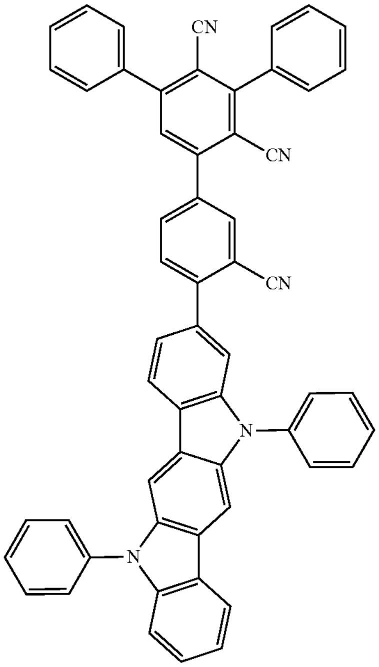

-continued
4-22
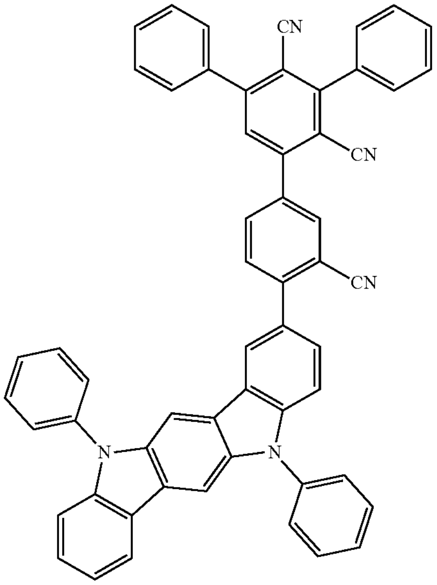
4-23
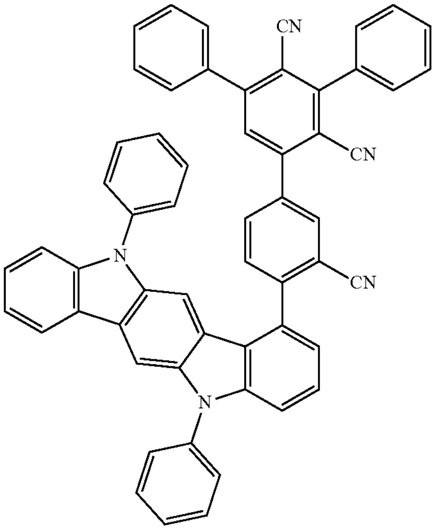
4-24
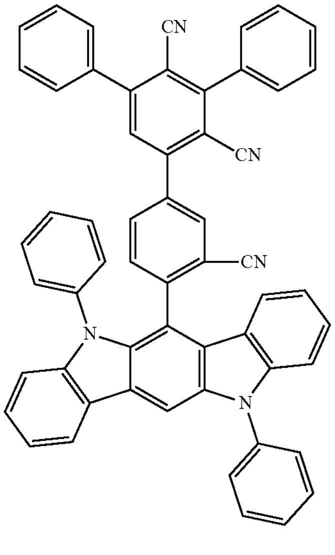
-continued
4-25
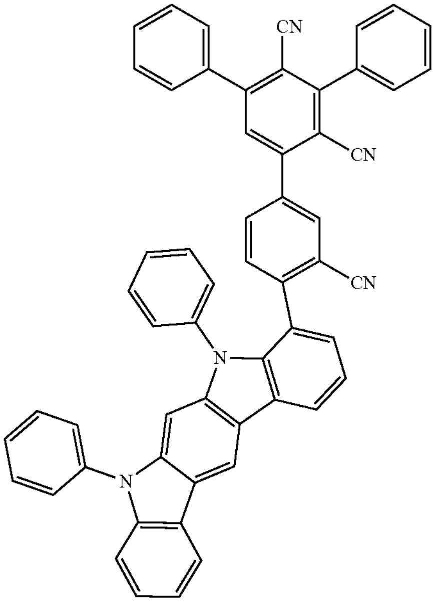
4-26
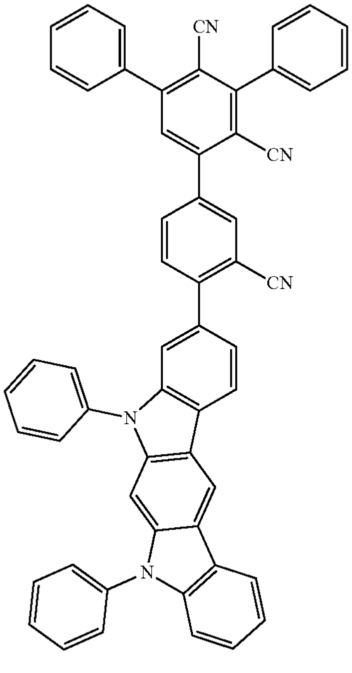

-continued
4-27
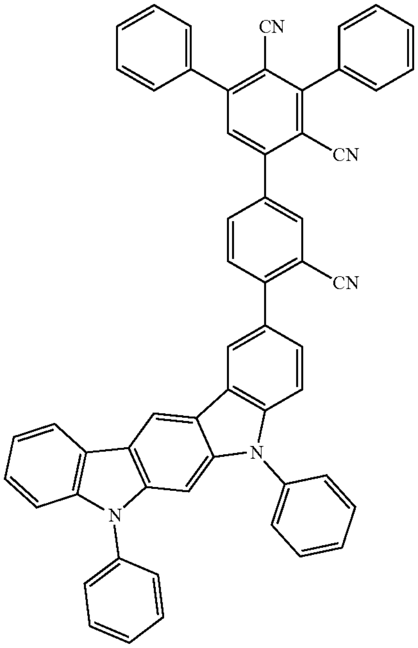
4-28
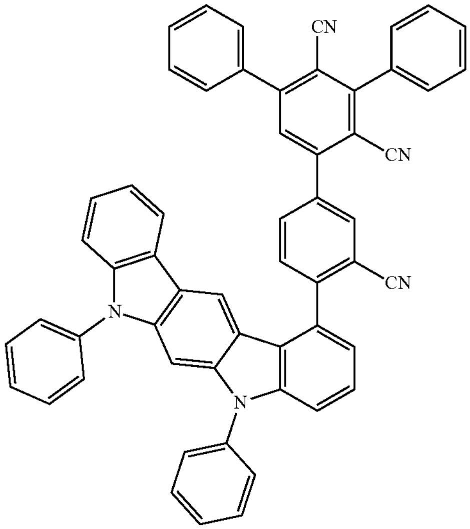
-continued
4-29
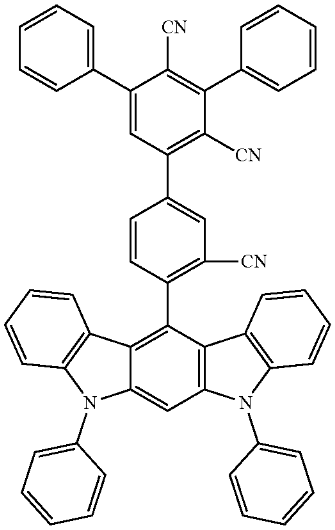
4-30
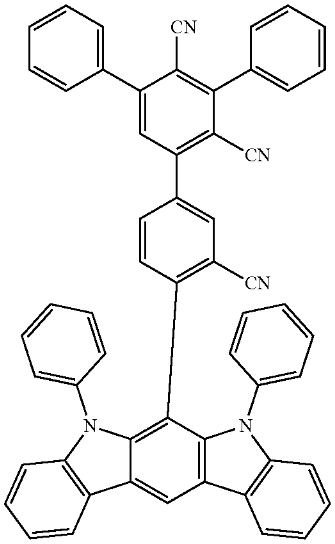
4-31
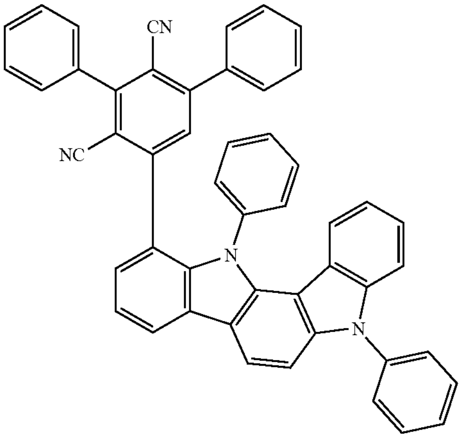

-continued
4-32
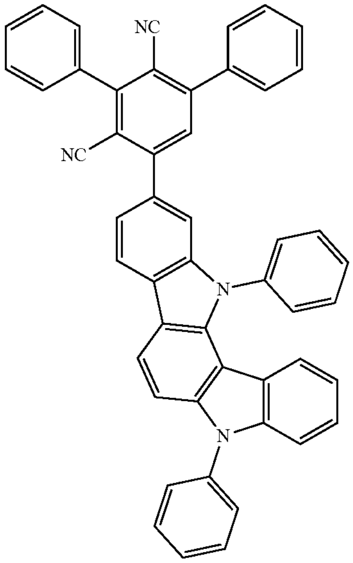
4-33
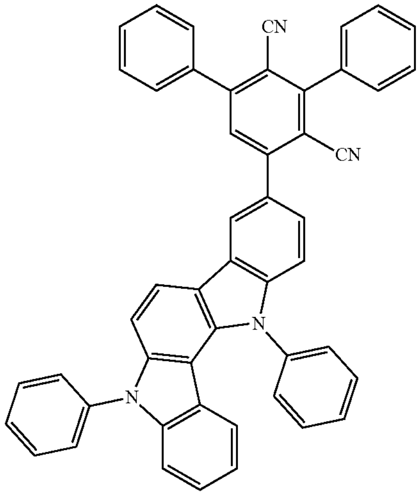
4-34
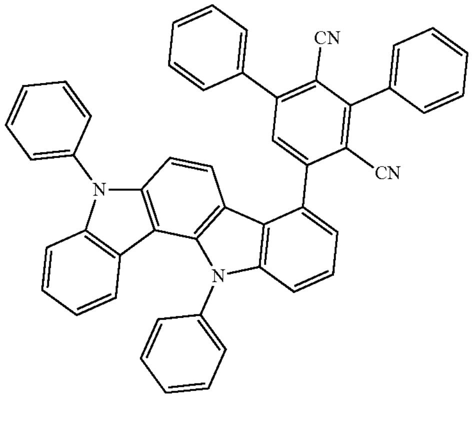
-continued
4-35
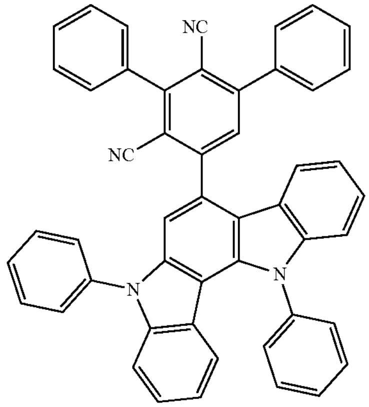
4-36
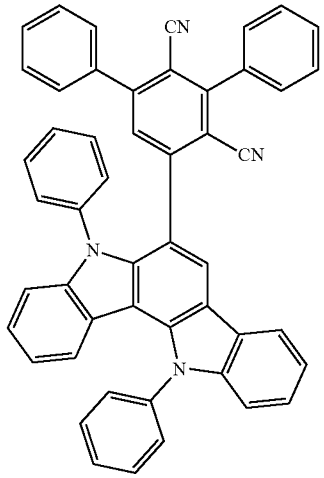
4-37
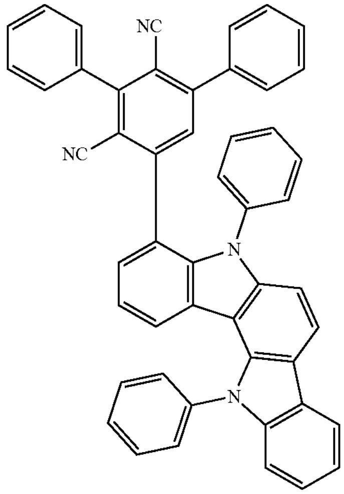

-continued
4-38
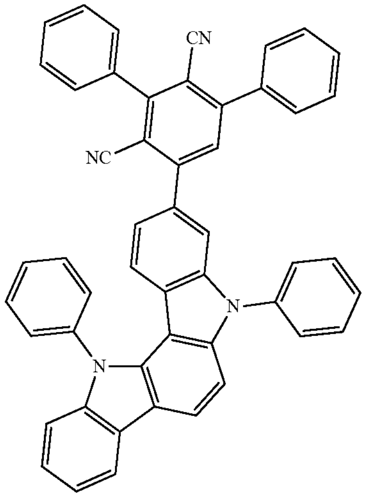
4-39
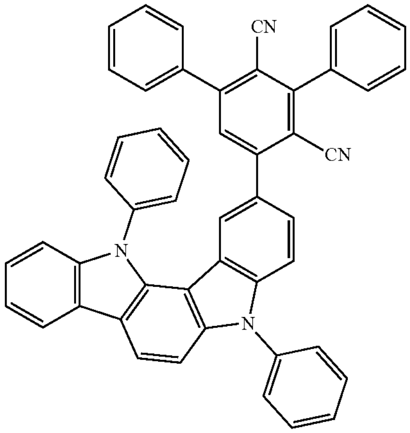
4-40
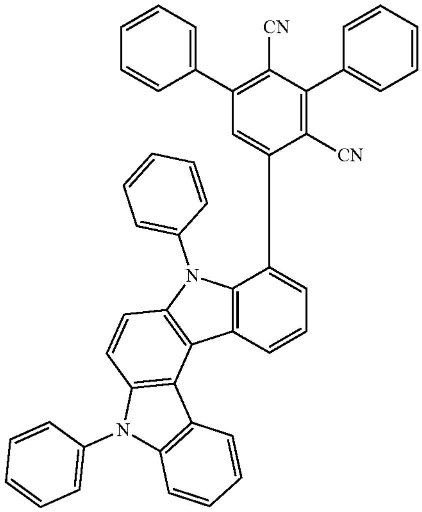
-continued
4-41
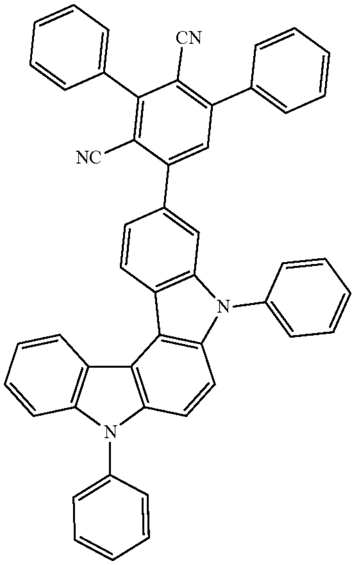
4-42
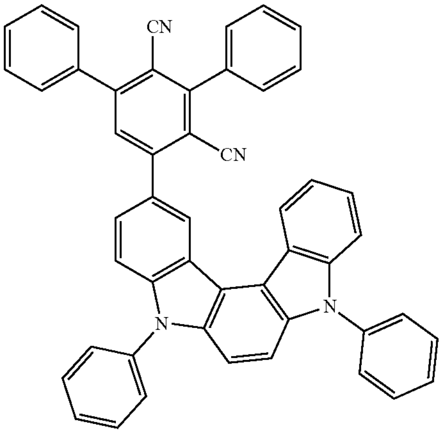
4-43
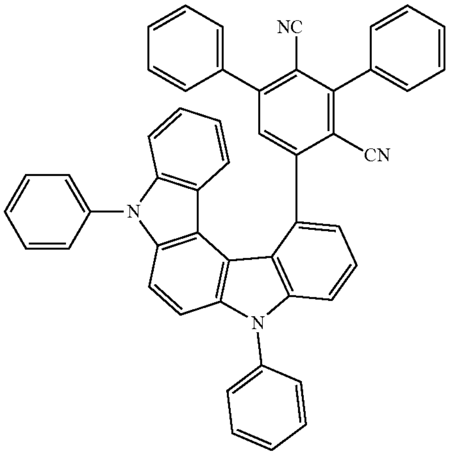

-continued
4-44
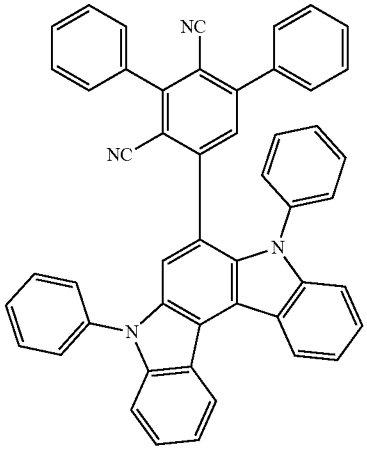
4-45
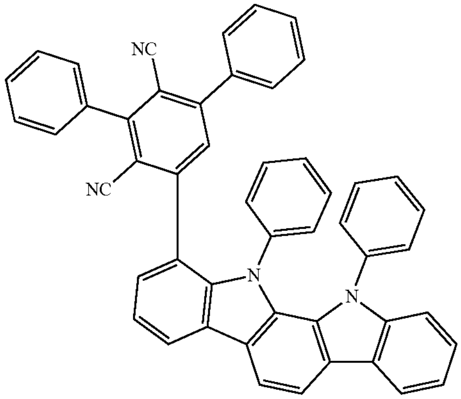
4-46
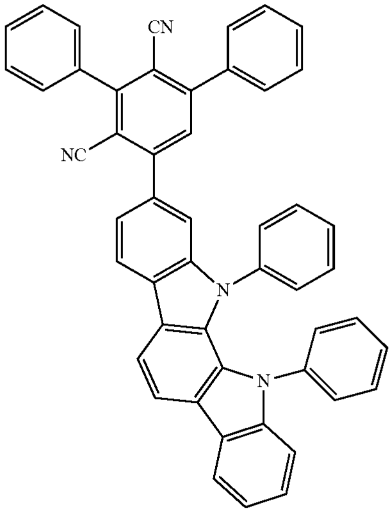
-continued
4-47
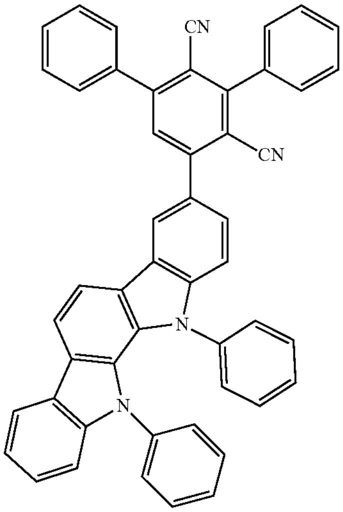
4-48
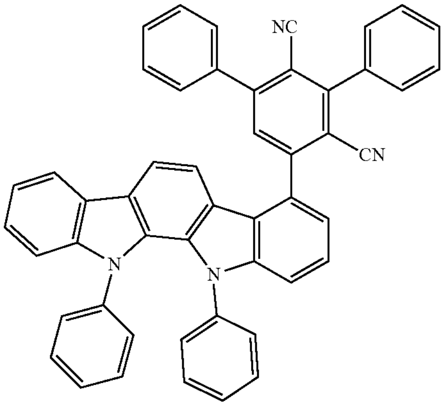
4-49
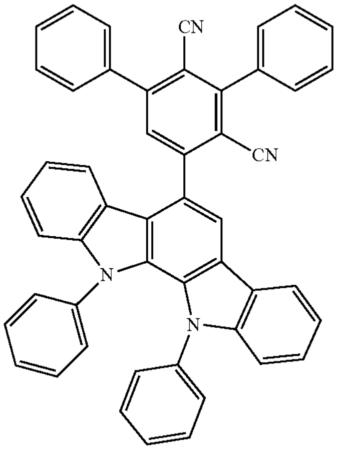

-continued
4-50
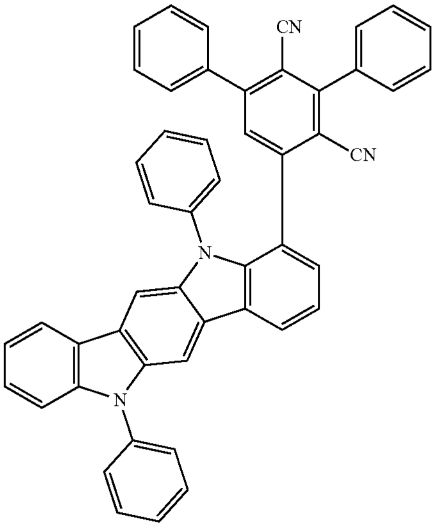
4-51
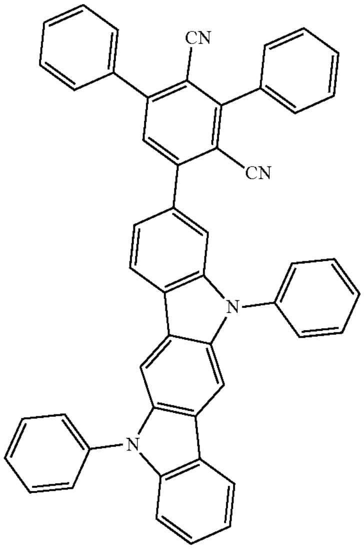
4-52
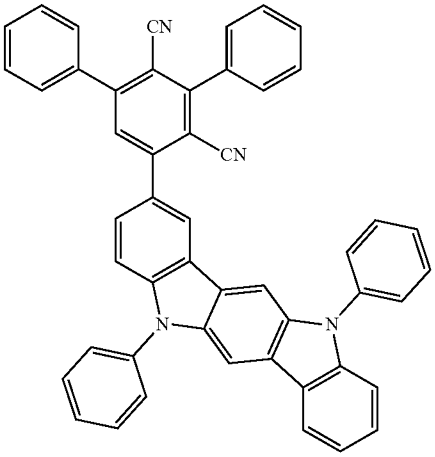
-continued
4-53
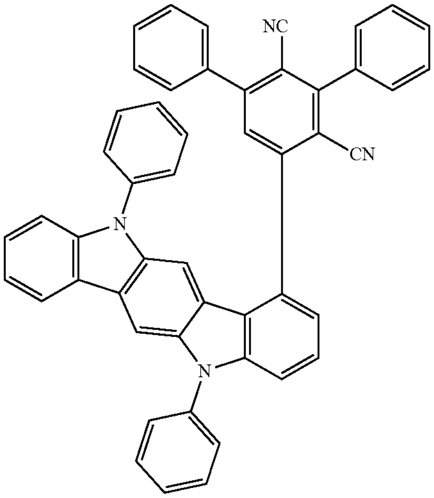
4-54
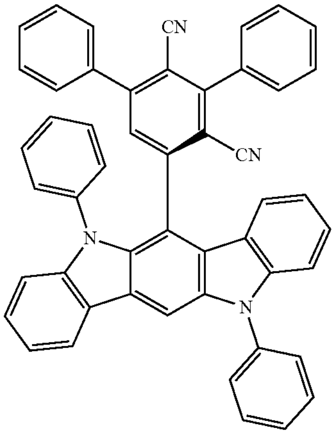
4-55
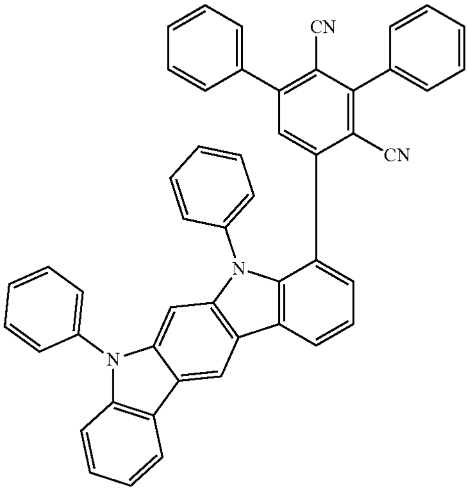

-continued 4-56

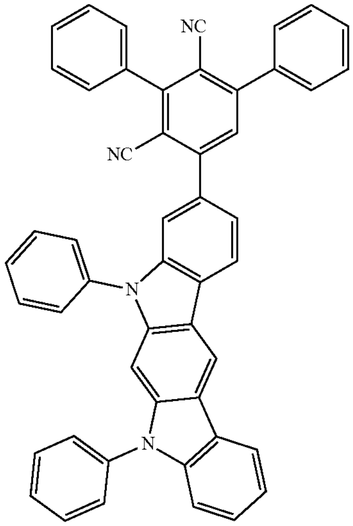

4-57

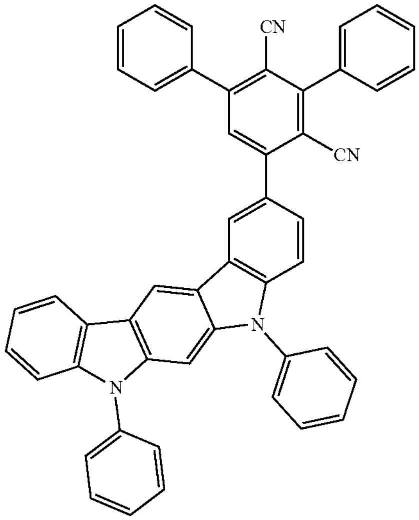

4-58

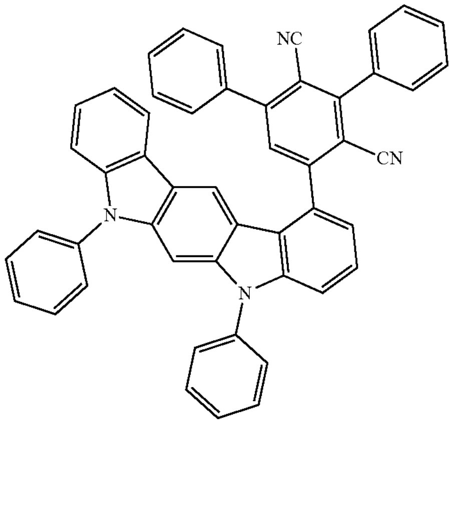

-continued 4-59

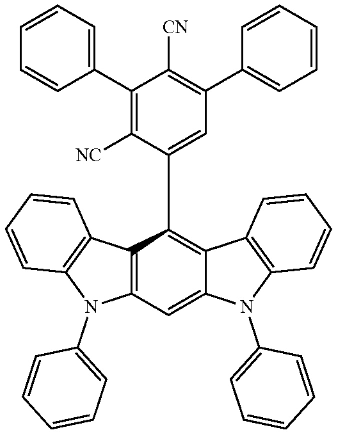

4-60

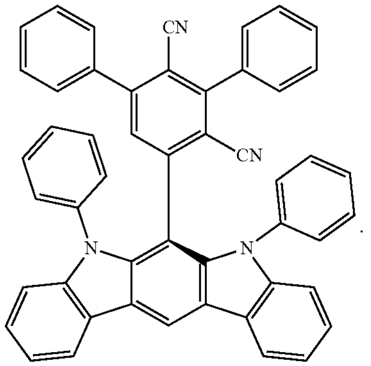

[Organic Light Emitting Device and OLED]

It is possible to realize an OLED having excellent luminous efficiency and improved luminous lifespan by applying the organic compound having the structure of Formulae 1 to 12 into an emissive layer, for example an emitting material layer of the OLED. The OLED of the present disclosure may be applied to an organic light emitting device such as an organic light emitting display device or an organic light emitting illumination device. An organic light emitting display device including the OLED will be explained. FIG. 1 is a schematic circuit diagram illustrating an organic light emitting display device in accordance with an exemplary aspect of the present disclosure.

As illustrated in FIG. 1, a gate line GL, a data line DL and power line PL, each of which cross each other to define a pixel region P, in the organic light display device. A switching thin film transistor Ts, a driving thin film transistor Td, a storage capacitor Cst and an organic light emitting diode D are formed within the pixel region P. The pixel region P may include a first pixel region P1, a second pixel region P2 and a third pixel region P3 (see, FIG. 11).

The switching thin film transistor Ts is connected to the gate line GL and the data line DL, and the driving thin film transistor Td and the storage capacitor Cst are connected between the switching thin film transistor Ts and the power line PL. The organic light emitting diode D is connected to the driving thin film transistor Td. When the switching thin film transistor Ts is turned on by a gate signal applied into the gate line GL, a data signal applied into the data line DL is applied into a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the organic light emitting diode D through the driving thin film transistor Td. And then, the organic light emitting diode D emits light having a luminance proportional to the current flowing through the driving thin film transistor Td. In this case, the storage capacitor Cst is charge with a voltage proportional to the data signal so that the voltage of the gate electrode in the driving thin film transistor Td is kept constant during one frame. Therefore, the organic light emitting display device can display a desired image.

Figure 2:
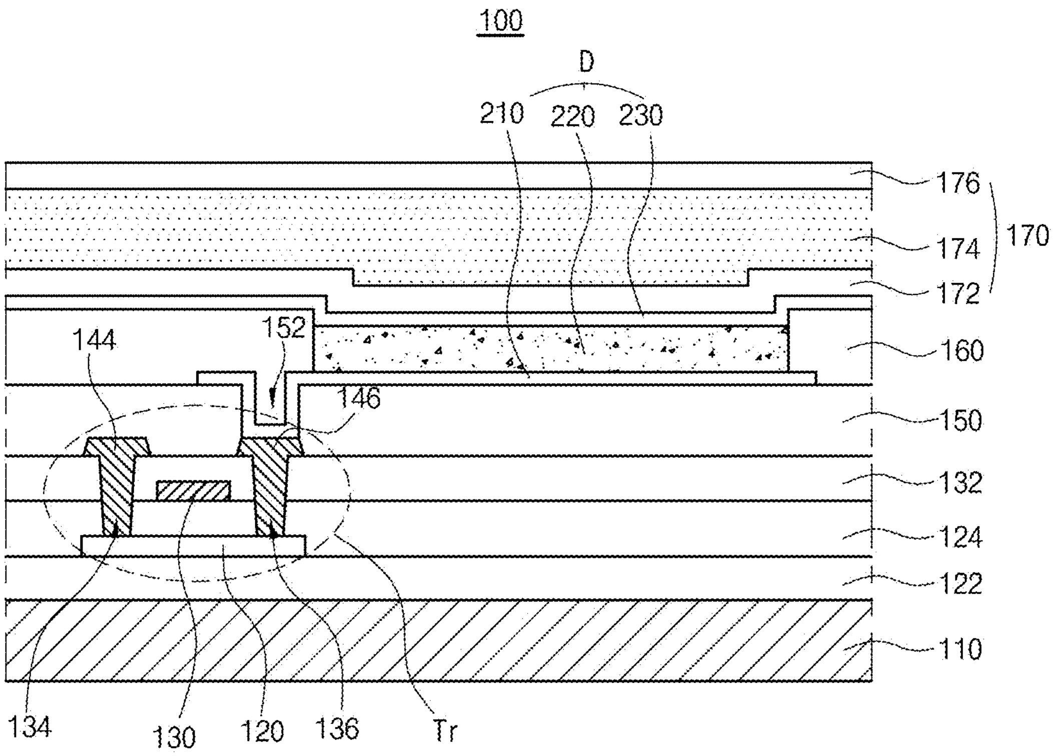
FIG. 2 is a schematic cross-sectional view illustrating an organic light emitting display device in accordance with an exemplary aspect of the present disclosure.

FIG. 2 is a schematic cross-sectional view of an organic light emitting display device 100 in accordance with an exemplary aspect of the present disclosure. All component of the organic light emitting display device in accordance with all aspects of the present disclosure are operatively couple and configured. As illustrated in FIG. 2, the organic light emitting display device 100 includes a substrate 110, a thin-film transistor Tr on the substrate 110, and an organic light emitting diode (OLED) D connected to the thin film transistor Tr.

The substrate 110 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 may be disposed over the substrate 110, and the thin film transistor Tr is disposed over the buffer layer 122. The buffer layer 122 may be omitted.

A semiconductor layer 120 is disposed over the buffer layer 122. In one exemplary aspect, the semiconductor layer 120 may include, but is not limited to, oxide semiconductor materials. In this case, a light-shield pattern may be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 may include, but is not limited to, polycrystalline silicon. In this case, opposite edges of the semiconductor layer 120 may be doped with impurities.

A gate insulating layer 124 formed of an insulating material is disposed on the semiconductor layer 120. The gate insulating layer 124 may include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 may be patterned identically as the gate electrode 130.

An interlayer insulating layer 132 formed of an insulating material is disposed on the gate electrode 130 with covering over an entire surface of the substrate 110. The interlayer insulating layer 132 may include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 2. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 2 has a coplanar structure in which the gate electrode 130, the source electrode 144 and the drain electrode 146 are disposed over the semiconductor layer 120. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

A gate line and a data line, which cross each other to define a pixel region, and a switching element, which is connected to the gate line and the data line, may be further formed in the pixel region of FIG. 1. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter that comprises dyes or pigments for transmitting specific wavelength light of light emitted from the OLED D. For example, the color filter can transmit light of specific wavelength such as red (R), green (G), blue (B) and/or white (W). Each of red, green, and blue color filter may be formed separately in each pixel region. In this case, the organic light emitting display device 100 can implement full-color through the color filter.

For example, when the organic light emitting display device 100 is a bottom-emission type, the color filter may be disposed on the interlayer insulating layer 132 with corresponding to the OLED D. Alternatively, when the organic light emitting display device 100 is a top-emission type, the color filter may be disposed over the OLED D, that is, a second electrode 230.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it may be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 including at least one emitting part and a second electrode 230 each of which is disposed sequentially on the first electrode 210.

The first electrode 210 is disposed in each pixel region. The first electrode 210 may be an anode and include a conductive material having a relatively high work function value. For example, the first electrode 210 may include, but is not limited to, a transparent conductive oxide (TCO) such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a bottom-emission type, the first electrode 210 may have a single-layered structure of the TCO. Alternatively, when the organic light emitting display device 100 is a top-emission type, a reflective electrode or a reflective layer may be disposed under the first electrode 210. For example, the reflective electrode or the reflective layer may include, but are not limited to, silver (Ag) or aluminum-palladium-copper (APC) alloy. In the OLED D of the top-emission type, the first electrode 210 may have a triple-layered structure of ITO/Ag/ITO or ITO/APC/ITO.

In addition, a bank layer 160 is disposed on the passivation layer 150 in order to cover edges of the first electrode 210. The bank layer 160 exposes a center of the first electrode 210.

An emissive layer 220 is disposed on the first electrode 210. In one exemplary aspect, the emissive layer 220 may have a single-layered structure of an emitting material layer (EML). Alternatively, the emissive layer 220 may have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 5, 7 and 9). In one aspect, the emissive layer 220 may have single emitting part. Alternatively, the emissive layer 220 may have multiple emitting parts to form a tandem structure.

The emissive layer 220 comprises anyone having the structure of Formulae 1 to 12. As an example, the organic compound having the structure of Formulae 1 to 12 may be applied into the dopant in the EML.

The second electrode 230 is disposed over the substrate 110 above which the emissive layer 220 is disposed. The second electrode 230 may be disposed over a whole display area and may include a conductive material with a relatively low work function value compared to the first electrode 210. The second electrode 230 may be a cathode. For example, the second electrode 230 may include, but is not limited to, aluminum (Al), magnesium (Mg), calcium (Ca), silver (Ag), alloy thereof or combination thereof such as aluminum-magnesium alloy (Al—Mg). When the organic light emitting display device 100 is a top-emission type, the second electrode 230 is thin so as to have light-transmissive (semi-transmissive) property.

In addition, an encapsulation film 170 may be disposed over the second electrode 230 in order to prevent outer moisture from penetrating into the OLED D. The encapsulation film 170 may have, but is not limited to, a laminated structure of a first inorganic insulating film 172, an organic insulating film 174 and a second inorganic insulating film 176.

Moreover, the organic light emitting display device 100 may have a polarizer in order to decrease external light reflection. For example, the polarizer may be a circular polarizer. When the organic light emitting display device 100 is a bottom-emission type, the polarizer may be disposed under the substrate 110. Alternatively, when the organic light emitting display device 100 is a top-emission type, the polarizer may be disposed over the encapsulation film 170. In addition, a cover window may be attached to the encapsulation film 170 or the polarizer. In this case, the substrate 110 and the cover window may have a flexible property, thus the organic light emitting display device 100 may be a flexible display device.

Figure 3:
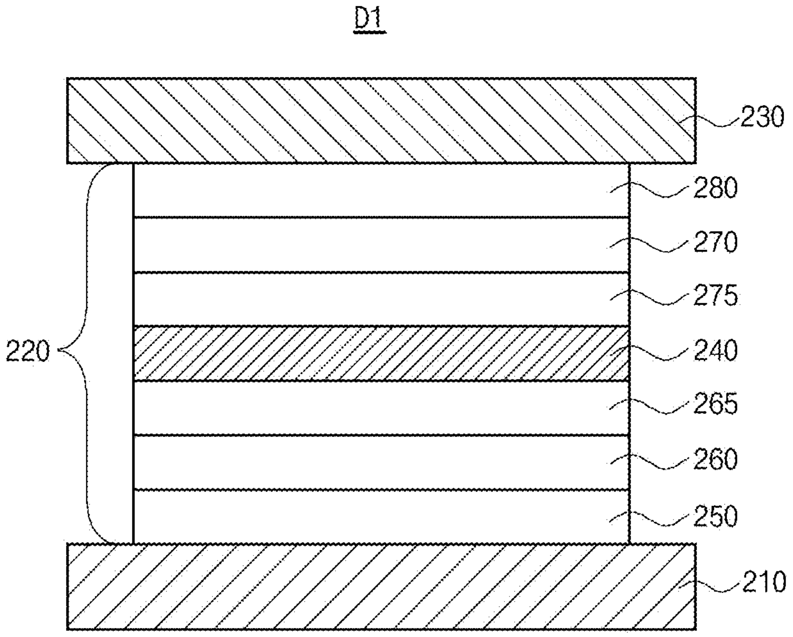
FIG. 3 is a schematic cross-sectional view illustrating an OLED in accordance with an exemplary aspect of the present disclosure.

We will describe the OLED in more detail. FIG. 3 is a schematic cross-sectional view illustrating an OLED in accordance with an exemplary aspect of the present disclosure. As illustrated in FIG. 3, the OLED D1 includes first and second electrodes 210 and 230 facing each other and an emissive layer 220 with single emitting part disposed between the first and second electrodes 210 and 230. The organic light emitting display device 100 includes a red pixel region, a green pixel region and a blue pixel region, and the OLED D1 may be disposed in the green pixel region.

In one exemplary aspect, the emissive layer 220 comprises an EML 240 disposed between the first and second electrodes 210 and 230. Also, the emissive layer 220 may comprise at least one of a HTL 260 disposed between the first electrode 210 and the EML 240 and an ETL 270 disposed between the second electrode 230 and the EML 240. Also, the emissive layer 220 may further comprise at least one of a HIL 250 disposed between the first electrode 210 and the HTL 260 and an EIL 280 disposed between the second electrode 230 and the ETL 270. Alternatively, the emissive layer 220 may further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 may be an anode that provides a hole into the EML 240. The first electrode 210 may include, but is not limited to, a conductive material having a relatively high work function value, for example, a transparent conductive oxide (TCO). In an exemplary aspect, the first electrode 210 may include, but is not limited to, ITO, IZO, ITZO, SnO, ZnO, ICO, AZO, and the like.

The second electrode 230 may be a cathode that provides an electron into the EML 240. The second electrode 230 may include, but is not limited to, a conductive material having a relatively low work function value, i.e., a highly reflective material such as Al, Mg, Ca, Ag, alloy thereof, combination thereof, and the like.

In this aspect, the EML 240 may comprise a first compound (Compound 1, H) and a second compound (Compound 2) DF. For example, the first compound may be a (first) host and the second compound DF may be a delayed fluorescent material. For example, the second compound DF in the EML 240 may comprise the organic compound having the structure of Formulae 1 to 12. As an example, the EML 240 may emit a green light. We will describe the kinds of the first compound and energy level relationships between the first and second compound H and DF below.

The HIL 250 is disposed between the first electrode 210 and the HTL 260 and improves an interface property between the inorganic first electrode 210 and the organic HTL 260. In one exemplary aspect, the HIL 250 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiophene)polystyrene sulfonate (PEDOT/PSS), N-(biphenyl-4-yl)-9,9-dimethyl-N-(4-(9-phenyl-9H-carbazol-3-yl)phenyl)-9H-fluoren-2-amine and combination thereof. The HIL 250 may be omitted in compliance with a structure of the OLED D1.

The HTL 260 is disposed adjacently to the EML 240 between the first electrode 210 and the EML 240. In one exemplary aspect, the HTL 260 may include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis (phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), 3,5-di(9H-carbazol-9-yl)-N,N-diphenylamine (DCDPA), N-(biphenyl-4-yl)-9,9-dimethyl-N-(4-(9-phenyl-9H-carbazol-3-yl)phenyl)-9H-fluoren-2-amine, N-(biphenyl-4-yl)-N-(4-(9-phenyl-9H-carbazol-3-yl)phenyl) biphenyl-4-amine and combination thereof.

The ETL 270 and the EIL 280 may be laminated sequentially between the EML 240 and the second electrode 230. The ETL 270 includes a material having high electron mobility so as to provide electrons stably with the EML 240 by fast electron transportation.

In one exemplary aspect, the ETL 270 may comprise, but is not limited to, at least one of oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 may comprise, but is not limited to, tris-(8-hydroxyquinoline aluminum) ($Alq_3$), Bis (2-methyl-8-quinolinolato-N1,O8)-(1,1'-biphenyl-4-olato) aluminum (BAlq), lithium quinolate (Liq), 2-biphenyl-4-yl-5-(4-t-butylphenyl)-1,3,4-oxadiazole (PBD), spiro-PBD, 1,3,5-Tris(N-phenylbenzimidazol-2-yl)benzene (TPBi), 4,7-diphenyl-1,10-phenanthroline (Bphen), 2,9-Bis(naphthalene-2-yl) 4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl) 1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ), diphenyl-4-triphenysilyl-phenylphosphine oxide (TSPO1) and combination thereof.

The EIL 280 is disposed between the second electrode 230 and the ETL 270, and can improve physical properties of the second electrode 230 and therefore, can enhance the lifetime of the OLED D1. In one exemplary aspect, the EIL 280 may comprise, but is not limited to, an alkali metal halide or an alkaline earth metal halide such as LiF, CsF, NaF, $BaF_2$ and the like, and/or an organic metal compound such as lithium quinolate, lithium benzoate, sodium stearate, and the like.

When holes are transferred to the second electrode 230 via the EML 240 and/or electrons are transferred to the first electrode 210 via the EML 240, the OLED D1 may have short lifetime and reduced luminous efficiency. In order to prevent these phenomena, the OLED D1 in accordance with this aspect of the present disclosure may have at least one exciton blocking layer adjacent to the EML 240.

For example, the OLED D1 may include the EBL 265 between the HTL 260 and the EML 240 so as to control and prevent electron transfers. In one exemplary aspect, the EBL 265 may comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-bis(carbazol-9-yl) benzene (mCP), 3,3'-bis(N-carbazolyl)-1,1'-biphenyl (mCBP), CuPc, N,N'-bis[4-(bis(3-methylphenyl)amino) phenyl]-N,N'-diphenyl-[1,1'-biphenyl]-4,4'-diamine (DNTPD), TDAPB, DCDPA, 2,8-bis(9-phenyl-9H-carbazol-3-yl)dibenzo[b,d]thiophene and combination thereof.

In addition, the OLED D1 may further include the HBL 275 as a second exciton blocking layer between the EML 240 and the ETL 270 so that holes cannot be transferred from the EML 240 to the ETL 270. In one exemplary aspect, the HBL 275 may comprise, but is not limited to, at least one of oxadiazole-based compounds, triazole-based compounds, phenanthroline-based compounds, benzoxazole-based compounds, benzothiazole-based compounds, benzimidazole-based compounds, and triazine-based compounds each of which can be used in the ETL 270.

For example, the HBL 275 may comprise a compound having a relatively low HOMO energy level compared to the luminescent materials in EML 240. The HBL 275 may comprise, but is not limited to, $Alq_3$, BAlq, Liq, PBD, spiro-PBD, BCP, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole, TSPO1 and combination thereof.

As described above, the EML 240 in the first aspect comprises the first compound H the second compound DF having the delayed florescent property and the structure of Formulae 1 to 12. Since there co-exist the electron donor moiety and the electron acceptor moiety in the organic compound having the structure of Formulae 1 to 12, the dipole moment in the molecule increases and the HOMO energy level is separated easily form the LUMO energy level, and therefore, the organic compound has the delayed fluorescent property. In addition, the organic compound has limited molecular conformation owing to the rigid structure of the fused aromatic or fused hetero aromatic moiety, thus energy loss in emitting light is decreased, and therefore, the organic compound can implement luminescence with excellent luminous efficiency and color purity.

The host for the delayed fluorescent can induce the triplet excitons of the dopant to participate in the luminous process without quenching as a non-radiative recombination. For this end, it is necessary to adjust energy levels among the first compound H of the host and the second compound DF of the delayed fluorescent material.

FIG. 4 is a schematic diagram illustrating luminous mechanism by energy level bandgap among luminous materials in accordance with an exemplary aspect of the present disclosure. As illustrated in FIG. 4, a singlet energy level $S_1^H$ of the first compound H of the host in the EML 240 is higher than a singlet energy level $S_1^{DF}$ of the second compound DF with the delayed fluorescent property. Optionally, a triplet energy level $T_1^H$ of the first compound H may be higher than a triplet energy level $T_1^{DF}$ of the second compound DF. As an example, the triplet energy level $T_1^H$ of the first compound H may be higher than the triplet energy level $T_1^{DF}$ of the second compound DF by at least about 0.2 eV, for example, at least about 0.3 eV, or at least about 0.5 eV.

When the triplet energy level $T_1^H$ and/or the singlet energy level $S_1^H$ of the first compound H is not high enough than the triplet energy level $T_1^{DF}$ and/or the singlet energy level $S_1^{DF}$ of the second compound DF, the triplet state exciton energy of the second compound DF may be reversely transferred to the triplet energy level $T_1^H$ of the first compound H. In this case, the triplet exciton reversely transferred to the first compound H where the triplet exciton cannot be emitted is quenched as non-emission so that the triplet exciton energy of the second compound DF having the delayed fluorescent property cannot contribute to luminescence. The second compound DF having the delayed fluorescent property may have the energy level bandgap $\Delta E_{ST}^{DF}$ between the singlet energy level $S_1^{DF}$ and the triplet energy level $T_1^{DF}$ equal to or less than about 0.3 eV, for example between about 0.05 eV and about 0.3 eV.

In addition, it is necessary to adjust properly HOMO energy levels and LUMO energy levels of the first compound H and the second compound DF. For example, an energy level bandgap ($|HOMO^H\text{-}HOMO^{DF}|$) between the HOMO energy level ($HOMO^H$) of the first compound H and the HOMO energy level ($HOMO^{DF}$) of the second compound DF, or an energy level bandgap ($|LUMO^H\text{-}LUMO^{DF}|$) between the LUMO energy level ($LUMO^H$) of the first compound H and the LUMO energy level ($LUMO^{DF}$) of the second compound DF may be equal to or less than about 0.5 eV, for example, between about 0.1 eV to about 0.5 eV.

When the EML 240 comprises the first compound H, the second compound DF having the delayed fluorescent property, the exciton energy can be transferred to the second compound DF from the first compound H without energy loss in the luminescence process. In this case, the first compound H of the host, which can be included in the EML 240 together with the second compound having the structure of Formulae 1 to 12, does not have to have high triplet energy level and/or wide energy bandgap. Accordingly, it is possible to minimize the delay of charge injections and transportations caused by using the host with wider energy bandgap.

In one exemplary aspect, the first compound H in the EML 240 may comprise, but is not limited to, 9-(3-(9H-carbazol-9-yl)phenyl)-9H-carbazole-3-carbonitrile (mCP-CN), CBP, mCBP, mCP, DPEPO, 2T-NATA, TCTA, 1,3,5-Tri[(3-pyridyl)-phen-3-yl]benzene (TmPyPB), 2,6-di(9H-carbazol-9-yl)pyridine (PYD-2Cz), 3',5'-di(carbazol-9-yl)-[1,1'-bipheyl]-3,5-dicarbonitrile (DCzTPA), 4'-(9H-carbazol-9-yl) biphenyl-3,5-dicarbonitrile (pCzB-2CN), 3'-(9H-carbazol-9-yl)biphenyl-3,5-dicarbonitrile (mCzB-2CN), 4-(3-(triphenylen-2-yl)phenyl)dibenzo[b,d] thiophene, 9-(4-(9H-carbazol-9-yl)phenyl)-9H-3,9'-bicarbazole, 9-(3-(9H-carbazol-9-yl)phenyl)-9H-3,9'-bicarbazole and combination thereof. For example, the first compound may be, but is not limited to, selected from the following compounds in Formula 13:

[Formula 13]

H1

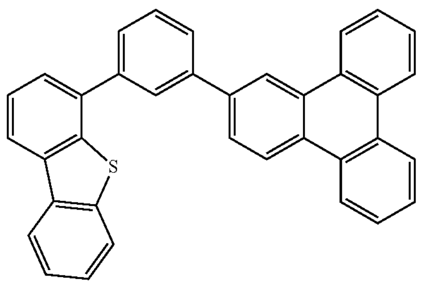

H2

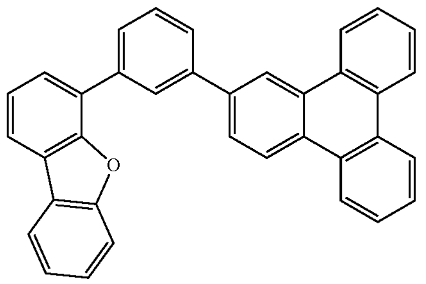

H3

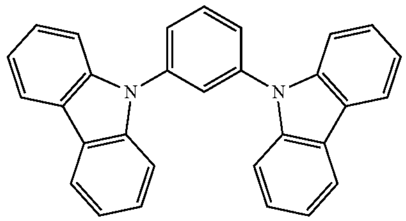

H4

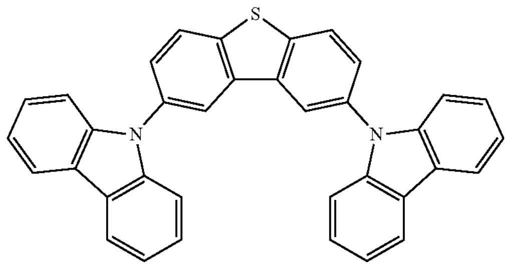

H5

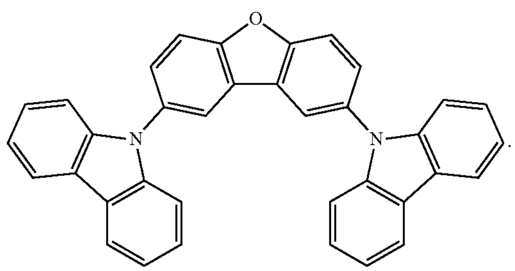

When the EML 240 includes the first compound H of the host and the second compound DF of the delayed fluorescent material, the contents of the second compound DF in the EML may be, but is not limited to, between about 10 wt % and about 70 wt %, for example, about 10 wt % and about 50 wt % such as about 20 wt % and about 50 wt %.

The organic compound having the structure of Formulae 1 to 12 has very excellent luminous properties. Accordingly, the OLED D1 including that organic compound in the emissive layer 220, for example, in the EML 240 can improve its luminous efficiency and luminous lifespan.

Figure 5:
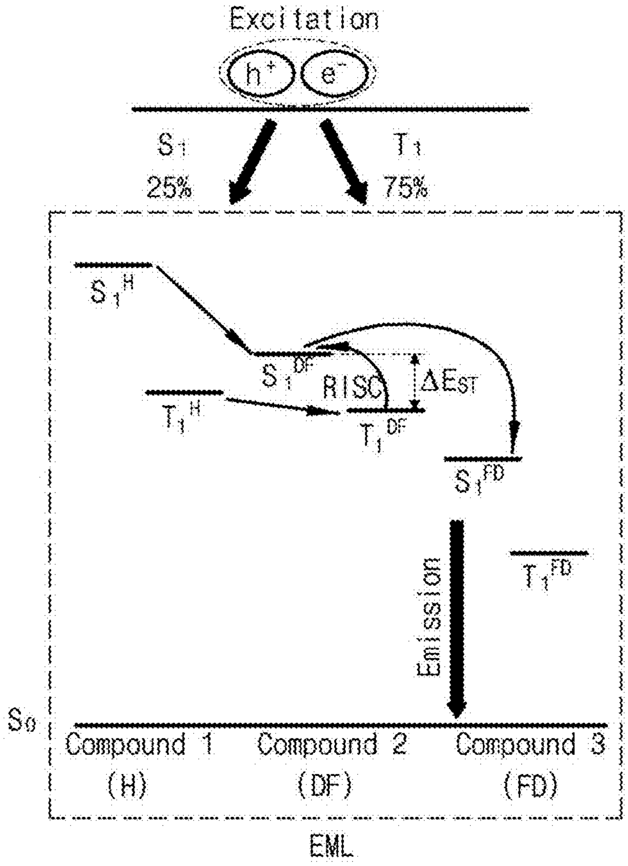
FIG. 5 is a schematic diagram illustrating luminous mechanism by energy level bandgap among luminous material in accordance with another exemplary aspect of the present disclosure.

In another exemplary aspect, the EML 240 may further comprise a third compound. FIG. 5 is a schematic diagram illustrating luminous mechanism by energy level bandgap among luminous material in accordance with another exemplary aspect of the present disclosure. The first compound H may be host, the second compound DF (first dopant) may be the delayed fluorescent material and the third compound (Compound 3, second dopant) may be fluorescent or phosphorescent material. The first and second compound H and DF may be identical to those compounds as described above. When the EML 240 further includes the fluorescent or phosphorescent material as well as the delayed fluorescent material, the OLED D1 can further improve its luminous efficiency and color purity by adjusting energy levels among those luminous materials.

When the EML includes only the second compound DF having the delayed fluorescent property, the EML may implement high internal quantum efficiency as the prior art phosphorescent materials because the second compound DF can exhibit 100% internal quantum efficiency in theory. However, because of the bond formation between the electron acceptor and the electron donor and conformational twists within the delayed fluorescent material, additional charge transfer transition (CT transition) within the delayed fluorescent material is caused thereby, and the delayed fluorescent material has various geometries. As a result, the delayed fluorescent materials show emission spectra having very broad FWHM (full-width at half maximum) in the course of luminescence, which results in poor color purity. In addition, the delayed fluorescent material utilizes the triplet exciton energy as well as the singlet exciton energy in the luminescence process with rotating each moiety within its molecular structure, which results in twisted internal charge transfer (TICT). As a result, the luminous lifespan of an OLED including only the delayed fluorescent materials may be reduced owing to weakening of molecular bonding forces among the delayed fluorescent materials.

In accordance with this exemplary aspect, the EML further includes the third compound FD of fluorescent or phosphorescent material in order to prevent the color purity and luminous lifetime from being reduced in case of using only the delayed fluorescent material as the dopant. As illustrated in FIG. 5, the triplet exciton energy of the second compound DF having the delayed fluorescent property is converted upwardly to its own singlet exciton energy by RISC mechanism, then the converted singlet exciton energy of the second compound DF can be transferred to the third compound FD in the same EML by Forster Resonance Energy Transfer (FRET) mechanism to implement a hyper-fluorescence.

When the EML 240 includes the first compound H of the host, the second compound DF of the delayed fluorescent material and the third compound FD of the fluorescent or phosphorescent material, it is necessary to adjust properly energy levels among those luminous materials. As illustrated in FIG. 5, an energy level bandgap $\Delta E_{ST}^{DF}$ between the singlet energy level $S_1^{DF}$ and the triplet energy level $T_1^{DF}$ of the second compound DF of the delayed fluorescent material may be equal to or less than about 0.3 eV in order to realize the delayed fluorescence. In addition, the singlet energy level $S_1^{H}$ of the first compound H of the host is higher than the singlet energy level $S_1^{DF}$ of the second compound DF of the delayed fluorescent material. Also, the triplet energy level $T_1^{H}$ of the first compound H may be higher than the triplet energy level $T_1^{Df}$ of the second compound DF.

In addition, the singlet energy level $S_1^{DF}$ of the second compound DF is higher than a single energy level $S_1^{FD}$ of the third compound FD of the fluorescent or phosphorescent material. Alternatively, the triplet energy level $T_1^{DF}$ of the second compound DF may be higher than a triplet energy level $T_1^{FD}$ of the third compound FD.

Moreover, the exciton energy should be effectively transferred from the second compound DF of the delayed fluorescent material to the third compound FD of the fluorescent or phosphorescent material in order to implement hyper-fluorescence. As an example, fluorescent or phosphorescent material having the absorption spectrum with large overlapping area with the photoluminescence spectrum of the second compound DF having the delayed fluorescent property may be used as the third compound FD in order to transfer exciton energy efficiently from the second compound to the third compound.

As an example, the third compound FD emits a green light. For example, the third compound FD emitting a green light may have, but is not limited to, a boron-dipyrromethene (BODIPY, 4,4,-difluoro-4-bora-3a,4a-diaza-s-indacene) core. As an example, the third compound FD may comprise, but is not limited to, 5,12-dimethylquinolino[2,3-b]acridine-7,14(5H,12H)-dione, 5,12-diethylquinolino[2,3-b]acridine-7,14(5H,12H)-dione, 5,12-dibutyl-3,10-difluoro-quinolino[2,3-b]acridine-7,14(5H,12H)-dione, 5,12-dibutyl-3,10-bis(trifluoromethyl)quinolino[2,3-b]acridine-7,14(5H,12H)-dione, 5,12-dibutyl-2,3,9,10-tetrafluoroquinolino[2,3-b]acridine-7,14(5H,12H)-dione, 1,1,7,7-tetramethyl-2,3,6,7-tetrahydro-1H,5H-benzo[ij]quinolizin-9-yl)ethenyl]-4H-pyran-4-ylidene}propanedinitrile (DCJTB). Alternatively, the third compound may include phosphorescent material of a metal complex emitting a green light.

When the EML 240 includes the first compound H, the second compound DF and the third compound FD, the contents of the first compound H may be larger than the contents of the second compound DF in the EML, and the consents of the second compound DF is larger than the contents of the third compound FD in the EML. In this case, exciton energy can be transferred efficiently from the second compound DF to the third compound FD via FRET mechanism. As an example, each of the contents of the first to third compounds H, DF and FD in the EML 240 may be, but is not limited to, about 60 wt % to about 75 wt %, about 20 wt % to about 40 wt % and about 0.1 wt % to about 5 wt %, respectively.

Figure 6:
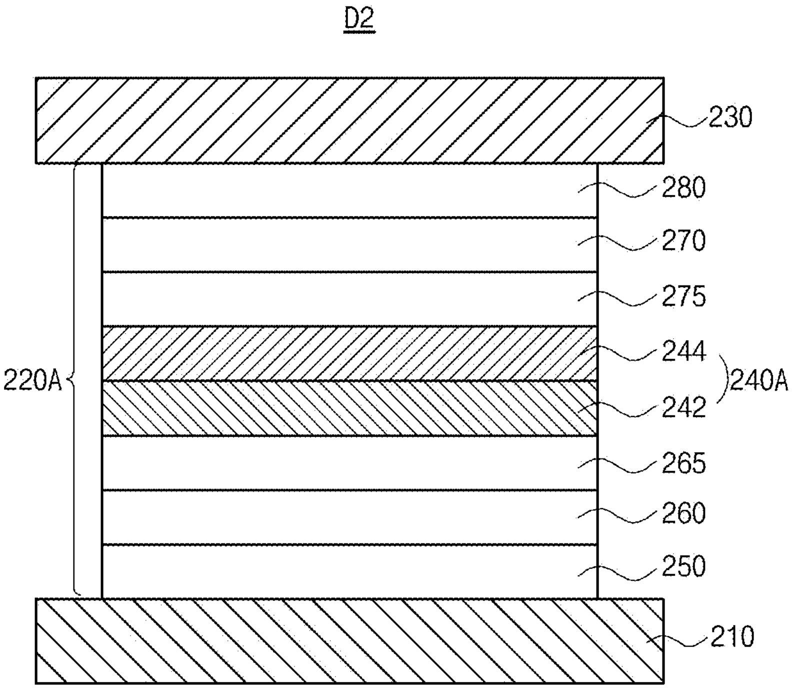
FIG. 6 is a schematic cross-sectional view illustrating an OLED in accordance with still another exemplary aspect of the present disclosure.
Figure 7:
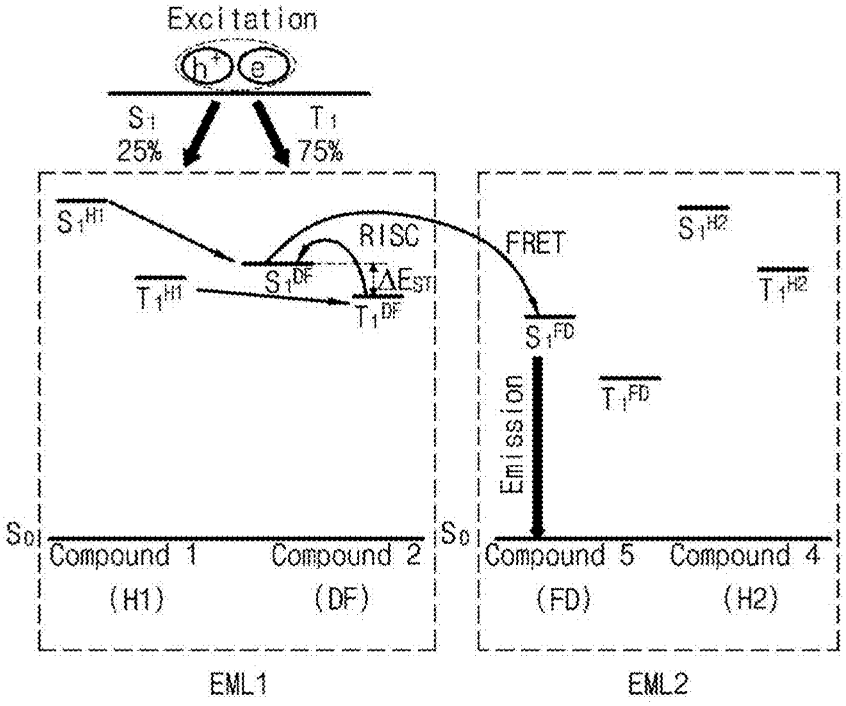
FIG. 7 is a schematic diagram illustrating luminous mechanism by energy level bandgap among luminous materials in accordance with still another exemplary aspect of the present disclosure.

Alternatively, an OLED in accordance with the present disclosure may include multiple-layered EML. FIG. 6 is a schematic cross-sectional view illustrating an OLED having a double-layered EML in accordance with another exemplary aspect of the present disclosure. FIG. 7 is a schematic diagram illustrating luminous mechanism by energy level bandgap among luminous materials in accordance with another exemplary aspect of the present disclosure.

As illustrated in FIG. 6, the OLED D2 includes first and second electrodes 210 and 230 facing each other and an emissive layer 220A with single emitting part disposed between the first and second electrodes 210 and 230. The organic light emitting display device 100 includes a red pixel region, a green pixel region and a blue pixel region, and the OLED D2 may be disposed in the green pixel region.

In one exemplary aspect, the emissive layer 220A comprises an EML 240A. The emissive layer 220A may comprise at least one of an HTL 260 disposed between the first electrode 210 and the EML 240A and an ETL 270 disposed between the second electrode 230 and the EML 240A. Also, the emissive layer 220A may further comprise at least one of an HIL 250 disposed between the first electrode 210 and the HTL 260 and an EIL 280 disposed between the second electrode 230 and the ETL 270. Alternatively, the emissive layer 220A may further comprise an EBL 265 disposed between the HTL 260 and the EML 240A and/or an HBL 275 disposed between the EML 240A and the ETL 270. The configurations of the first and second electrodes 210 and 230 as well as other layers except the EML 240A in the emissive layer 220A is substantially identical to the corresponding electrodes and layers in the OLED D1.

The EML 240A includes a first EML (EML1, lower EML, first layer) 242 and a second EML (EML2, upper EML, second layer) 244. The EML1 242 is disposed between the EBL 265 and the HBL 275 and the EML2 244 is disposed between the EML1 242 and the HBL 275. One of the EML1 242 and the EML2 244 includes the second compound (first dopant) DF of the delayed fluorescent material, and the other of the EML1 242 and the EML2 244 includes a fifth compound (Compound 5, second dopant) FD of the fluorescent or phosphorescent material. Also, each of the EML1 242 and the EML2 244 comprises the first compound (first host) H1 and a fourth compound (Compound 4, second host) H2, respectively. In the exemplary this aspect, the EML1 242 includes the first compound H1 of the first host and the second compound DF of the delayed fluorescent material. The EML2 244 includes the fourth compound H2 of the second host and the fifth compound FD of the fluorescent or phosphorescent material.

The triplet exciton energy of the second compound DF in the EML1 242 can be converted upwardly its own singlet exciton energy via RISC mechanism. While the second compound DF has a high internal quantum efficiency, its color purity is bad owing to wide FWHM. On the contrary, the fifth compound FD of the fluorescent or phosphorescent material has an advantage in terms of color purity due to its narrow FWHM, but its internal quantum efficiency is low because its triplet exciton cannot be involved in the luminescence process.

However, in this exemplary aspect, the singlet exciton energy and the triplet exciton energy of the second compound DF having the delayed fluorescent property in the EML1 242 can be transferred to the fifth compound FD of the fluorescent or phosphorescent material, in the EML2 244 disposed adjacently to the EML1 242 by FRET mechanism, which transfers energy non-radially through electrical fields by dipole-dipole interactions. Accordingly, the ultimate light emission occurs in the fifth compound FD within the EML2 244.

In other words, the triplet exciton energy of the second compound DF in the EML1 242 is converted upwardly to its own singlet exciton energy by RISC mechanism. Then, the converted singlet exciton energy of the second compound DF is transferred to the singlet exciton energy of the fifth compound FD in the EML2 244. The fifth compound FD in the EML2 244 can emit light utilizing the triplet exciton energy as well as the singlet exciton energy. As the exciton energy which is generated at the second compound DF having the delayed fluorescent property in the EML1 242 is efficiently transferred from the second compound DF to the fifth compound FD of the fluorescent or phosphorescent material in the EML2 244, hyper-fluorescence can be realized. In this case, the substantial light emission is occurred in the EML2 244 including the fifth compound FD of the fluorescent or phosphorescent material and with a narrow FWHM. Accordingly, the OLED D2 can enhance its quantum efficiency and improve its color purity due to narrow FWHM.

Each of the EML1 242 and the EML2 244 includes the first compound H1 and the fourth compound H2, respectively. The exciton energies generated at the first and fourth compounds H1 and H2 should be transferred to the second compound DF of the delayed fluorescent material to emit light. As illustrated in FIG. 7, each of singlet energy levels $S_1^{H1}$ and $S_1^{H2}$ of the first and fourth compounds H1 and H2 is higher than the singlet energy level SIDE of the second compound DF of the delayed fluorescent material. Alternatively, each of triplet energy levels $T_1^{H1}$ and $T_1^{H2}$ of the first and fourth compounds H1 and H2 may be higher than the triplet energy level $T_1^{DF}$ of the second compound DF. As an example, each of the triplet energy levels $T_1^{H1}$ and $T_1^{H2}$ of the first and fourth compounds H1 and H2 may be higher than the triplet energy level $T_1^{Df}$ of the second compound DF by at least about 0.2 eV, for example by at least about 0.3 eV, or by at least about 0.5 eV.

Also, the singlet energy level $S_1^{H2}$ of the fourth compound H2 is higher than the singlet energy level $S_1^{FD}$ of the fifth compound FD. In this case, the singlet exciton energy generated at the fourth compound H2 can be transferred to the singlet energy level $S_1^{FD}$ of the fifth compound FD. Optionally, the triplet energy level $T_1^{H2}$ of the fourth compound H2 may be higher than the triplet energy level $T_1^{FD}$ of the fifth compound FD.

In addition, it is necessary for the EML 240A to implement high luminous efficiency and color purity as well as to transfer exciton energy efficiently from the second compound DF, which is converted to ICT complex state by RISC mechanism in the EML1 242, to the fifth compound FD of the fluorescent or phosphorescent material in the EML2 244. In order to realize such an OLED D2, the singlet energy level $S_1^{DF}$ of the second compound DF is higher than the singlet energy level $S_1^{FD}$ of the fifth compound FD of the florescent or phosphorescent material. Optionally, the triplet energy level $T_1^{DF}$ of the second compound DF may be higher than the triplet energy level $T_1^{FD}$ of the fifth compound FD.

Moreover, the energy level bandgap ($|HOMO^{H}$-$HOMO^{DF}|$) between the HOMO energy level ($HOMO^{H}$) of the first and/or fourth compounds H1 and H2 and the HOMO energy level ($HOMO^{DF}$) of the second compound DF, or the energy level bandgap ($|LUMO^{H}$-$LUMO^{DF}|$) between a LUMO energy level ($LUMO^{H}$) of the first and/or fourth compounds H1 and H2 and the LUMO energy level ($LUMO^{DF}$) of the second compound DF may be equal to or less than about 0.5 eV. When the luminous materials do not satisfy the required energy levels as described above, exciton energies are quenched at the second and fifth compounds DF and FD or exciton energies cannot transferred efficiently from the first and fourth compounds H1 and H2 to the second and fifth compounds DF and FD, so that OLED D2 may have reduced quantum efficiency.

The first compound H1 and the fourth compound H2 may be the same or different from each other. For example, each of the first compound H1 and the fourth compound H2 may be independently identical to the first compound H as described above. The second compound DF may be the organic compound having the structure of Formulae 1 to 12. The fifth compound FD may have narrow FWHM and have an absorption spectrum with large overlapping area with a luminescent spectrum of the second compound DF. The fifth compound FD may be the fluorescent or phosphorescent material emitting a green light. For example, the fifth compound FD may be the fluorescent or phosphorescent material of the third compound as described above.

In one exemplary aspect, the contents of the first and fourth compounds H1 and H2 in the EML1 242 and the EML2 244 may be larger than or equal to the contents of the second and fifth compounds DF and FD in the same layer. Also, the contents of the second compound DF in the EML1 242 may be larger than the contents of the fifth compound FD in the EML2 244. In this case, exciton energy can be transferred efficiently from the second compound DF to the fifth compound FD via FRET mechanism. As an example, the contents of the second compound DF in the EML1 242 may be, but is not limited to, about 1 wt % to about 70 wt %, about 10 wt % to about 50 wt %, or about 20 wt % to about 50 wt %. In addition, the contents of the fifth compound FD in the EML2 244 may be about 1 wt % to about 10 wt %, or about 1 wt % to about 5 wt %.

When the EML2 244 is disposed adjacently to the HBL 275 in one exemplary aspect, the fourth compound H2 in the EML2 244 may be the same material as the HBL 275. In this case, the EML2 244 may have a hole blocking function as well as an emission function. In other words, the EML2 244 can act as a buffer layer for blocking holes. In one aspect, the HBL 275 may be omitted where the EML2 244 may be a hole blocking layer as well as an emitting material layer.

When the EML2 244 is disposed adjacently to the EBL 265 in another exemplary aspect, the fourth compound H2 may be the same material as the EBL 265. In this case, the EML2 244 may have an electron blocking function as well as an emission function. In other words, the EML2 244 can act as a buffer layer for blocking electrons. In one aspect, the EBL 265 may be omitted where the EML2 244 may be an electron blocking layer as well as an emitting material layer.

Figure 8:
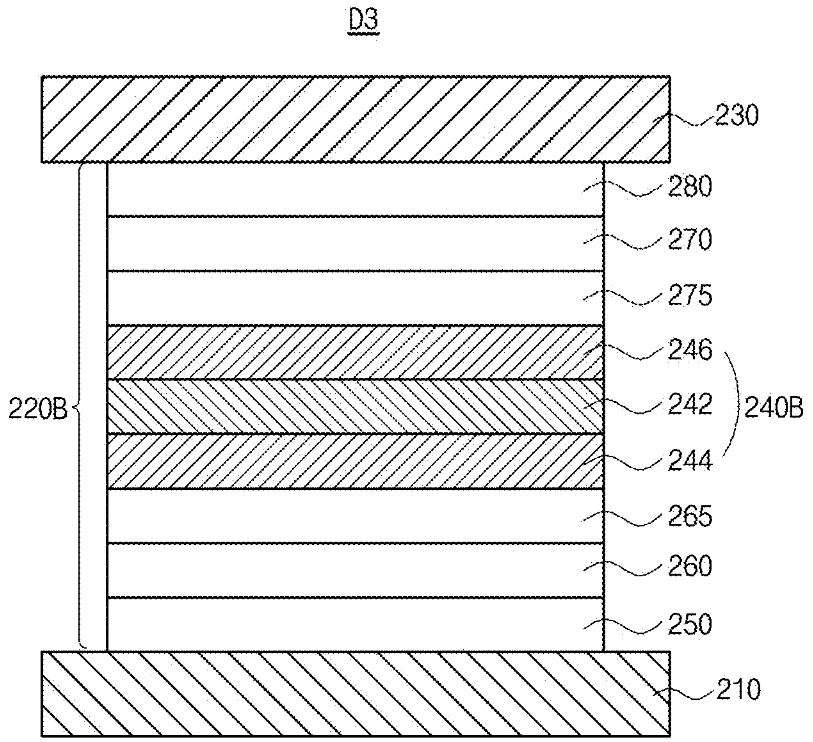
FIG. 8 is a schematic cross-sectional view illustrating an OLED in accordance with still another exemplary aspect of the present disclosure.
Figure 9:
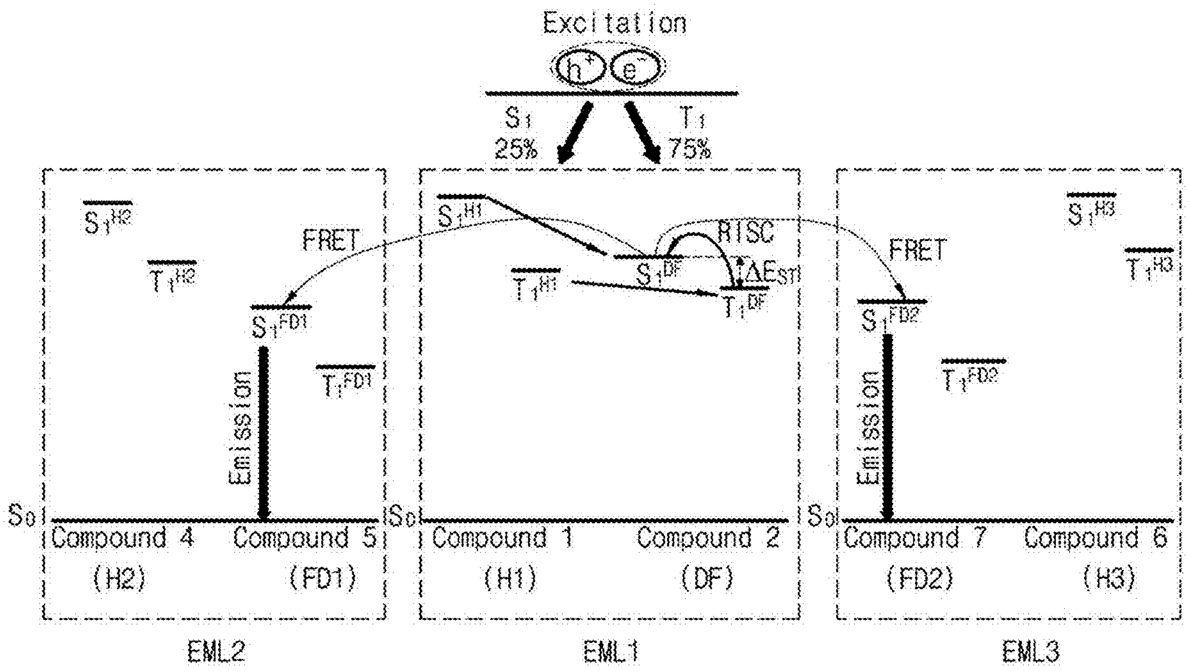
FIG. 9 is a schematic diagram illustrating luminous mechanism by energy level bandgap among luminous materials in accordance with still another exemplary aspect of the present disclosure.

An OLED having a triple-layered EML will be explained. FIG. 8 is a schematic cross-sectional view illustrating an OLED having a triple-layered EML in accordance with another exemplary aspect of the present disclosure. FIG. 9 is a schematic diagram illustrating luminous mechanism by energy level bandgap among luminous materials in accordance with another exemplary aspect of the present disclosure.

As illustrated in FIG. 8, the OLED D3 comprises first and second electrodes 210 and 230 facing each other and an emissive layer 220B with single emitting part disposed between the first and second electrodes 210 and 230. The organic light emitting display device 100 (FIG. 2) includes a red pixel region, a green pixel region and a blue pixel region, and the OLED D3 may be disposed in the green pixel region.

In one exemplary aspect, the emissive layer 220B comprises a three-layered EML 240B. The emissive layer 220B may comprise at least one of an HTL 260 disposed between the first electrode 210 and the EML 240B and an ETL 270 disposed between the second electrode 230 and the EML 240B. Also, the emissive layer 220B may further comprise at least one of an HIL 250 disposed between the first electrode 210 and the HTL 260 and an EIL 280 disposed between the second electrode 230 and the ETL 270. Alternatively, the emissive layer 220B may further comprise an EBL 265 disposed between the HTL 260 and the EML 240B and/or an HBL 275 disposed between the EML 240B and the ETL 270. The configurations of the first and second electrodes 210 and 230 as well as other layers except the EML 240B in the emissive layer 220B is substantially identical to the corresponding electrodes and layers in the OLEDs D1 and D2.

The EML 240B comprises a first EML (EML1, middle EML, first layer) 242, a second EML (EML2, lower EML, second layer) 244 and a third EML (EML3, upper EML, third layer) 246. The EML1 242 is disposed between the EBL 265 and the HBL 275, the EML2 244 is disposed between the EBL 265 and the EML1 242 and the EML3 246 is disposed between the EML1 242 and the HBL 275.

The EML1 242 comprises the second compound (first dopant) DF of the delayed fluorescent material. Each of the EML2 244 and the EML3 246 comprises the fifth compound (second dopant) FD1 and a seventh compound (Compound 7, third dopant) FD2 each of which may be the fluorescent or phosphorescent material, respectively. In addition, each of the EML1 242, EML2 244 and EML3 246 further includes the first compound (Host 1) H1, the fourth compound (Host 2) H2 and the sixth compound (Compound 6, Host 3) H3 each of which may be the first to third hosts, respectively.

In accordance with this aspect, the singlet energy as well as the triplet energy of the second compound DF of the delayed fluorescent material in the EML1 242 can be transferred to the fifth and seventh compounds FD1 and FD2 of the fluorescent or phosphorescent materials each of which is included in the EML2 244 and EML3 246 disposed adjacently to the EML1 242 by FRET mechanism. Accordingly, the ultimate emission occurs in the fifth and seventh compounds FD1 and FD2 in the EML2 244 and the EML3 246.

The triplet exciton energy of the second compound DF in the EML1 242 is converted upwardly to its own singlet exciton energy by RISC mechanism, then the singlet exciton energy of the second compound DF is transferred to the singlet exciton energy of the fifth and seventh compounds FD1 and FD2 in the EML2 244 and the EML3 246 because the second compound DF has the singlet energy level $S_1^{DF}$ higher than each of the singlet energy levels $S_1^{FD1}$ and $S_1^{FD2}$ of the fifth and seventh compounds FD1 and FD2 (FIG. 9). The singlet exciton energy of the second compound DF in the EML1 242 is transferred to the fifth and seventh compounds FD1 and FD2 in the EML2 244 and the EML3 246 which are disposed adjacently to the EML1 242 by FRET mechanism.

The fifth and seventh compounds FD1 and FD2 in the EML2 244 and EML3 246 can emit light utilizing the singlet exciton energy and the triplet exciton energy derived from the second compound DF. Each of the fifth and seventh compounds FD1 and FD2 may have narrower FWHM compared to the second compound DF. As the exciton energy, which is generated at the second compound DF having the delayed fluorescent property in the EML1 242, is transferred to the fifth and seventh compounds FD1 and FD2 in the EML2 244 and the EML3 246, hyper-fluorescence can be realized. Particularly, each of the fifth and seventh compounds FD1 and FD2 may have a luminescent spectrum having a large overlapping area with an absorption spectrum of the second compound DF, so that exciton energy of the second compound DF may be transferred efficiently to each of the fifth and seventh compounds FD1 and FD2. In this case, substantial light emission is occurred in the EML2 244 and in the EML3 246.

To implement efficient luminescence in the EML 240B, it is necessary to adjust properly energy levels among luminous materials in the EML1 242, the EML2 244 and the EML3 246. As illustrated in FIG. 9, each of singlet energy levels $S_1^{H1}$, $S_1^{H2}$ and $S_1^{H3}$ of the first, fourth and sixth compounds H1, H2 and H3, each of which may be the first to third hosts, respectively, is higher than the singlet energy level $S_1^{DF}$, respectively. Alternatively, each of triplet energy levels $T_1^{H1}$, $T_1^{H2}$ and $T_1^{H3}$ of the first, fourth and sixth compounds H1, H2 and H3 may be higher than the triplet energy level $T_1^{DF}$ of the second compound DF.

Also, it is necessary for the EML 240B to implement high luminous efficiency and color purity as well as to transfer exciton energy efficiently from the second compound DF, which is converted to ICT complex state by RISC mechanism in the EML1 242, to the fifth and seventh compounds FD1 and FD2 each of which is the fluorescent or phosphorescent material in the EML2 244 and the EML3 246. In order to realize such an OLED D3, the singlet energy level $S_1^{DF}$ of the second compound DF is higher than each of singlet energy levels $S_1^{FD1}$ and $S_1^{FD2}$ of the fifth and seventh compounds FD1 and FD2 of the fluorescent or phosphorescent material. Alternatively, the triplet energy level $T_1^{DF}$ of the second compound DF may be higher than each of triplet energy levels $T_1^{FD1}$ and $T_1^{FD2}$ of the fifth and seventh compounds FD1 and FD2.

In addition, the exciton energy, which is transferred from the second compound DF to each of the fifth and seventh compounds FD1 and FD2, should not be transferred to the fourth and sixth compounds H2 and H3 in order to realize efficient light emission. To this end, each of the singlet energy levels $S_1^{H2}$ and $S_1^{H3}$ of the fourth and sixth compounds H2 and H3 is higher than each of the excited singlet energy levels $S_1^{FD1}$ and $S_1^{FD2}$ of the fifth and seventh compounds FD1 and FD2, respectively. Alternatively, each of the triplet energy levels $T_1^{H2}$ and $T_1^{H3}$ of the fourth and sixth compounds H2 and H3 may be higher than each of the triplet energy levels $T_1^{FD1}$ and $T_1^{FD2}$ of the fifth and seventh compounds FD1 and FD2, respectively.

As described above, each of the EML1 242, the EML2 244 and the EML3 246 may include the first, fourth and sixth compounds H1, H2 and H3, respectively. For example, each of the first, fourth and sixth compounds H1, H2 and H3 may be the same or different from each other. For Example, each of the first, fourth and sixth compounds H1, H2 and H3 may be independently identical to the first compound H as described above. The second compound DF of the delayed fluorescent material may be the organic compound having the structure of Formulae 1 to 12. Also, each of the fifth and seventh compounds FD1 and FD2 may be identical to the third compound FD of the fluorescent or phosphorescent material.

In one exemplary aspect, the contents of the second compound DF in the EML1 242 may be larger than each of the contents of the fifth and seventh compounds FD1 and FD2 in the EML2 244 and in the EML3 246, respectively. In this case, exciton energy can be transferred efficiently from the second compound DF to the fifth and seventh compounds FD1 and FD2 via FRET mechanism. As an example, the contents of the second compound DF in the EML1 242 may be, but is not limited to, about 1 wt % to about 70 wt %, or about 10 wt % to about 50 wt %, or about 20 wt % to about 50 wt %. In addition, each of the contents of the fifth and seventh compounds FD1 and FD2 in the EML2 244 and in the EML3 246 may be about 1 wt % to about 10 wt %, or about 1 wt % to about 5 wt %.

When the EML2 244 is disposed adjacently to the EBL 265 in one exemplary aspect, the fourth compound H2 in the EML2 244 may be the same material as the EBL 265. In this case, the EML2 244 may have an electron blocking function as well as an emission function. In other words, the EML2 244 can act as a buffer layer for blocking electrons. In one aspect, the EBL 265 may be omitted where the EML2 244 may be an electron blocking layer as well as an emitting material layer.

When the EML3 246 is disposed adjacently to the HBL 275 in another exemplary aspect, the sixth compound H3 in the EML3 246 may be the same material as the HBL 275. In this case, the EML3 246 may have a hole blocking function as well as an emission function. In other words, the EML3 246 can act as a buffer layer for blocking holes. In one aspect, the HBL 275 may be omitted where the EML3 246 may be a hole blocking layer as well as an emitting material layer.

In still another exemplary aspect, the fourth compound H2 in the EML2 244 may be the same material as the EBL 265 and the sixth compound H3 in the EML3 246 may be the same material as the HBL 275. In this aspect, the EML2 244 may have an electron blocking function as well as an emission function, and the EML3 246 may have a hole blocking function as well as an emission function. In other words, each of the EML2 244 and the EML3 246 can act as a buffer layer for blocking electrons or hole, respectively. In one aspect, the EBL 265 and the HBL 275 may be omitted where the EML2 244 may be an electron blocking layer as well as an emitting material layer and the EML3 246 may be a hole blocking layer as well as an emitting material layer.

Figure 10:
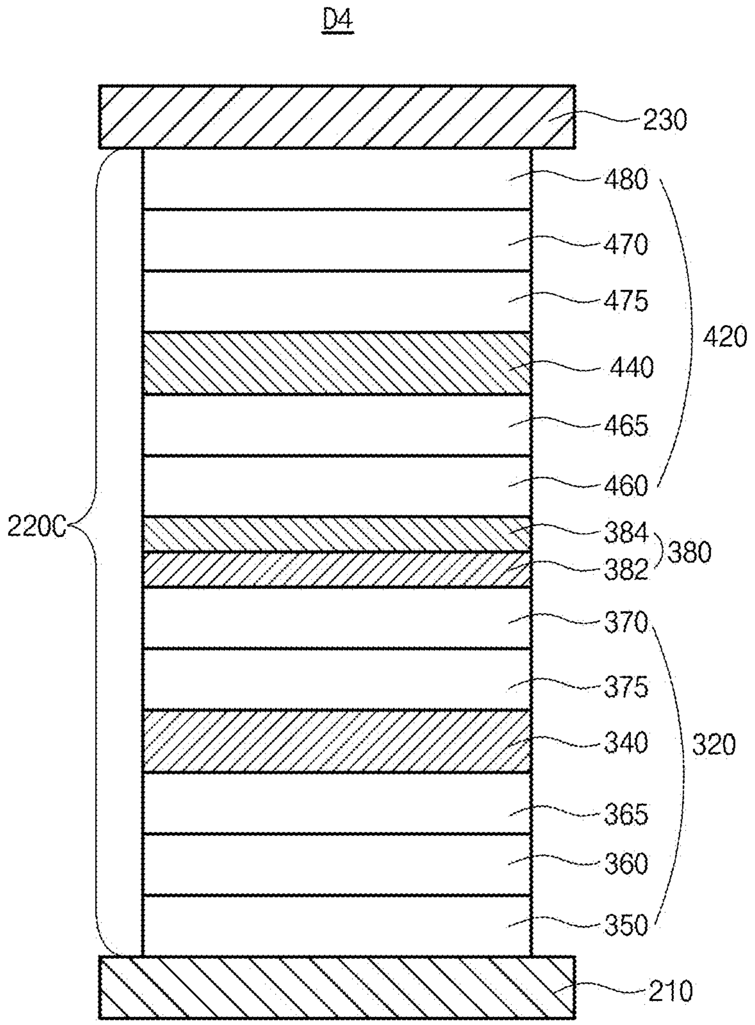
FIG. 10 is a schematic cross-sectional view illustrating an OLED in accordance with still another exemplary aspect of the present disclosure.

In an alternative aspect, an OLED may include multiple emitting parts. FIG. 10 is a schematic cross-sectional view illustrating an OLED in accordance with still another exemplary aspect of the present disclosure.

As illustrated in FIG. 10, the OLED D4 comprises first and second electrodes 210 and 230 facing each other and an emissive layer 220C with two emitting parts disposed between the first and second electrodes 210 and 230. The organic light emitting display device 100 (FIG. 2) includes a red pixel region, a green pixel region and a blue pixel region, and the OLED D4 may be disposed in the green pixel region. The first electrode 210 may be an anode and the second electrode 230 may be a cathode.

The emissive layer 220C includes a first emitting part 320 that includes a first EML (EML1) 340, and a second emitting part 420 that includes a second EML (EML2) 440. Also, the emissive layer 220C may further comprise a charge generation layer (CGL) 380 disposed between the first emitting part 320 and the second emitting part 420.

The CGL 380 is disposed between the first and second emitting parts 320 and 420 so that the first emitting part 320, the CGL 380 and the second emitting part 420 are sequentially disposed on the first electrode 210. In other words, the first emitting part 320 is disposed between the first electrode 210 and the CGL 380 and the second emitting part 420 is disposed between the second electrode 230 and the CGL 380.

The first emitting part 320 comprises the EML1 340. The first emitting part 320 may further comprise at least one of a first HTL (HTL1) 360 disposed between the first electrode 210 and the EML1 340, an HIL 350 disposed between the first electrode 210 and the HTL1 360 and a first ETL (ETL1) 370 disposed between the EML1 340 and the CGL 380. Alternatively, the first emitting part 320 may further comprise a first EBL (EBL1) 365 disposed between the HTL1 360 and the EML1 340 and/or a first HBL (HBL1) 375 disposed between the EML1 340 and the ETL 1 370.

The second emitting part 420 comprises the EML2 440. The second emitting part 420 may further comprise at least one of a second HTL (HTL2) 460 disposed between the CGL 380 and the EML2 440, a second ETL (ETL2) 470 disposed between the EML2 440 and the second electrode 230 and an EIL 480 disposed between the ETL2 470 and the second electrode 230. Alternatively, the second emitting part 420 may further comprise a second EBL (EBL2) 465 disposed between the HTL2 460 and the EML2 440 and/or a second HBL (HBL2) 475 disposed between the EML2 440 and the ETL2 470.

The CGL 380 is disposed between the first emitting part 320 and the second emitting part 420. The first emitting part 320 and the second emitting part 420 are connected via the CGL 380. The CGL 380 may be a PN-junction CGL that junctions an N-type CGL (N-CGL) 382 with a P-type CGL (P-CGL) 384.

The N-CGL 382 is disposed between the ETL1 370 and the HTL2 460 and the P-CGL 384 is disposed between the N-CGL 382 and the HTL2 460. The N-CGL 382 transports electrons to the EML1 340 of the first emitting part 320 and the P-CGL 384 transport holes to the EML2 440 of the second emitting part 420.

In this aspect, each of the EML1 340 and the EML2 440 may be a green emitting material layer. For example, at least one of the EML1 340 and the EML2 440 comprise the first compound H of the host, the second compound DF of the delayed fluorescent material, and optionally the third compound FD of the fluorescent or phosphorescent material.

When the EML1 340 includes the first compound H, the second compound DF and the third compound FD, the contents of the first compound H may be larger than the contents of the second compound DF, and the consents of the second compound DF is larger than the contents of the third compound FD. In this case, exciton energy can be transferred efficiently from the second compound DF to the third compound FD. As an example, each of the contents of the first to third compounds H, DF and FD in the EML1 340 may be, but is not limited to, about 60 wt % to about 75 wt %, about 20 wt % to about 40 wt % and about 0.1 wt % to about 5 wt %, respectively.

In one exemplary aspect, the EML2 440 may comprise the first compound H of the host, the second compound DF of the delayed fluorescent material, and optionally the third compound FD of the fluorescent or phosphorescent material. Alternatively, the EML2 440 may include another compound that is different from at least one of the second compound DF and the third compound FD in the EML1 340, and thus the EML2 440 may emit light different from the light emitted from the EML1 340 or may have different luminous efficiency different from the luminous efficiency of the EML1 340.

In FIG. 10, each of the EML1 340 and the EML2 440 has a single-layered structure. Alternatively, each of the EML1 340 and the EML2 440, each of which may include the first to third compounds H, DF and FD, may have a double-layered structure (FIG. 6) or a triple-layered structure (FIG. 8), respectively.

In the OLED D4, the singlet exciton energy of the second compound DF of the delayed fluorescent material is transferred to the third compound FD of the fluorescent or phosphorescent material, and the final emission is occurred at the third compound FD. Accordingly, the OLED D4 can have excellent luminous efficiency and color purity. In addition, the OLED D4 has a double stack structure of the green emitting material layers, the OLED D4 can improve its color sense or optimize its luminous efficiency.

Figure 11:
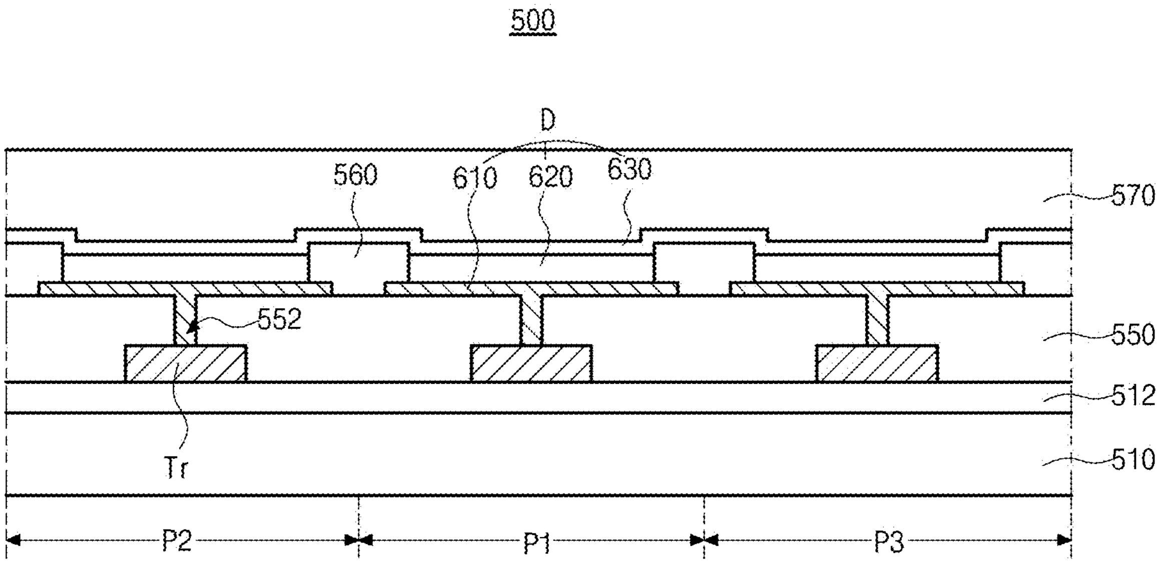
FIG. 11 is a schematic cross-sectional view illustrating an organic light emitting display device in accordance with another exemplary aspect of the present disclosure.

FIG. 11 is a schematic cross-sectional view illustrating an organic light emitting display device in accordance with another exemplary aspect of the present disclosure. As illustrated in FIG. 11, an organic light emitting display device 500 includes a substrate 510 that defines first to third pixel regions P1, P2 and P3, a thin film transistor Tr disposed over the substrate 510 and an OLED D disposed over the thin film transistor Tr and connected to the thin film transistor Tr. As an example, the first pixel region P1 may be a green pixel region, the second pixel region P2 may be a red pixel region and the third pixel region P3 may be a blue pixel region.

The substrate 510 may be a glass substrate or a flexible substrate. For example, the flexible substrate may be any one of a P1 substrate, a PES substrate, a PEN substrate, a PET substrate and a PC substrate.

A buffer layer 512 is disposed over the substrate 510 and the thin film transistor Tr is disposed over the buffer layer 512. The buffer layer 512 may be omitted. As illustrated in FIG. 2, the thin film transistor Tr includes a semiconductor layer, a gate electrode, a source electrode and a drain electrode and acts as a driving element.

A passivation layer 550 is disposed over the thin film transistor Tr. The passivation layer 550 has a flat top surface and has a drain contact hole 552 that exposes a drain electrode of the thin film transistor Tr.

The OLED D is disposed over the passivation layer 550, and includes a first electrode 610 that is connected to the drain electrode of the thin film transistor Tr, and an emissive layer 620 and a second electrode 630 each of which is disposed sequentially on the first electrode 610. The OLED D is disposed in each of the first to third pixel regions P1, P2 and P3 and emits different light in each pixel region. For example, the OLED D in the first pixel region P1 may emit a green light, the OLED D in the second pixel region P2 may emit a red light and the OLED D in the third pixel region P3 may emit a blue light.

The first electrode 610 is separately formed for each of the first to third pixel regions P1, P2 and P3, and the second electrode 630 corresponds to the first to third pixel regions P1, P2 and P3 and is formed integrally.

The first electrode 610 may be one of an anode and a cathode, and the second electrode 630 may be the other of the anode and the cathode. In addition, one of the first electrode 610 and the second electrode 630 is a transmissive (or semi-transmissive) electrode and the other of the first electrode 610 and the second electrode 630 is a reflective electrode.

For example, the first electrode 610 may be an anode and may include conductive material having a relatively high work function value, e.g., a transparent conductive oxide layer of transparent conductive oxide (TCO). The second electrode 630 may be a cathode and may include conductive material having relatively low work function value, e.g., a metal material layer of low-resistant metal. For example, the first electrode 610 may include any one of ITO, IZO, ITZO, SnO, ZnO, ICO and AZO, and the second electrode 630 may include Al, Mg, Ca, Ag, alloy thereof or combination thereof.

When the organic light emitting display device 500 is a bottom-emission type, the first electrode 610 may have a single-layered structure of a transparent conductive oxide layer.

Alternatively, when the organic light emitting display device 500 is a top-emission type, a reflective electrode or a reflective layer may be disposed under the first electrode 610. For example, the reflective electrode or the reflective layer may include, but is not limited to, Ag or APC alloy. In the OLED D of the top-emission type, the first electrode 610 may have a triple-layered structure of ITO/Ag/ITO or ITO/APC/ITO. Also, the second electrode 630 is thin so as to have light-transmissive (or semi-transmissive) property.

A bank layer 560 is disposed over the passivation layer 550 in order to cover edges of the first electrode 610. The bank layer 560 exposes the center of the first electrode 610 corresponding to each of the first to third pixel regions P1, P2 and P3, respectively.

An emissive layer 620 is disposed on the first electrode 610. In one exemplary aspect, the emissive layer 620 may have a single-layered structure of an EML. Alternatively, the emissive layer 620 may include at least one of an HIL, an HTL, and an EBL disposed sequentially between the first electrode 610 and the EML and/or an HBL, an ETL and an EIL disposed sequentially between the EML and the second electrode 630.

In one exemplary aspect, the EML of the emissive layer 620 in the first pixel region P1 of the green pixel region may comprise the first compound H of the host, the second compound DF of the delayed fluorescent material, and optionally the third compound FD of the fluorescent or phosphorescent material.

An encapsulation film 570 is disposed over the second electrode 630 in order to prevent outer moisture from penetrating into the OLED D. The encapsulation film 570 may have, but is not limited to, a triple-layered structure of a first inorganic insulating film, an organic insulating film and a second inorganic insulating film.

Moreover, the organic light emitting display device 500 may have a polarizer in order to decrease external light reflection. For example, the polarizer may be a circular polarizer. When the organic light emitting display device 500 is a bottom-emission type, the polarizer may be disposed under the substrate 510. Alternatively, when the organic light emitting display device 500 is a top emission type, the polarizer may be disposed over the encapsulation film 570.

Figure 12:
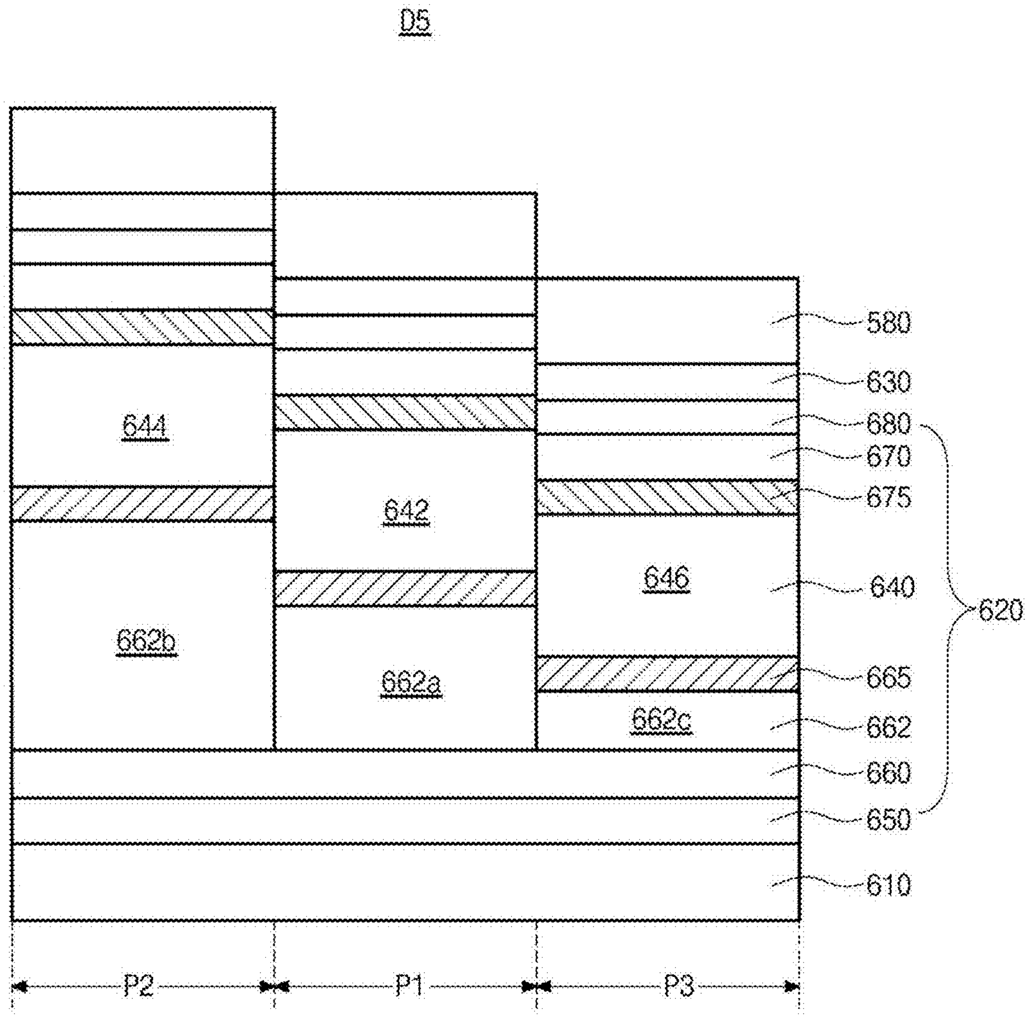
FIG. 12 is a schematic cross-sectional view illustrating an OLED in accordance with still another exemplary aspect of the present disclosure.

FIG. 12 is a schematic cross-sectional view illustrating an OLED in accordance with still another exemplary aspect of the present disclosure. As illustrated in FIG. 12, the OLED D5 comprises a first electrode 610, a second electrode 630 facing the first electrode 610 and an emissive layer 620 disposed between the first and second electrodes 610 and 630.

The first electrode 610 may be an anode and the second electrode 630 may be a cathode. As an example, the first electrode 610 may be a reflective electrode and the second electrode 630 may be a transmissive (or semi-transmissive) electrode.

The emissive layer 620 comprises an EML 640. The emissive layer 620 may comprise at least one of an HTL 660 disposed between the first electrode 610 and the EML 640 and an ETL 670 disposed between the second electrode 630 and the EML 640. Also, the emissive layer 620 may further comprise at least one of an HIL 650 disposed between the first electrode 610 and the HTL 660 and an EIL 680 disposed between the second electrode 630 and the ETL 670. Alternatively, the emissive layer 620 may further comprise an EBL 665 disposed between the HTL 660 and the EML 640 and/or an HBL 675 disposed between the EML 640 and the ETL 670.

In addition, the emissive layer 620 may further comprise an auxiliary hole transport layer (auxiliary HTL) 662 disposed between the HTL 660 and the EBL 665. The auxiliary HTL 662 may comprise a first auxiliary HTL 662*a* located in the first pixel region P1, a second auxiliary HTL 662*b* located in the second pixel region P2 and a third auxiliary HTL 662*c* located in the third pixel region P3.

The first auxiliary HTL 662*a* has a first thickness, the second auxiliary HTL 662*b* has a second thickness and the third auxiliary HTL 662*c* has a third thickness. The first thickness is less than the second thickness and more than the third thickness. Accordingly, the OLED D5 has a micro-cavity structure.

Owing to the first to third auxiliary HTLs 662*a*, 662*b* and 662*c* having different thickness to each other, the distance between the first electrode 610 and the second electrode 630 in the first pixel region P1 emitting light in the first wavelength range (green light) is smaller than the distance between the first electrode 610 and the second electrode 630 in the second pixel region P2 emitting light in the second wavelength (red light), but is larger than the distance between the first electrode 610 and the second electrode 630 in the third pixel region P3 emitting light in the third wavelength (blue light). Accordingly, the OLED D5 has improved luminous efficiency.

In FIG. 12, the third auxiliary HTL 662*c* is located in the third pixel region P3. Alternatively, the OLED D5 may implement the micro-cavity structure without the third auxiliary HTL 662*c*. In addition, a capping layer 580 may be disposed over the second electrode 630 in order to improve out-coupling of the light emitted from the OLED D5.

The EML 640 comprises a first EML (EML1) 642 located in the first pixel region P1, a second EML (EML2) 644 located in the second pixel region P2 and a third EML (EML3) 646 located in the third pixel region P3. Each of the EML1 642, the EML2 644 and the EML3 646 may be a green EML, a red EML and a blue EML, respectively In one exemplary aspect, the EML1 642 located in the first pixel region P1 may comprise the first compound H of the host, the second compound DF of the delayed fluorescent material, and optionally the third compound FD of the fluorescent or phosphorescent material. The EML1 642 may have a single-layered structure, a double-layered structure (FIG. 6) or a triple-layered structure (FIG. 8).

In an exemplary aspect, the contents of the first compound H may be larger than the contents of the second compound DF, and the consents of the second compound DF is larger than the contents of the third compound FD in the EML1 642. In this case, exciton energy can be transferred efficiently from the second compound DF to the third compound FD. As an example, each of the contents of the first to third compounds H, DF and FD in the EML1 642 may be, but is not limited to, about 60 wt % to about 75 wt %, about 20 wt % to about 40 wt % and about 0.1 wt % to about 5 wt %, respectively.

The EML2 644 in the second pixel region P2 may comprises a host and a red dopant and the EML3 646 in the third pixel region P3 may comprise a host and a blue dopant. For example, the host in each of the EML2 644 and the EML3 646 may comprise the first compound H, and each of the red and blue dopants may comprise at least one of a red or blue phosphorescent material, a red or blue fluorescent material and a red or blue delayed fluorescent material, respectively.

For example, the host in the EML2 644 may comprise, but is not limited to, 9,9'-Diphenyl-9H,9'H-3,3'-bicarbazole (BCzPh), CBP, 1,3,5-Tris(carbazole-9-yl)benzene (TCP), TCTA, 4,4'-Bis(carbazole-9-yl)-2,2'-dimethylbipheyl (CDBP), 2,7-Bis(carbazole-9-yl)-9,9-dimethylfluorene (DMFL-CBP), 2,2',7,7'-Tetrakis(carbazole-9-yl)-9,9-spiorofluorene (spiro-CBP), DPEPO, 4'-(9H-carbazol-9-yl)biphenyl-3,5-dicarbonitrile (PCzB-2CN), 3'-(9H-carbazol-9-yl)biphenyl-3,5-dicarbonitrile (mCzB-2CN), 3,6-Bis(carbazole-9-yl)-9-(2-ethyl-hexyl)-9H-carbazole (TCz1), $Bepp_2$, Bis(10-hydroxylbenzo[h]quinolinato)beryllium ($Bebq_2$), 1,3,5-Tris(1-pyrenyl)benzene (TPB3) and combination thereof.

The red dopant in the EML2 644 may comprise, but is not limited to, a red phosphorescent dopant and/or a red fluorescent dopant such as [Bis(2-(4,6-dimethyl)phenylquinoline)](2,2,6,6-tetramethylheptane-3,5-dionate)iridium(III), Bis[2-(4-n-hexylphenyl)quinoline](acetylacetonate)iridium (III) (Hex-Ir(phq)$_2$(acac)), Tris[2-(4-n-hexylphenyl)quinoline]iridium(III) (Hex-Ir(phq)$_3$), Tris[2-phenyl-4-methylquinoline]iridium(III) (Ir(Mphq)$_3$), Bis(2-phenylquinoline)(2,2,6,6-tetramethylheptene-3,5-dionate)iridium(III) (Ir(dpm)PQ$_2$), Bis(phenylisoquinoline)(2,2,6,6-tetramethylheptene-3,5-dionate)iridium(III) (Ir(dpm)(piq)$_2$), Bis[(4-n-hexylphenyl) isoquinoline](acetylacetonate)iridium(III) (Hex-Ir(piq)$_2$(acac)), Tris[2-(4-n-hexylphenyl)quinoline] iridium(III) (Hex-Ir(piq)$_3$), Tris(2-(3-methylphenyl)-7-methyl-quinolato) iridium (Ir(dmpq)$_3$), Bis[2-(2-methylphenyl)-7-methylquinoline](acetylacetonate) iridium (III) (Ir (dmpq)$_2$(acac)), Bis[2-(3,5-dimethylphenyl)-4-methylquinoline](acetylacetonate) iridium (III) (Ir(mphmq)$_2$(acac)), Tris(dibenzoylmethane)mono(1,10-phenanthroline)europium(III) (Eu(dbm)$_3$(phen)) and combination thereof.

The host in the EML3 646 may comprise, but is not limited to, mCP, mCP-CN, mCBP, CBP-CN, 9-(3-(9H-Carbazol-9-yl)phenyl)-3-(diphenylphosphoryl)-9H-carbazole (mCPPO1) 3,5-Di(9H-carbazol-9-yl) biphenyl (Ph-mCP), TSPO1, 9-(3'-(9H-carbazol-9-yl)-[1,1'-biphenyl]-3-yl)-9H-pyrido[2,3-b]indole (CzBPCb), Bis(2-methylphenyl)diphenylsilane (UGH-1), 1,4-Bis (triphenylsilyl)benzene (UGH-2), 1,3-Bis(triphenylsilyl) benzene (UGH-3), 9,9-Spiorobifluoren-2-yl-diphenyl-phosphine oxide (SPPO1), 9,9'-(5-(Triphenylsilyl)-1,3-phenylene)bis(9H-carbazole) (SimCP) and combination thereof.

The blue dopant in the EML3 646 may comprise, but is not limited to, a blue phosphorescent dopant and/or a blue fluorescent dopant such as perylene, 4,4'-Bis[4-(di-p-tolylamino)styryl]biphenyl (DPAVBi), 4-(Di-p-tolylamino)-4-4'-[(di-p-tolylamino)styryl]stilbene (DPAVB), 4,4'-Bis[4-(diphenylamino)styryl]biphenyl (BDAVBi), 2,7-Bis(4-diphenylamino)styryl)-9,9-spiorfluorene (spiro-DPVBi), [1,4-bis[2-[4-[N,N-di(p-tolyl)amino]phenyl]vinyl]benzene (DSB), 1-4-di-[4-(N,N-diphenyl)amino]styryl-benzene (DSA), 2,5,8,11-Tetra-tetr-butylperylene (TBPe), Bis(2-hydroxylphenyl)-pyridine)beryllium ($Bepp_2$), 9-(9-Phenylcarbazole-3-yl)-10-(naphthalene-1-yl)anthracene (PCAN), mer-Tris(1-phenyl-3-methylimidazolin-2-ylidene-C,C(2)'iridium(III) (mer-Ir(pmi)$_3$), fac-Tris(1,3-diphenyl-benzimidazolin-2-ylidene-C,C(2)'iridium(III) (fac-Ir(dpbic)$_3$), Bis (3,4,5-trifluoro-2-(2-pyridyl)phenyl-(2-carboxypyridyl) iridium(III) (Ir(tfpd)$_2$pic), tris(2-(4,6-difluorophenyl) pyridine))iridium(III) (Ir(Fppy)$_3$), Bis[2-(4,6-difluorophenyl)pyridinato-C$^2$,N](picolinato)iridium(III) (FIrpic) and combination thereof.

The OLED D5 emits a green light, a red light and a blue light in each of the first to third pixel regions P1, P2 and P3 so that the organic light emitting display device 500 (FIG. 11) may implement a full-color image.

The organic light emitting display device 500 may further comprise a color filter layer corresponding to the first to third pixel regions P1, P2 and P3 for improving color purity of the light emitted from the OLED D. As an example, the color filter layer may comprise a first color filter layer (green color filter layer) corresponding to the first pixel region P1, the second color filter layer (red color filter layer) corresponding to the second pixel region P2 and the third color filter layer (blue color filter layer) corresponding to the third pixel region P3.

When the organic light emitting display device 500 is a bottom-emission type, the color filter layer may be disposed between the OLED D and the substrate 510. Alternatively, when the organic light emitting display device 500 is a top-emission type, the color filter layer may be disposed over the OLED D.

Figure 13:
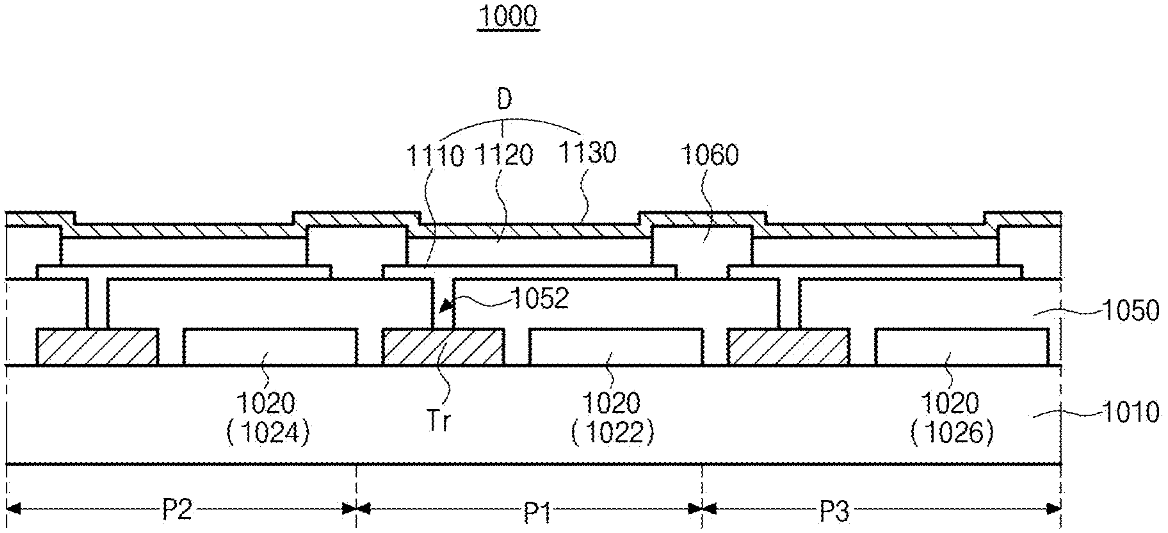
FIG. 13 is a schematic cross-sectional view illustrating an organic light emitting display device in accordance with still another exemplary aspect of the present disclosure.

FIG. 13 is a schematic cross-sectional view illustrating an organic light emitting display device in accordance with still another exemplary aspect of the present disclosure. As illustrated in FIG. 13, the organic light emitting display device 1000 comprise a substrate 1010 defining a first pixel region P1, a second pixel region P2 and a third pixel region P3, a thin film transistor Tr disposed over the substrate 1010, an OLED D disposed over the thin film transistor Tr and connected to the thin film transistor Tr and a color filter layer 1020 corresponding to the first to third pixel regions P1, P2 and P3. As an example, the first pixel region P1 may be a green pixel region, the second pixel region P2 may be a red pixel region and the third pixel region P3 may be a blue pixel region.

The substrate 1010 may be a glass substrate or a flexible substrate. For example, the flexible substrate may be any one of a PI substrate, a PES substrate, a PEN substrate, a PET substrate and a PC substrate. The thin film transistor Tr is located over the substrate 1010. Alternatively, a buffer layer may be disposed over the substrate 1010 and the thin film transistor Tr may be disposed over the buffer layer. As illustrated in FIG. 2, the thin film transistor Tr includes a semiconductor layer, a gate electrode, a source electrode and a drain electrode and acts as a driving element.

The color filter layer 1020 is located over the substrate 1010. As an example, the color filter layer 1020 may comprise a first color filter layer 1022 corresponding to the first pixel region P1, a second color filter layer 1024 corresponding to the second pixel region P2 and a third color filter layer 1026 corresponding to the third pixel region P3. The first color filter layer 1022 may be a green color filter layer, the second color filter layer 1024 may be a red color filter layer and the third color filter layer 1026 may be a blue color filter layer. For example, the first color filter layer 1022 may comprise at least one of green dye or blue pigment, the second color filter layer 1024 may comprise at least one of red dye or green pigment and the third color filter layer 1026 may comprise at least one of blue dye or red pigment.

A passivation layer 1050 is disposed over the thin film transistor Tr and the color filter layer 1020. The passivation layer 1050 has a flat top surface and a drain contact hole 1052 that exposes a drain electrode of the thin film transistor Tr.

The OLED D is disposed over the passivation layer 1050 and corresponds to the color filter layer 1020. The OLED D includes a first electrode 1110 that is connected to the drain electrode of the thin film transistor Tr, and an emissive layer 1120 and a second electrode 1130 each of which is disposed sequentially on the first electrode 1110. The OLED D emits white light in the first to third pixel regions P1, P2 and P3.

The first electrode 1110 is separately formed for each of the first to third pixel regions P1, P2 and P3, and the second electrode 1130 corresponds to the first to third pixel regions P1, P2 and P3 and is formed integrally.

The first electrode 1110 may be one of an anode and a cathode, and the second electrode 1130 may be the other of the anode and the cathode. In addition, the first electrode 1110 may be a transmissive (or semi-transmissive) electrode and the second electrode 1130 may be a reflective electrode.

For example, the first electrode 1110 may be an anode and may include conductive material having a relatively high work function value, e.g., a transparent conductive oxide layer of transparent conductive oxide (TCO). The second electrode 1130 may be a cathode and may include conductive material having relatively low work function value, e.g., a metal material layer of low-resistant metal. For example, the transparent conductive oxide layer of the first electrode 1110 may include any one of ITO, IZO, ITZO, SnO, ZnO, ICO and AZO, and the second electrode 1130 may include Al, Mg, Ca, Ag, alloy thereof (e.g. Mg—Ag) or combination thereof.

The emissive layer 1120 is disposed on the first electrode 1110. The emissive layer 1120 includes at least two emitting parts emitting different colors. Each of the emitting part may have a single-layered structure of an EML. Alternatively, each of the emitting parts may include at least one of an HIL, an HTL, and an EBL, an HBL, an ETL and an EIL. In addition, the emissive layer may further comprise a CGL disposed between the emitting parts.

At least one of the at least two emitting parts may comprise the first compound H of the host, the second compound DF of the delayed fluorescent material, and optionally the third compound FD of the fluorescent or phosphorescent material.

A bank layer 1060 is disposed on passivation layer 1050 in order to cover edges of the first electrode 1110. The bank layer 1060 corresponds to each of the first to third pixel regions P1, P2 and P3 and exposes a center of the first electrode 1110. As described above, since the OLED D emits white light in the first to third pixel regions P1, P2 and P3, the emissive layer 1120 may be formed as a common layer without being separated in the first to third pixel regions P1, P2 and P3. The bank layer 1060 is formed to prevent current leakage from the edges of the first electrode 1110, and the bank layer 1060 may be omitted.

Moreover, the organic light emitting display device 1000 may further comprise an encapsulation film disposed on the second electrode 1130 in order to prevent outer moisture from penetrating into the OLED D. In addition, the organic light emitting display device 1000 may further comprise a polarizer disposed under the substrate 1010 in order to decrease external light reflection.

In the organic light emitting display device 1000 in FIG. 13, the first electrode 1110 is a transmissive electrode, the second electrode 1130 is a reflective electrode, and the color filter layer 1020 is disposed between the substrate 1010 and the OLED D. That is, the organic light emitting display device 1000 is a bottom-emission type. Alternatively, the first electrode 1110 may be a reflective electrode, the second electrode 1130 may be a transmissive electrode (or semi-transmissive electrode) and the color filter layer 1020 may be disposed over the OLED D in the organic light emitting display device 1000.

In the organic light emitting display device 1000, the OLED D located in the first to third pixel regions P1, P2 and P3 emits white light, and the white light passes through each of the first to third pixel regions P1, P2 and P3 so that each of a green color, a red color and a blue color is displayed in the first to third pixel regions P1, P2 and P3, respectively.

A color conversion film may be disposed between the OLED D and the color filter layer 1020. The color conversion film corresponds to the first to third pixel regions P1, P2 and P3, and comprises a blue color conversion film, a green color conversion film and a red color conversion film each of which can convert the white light emitted from the OLED D into blue light, green light and red light, respectively. For example, the color conversion film may comprise quantum dots. Accordingly, the organic light emitting display device 1000 may further enhance its color purity. Alternatively, the color conversion film may displace the color filter layer 1020.

Figure 14:
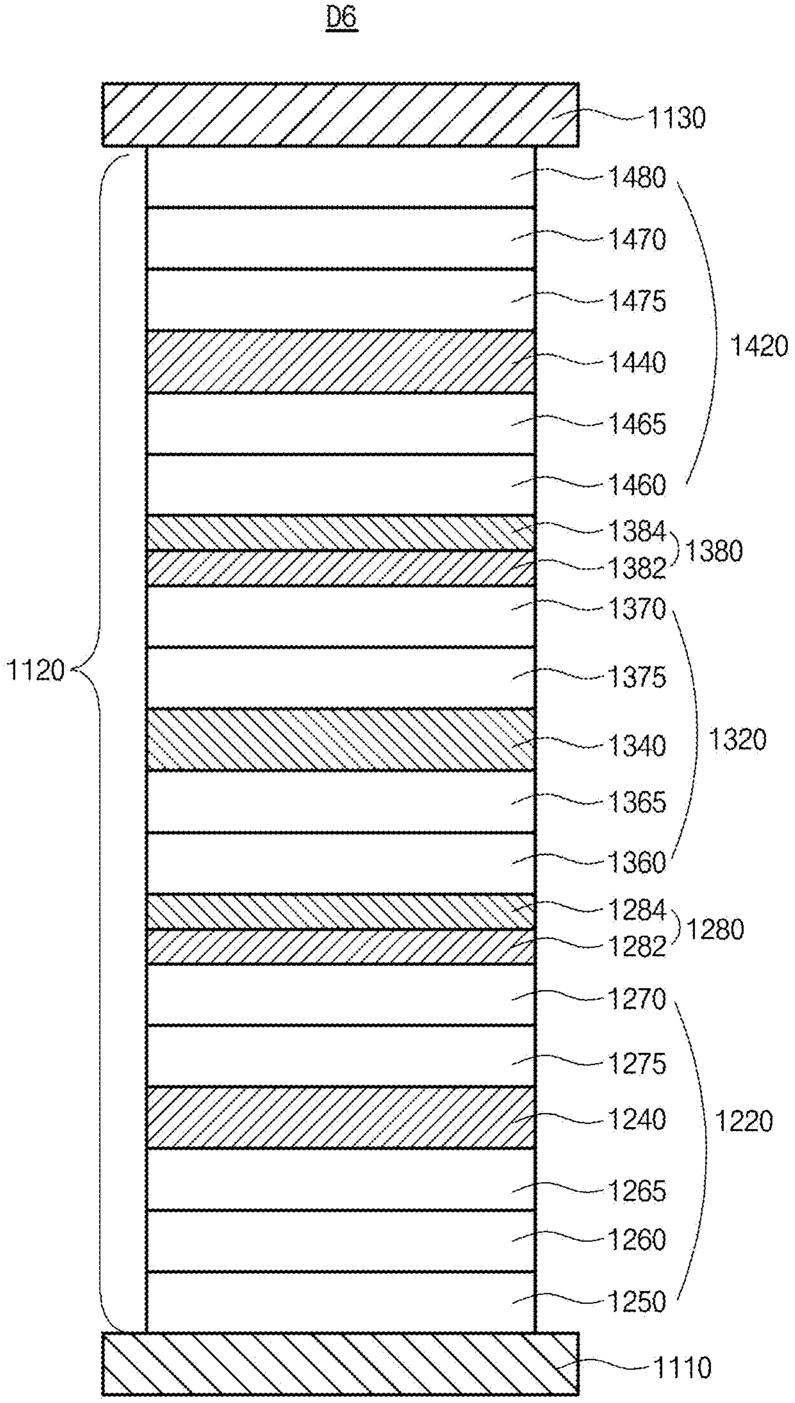
FIG. 14 is a schematic cross-sectional view illustrating an OLED in accordance with still another exemplary aspect of the present disclosure.

FIG. 14 is a schematic cross-sectional view illustrating an OLED in accordance with still another exemplary aspect of the present disclosure. As illustrated in FIG. 14, the OLED D6 comprises first and second electrodes 1110 and 1130 facing each other and an emissive layer 1120 disposed between the first and second electrodes 1110 and 1130. The first electrode 1110 may be an anode and the second electrode 1130 may be a cathode. For example, the first electrode 1110 may be a transmissive electrode and the second electrode 1130 may be a reflective electrode.

The emissive layer 1120 includes a first emitting part 1220 comprising a first EML (EML1) 1240, a second emitting part 1320 comprising a second EML (EML2) 1340 and a third emitting part 1420 comprising a third EML (EML3) 1440. In addition, the emissive layer 1120 may further comprise a first charge generation layer (CGL1) 1280 disposed between the first emitting part 1220 and the second emitting part 1320 and a second charge generation layer (CGL2) 1380 disposed between the second emitting part 1320 and the third emitting part 1420. Accordingly, the first emitting part 1220, the CGL1 1280, the second emitting part 1320, the CGL2 1380 and the third emitting part 1420 are disposed sequentially on the first electrode 1110.

The first emitting part 1220 may further comprise at least one of a first HTL (HTL1) 1260 disposed between the first electrode 1110 and the EML1 1240, an HIL 1250 disposed between the first electrode 1110 and the HTL1 1260 and a first ETL (ETL1) 1270 disposed between the EML1 1240 and the CGL1 1280. Alternatively, the first emitting part 1220 may further comprise a first EBL (EBL1) 1265 disposed between the HTL1 1260 and the EML1 1240 and/or a first HBL (HBL1) 1275 disposed between the EML1 1240 and the ETL1 1270.

The second emitting part 1320 may further comprise at least one of a second HTL (HTL2) 1360 disposed between the CGL1 1280 and the EML2 1340, a second ETL (ETL2) 1370 disposed between the EML2 1340 and the CGL2 1380. Alternatively, the second emitting part 1320 may further comprise a second EBL (EBL2) 1365 disposed between the HTL2 1360 and the EML2 1340 and/or a second HBL (HBL2) 1375 disposed between the EML2 1340 and the ETL2 1370.

The third emitting part 1420 may further comprise at least one of a third HTL (HTL3) 1460 disposed between the CGL2 1380 and the EML3 1440, a third ETL (ETL3) 1470 disposed between the EML3 1440 and the second electrode 1130 and an EIL 1480 disposed between the ETL3 1470 and the second electrode 1130. Alternatively, the third emitting part 1420 may further comprise a third EBL (EBL3) 1465 disposed between the HTL3 1460 and the EML3 1440 and/or a third HBL (HBL3) 1475 disposed between the EML3 1440 and the ETL3 1470.

The CGL1 1280 is disposed between the first emitting part 1220 and the second emitting part 1320. That is, the first emitting part 1220 and the second emitting part 1320 are connected via the CGL1 1280. The CGL1 1280 may be a PN-junction CGL that junctions a first N-type CGL (N-CGL1) 1282 with a first P-type CGL (P-CGL1) 1284.

The N-CGL1 1282 is disposed between the ETL1 1270 and the HTL2 1360 and the P-CGL1 1284 is disposed between the N-CGL1 1282 and the HTL2 1360. The N-CGL1 1282 transports electrons to the EML1 1240 of the first emitting part 1220 and the P-CGL1 1284 transport holes to the EML2 1340 of the second emitting part 1320.

The CGL2 1380 is disposed between the second emitting part 1320 and the third emitting part 1420. That is, the second emitting part 1320 and the third emitting part 1420 are connected via the CGL2 1380. The CGL2 1380 may be a PN-junction CGL that junctions a second N-type CGL (N-CGL2) 1382 with a second P-type CGL (P-CGL2) 1384.

The N-CGL2 1382 is disposed between the ETL2 1370 and the HTL3 1460 and the P-CGL2 1384 is disposed between the N-CGL2 1382 and the HTL3 1460. The N-CGL2 1382 transports electrons to the EML2 1340 of the second emitting part 1320 and the P-CGL2 1384 transport holes to the EML3 1440 of the third emitting part 1420.

In this aspect, one of the first to third EMLs 1240, 1340 and 1440 may be a blue EML, another of the first to third EMLs 1240, 1340 and 1440 may be a green EML and the third of the first to third EMLs 1240, 1340 and 1440 may be a red EML.

As an example, the EML1 1240 may be a blue EML, the EML2 1340 may be a green EML and the EML3 1440 may be a red EML. Alternatively, the EML1 1240 may be a red EML, the EML2 1340 may be a green EML and the EML3 1440 may be a blue EML1.

The EML1 1240 includes a host and a blue dopant (or red dopant) and the EML3 1440 includes a host and a red dopant (or blue dopant). As an example, the host in each of the EML1 1240 and the EML3 1440 may include the blue or red host, and the blue or red dopant may include at least one of the blue or red phosphorescent material, the blue or red fluorescent material and the blue or red delayed fluorescent material, as described above.

The EML2 1340 may comprise the first compound H of the host, the second compound DF of the delayed fluorescent material, and optionally the third compound FD of the fluorescent or phosphorescent material. The EML2 1340 including the first to third compounds H, DF and FD may have a single-layered structure, a double-layered structure (FIG. 6) or a triple-layered structure (FIG. 8).

When the EML2 1340 includes the first compound H, the second compound DF and the third compound FD, the contents of the first compound H may be larger than the contents of the second compound DF, and the consents of the second compound DF is larger than the contents of the third compound FD. In this case, exciton energy can be transferred efficiently from the second compound DF to the third compound FD. As an example, each of the contents of the first to third compounds H, DF and FD in the EML2 1340 may be, but is not limited to, about 60 wt % to about 75 wt %, about 20 wt % to about 40 wt % and about 0.1 wt % to about 5 wt %, respectively.

The OLED D6 emits white light in each of the first to third pixel regions P1, P2 and P3 and the white light passes though the color filter layer 1020 (FIG. 13) correspondingly disposed in the first to third pixel regions P1, P2 and P3. Accordingly, the OLED D6 can implement a full-color image.

Figure 15:
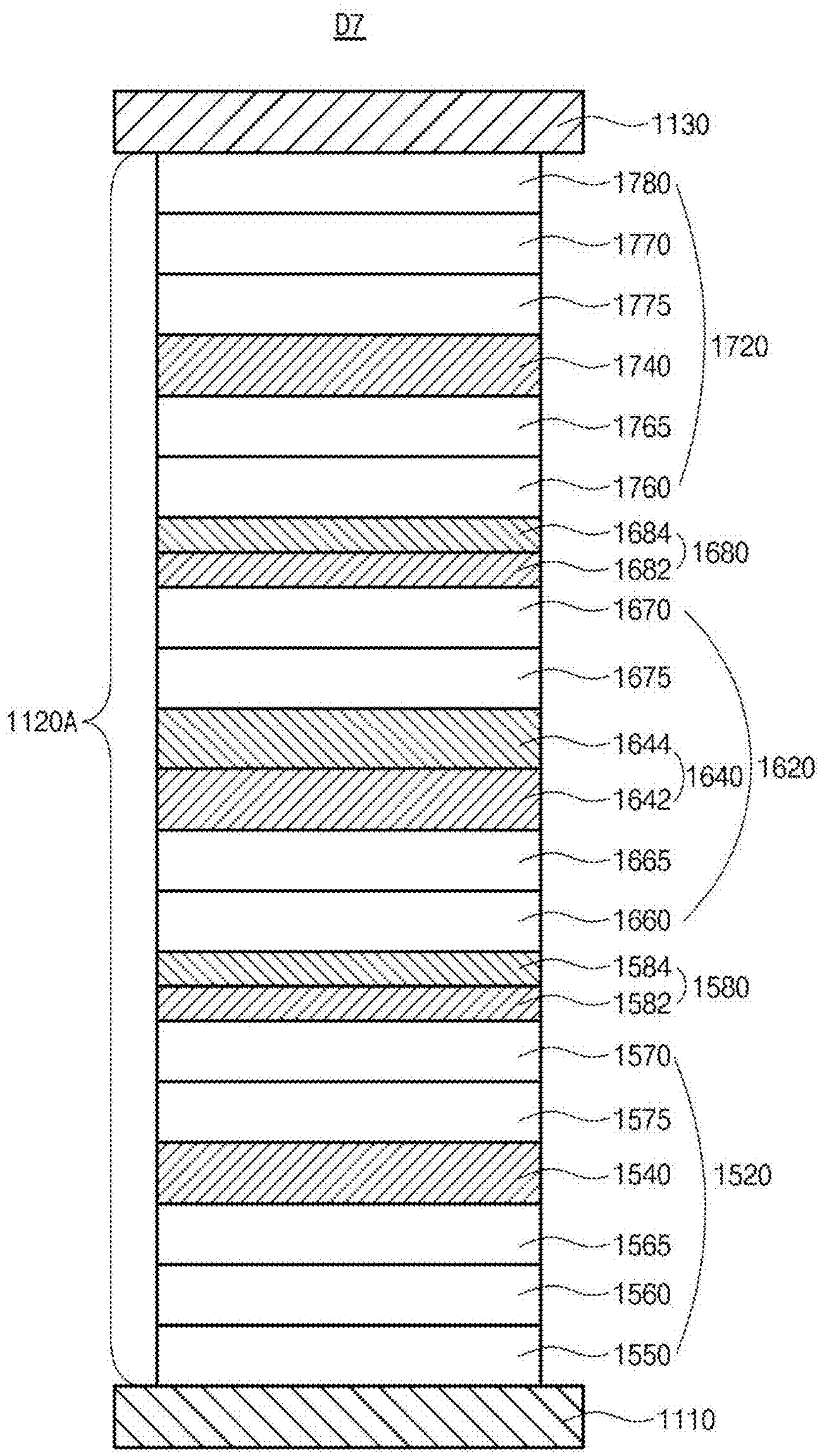
FIG. 15 is a schematic cross-sectional view illustrating an OLED in accordance with still another exemplary aspect of the present disclosure.

FIG. 15 is a schematic cross-sectional view illustrating an OLED in accordance with still another exemplary aspect of the present disclosure. As illustrated in FIG. 15, the OLED D7 comprises first and second electrodes 1110 and 1130 facing each other and an emissive layer 1120A disposed between the first and second electrodes 1110 and 1130. The first electrode 1110 may be an anode and the second electrode 1130 may be a cathode. For example, the first electrode 1110 may be a transmissive electrode and the second electrode 1130 may be a reflective electrode.

The emissive layer 1120A includes a first emitting part 1520 comprising an EML1 1540, a second emitting part 1620 comprising an EML2 1640 and a third emitting part 1720 comprising an EML3 1740. In addition, the emissive layer 1120A may further comprise a CGL1 1580 disposed between the first emitting part 1520 and the second emitting part 1620 and a CGL2 1680 disposed between the second emitting part 1620 and the third emitting part 1720. Accordingly, the first emitting part 1520, the CGL1 1580, the second emitting part 1620, the CGL2 1680 and the third emitting part 1720 are disposed sequentially on the first electrode 1110.

The first emitting part 1520 may further comprise at least one of an HTL1 1560 disposed between the first electrode 1110 and the EML1 1540, an HIL 1550 disposed between the first electrode 1110 and the HTL1 1560 and an ETL1 1570 disposed between the EML1 1540 and the CGL1 1580. Alternatively, the first emitting part 1520 may further comprise an EBL1 1565 disposed between the HTL1 1560 and the EML1 1540 and/or an HBL1 1575 disposed between the EML1 1540 and the ETL1 1570.

The EML2 1640 of the second emitting part 1620 comprises a lower EML 1642 and an upper EML 1644. The lower EML 1642 is located adjacently to the first electrode 1110 and the upper EML 1644 is located adjacently too the second electrode 1130. In addition, the second emitting part 1620 may further comprise at least one of an HTL2 1660 disposed between the CGL1 1580 and the EML2 1640, an ETL2 1670 disposed between the EML2 1640 and the CGL2 1680. Alternatively, the second emitting part 1620 may further comprise an EBL2 1665 disposed between the HTL2 1660 and the EML2 1640 and/or an HBL2 1675 disposed between the EML2 1640 and the ETL2 1670.

The third emitting part 1720 may further comprise at least one of an HTL3 1760 disposed between the CGL2 1680 and the EML3 1740, an ETL3 1770 disposed between the EML3 1740 and the second electrode 1130 and an EIL 1780 disposed between the ETL3 1770 and the second electrode 1130. Alternatively, the third emitting part 1720 may further comprise an EBL3 1765 disposed between the HTL3 1760 and the EML3 1740 and/or an HBL3 1775 disposed between the EML3 1740 and the ETL3 1770.

The CGL1 1580 is disposed between the first emitting part 1520 and the second emitting part 1620. That is, the first emitting part 1520 and the second emitting part 1620 are connected via the CGL1 1580. The CGL1 1580 may be a PN-junction CGL that junctions an N-CGL1 1582 with a P-CGL1 1584. The N-CGL1 1582 is disposed between the ETL1 1570 and the HTL2 1660 and the P-CGL1 1584 is disposed between the N-CGL1 1582 and the HTL2 1660.

The CGL2 1680 is disposed between the second emitting part 1620 and the third emitting part 1720. That is, the second emitting part 1620 and the third emitting part 1720 are connected via the CGL2 1680. The CGL2 1680 may be a PN-junction CGL that junctions an N-CGL2 1682 with a P-CGL2 1684. The N-CGL2 1682 is disposed between the ETL2 1670 and the HTL3 1760 and the P-CGL2 1684 is disposed between the N-CGL2 1682 and the HTL3 1760. In one exemplary aspect, at least one of the N-CGL1 1582 and the N-CGL2 1682 may include any organic compound having the structure of Formulae 1 to 3.

In this aspect, each of the EML1 1540 and the EML3 1740 may be a blue EML. Each of the EML1 1540 and the EML3 1740 may comprise a host and a blue dopant. The host in each of the EML1 1540 and the EML3 1740 may comprise the blue host and the blue dopant may comprise at least one of the blue phosphorescent material, the blue fluorescent material and the blue delayed fluorescent material, as described above. Each of the host and the blue dopant in the EML1 1540 may be independently identical to or different from each of the host and the blue dopant in the EML3 1740. As an example, the blue dopant in the EML1 1540 may be different from the blue dopant in the EML3 1740 in terms of luminous efficiency and/or emission wavelength.

One of the lower EML 1642 and the upper EML 1644 in the EML2 1640 may be a green EML and the other of the lower EML 1642 and the upper EML 1644 in the EML2 1640 may be a red EML. The green EML and the red EML is sequentially disposed to form the EML2 1640.

In one exemplary aspect, the lower EML 1642 as the green EML may comprise the first compound H of the host, the second compound DF of the delayed fluorescent material having the structure of Formulae 1 to 12, and optionally the third compound FD of the fluorescent or phosphorescent material.

The upper EML 1644 as the red EML may comprise a host and the red dopant. The host in the upper EML 1644 may comprise the red host and the red dopant ion the upper EML 1644 may comprise at least one of the red phosphorescent material, the red fluorescent material and the red delayed fluorescent material, as described above.

As an example, when the lower EML 1642 includes the first compound H, the second compound DF and the third compound FD, the contents of the first compound H may be larger than the contents of the second compound DF, and the consents of the second compound DF is larger than the contents of the third compound FD. In this case, exciton energy can be transferred efficiently from the second compound DF to the third compound FD. As an example, each of the contents of the first to third compounds H, DF and FD in the lower EML 1642 may be, but is not limited to, about 60 wt % to about 75 wt %, about 20 wt % to about 40 wt % and about 0.1 wt % to about 5 wt %, respectively.

The OLED D7 emits white light in each of the first to third pixel regions P1, P2 and P3 and the white light passes though the color filter layer 1020 (FIG. 13) correspondingly disposed in the first to third pixel regions P1, P2 and P3. Accordingly, the OLED D7 can implement a full-color image.

In FIG. 15, the OLED D7 has a three-stack structure including the first to three emitting parts 1520, 1620 and 1720 which includes the EML1 1540 and the EML3 1740 as the blue EML. Alternatively, the OLED D7 may have a two-stack structure where one of the first emitting part 1520 and the third emitting part 1720 each of which includes the EML1 1540 and the EML3 1740 as the blue EML is omitted.

Comparative Synthesis Example 1: Synthesis of Compound Ref. 1

(1) Synthesis of Intermediate A

[Comparative Reaction Formula 1-1]

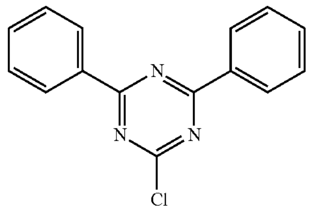

+

-continued

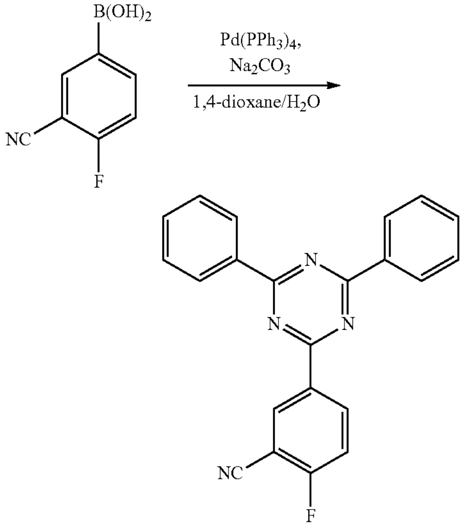

A 2-chloro-4,6-diphenyl-1,3,5-triazine (2.00 g, 7.47 mmol), 3-cyano-4-fluorophenylboronic acid (1.38 g, 8.22 mmol), $Na_2CO_3$ (3.96 g, 37.35 mmol), Tetrakis(triphenylphosphine) palladium (0) ($Pd(PPh_3)_4$, 0.26 g, 0.22 mmol) were put into a two-neck flask, and then the mixture was dissolved in 200 mL of a mixed solvent 1,4-doxane/$H_2O$ (4:1 by volume ratio). Then, the solution was refluxed for 12 hours with stirring. After the reaction was complete, the crude product was purified with column chromatography using methylene chloride (MC) and hexane (3:7 by volume ratio) as an eluent to give an Intermediate A of a solid state (2.10 g, yield: 79.78%).

(2) Synthesis of Compound Ref. 1

[Comparative Reaction Formula 1-2]

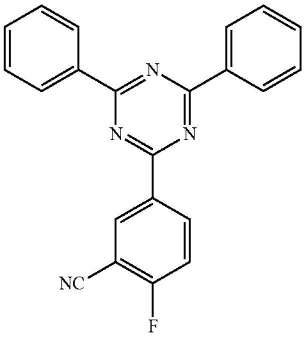

A

+

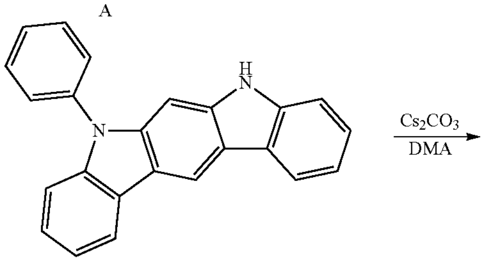

-continued

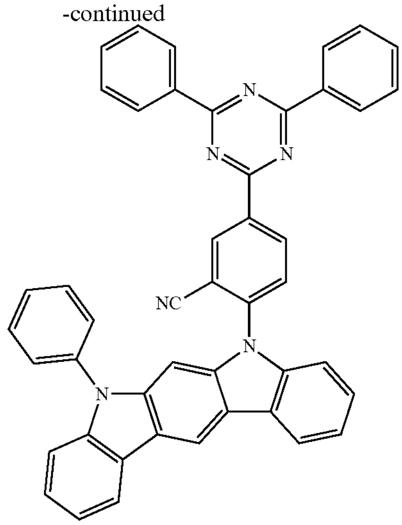

Ref. 1

The Intermediate A (5.0 g, 14.19 mmol), 5-phenyl-5,12-dihydroindolo[3,2-a]carbazole (5.2 g, 15.91 mmol) and $Cs_2CO_3$ (9.2 g, 28.38 mmol) dissolved in 150 mL of DMA (dimethylacetamide) were put into a two-neck flask, and then the solution was heated at 150° C. for 3 hours with stirring. After the reaction was complete, the reactants were extracted with $MC/H_2O$, dried with $MgSO_4$ and then filtered. After the reactants were concentrated, the crude product was solidified with methanol, and then filtered to give Compound Ref. 1 of a solid state (7.2 g, yield: 77%).

Comparative Synthesis Example 2: Synthesis of Compound Ref. 2

(1) Synthesis of Intermediate B

[Comparative Reaction Formula 2-1]

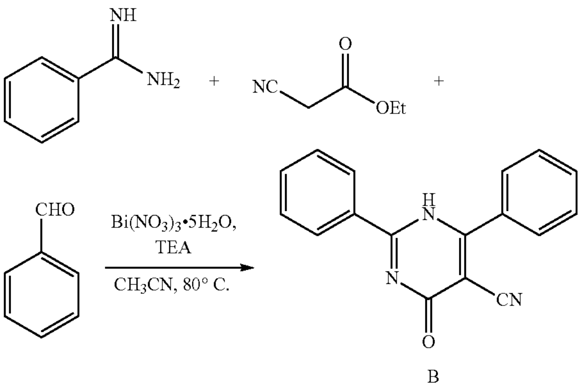

Benzamidine hydrochloride (50 g, 322.56 mmol), ethyl cyanoacetate (36.5 g, 322.56 mmol), benzaldehyde (59 g, 322.56 mmol), $Bi(NO_3)_3{\cdot}5H_2O$ (7.8 g, 16.13 mmol) and trimethylamine (230 mL, 16.13 mmol) dissolved in 800 mL of acetonitrile were put into a two-neck flask, and then the solution was heated at 80° C. for 4 hours with stirring. After the reaction was complete, the mixed solution was cooled to room temperature, was extracted with $H_2O/MC$, dried with $MgSO_4$ and filtered. The solvent was concentrated under vacuum distillation and recrystallized with ethanol to give the Intermediate B of white solid (35 g, yield: 40%).

(2) Synthesis of Intermediate C

[Comparative Reaction Formula 2-2]

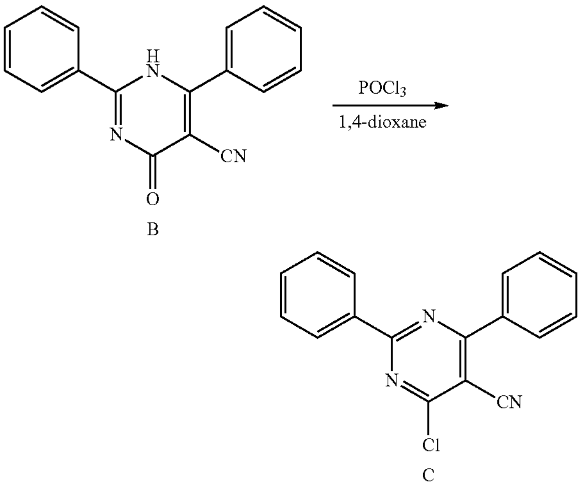

The intermediate B (35 g, 128.06 mmol), $POCl_3$ (30 mL, 320.16 mmol) dissolved in 60 mL of 1,4-dioxane was put into a two-neck flask, and then the solution was heated overnight at 120° C. with stirring. After the reaction was complete, the reactants were cooled to 0° C., and then water was added drop-wisely into the solution to quench the reaction. The reactants were extracted with $MC/H_2O$, dried with $MgSO_4$ and filtered. After the reactants were concentrated, the crude product was solidified with methanol, and then filtered to give the Intermediated C of solid (34.5 g, yield: 92%).

(3) Synthesis of Compound Ref. 2

[Comparative Reaction Formula 2-3]

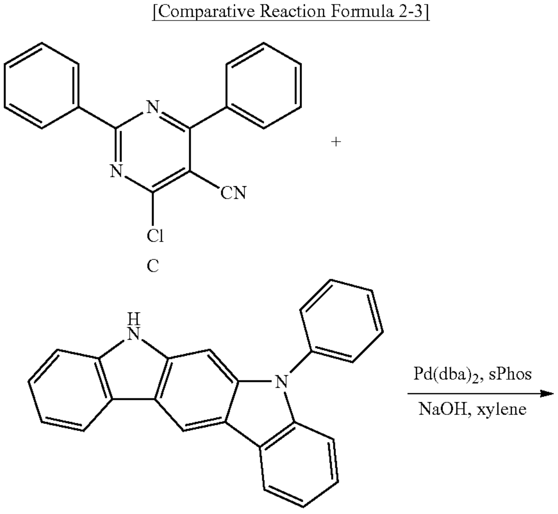

-continued

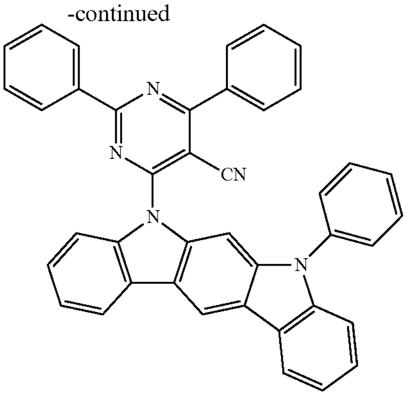

Ref. 2

The Intermediate C (3.2 g, 10.83 mmol), 5-phenyl-5,7-dihydroindolo[2,3-b]carbazole (3.0 g, 9.03 mmol), bis(dibenzylideneacetone) palladium(0) ($Pd(dba)_2$, 260 mg, 0.45 mmol), 2-dicyclohexylphosphino-2',6'-dimethoxybiphenyl (sPhos, 370 mg, 0.90 mmol) and sodium hydroxide (1.1 g, 27.08 mmol) dissolved in 90 mL of xylene were put into a two-neck flask, the reactants were reacted at 150° C. for 2.5 hours with stirring. After the solution was cooled to room temperature, the reactants were extracted with $MC/H_2O$, dried with $MgSO_4$ and then filtered. After the reactants were concentrated, the crude product was purified with column chromatography (eluent: ethyl acetate/MC) to give Compound Ref. 2 of a solid state (5.6 g, yield: 79%).

Comparative Synthesis Example 3: Synthesis of Compound Ref. 3

(1) Synthesis of Intermediate D

[Comparative Reaction Formula 3-1]

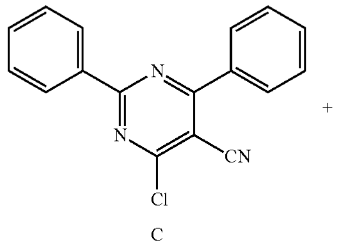

C

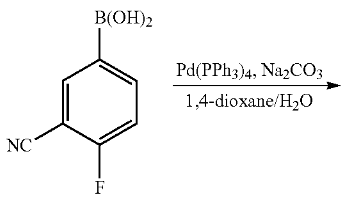

-continued

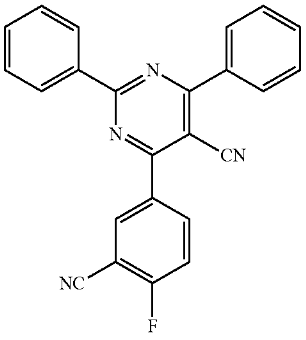

D

The Intermediate D was obtained by repeating the synthesis process of the Intermediate A except that the Intermediate C as the reactant was used instead of 2-chloro-4,6-diphenyl-1,3,5-triazine (2.01 g, yield: 78%).

(2) Synthesis of Compound Ref. 3

[Comparative Reaction Formula 3-2]

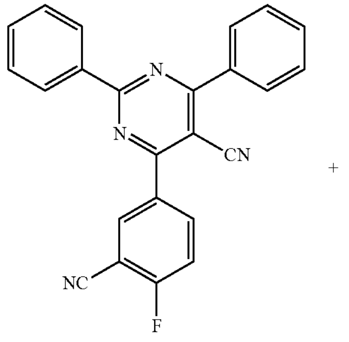

D

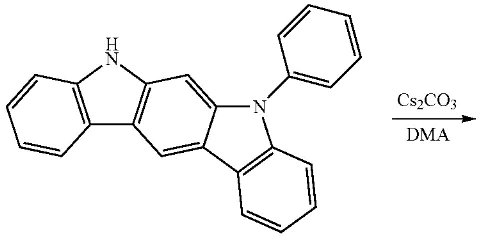

-continued

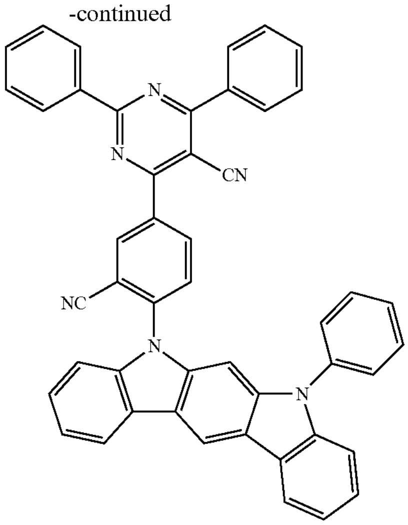

Ref. 3

The Compound Ref. 3 was obtained by repeating the synthesis process of the Compound Ref. 1 except that the Intermediate D as the reactant was used instead of the Intermediate A (2.28 g, yield: 77%)

Synthesis Example 1: Synthesis of Compound 1-27

(1) Synthesis of Intermediate E

[Reaction Formula 1-1]

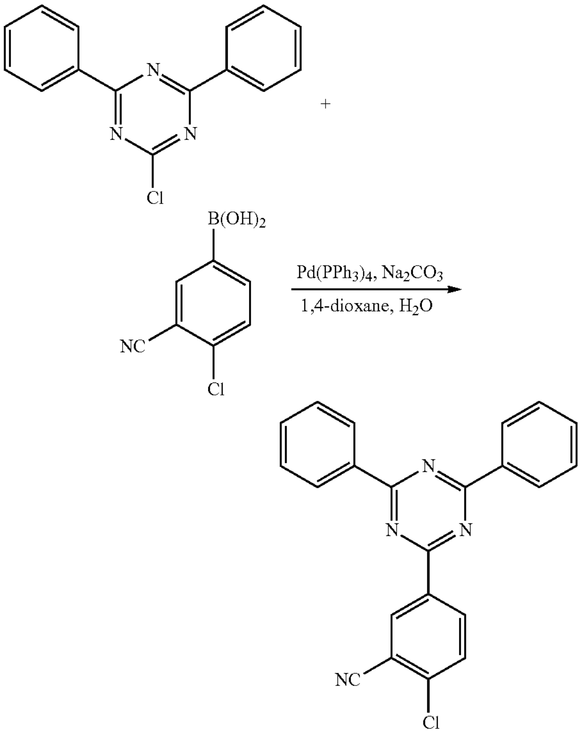

E 2-chloro-4,6-diphenyl-1,3,6-triazine (13.8 g, 51.41 mmol), 3-cyano-4-chlorophenylboronic acid (11.2 g, 61.69 mmol), $Pd(PPh_3)_4$ (3.0 g, 2.571 mmol) and $Na_2CO_3$ (16.3 g, 154.23 mmol) dissolved sequentially in 510 mL of mixed solvent 1,4-dioxane/$H_2O$ (4:1 by volume ratio) were put into a two-neck flask, and then the solution was reacted overnight at 120° C. As a gray solid is obtained, the reactants were washed with water and methanol and filtered to give the Intermediate E of solid (9.3 g, yield: 49%).

(2) Synthesis of Intermediate F

[Reaction Formula 1-2]

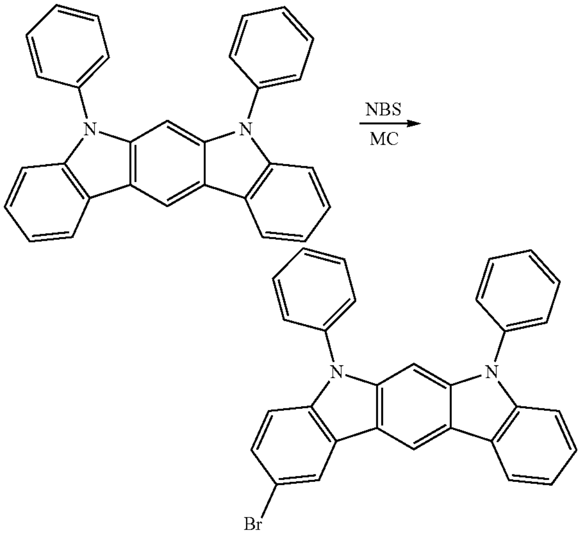

F 5,7-diphenyl-5,7-dihydroindolo[2,3-b]carbazole (5.9 g, 14.44 mmol) dissolved in 140 mL of dimethylformamide (DMF) was put into a two-neck flask, then N-bromosuccinimide (NBS, 2.6 g, 14.44 mmol) was added drop-wisely to the solution slowly. The reactants were reacted at room temperature for 6 hours. After the reaction was complete, the reactants were extracted with MC/$H_2O$, dried with $MgSO_4$ and filtered. After the reactants were concentrated, the crude product was dissolved in MC, and then recrystallized with methanol to give the Intermediate F of solid (5.0 g, yield: 71%).

(3) Synthesis of Intermediate G

[Reaction Formula 1-3]

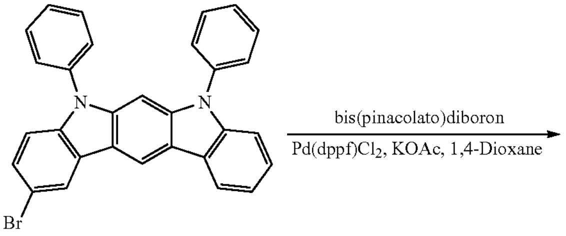

F

-continued

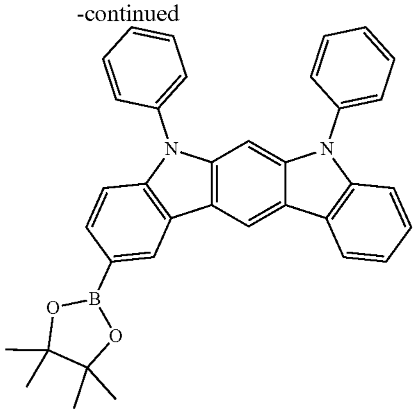

G

The Intermediate F (5.0 g, 10.26 mmol), bis(pinacolato) diboron (3.9 g, 15.39 mmol), potassium acetate (KOAc, 3.0 g, 30.78 mmol), [1,1'-bis(diphenylphosphino)dichloropalladium(II) ($PdCl_2$(dppf), 375 mg, 0.51 mmol) dissolved in 100 mL of a solvent 1,4-dioxane were put into a two-neck flask, and then the solution was refluxed for 3.5 hours with stirring. After the reactants were cooled down to room temperature, the reactants were extracted with MC/$H_2O$, dried with $MgSO_4$ and filtered. After the reactants were concentrated, the crude product was dissolved in MC and recrystallized with methanol to give the Intermediate G of solid (3.3 g, yield: 60%).

(4) Synthesis of Compound 1-27

[Reaction Formula 1-4]

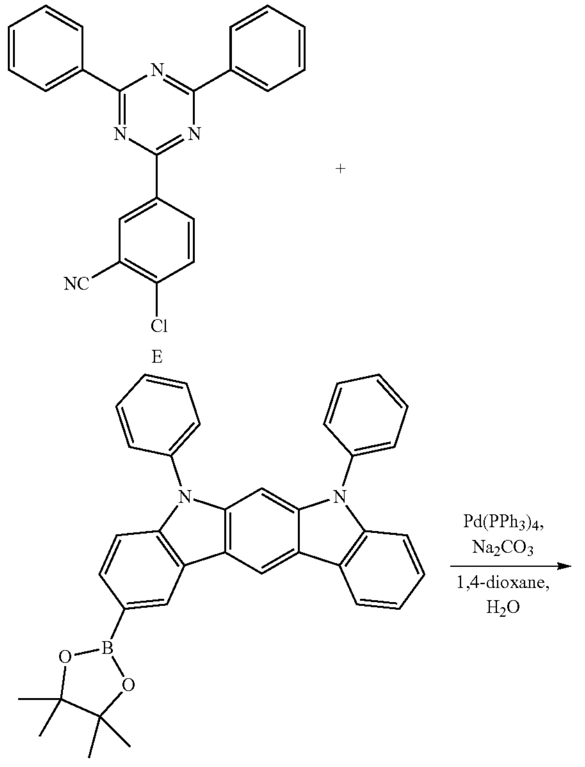

-continued

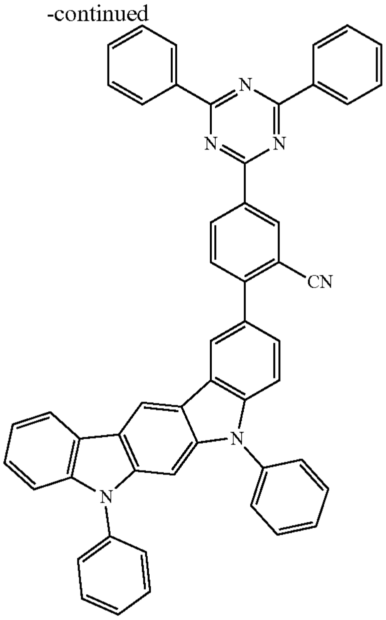

1-27

The Intermediate E (2.73 g, 7.40 mmol), the Intermediate G (3.3 g, 6.17 mmol), $Pd(PPh_3)_4$ (0.36 g, 0.31 mmol) and $Na_2CO_3$ (2.0 g, 18.52 mmol) dissolved in 62 mL of a mixed solvent 1,4-dioxane/$H_2O$ (4:1 by volume ratio) were put into a two-neck flaks, then the reactants were reacted overnight at 120° C. with stirring. After the reaction was complete, the reactants were extracted with MC/$H_2O$, dried with $MgSO_4$ and filtered. After the reactants were concentrated, the crude product was dissolved in MC and recrystallized with methanol to give Compound 1-27 of solid (5.2 g, yield: 95%)

Synthesis Example 2: Synthesis of Compound 1-12

(1) Synthesis of Intermediate H

[Reaction Formula 2-1]

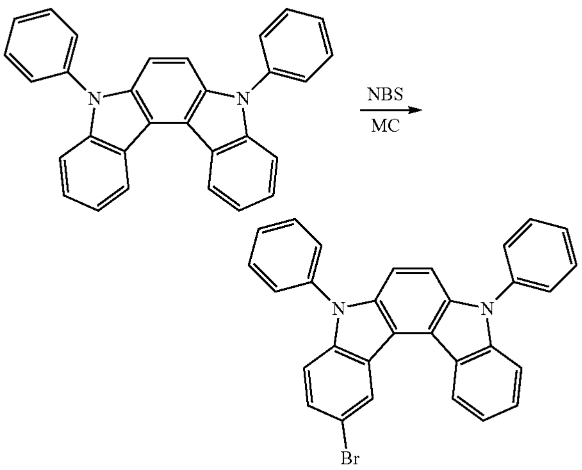

H

The Intermediate H was obtained by repeating the synthesis process of the Intermediate F except that 5,8-diphenyl-5,8-dihydroindolo[2,3-c]carbazole (10.0 g, 24.48 mmol) as the reactant was used instead of 5,7-diphenyl-5,7-dihydroindolo[2,3-b]carbazole (7.40 g, yield: 62%).

(2) Synthesis of Intermediate I

[Reaction Formula 2-2]

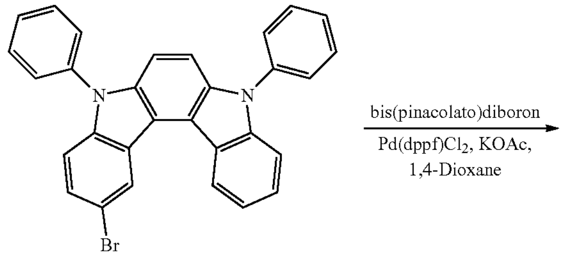

H

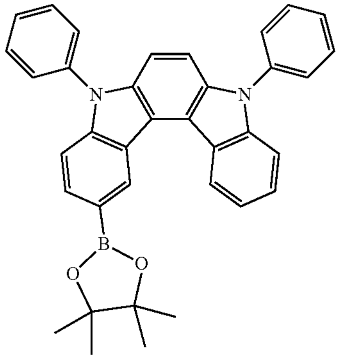

I

The Intermediate I was obtained by repeating the synthesis process of the Intermediate G except that the Intermediate H (5.0 g, 10.25 mmol) as the reactant was used instead of the Intermediate F (3.40 g, yield: 62%).

(3) Synthesis of Compound 1-12

[Reaction Formula 2-3]

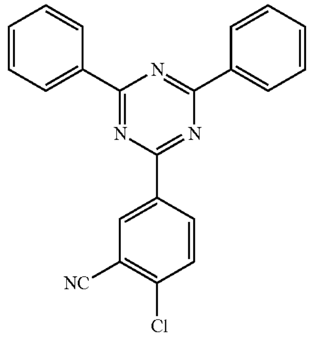

E

+

-continued

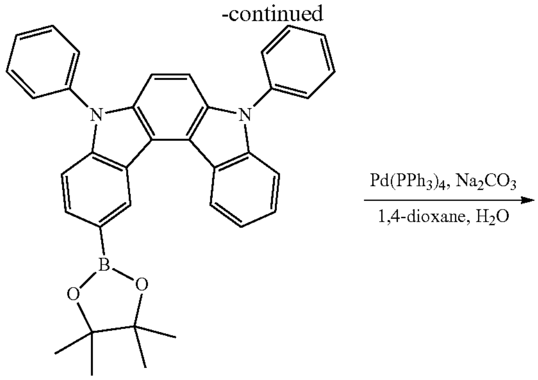

I

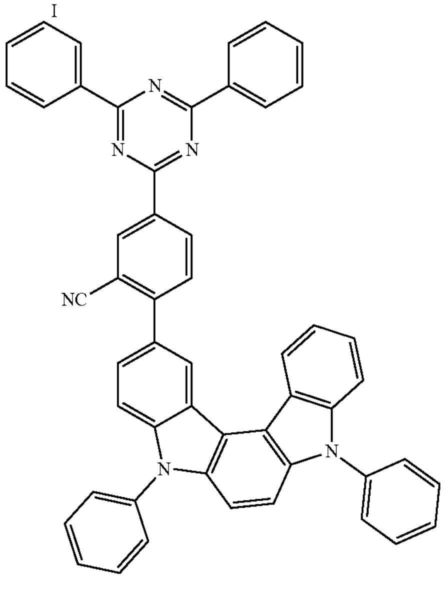

1-12

The Compound 1-12 was obtained by repeating the synthesis process of the Compound 1-27 except that the Intermediate I (2.0 g, 3.74 mmol) as the reactant was used instead of the Intermediate G (2.11 g, yield: 76%).

Synthesis Example 3: Synthesis of Compound 1-22

(1) Synthesis of Intermediate J

[Reaction Formula 3-1]

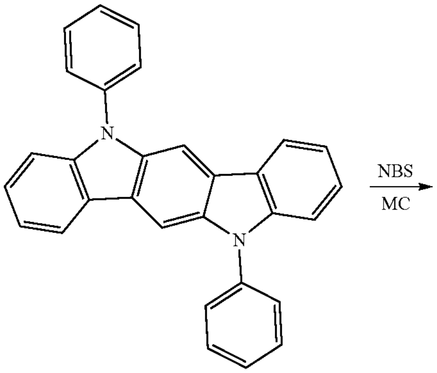

-continued

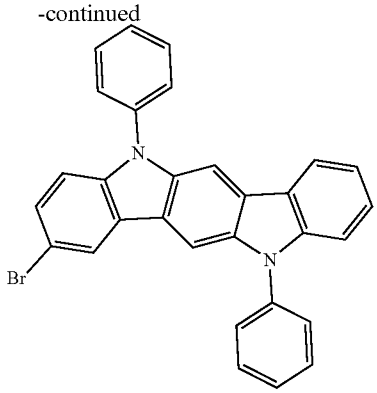

J

The Intermediate J was obtained by repeating the synthesis process of the Intermediate F except that 5,11-diphenyl-5,11-dihydroindolo[2,3-b]carbazole (10.0 g, 24.48 mmol) as the reactant was used instead of 5,7-diphenyl-5,7-dihydroindolo[2,3-b]carbazole (7.99 g, yield: 67%).

(2) Synthesis of Intermediate K

[Reaction Formula 3-2]

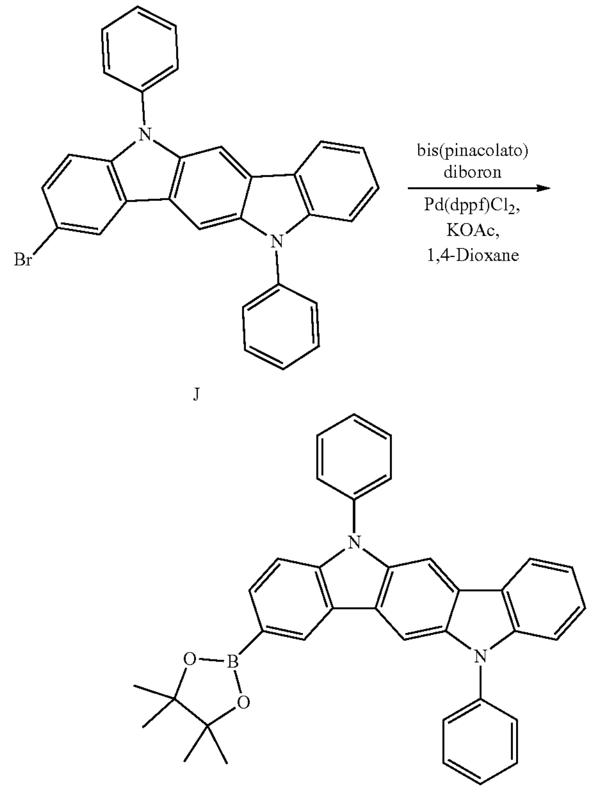

J

K

The Intermediate K was obtained by repeating the synthesis process of the Intermediate G except that the Intermediate J (5.0 g, 10.25 mmol) as the reactant was used instead of the Intermediate F (3.18 g, yield: 58%).

(3) Synthesis of Compound 1-22

[Reaction Formula 3-3]

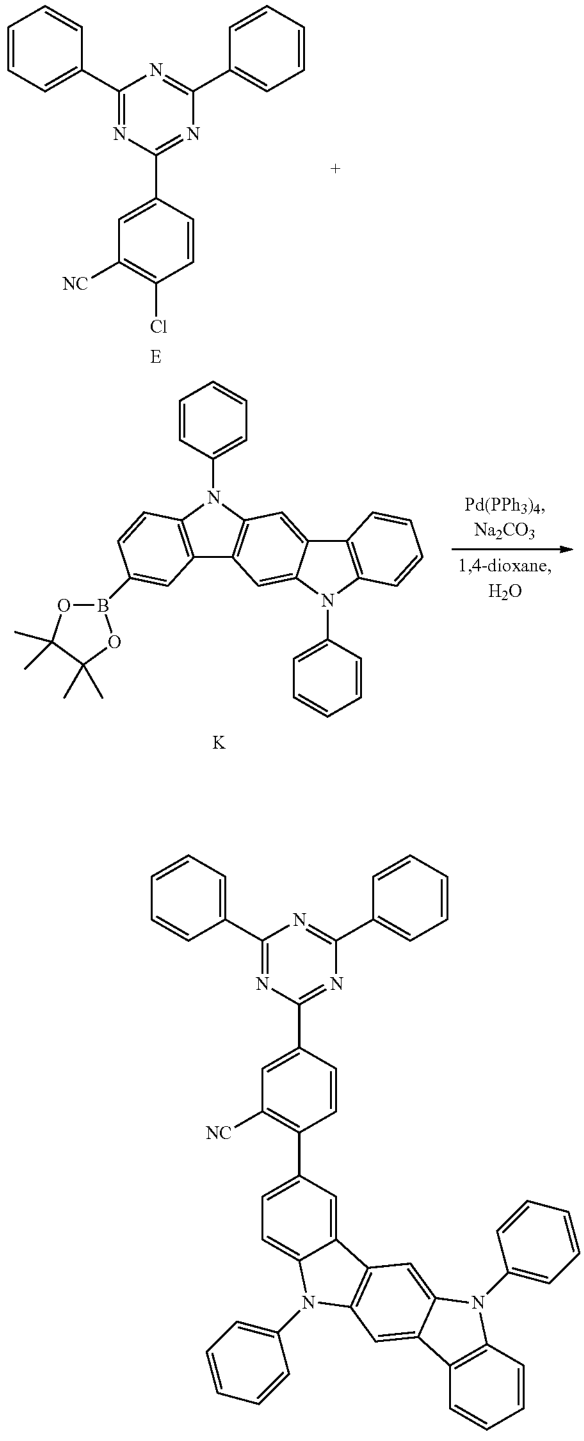

E

K 1-22

The Compound 1-22 was obtained by repeating the synthesis process of the Compound 1-27 except that the Intermediate K (2.0 g, 3.74 mmol) as the reactant was used instead of the Intermediate G.

Synthesis Example 4: Synthesis of Compound 2-57

[Reaction Formula 4]

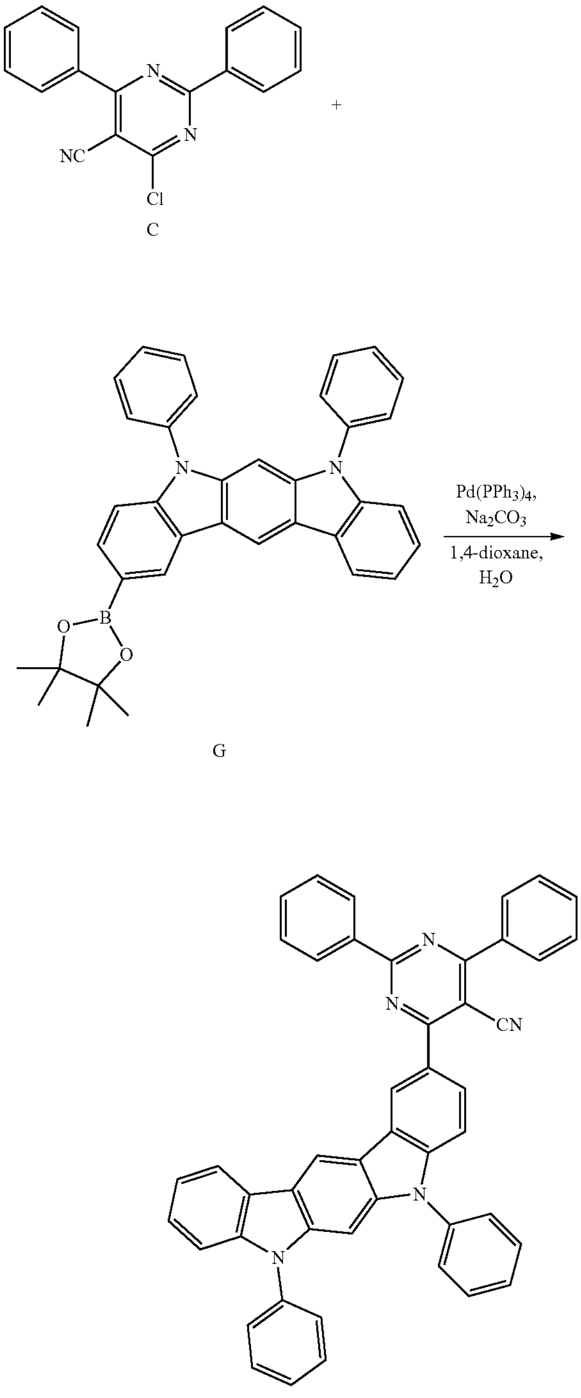

C

G 2-57

The Compound 2-57 was obtained by repeating the synthesis process of the Compound 1-27 except that the Intermediate C (2.0 g, 6.86 mmol) as the reactant was used instead of the Intermediate E (3.14 g, yield: 69%).

Synthesis Example 5: Synthesis of Compound 2-42

[Reaction Formula 5]

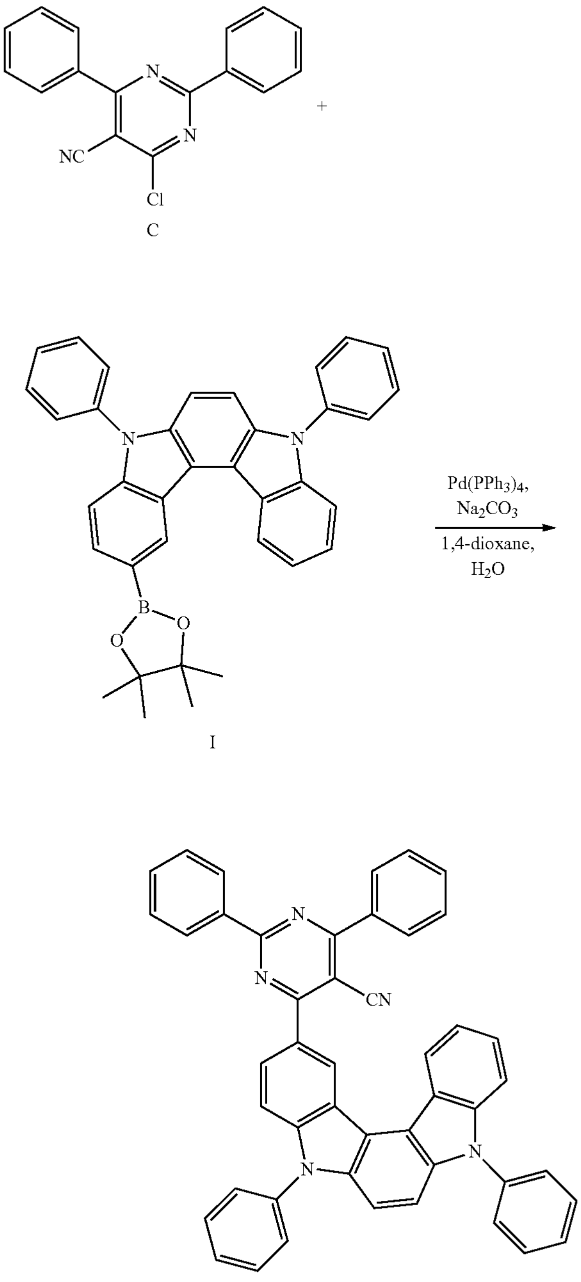

C

I 2-42

The Compound 2-42 was obtained by repeating the synthesis process of the Compound 2-57 except that the Intermediate I (2.0 g, 3.74 mmol) as the reactant was used instead of the Intermediate G (1.96 g, yield: 79%).

Synthesis Example 6: Synthesis of Compound 2-52

[Reaction Formula 6]

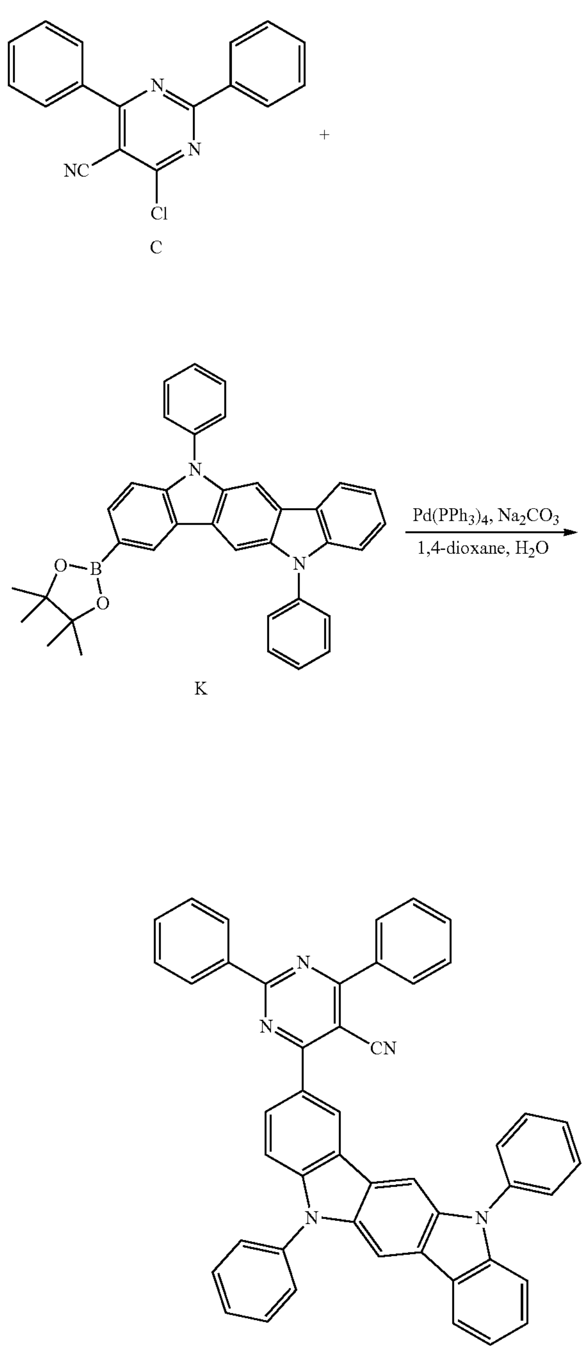

C

K 2-52

The Compound 2-52 was obtained by repeating the synthesis process of the Compound 2-57 except that the Intermediate K (2.0 g, 3.74 mmol) as the reactant was used instead of the Intermediate G.

Synthesis Example 7: Synthesis of Compound 2-27

(1) Synthesis of Intermediate L

[Reaction Formula 7-1]

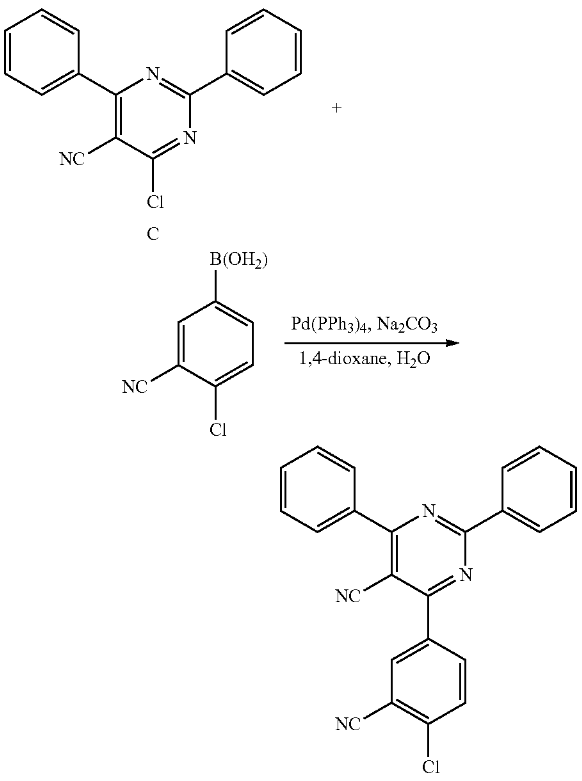

C

L

The Intermediate L was obtained by repeating the synthesis process of the Intermediate E except that the Intermediate C as the reactant was used instead of 2-chloro-4,6-diphenyl-1,3,5-triazine (5.12 g, yield: 38%)

(2) Synthesis of Compound 2-27

[Reaction Formula 7-2]

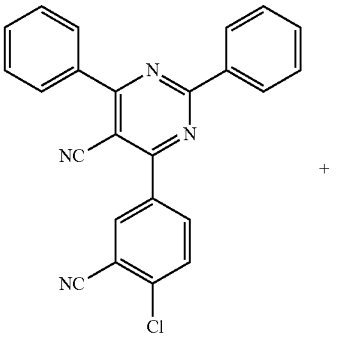

L

-continued

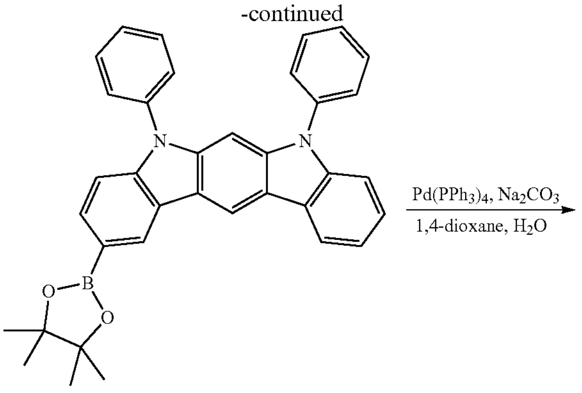

G

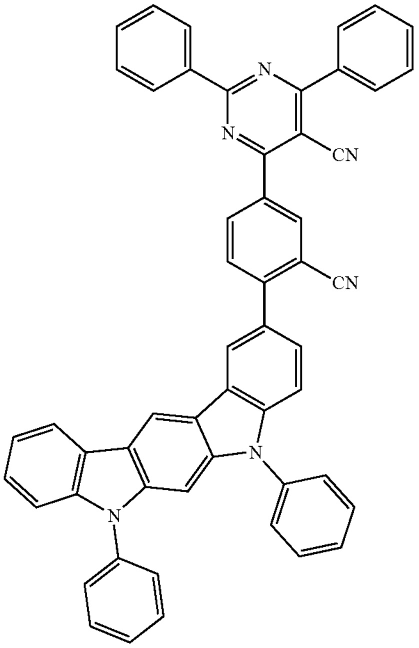

2-27

The Compound 2-27 was obtained by repeating the synthesis process of the Compound 1-27 except that the Intermediate L (2.0 g, 5.09 mmol) as the reactant was used instead of the Intermediate E (2.93 g, yield: 75%).

Synthesis Example 8: Synthesis of Compound 2-12

[Reaction Formula 8]

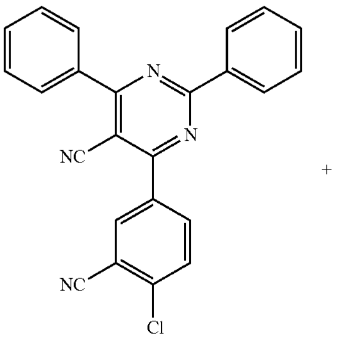

L

-continued

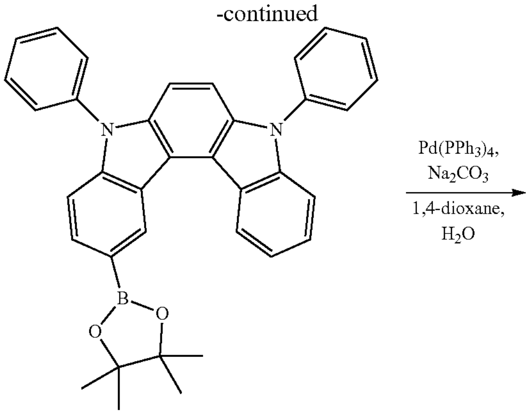

I

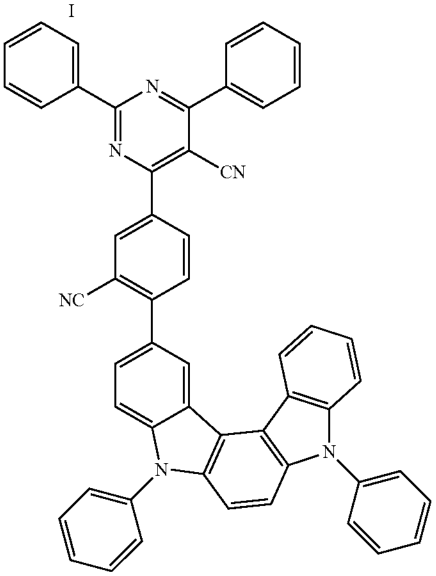

2-12

The Compound 2-12 was obtained by repeating the synthesis process of the Compound 2-27 except that the Intermediate I (2.5 g, 4.68 mmol) as the reactant was used instead of the Intermediate G (2.65 g, yield: 74%).

Synthesis Example 9: Synthesis of Compound 2-22

[Reaction Formula 9]

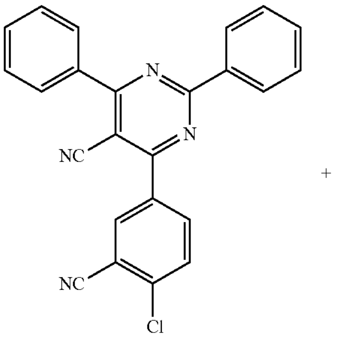

L

-continued

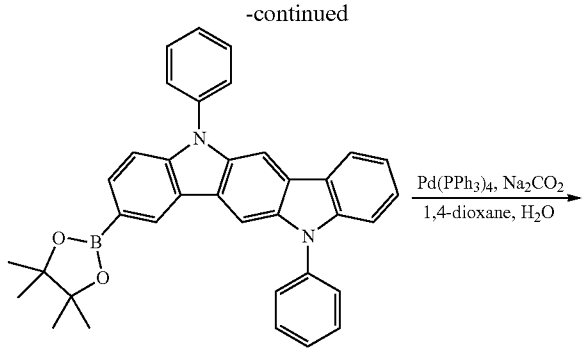

K

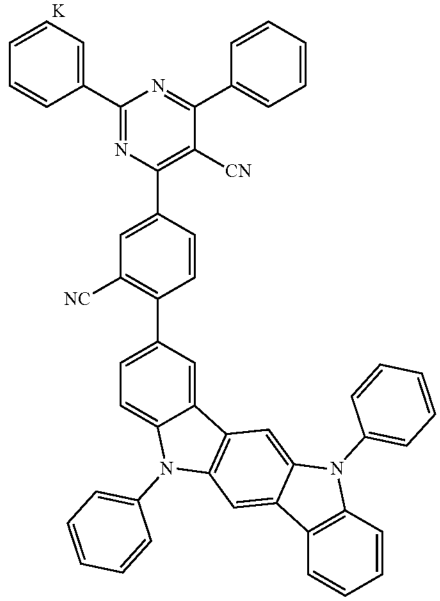

2-22

The Compound 2-22 was obtained by repeating the synthesis process of the Compound 2-27 except that the Intermediate K (2.5 g, 4.68 mmol) as the reactant was used instead of the Intermediate G (2.83 g, yield: 79%).

Example 1 (Ex. 1): Fabrication of OLED

An OLED in which the Compound 1-27 of the delayed fluorescent material (second compound) is applied into an EML was fabricated. An ITO attached glass substrate was washed with UV ozone and loaded into the vapor system, and then was transferred to a vacuum deposition chamber in order to deposit other layers on the substrate. An organic layer was deposited by evaporation by a heated boat under $10^{-7}$ torr at a deposition rate of 1 Å/s in the following order:

An anode (ITO, 50 nm); An HIL (HAT-CN, 7 nm); an HTL (TAPC, 78 nm); an EBL (DCDPA, 15 nm); an EML (mCBP (host, 50 wt %), Compound 1-27 (dopant, 50 wt %), 40 nm); an HBL (B3PYMPM, 10 nm); an ETL (TPBi, 30 nm); an EIL (LiF, 1.0 nm); and a cathode (Al, 100 nm).

And then, cappling layer (CPL) was deposited over the cathode and the device was encapsulated by glass. After deposition of emissive layer and the cathode, the OLED was transferred from the deposition chamber to a dry box for film formation, followed by encapsulation using UV-curable epoxy resin and moisture getter.

Examples 2-9 (Ex. 2-9): Fabrication of OLED

An OLED was fabricated using the same materials as Example 1, except that Compound 1-12 (Ex. 2), Compound 1-22 (Ex. 3), Compound 2-57 (Ex. 4), Compound 2-42 (Ex. 5), Compound 2-52 (Ex. 6), Compound 2-27 (Ex. 7), Compound 2-12 (Ex. 8) or Compound 2-22 (Ex. 9) as the second compound in the EML was used instead of Compound 1-27.

Comparative Examples 1-3 (Ref. 1-3): Fabrication of OLED

An OLED was fabricated using the same materials as Example 1, except that Compound Ref. 1 (Ref. 1), Compound Ref. 2 (Ref. 2) or Compound Ref. 3 (Ref. 3) as the second compound in the EML was used instead of Compound 1-27.

Experimental Example 1: Measurement of Luminous Properties of OLED

Each of the OLED fabricated by Ex. 1-9 and Ref. 1-3 having 9 $mm^2$ of luminous area was connected to an external power source and then luminous properties for all the diodes were evaluated using a constant current source (KEITHLEY) and a photometer PR650 at a room temperature. In particular, driving voltage (V), external quantum efficiency (EQE, %), maximum electroluminescence wavelength (EL $\lambda_{max}$, nm) at a current density of 6 $mA/cm^2$ and $T_{95}$ (time period from initial luminescence to 95% of luminescence, hour) at a current density of 12 $mA/cm^2$ were measured. The results thereof are shown in the following Table 1.

TABLE 1

Luminous Properties of OLED

| Sample | Second Compound | V | EQE | EL $\lambda_{max}$ | $T_{95}$ |
|---|---|---|---|---|---|
| Ref. 1 | Ref. 1 | 3.3 | 17.9 | 520 | 52 |
| Ref. 2 | Ref. 2 | 3.3 | 7.6 | 552 | 46 |
| Ref. 3 | Ref. 3 | 3.6 | 18.9 | 548 | 182 |
| Ex. 1 | 1-27 | 3.4 | 19.2 | 524 | 482 |
| Ex. 2 | 1-12 | 3.3 | 19.4 | 544 | 476 |
| Ex. 3 | 1-22 | 3.4 | 19.5 | 532 | 490 |
| Ex. 4 | 2-57 | 3.6 | 18.9 | 523 | 530 |
| Ex. 5 | 2-42 | 3.6 | 19.6 | 542 | 558 |
| Ex. 6 | 2-52 | 3.5 | 19.8 | 542 | 558 |
| Ex. 7 | 2-27 | 3.6 | 17.9 | 543 | 584 |
| Ex. 8 | 2-12 | 3.6 | 10.9 | 570 | 608 |
| Ex. 9 | 2-22 | 3.5 | 10.6 | 568 | 686 |

As indicated in Table 1, compared to the OLED fabricated in Ref. 1 in which the second compound having triazine moiety of the electron acceptor moiety is applied, the OLEDs in Ex. 1-3 in each of which different second compound having the same electron acceptor moiety is applied enhanced their EQE and $T_{95}$ up to 8.9% and 8.4 times, respectively. Compared to the OLED fabricated in Ref. 2-3 in which the second compound having pyrimidine moiety of the electron acceptor moiety is applied, the OLEDs in Ex. 4-9 in each of which different second compound having the same electron acceptor moiety is applied enhanced their EQE and $T_{95}$ up to 160.5% and 13.9 times, respectively.

It will be apparent to those skilled in the art that various modifications and variations can be made in the present disclosure without departing from the scope of the disclosure. Thus, it is intended that the present disclosure cover the modifications and variations of the present disclosure provided they come within the scope of the appended claims.

What is claimed is:

1. An organic compound having the following structure of Formula 1:

A-[L-D]$_m$ [Formula 1]

wherein A is a hetero aromatic ring having the following structure of Formula 2; L is a single bond or an aromatic ring or a hetero aromatic ring having the following structure of Formula 3; D is a fused aromatic ring or a fused hetero aromatic ring having the following structure of Formula 4; and m is 1;

[Formula 2]

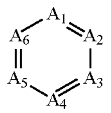

wherein one of $A_1$ to $A_6$ is a carbon atom linked to L or D, and the rest of $A_1$ to $A_6$ is independently $CR_1$ or N, wherein three of the rest of $A_1$ to $A_6$ is independently $CR_1$ and two of the rest of $A_1$ to $A_6$ is independently N, wherein $R_1$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two $R_1$ form an unsubstituted or substituted $C_6$-$C_{20}$ aromatic ring or an unsubstituted or substituted $C_3$-$C_{20}$ hetero aromatic ring, and wherein one of $R_1$ is the cyano group, the nitro group or the halogen atom;

[Formula 3]

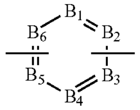

wherein two of $B_1$ to $B_6$ are carbon atoms each of which is linked to A and D, respectively, and the rest of $B_1$ to $B_6$ is independently $CR_2$ or N, wherein $R_2$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two $R_2$ of the rest of $B_1$ to $B_6$ form an unsubstituted or substituted $C_6$-$C_{20}$ aromatic ring or an unsubstituted or substituted $C_3$-$C_{20}$ hetero aromatic ring, and wherein at least one of $R_2$ is the cyano group, the nitro group or the halogen atom;

[Formula 4]

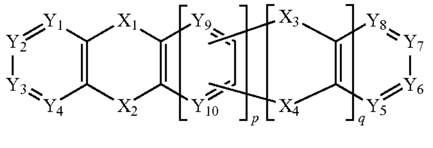

wherein each of $X_1$ to $X_4$ is independently a single bond, $CR_3R_4$ or $NR_5$, wherein each of $R_3$ to $R_5$ is independently hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, and wherein at least one of $X_1$ and $X_2$ is not a single bond and at least one of $X_3$ and $X_4$ is not a single bond; one of $Y_1$ to $Y_{10}$ is a carbon atom linked to A or L and the rest of $Y_1$ to $Y_{10}$ is independently $CR_6$ or N, wherein $R_6$ is independently is hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, or two of the rest of $Y_1$ to $Y_{10}$ form an unsubstituted or substituted $C_6$-$C_{20}$ aromatic ring or an unsubstituted or substituted $C_3$-$C_{20}$ hetero aromatic ring; and each of p and q is independently an integer of 1 to 2.

2. The organic compound of claim 1, wherein one of $X_1$ and $X_2$ is a single bond and the other of $X_1$ and $X_2$ is $NR_5$, one of $X_3$ and $X_4$ is a single bond and the other of $X_3$ and $X_4$ is $NR_5$, each of p and q is 1, and one of $Y_1$ to $Y_{10}$ is a carbon atom linked to L and the rest of $Y_1$ to $Y_{10}$ is independently $CR_6$, wherein $R_5$ and $R_6$ are the same as defined in claim 1.

3. The organic compound of claim 1, wherein D has the following structure of Formula 5 or Formula 6:

[Formula 5]

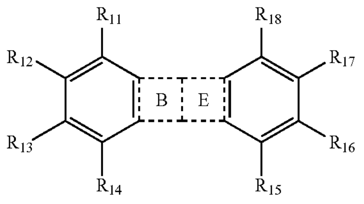

[Formula 6]

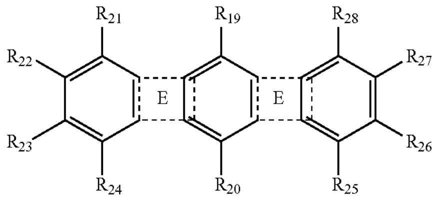

wherein B has the following structure of Formula 7; E has the following structure of Formula 8; one of $R_{11}$ to $R_{18}$ is a carbon atom linked to A or L and the rest of $R_{11}$ to $R_{18}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group; one of $R_{19}$ to $R_{28}$ is a carbon atom linked to A or L and the rest of $R_{19}$ to $R_{28}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group;

[Formula 7]

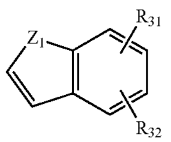

-continued

[Formula 8]

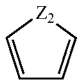

wherein each of $R_{31}$ and $R_{32}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group; each of $Z_1$ and $Z_2$ is independently $NR_{33}$, wherein $R_{33}$ is hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group.

4. The organic compound of claim 1, wherein the organic compound is selected from the following compounds:

2-1

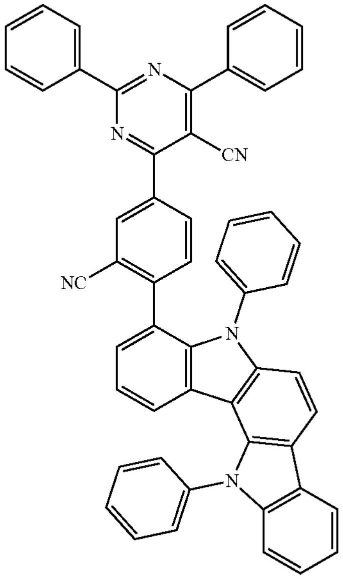

2-2

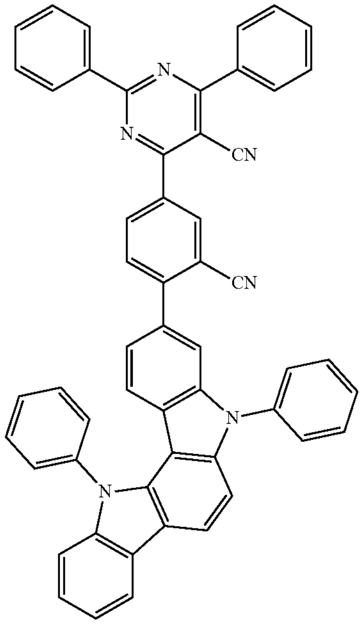

-continued 2-3

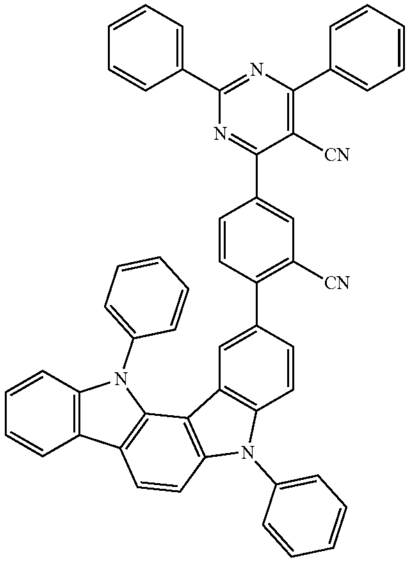

2-4

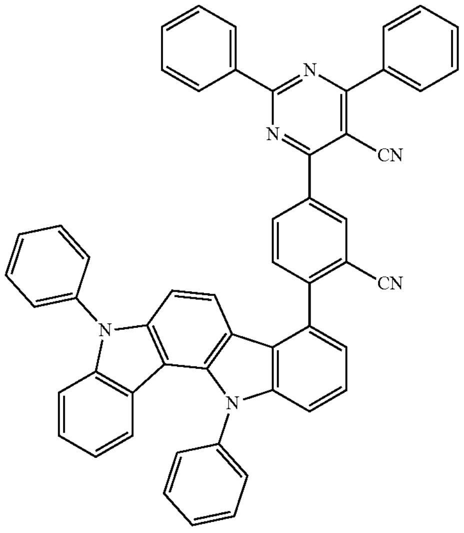

2-5

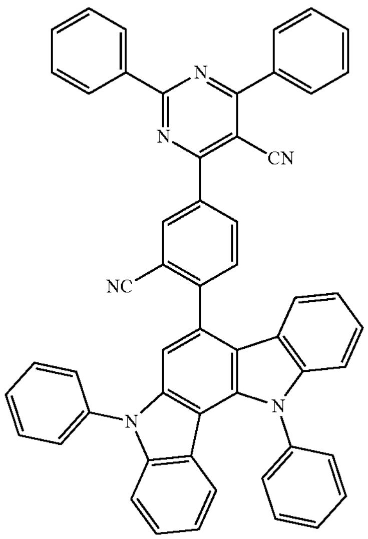

-continued
2-6
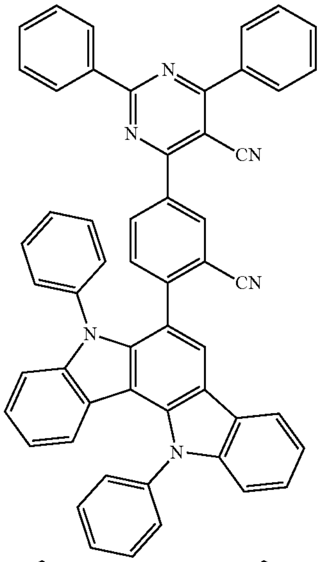
2-7
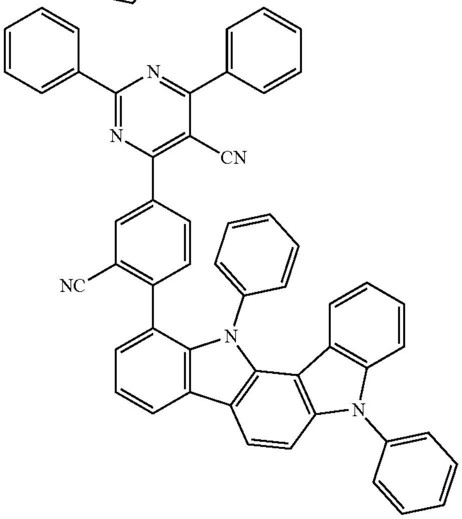
2-8
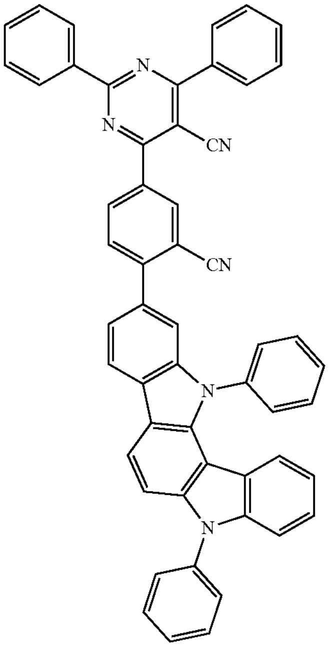
-continued
2-9
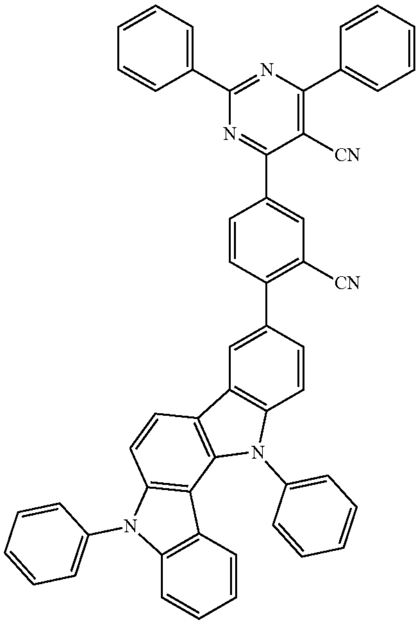
2-10
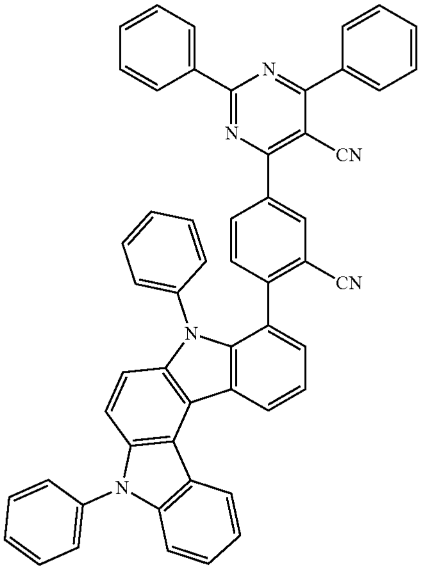

2-11
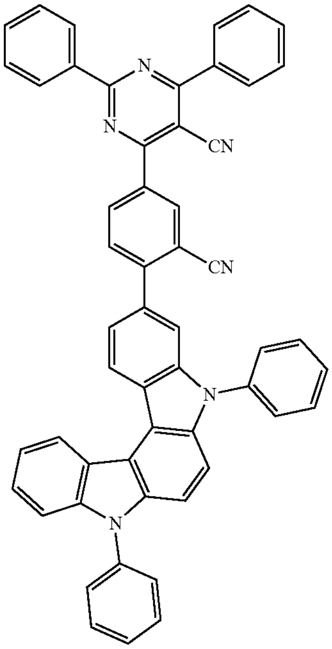
2-12
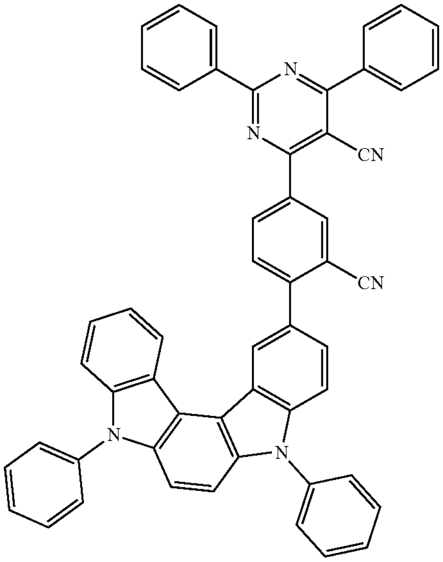
2-13
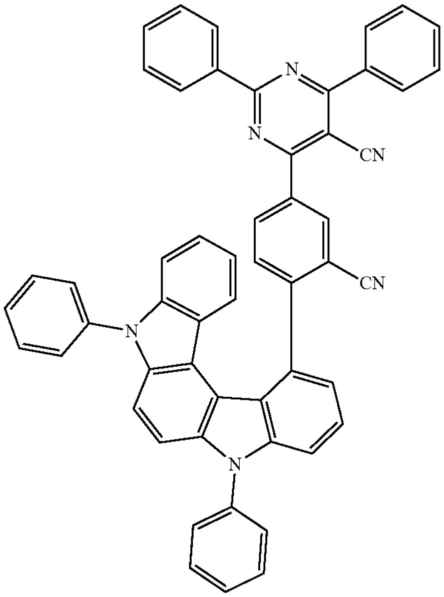
2-14
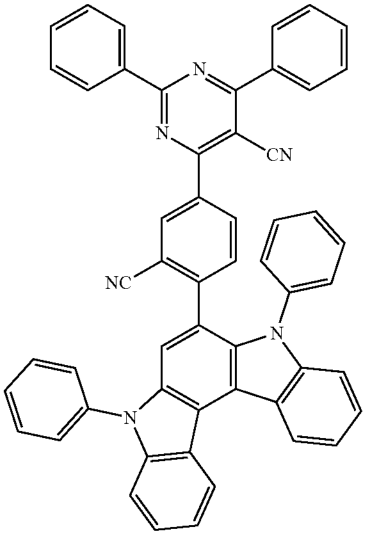
2-15
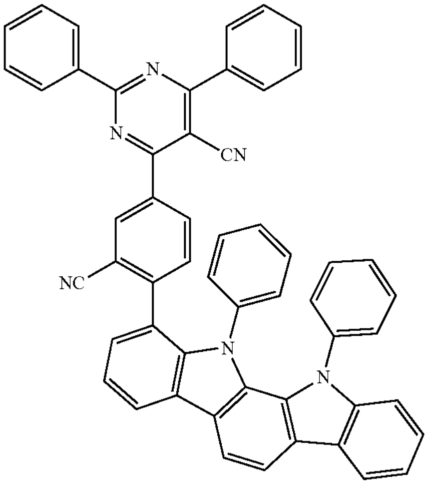

-continued
2-16
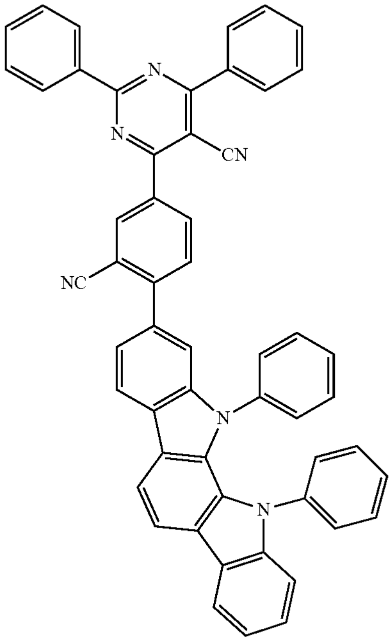
2-17
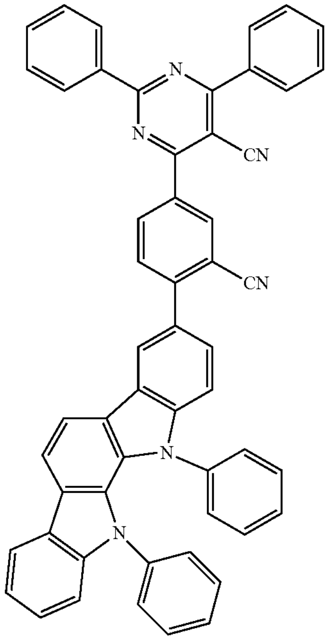
-continued
2-18
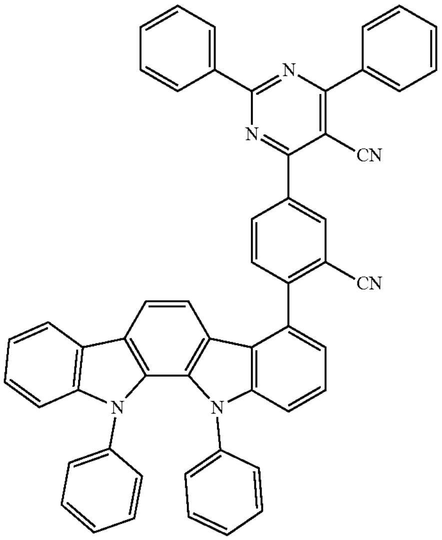
2-19
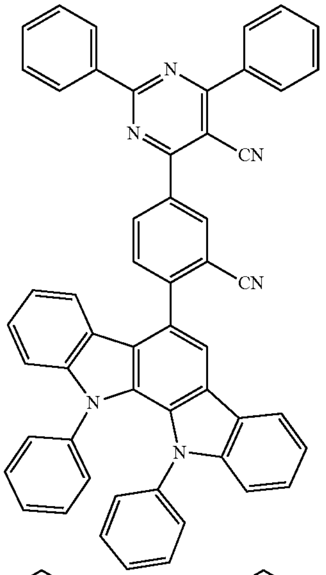
2-20
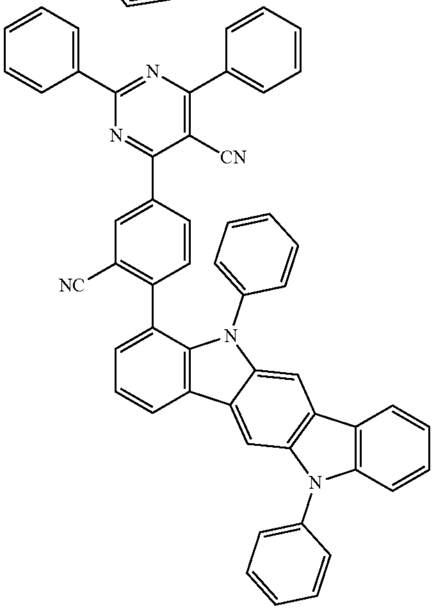

-continued
2-21
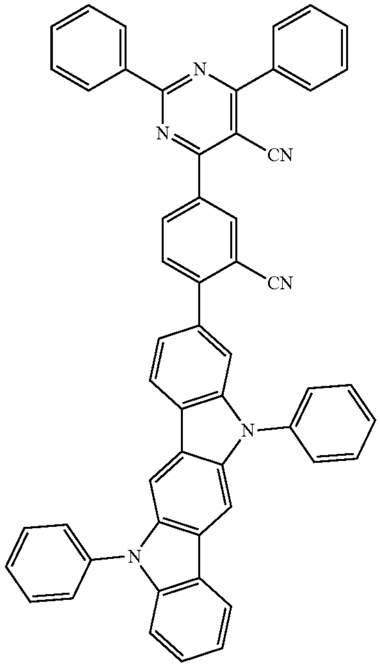
2-22
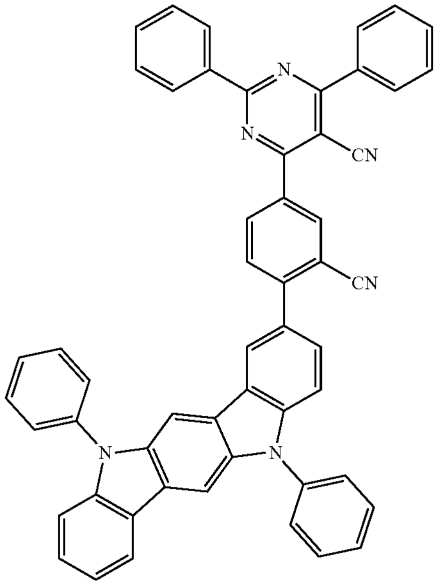
-continued
2-23
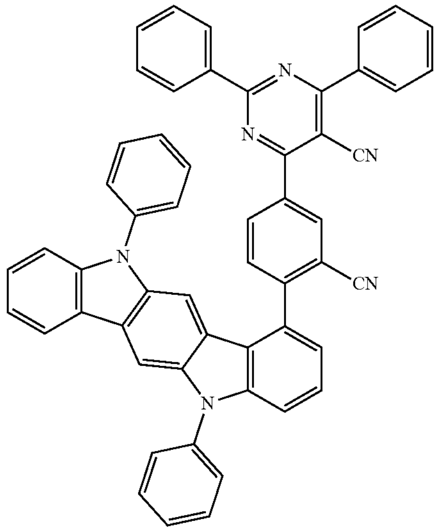
2-24
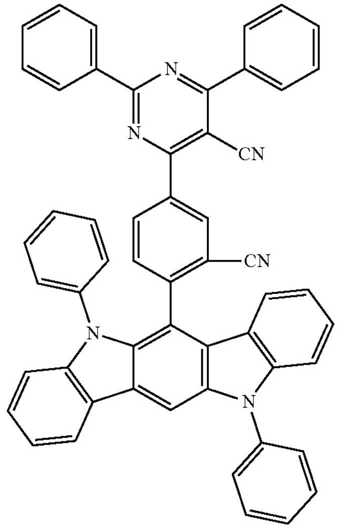
2-25
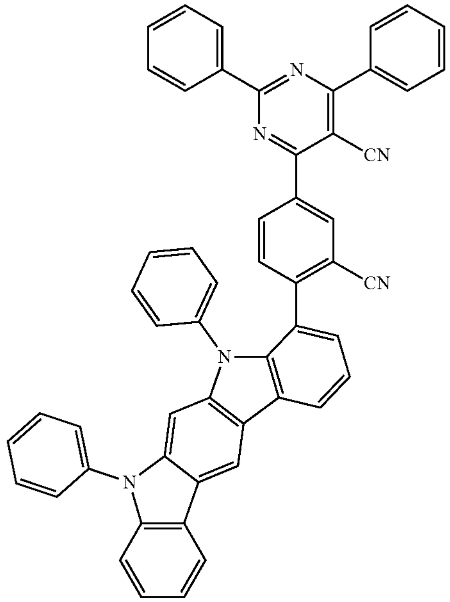

-continued
2-26
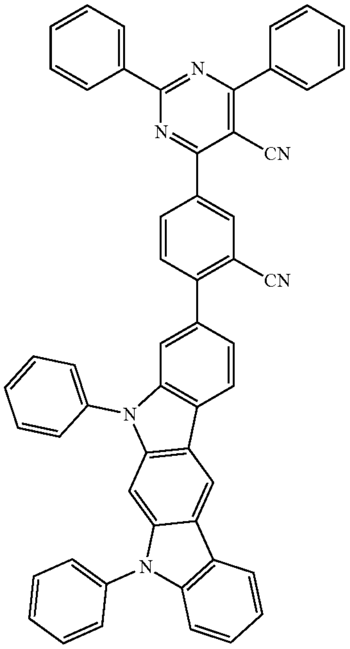
2-27
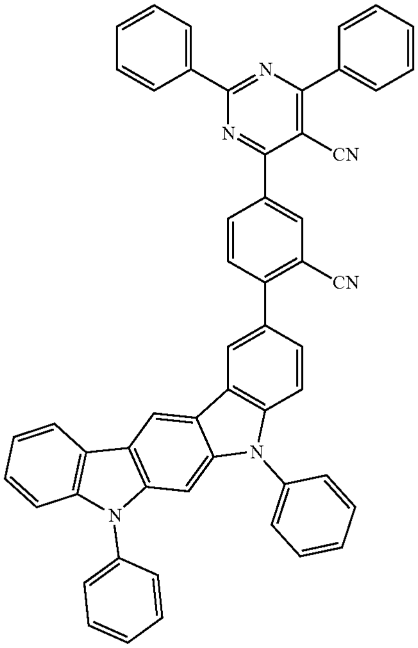
-continued
2-28
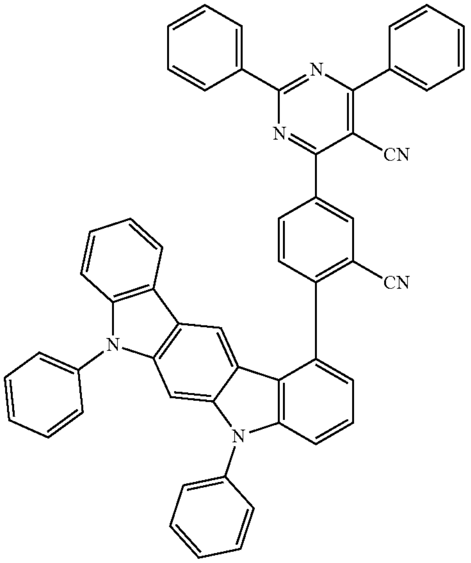
2-29
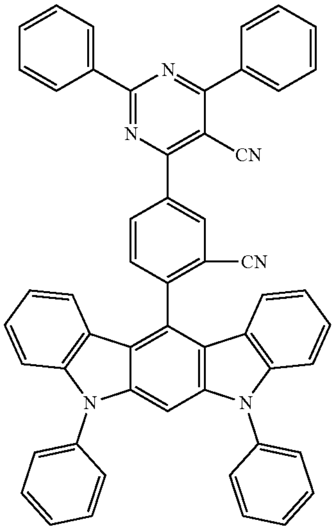
2-30
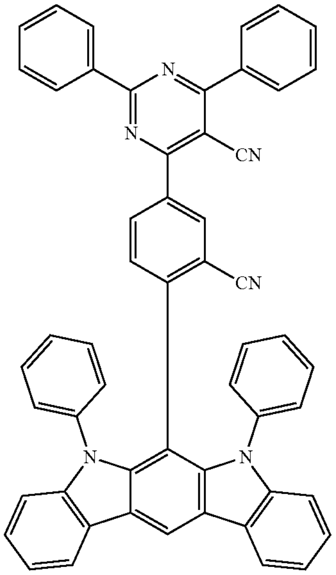

-continued
2-31
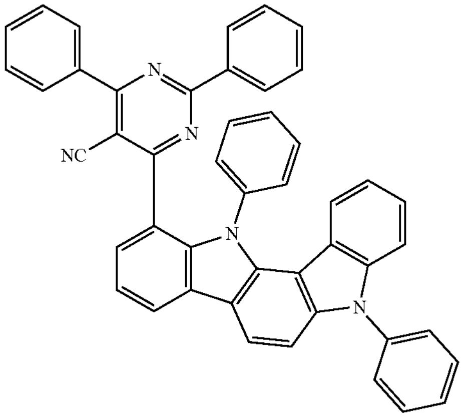
2-32
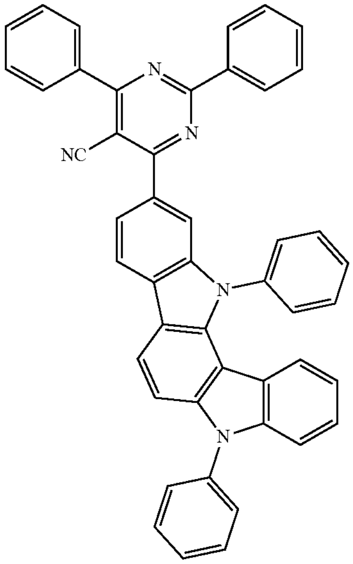
2-33
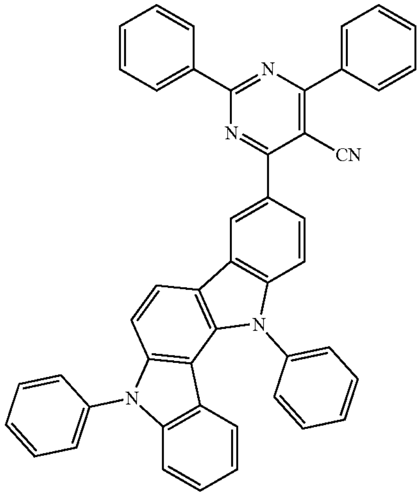
-continued
2-34
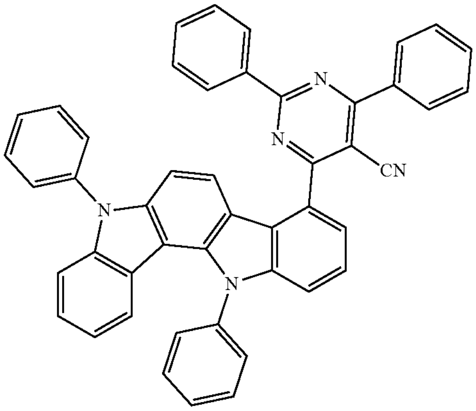
2-35
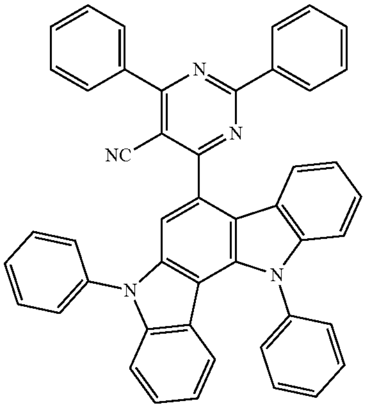
2-36
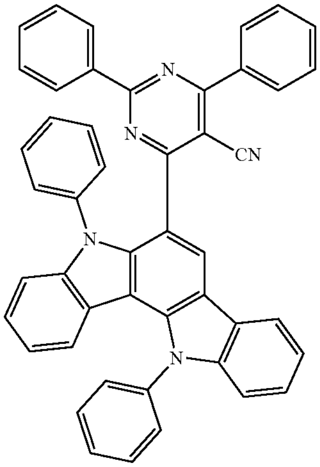

-continued
2-37
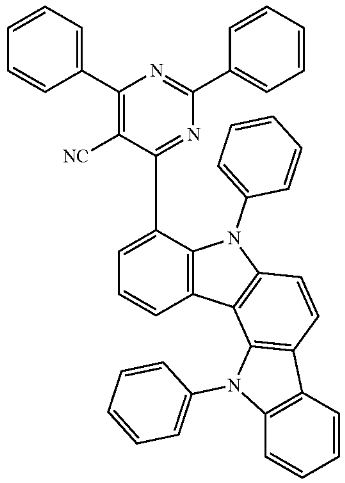
2-38
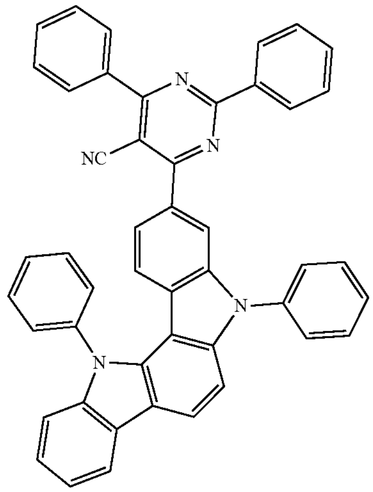
2-39
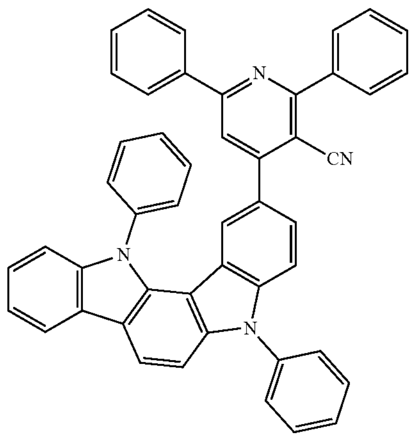
-continued
2-40
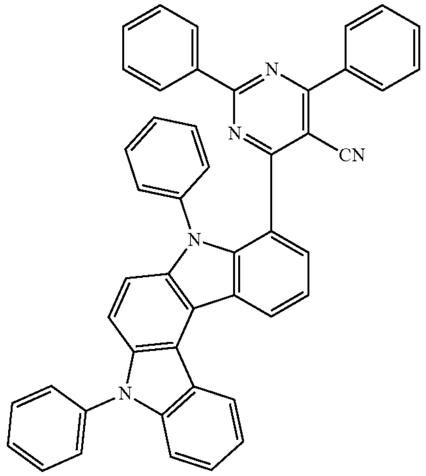
2-41
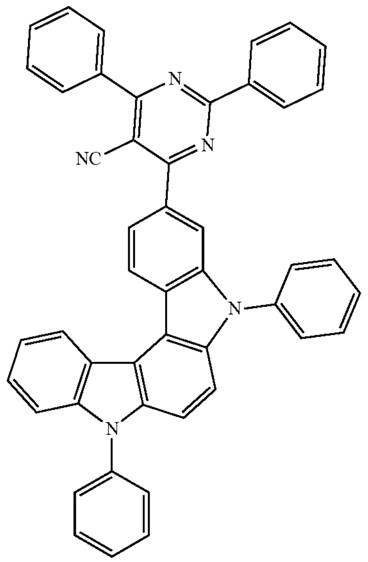
2-42
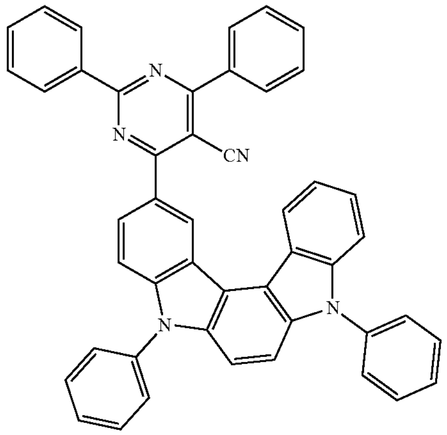

-continued
2-43
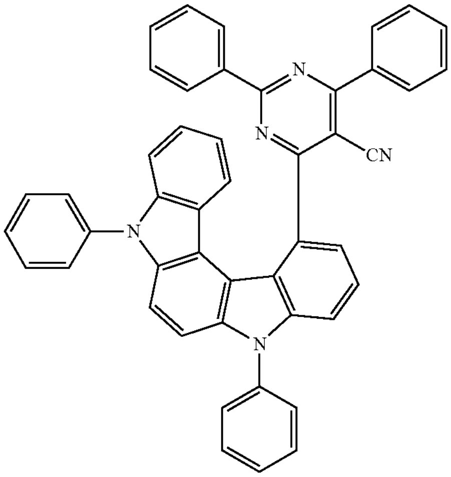
2-44
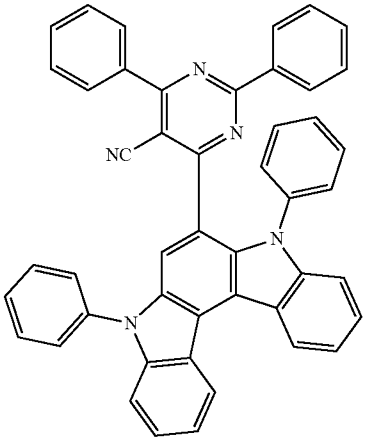
2-45
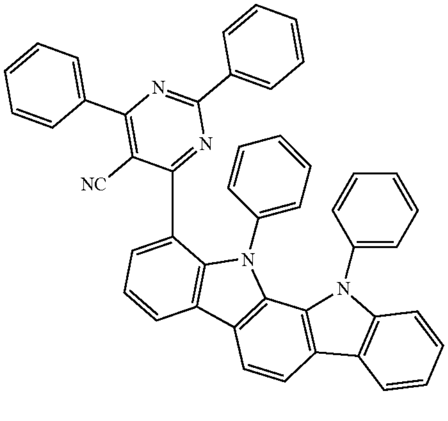
-continued
2-46
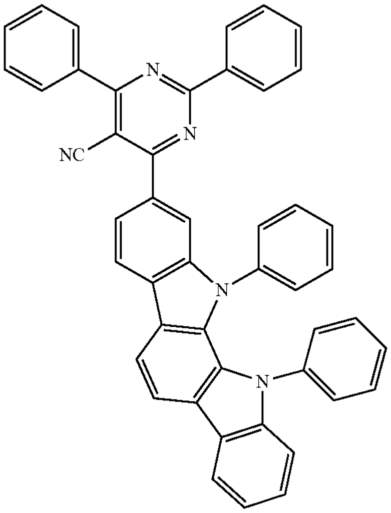
2-47
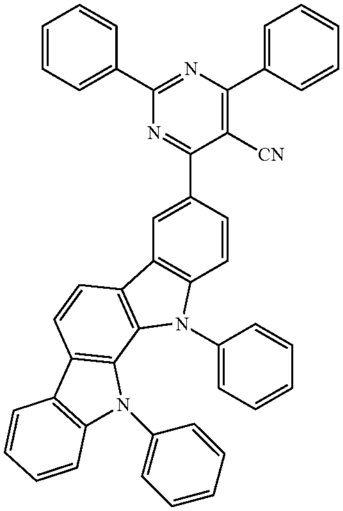
2-48
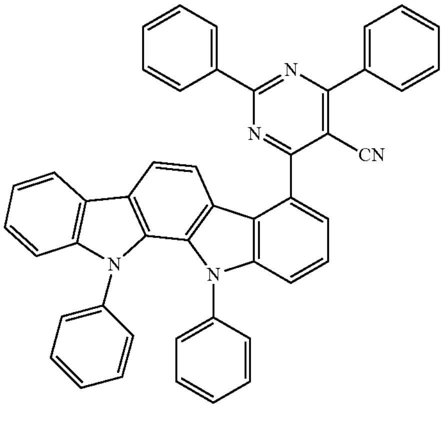

-continued
2-49
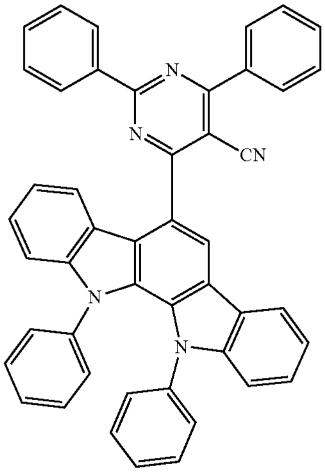
2-50
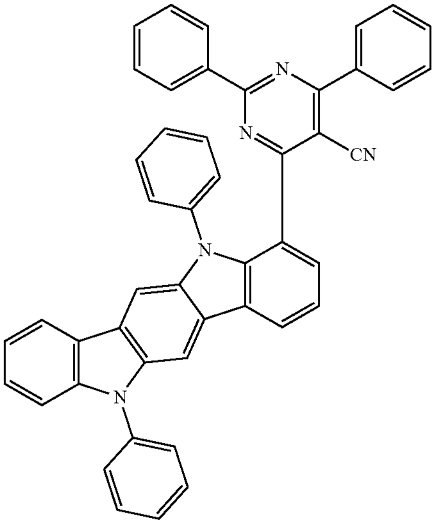
2-51
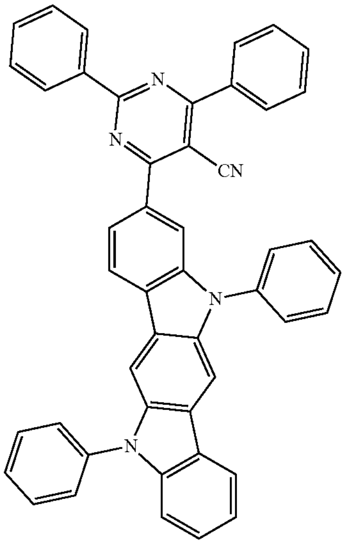
-continued
2-52
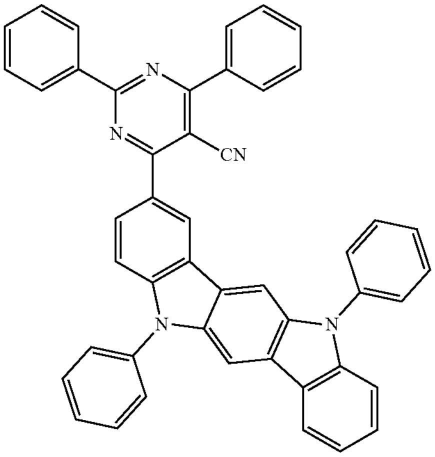
2-53
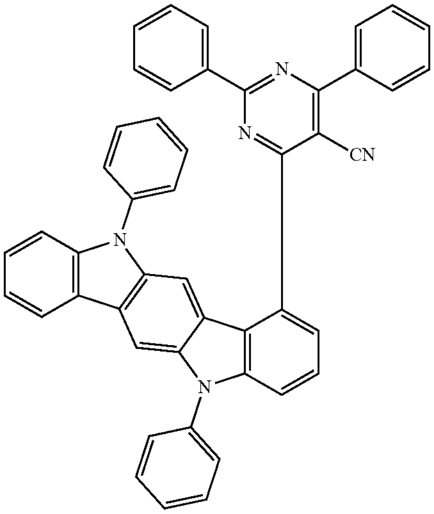
2-54
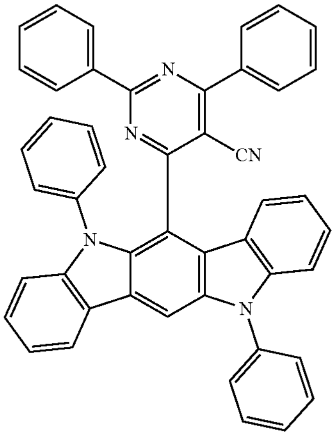

2-55
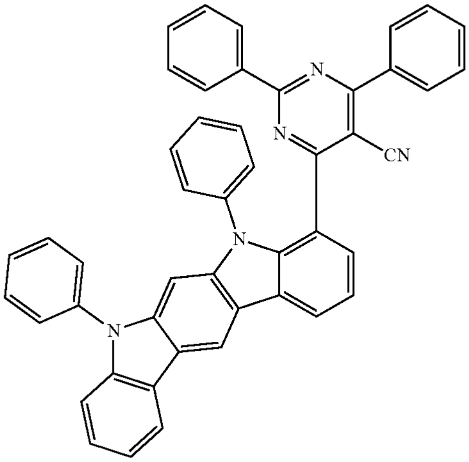
2-56
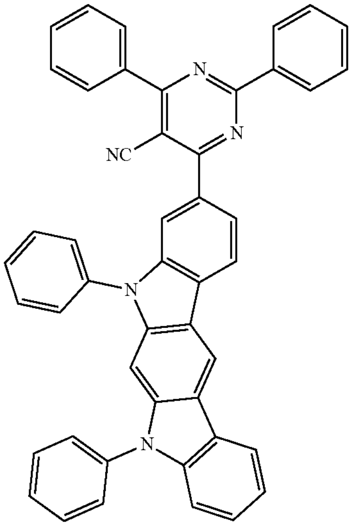
2-57
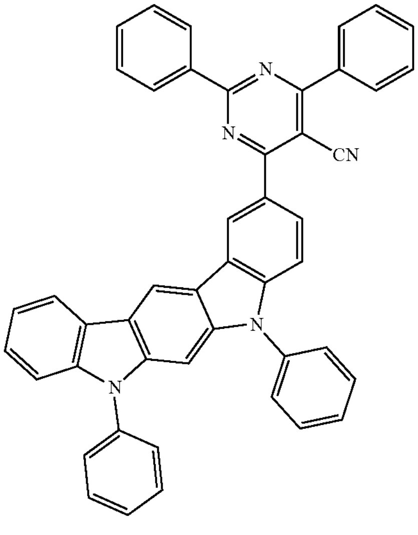
2-58
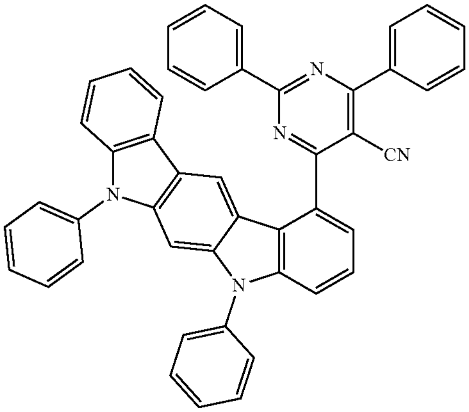
2-59
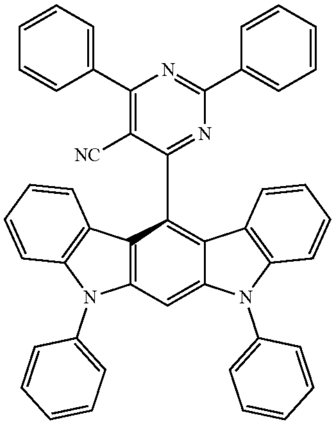
2-60
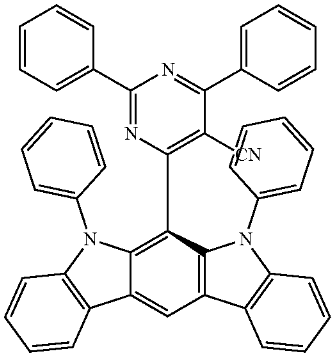

-continued
2-61
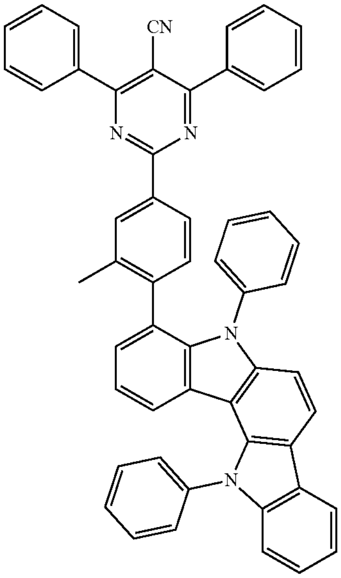
2-62
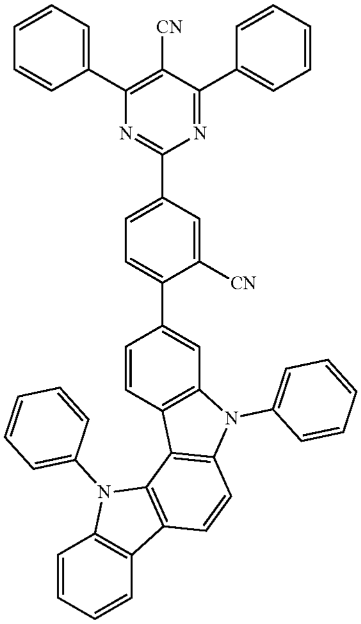
-continued
2-63
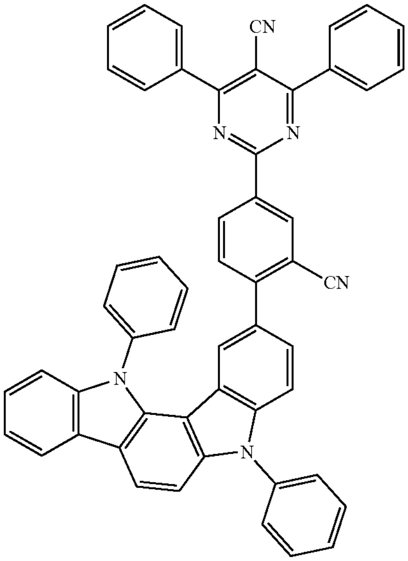
2-64
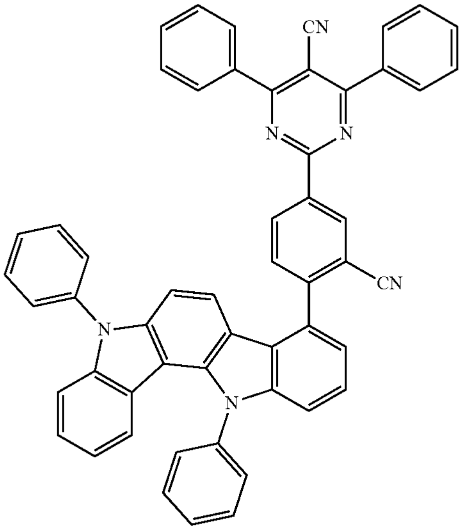

-continued
2-65
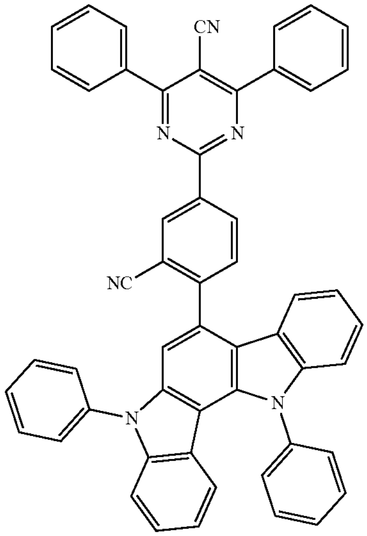
2-66
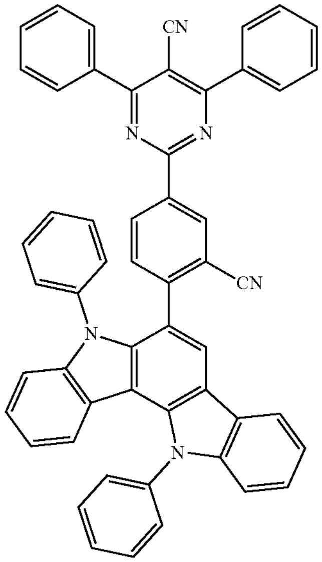
2-67
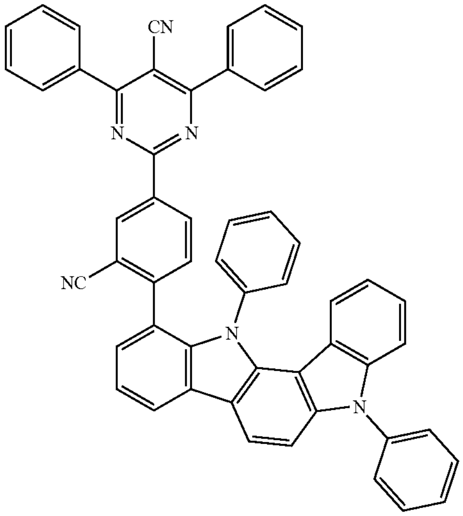
-continued
2-68
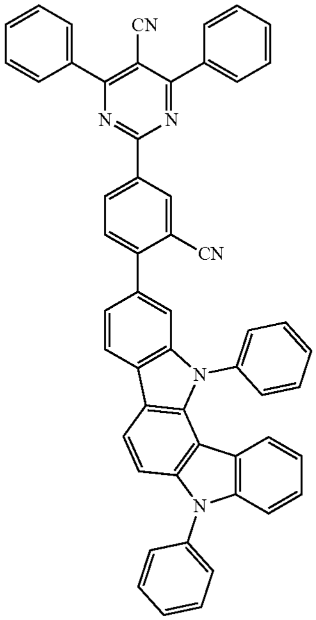
2-69
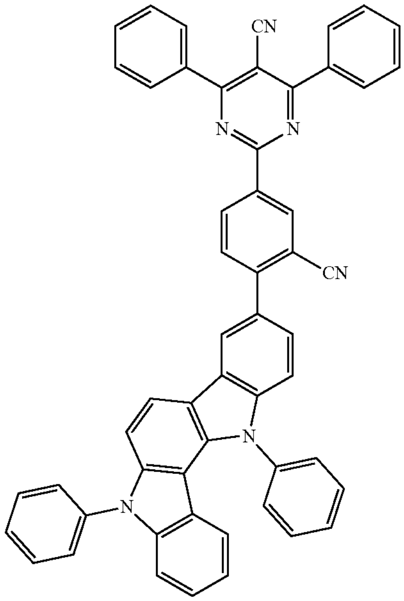

-continued
2-70
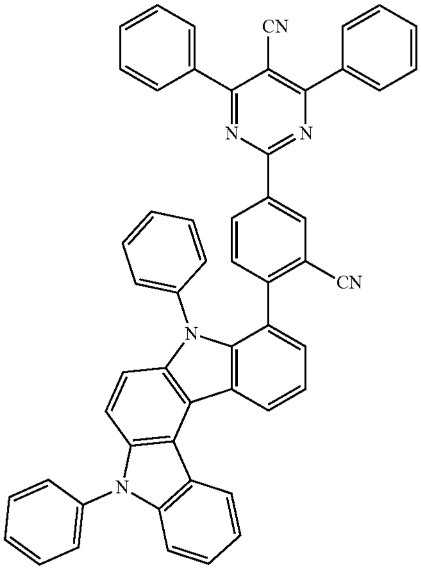
2-71
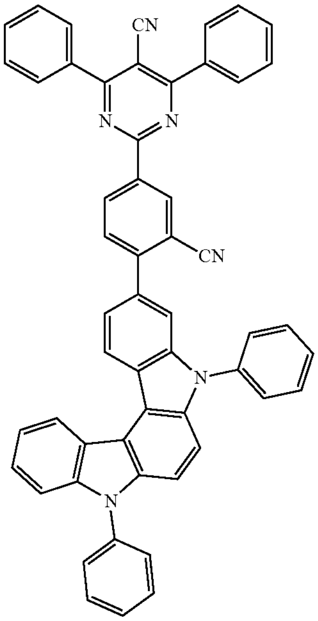
-continued
2-72
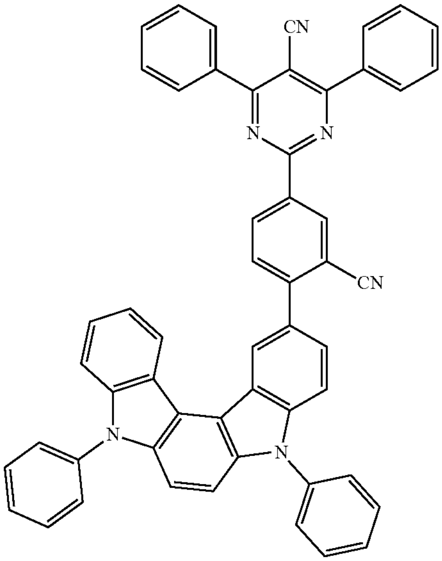
2-73
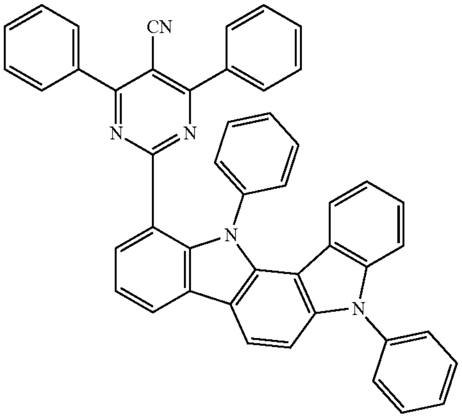
2-74
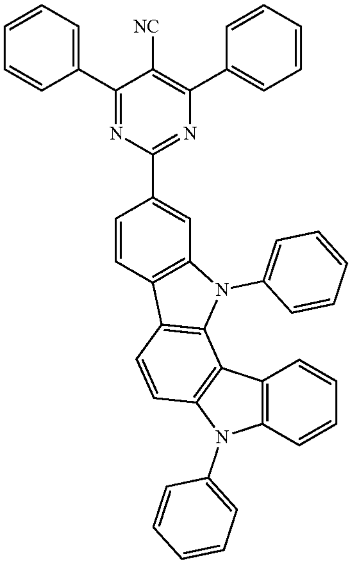

-continued
2-75
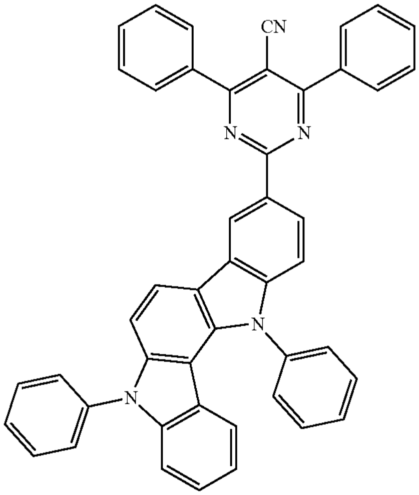
2-76
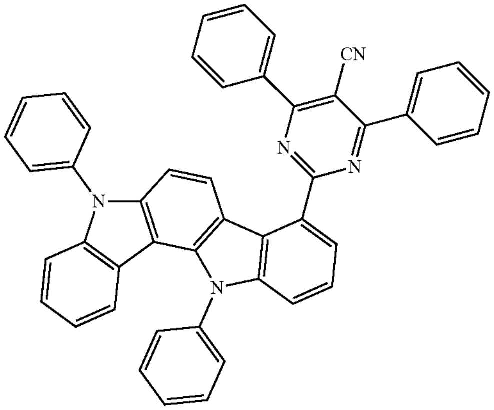
2-77
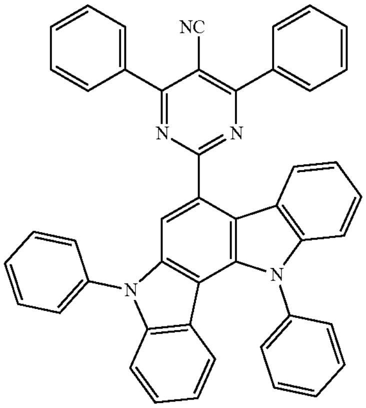
-continued
2-78
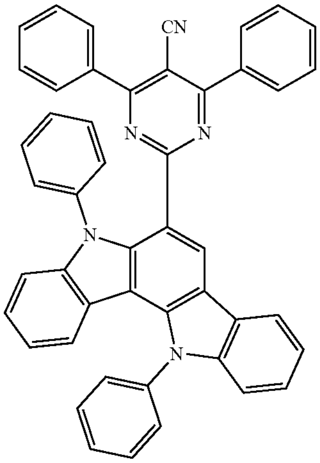
2-79
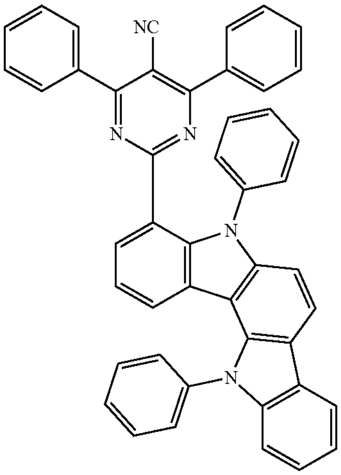
2-80
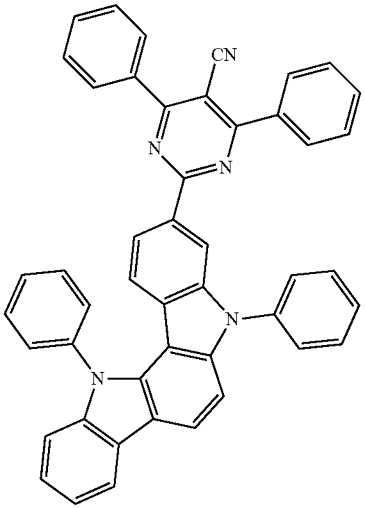

-continued
2-81
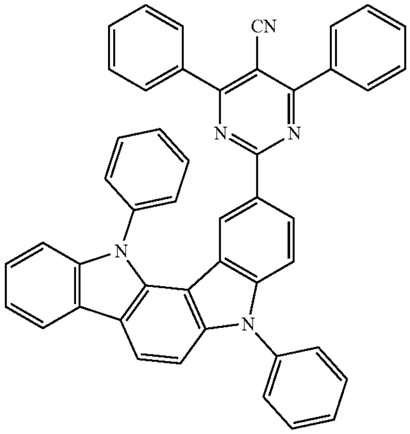
2-82
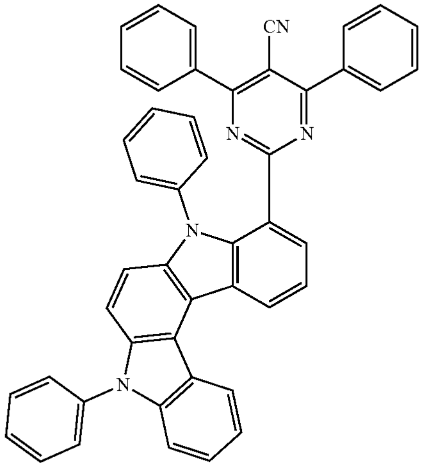
2-83
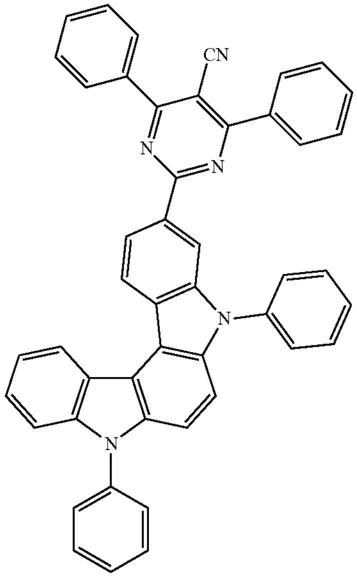
-continued
2-84
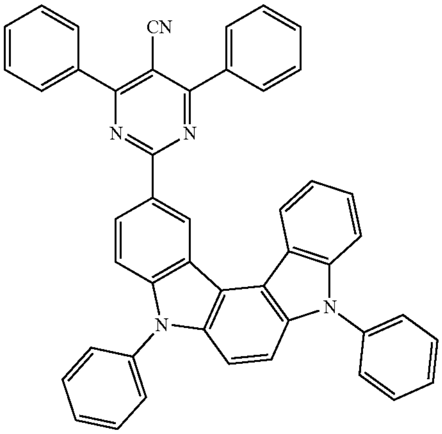
2-85
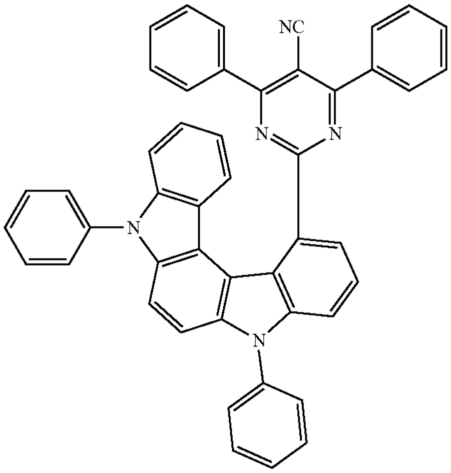
2-86
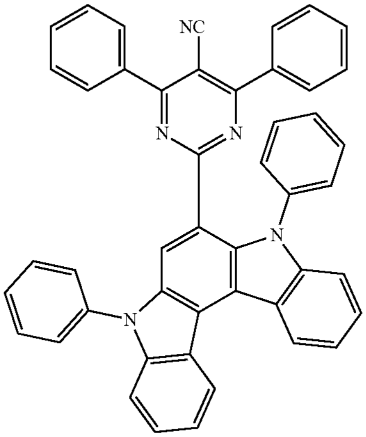

-continued
2-87
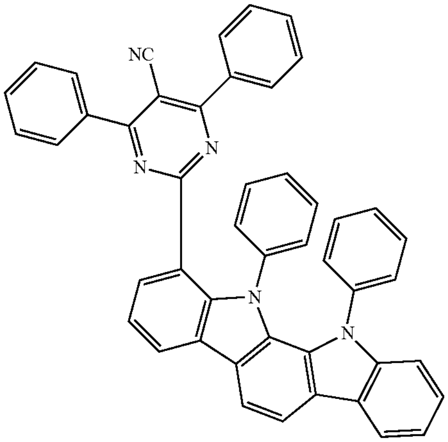
2-88
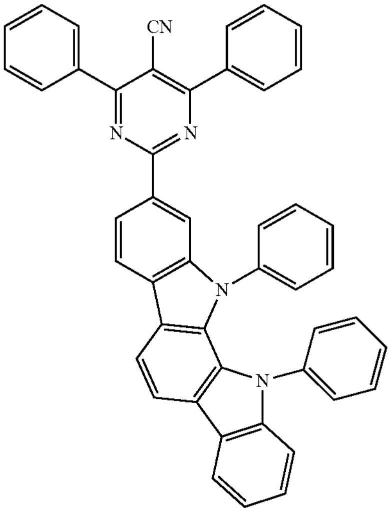
2-89
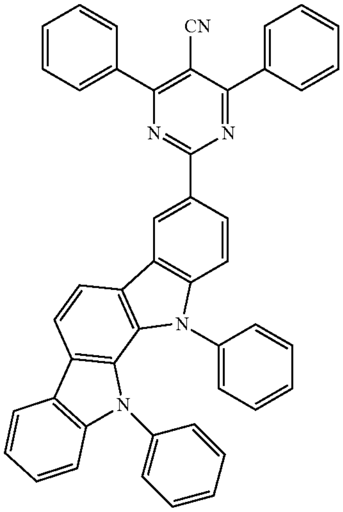
-continued
2-90
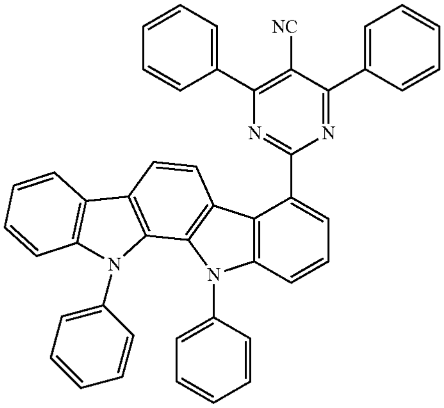
2-91
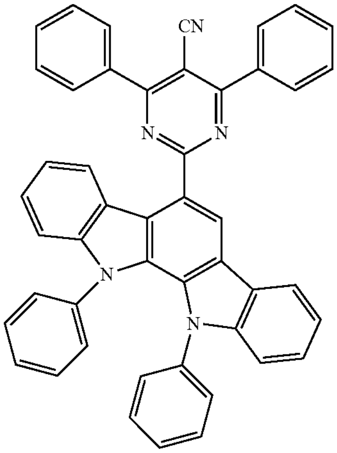
2-92
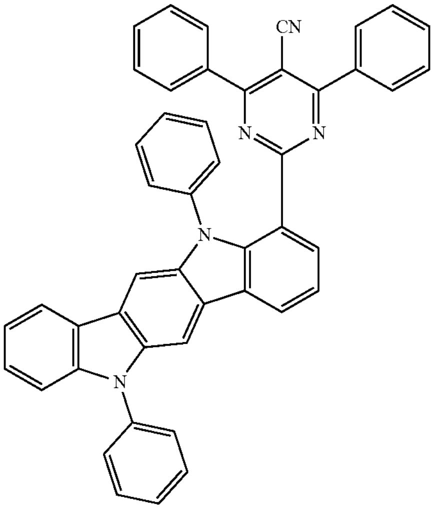

-continued
2-93
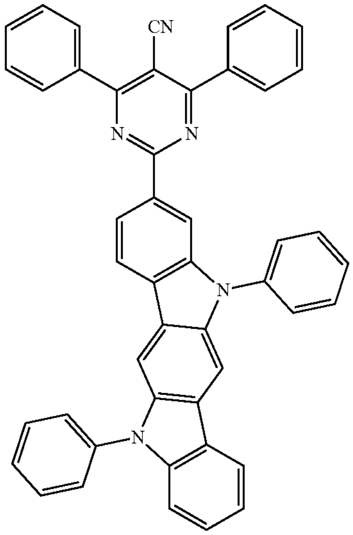
2-94
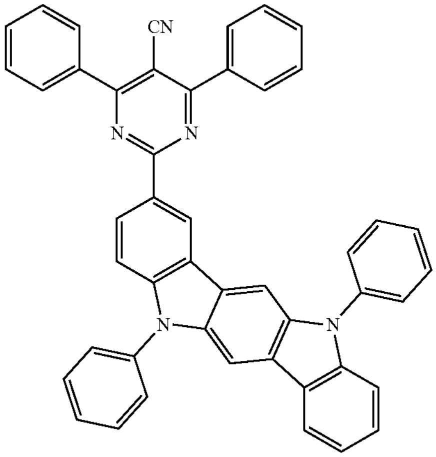
2-95
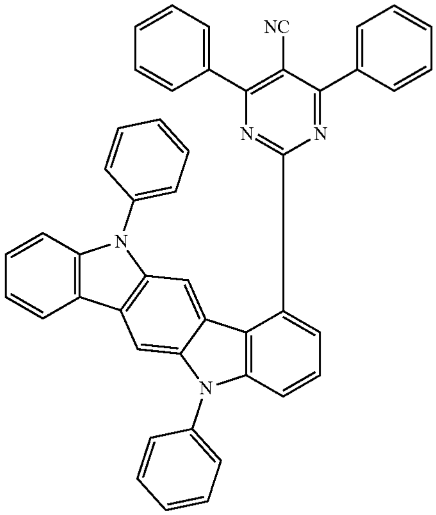
-continued
2-96
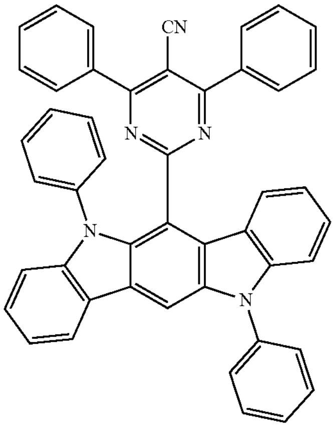
2-97
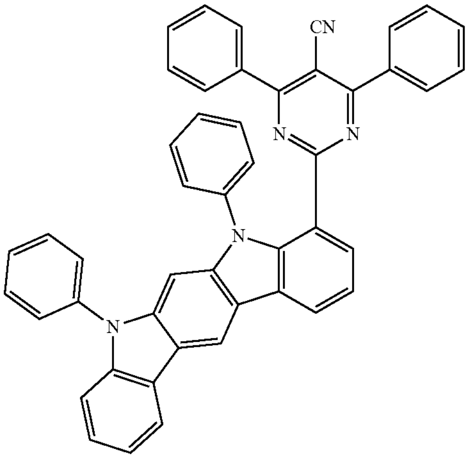
2-98
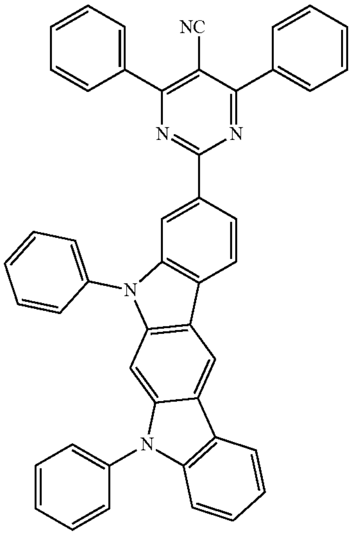

-continued 2-99

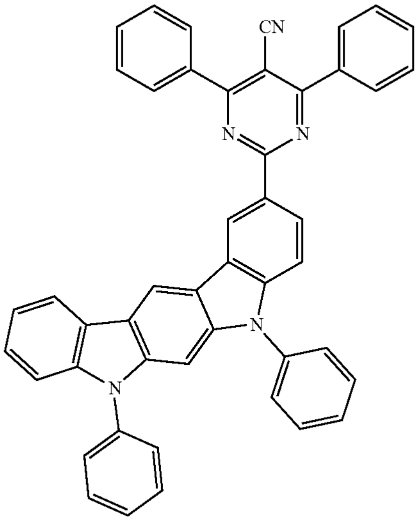

2-100

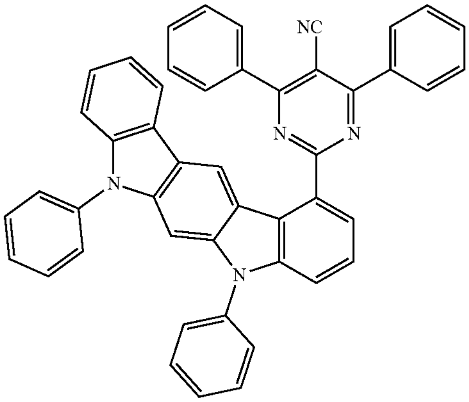

2-101

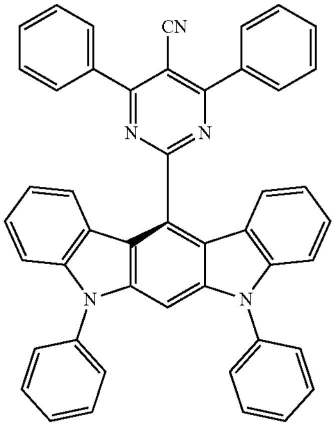

-continued 2-102

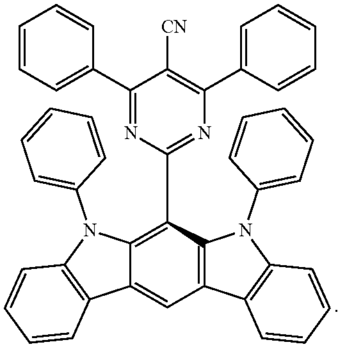

5. An organic light emitting diode comprising:

a first electrode;

a second electrode facing the first electrode; and an emissive layer disposed between the first and second electrodes, wherein the emissive layer comprise an organic compound having the following structure of Formula 1:

A-[L-D]$_m$ [Formula 1]

wherein A is a hetero aromatic ring having the following structure of Formula 2; L is a single bond or an aromatic ring or a hetero aromatic ring having the following structure of Formula 3; D is a fused aromatic ring or a fused hetero aromatic ring having the following structure of Formula 4; and m is 1;

[Formula 2]

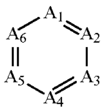

wherein one of $A_1$ to $A_6$ is a carbon atom linked to L or D and the rest of $A_1$ to $A_6$ is independently $CR_1$ or N, wherein three of the rest of $A_1$ to $A_6$ is independently $CR_1$ and two of the rest of $A_1$ to $A_6$ is independently N, wherein $R_1$ is independently a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two $R_1$ form an unsubstituted or substituted $C_6$-$C_{20}$ aromatic ring or an unsubstituted or substituted $C_3$-$C_{20}$ hetero aromatic ring, and wherein one of $R_1$ is the cyano group, the nitro group or the halogen atom;

[Formula 3]

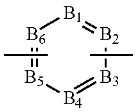

wherein two of $B_1$ to $B_6$ are carbon atoms each of which is linked to A and D, respectively, and the rest of $B_1$ to $B_6$ is independently $CR_2$ or N, wherein $R_2$ is independently hydrogen, a cyano group, a nitro group, a halogen atom, an unsubstituted or substituted $C_1$-$C_{20}$ alkyl group, an unsubstituted or substituted $C_1$-$C_{20}$ alkyl amino group, an unsubstituted or substituted $C_6$-$C_{30}$ aromatic group or an unsubstituted or substituted $C_3$-$C_{20}$ hetero aromatic group, or adjacent two $R_2$ of the rest of $B_1$ to $B_6$ form an unsubstituted or substituted $C_6$-$C_{20}$ aromatic ring or an unsubstituted or substituted $C_3$-$C_{20}$ hetero aromatic ring, and wherein at least one of $R_2$ is the cyano group, the nitro group or the halogen atom;

[Formula 4]

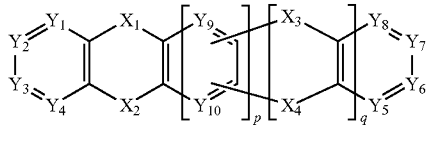

wherein each of $X_1$ to $X_4$ is independently a single bond, $CR_3R_4$ or $NR_5$, wherein each of $R_3$ to $R_5$ is independently hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, and wherein at least one of $X_1$ and $X_2$ is not a single bond and at least one of $X_3$ and $X_4$ is not a single bond; one of $Y_1$ to $Y_{10}$ is a carbon atom linked to A or L and the rest of $Y_1$ to $Y_{10}$ is independently $CR_6$ or N, wherein $R_6$ is independently is hydrogen, an unsubstituted or substituted $C_1$-$C_{20}$ alkyl group, an unsubstituted or substituted $C_6$-$C_{30}$ aromatic group or an unsubstituted or substituted $C_3$-$C_{20}$ hetero aromatic group, or two of the rest of $Y_1$ to $Y_{10}$ form an unsubstituted or substituted $C_6$-$C_{20}$ aromatic ring or an unsubstituted or substituted $C_3$-$C_{20}$ hetero aromatic ring; and each of p and q is independently an integer of 1 to 2.

6. The organic light emitting diode of claim 5, wherein one of $X_1$ and $X_2$ is a single bond and the other of $X_1$ and $X_2$ is $NR_5$, one of $X_3$ and $X_4$ is a single bond and the other of $X_3$ and $X_4$ is $NR_5$, each of p and q is 1, and one of $Y_1$ to $Y_{10}$ is a carbon atom linked to L and the rest of $Y_1$ to $Y_{10}$ is independently $CR_6$, wherein $R_5$ and $R_6$ are the same as defined in claim 5.

7. The organic light emitting diode of claim 5, wherein D has the following structure of Formula 5 or Formula 6:

[Formula 5]

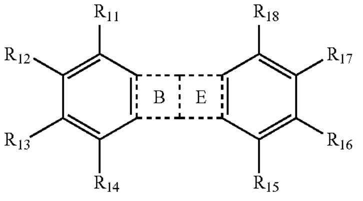

[Formula 6]

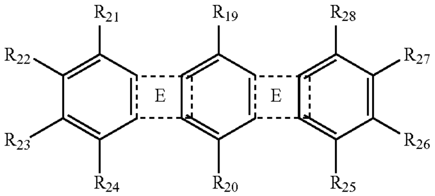

wherein B has the following structure of Formula 7; E has the following structure of Formula 8; one of $R_{11}$ to $R_{18}$ is a carbon atom linked to A or L and the rest of $R_{11}$ to $R_{18}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group; one of $R_{19}$ to $R_{28}$ is a carbon atom linked to A or L and the rest of $R_{19}$ to $R_{28}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group;

[Formula 7]

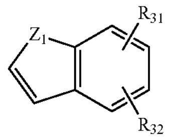

[Formula 8]

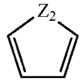

wherein each of $R_{31}$ and $R_{32}$ is independently hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group; each of $Z_1$ and $Z_2$ is independently $NR_{33}$, wherein $R_{33}$ is hydrogen, an unsubstituted or substituted $C_1$-$C_{20}$ alkyl group, an unsubstituted or substituted $C_6$-$C_{30}$ aryl group or an unsubstituted or substituted $C_3$-$C_{20}$ hetero aryl group.

8. The organic light emitting diode of claim 5, wherein the emissive layer includes at least one emitting material layer, and wherein the at least one emitting material layer includes the organic compound.

9. The organic light emitting diode of claim 8, wherein the at least one emitting material layer includes a first compound and a second compound, and wherein the second compound includes the organic compound.

10. The organic light emitting diode of claim 9, wherein the at least one emitting material layer further comprises a third compound.

11. The organic light emitting diode of claim 9, wherein the at least one emitting material layer includes a first emitting material layer disposed between the first electrode and the second electrode and a second emitting material layer disposed between the first electrode and the first emitting material layer or disposed between the first emitting material layer and the second electrode.

12. The organic light emitting diode of claim 11, wherein the at least one emitting material layer further comprises a third emitting material layer disposed oppositely to the second emitting material layer with respect to the first emitting material layer.

13. An organic light emitting device comprising:

a substrate; and an organic light emitting diode of claim 5 disposed over the substrate.

14. The organic compound of claim 1, wherein each of the rest of $R_1$ in Chemical Formula 2 is independently the unsubstituted or substituted $C_6$-$C_{30}$ aromatic group or the unsubstituted or substituted $C_3$-$C_{20}$ hetero aromatic group.

15. The organic light emitting diode of claim 5, wherein each of the rest of $R_1$ in Chemical Formula 2 is independently the unsubstituted or substituted $C_6$-$C_{30}$ aromatic group or the unsubstituted or substituted $C_3$-$C_{20}$ hetero aromatic group.

* * * * *